(12) United States Patent
Lyman et al.

(10) Patent No.: US 12,653,972 B2
(45) Date of Patent: Jun. 16, 2026

(54) COMPOSITIONS, DEVICES, AND METHODS FOR INTRANASAL DELIVERY OF DRY POWDER EPINEPHRINE

(71) Applicant: Belhaven BioPharma Inc., Raleigh, NC (US)

(72) Inventors: Scott Lyman, Raleigh, NC (US); Brian Taubenheim, Elkhart Lake, WI (US)

(73) Assignee: Belhaven BioPharma Inc., Raleigh, NC (US)

( * ) Notice: Subject to any disclaimer, the term of this patent is extended or adjusted under 35 U.S.C. 154(b) by 0 days.

(21) Appl. No.: 19/243,323

(22) Filed: Jun. 19, 2025

(65) Prior Publication Data

US 2026/0108459 A1     Apr. 23, 2026

Related U.S. Application Data

(60) Provisional application No. 63/709,741, filed on Oct. 21, 2024.

(51) Int. Cl.
*A61K 9/00* (2006.01)
*A61K 9/14* (2006.01)
(Continued)

(52) U.S. Cl.
CPC .............. *A61K 9/0075* (2013.01); *A61K 9/14* (2013.01); *A61M 11/001* (2014.02); *A61M 15/08* (2013.01)

(58) Field of Classification Search
CPC .... A61K 9/0075; A61K 9/007; A61K 9/0073; A61K 9/14; A61K 31/137;
(Continued)

(56) References Cited

U.S. PATENT DOCUMENTS 6,887,475 B1 * 5/2005 Lamb ................... G01N 33/505
435/373
7,947,742 B2 5/2011 Batycky et al.
(Continued)

FOREIGN PATENT DOCUMENTS

CA 3222781 A1 12/2022
CA 3238850 A1 6/2023
(Continued)

OTHER PUBLICATIONS

Casale, Thomas B. et al., Pharmacokinetics/pharmacodynamics of epinephrine after single and repeat administration of neffy, EpiPen, and manual intramuscular injection, Journal of Allergy and Clinical Immunology, Dec. 2023, pp. 1587-1596, vol. 152, No. 6.
(Continued)

*Primary Examiner* — James D Ponton
(74) *Attorney, Agent, or Firm* — Neo IP

(57) ABSTRACT

Intranasal dry powder epinephrine compositions are described herein. The compositions include epinephrine or a pharmaceutically acceptable salt thereof, as well as a stabilizing agent and a carrier. The stabilizing agent is operable to include citric acid, or a pharmaceutically acceptable salt derived therefrom. Such intranasal compositions as described herein are useful in the treatment of health conditions which threaten the central nervous system (CNS) and impede the actions of alpha and beta-adrenergic receptors. Such health conditions include anaphylaxis, bronchospasms, respiratory impairment, organophosphate poisoning, and major adverse cardiac events (MACE).

20 Claims, 106 Drawing Sheets
(39 of 106 Drawing Sheet(s) Filed in Color)

(51) Int. Cl.
　　*A61M 11/00* 　　　(2006.01)
　　*A61M 15/08* 　　　(2006.01)

(58) Field of Classification Search
　　CPC ............ A61M 2202/064; A61M 15/08; A61M
　　　　　　　11/007; A61M 11/02; A61M 11/001
　　See application file for complete search history.

(56) References Cited

U.S. PATENT DOCUMENTS

| | | |
|---|---|---|
| 7,954,491 B2 | 6/2011 | Hrkach |
| 8,415,397 B2 | 4/2013 | Batycky et al. |
| 8,747,813 B2 | 6/2014 | Batycky et al. |
| 9,789,071 B2 | 10/2017 | Fleming |
| 10,576,156 B2 | 3/2020 | Maggio |
| 10,682,414 B2 | 6/2020 | Lowenthal et al. |
| 10,688,044 B2 | 6/2020 | Hartman et al. |
| 10,806,709 B2 | 10/2020 | Fleming |
| 11,013,691 B2 | 5/2021 | Fabio et al. |
| 11,173,209 B2 | 11/2021 | Maggio |
| 11,191,838 B2 | 12/2021 | Lowenthal et al. |
| 11,400,045 B2 | 8/2022 | Temtsin-Krayz et al. |
| 11,433,063 B1 | 9/2022 | Bleske et al. |
| 11,617,716 B2 | 4/2023 | Lyman et al. |
| 11,717,571 B2 | 8/2023 | Lowenthal et al. |
| 11,737,980 B2 | 8/2023 | Sävmarker et al. |
| 11,744,895 B2 | 9/2023 | Lowenthal et al. |
| 11,865,252 B2 | 1/2024 | Norrant et al. |
| 11,872,308 B2 | 1/2024 | Lyman et al. |
| 11,918,655 B2 | 3/2024 | Lowenthal et al. |
| 11,957,647 B2 | 4/2024 | Sävmarker et al. |
| 12,005,185 B2 | 6/2024 | Lyman et al. |
| 12,029,709 B2 | 7/2024 | Fraser et al. |
| 12,037,336 B2 | 7/2024 | McCarthy et al. |
| 12,042,472 B2 | 7/2024 | Howard et al. |
| 12,090,139 B2 | 9/2024 | Gandhi et al. |
| 12,097,287 B2 | 9/2024 | Lyman et al. |
| 12,102,629 B1 | 10/2024 | Bleske et al. |
| 12,102,754 B2 | 10/2024 | Haruta |
| 12,133,837 B2 | 11/2024 | Akasapu et al. |
| 12,134,588 B2 | 11/2024 | Sommadossi et al. |
| 12,138,348 B2 | 11/2024 | Eber et al. |
| 12,150,921 B2 | 11/2024 | Hartman et al. |
| 12,186,426 B2 | 1/2025 | Lim et al. |
| 12,214,121 B2 | 2/2025 | Meliniotis et al. |
| 12,214,122 B2 | 2/2025 | Clarke et al. |
| 12,239,823 B2 | 3/2025 | Buchine et al. |
| 12,245,995 B2 | 3/2025 | Hartman et al. |
| 12,268,684 B2 | 4/2025 | Sävmarker et al. |
| 12,295,921 B2 | 5/2025 | Hartman et al. |
| 12,303,472 B2 | 5/2025 | Sävmarker et al. |
| 12,318,486 B2 | 6/2025 | Eber et al. |
| 12,324,838 B2 | 6/2025 | Lowenthal et al. |
| 12,414,916 B2 | 9/2025 | Lyman et al. |
| 2002/0170928 A1* | 11/2002 | Grychowski ........ B65D 83/386 |
| | | 222/251 |
| 2008/0269347 A1 | 10/2008 | Bruss et al. |
| 2010/0258118 A1* | 10/2010 | Morton ............. A61M 15/0078 |
| | | 264/9 |
| 2016/0220489 A1* | 8/2016 | Fleming ............... A61K 31/137 |
| 2017/0304459 A1 | 10/2017 | Jadhav et al. |
| 2020/0085765 A1 | 3/2020 | Rubin |
| 2021/0069126 A1 | 3/2021 | Fleming |
| 2021/0205238 A1 | 7/2021 | Augustin et al. |
| 2022/0087938 A1* | 3/2022 | Sävmarker ........... A61K 9/1682 |
| 2022/0218629 A1 | 7/2022 | Rawas-Qalaji et al. |
| 2022/0257884 A1 | 8/2022 | Poullain et al. |
| 2022/0362491 A1 | 11/2022 | Petit et al. |
| 2023/0105615 A1 | 4/2023 | Temtsin-Krayz et al. |
| 2023/0144040 A1 | 5/2023 | Brouet et al. |
| 2023/0225994 A1 | 7/2023 | Howard et al. |
| 2023/0302137 A1 | 9/2023 | Lowenthal et al. |
| 2024/0100272 A1 | 3/2024 | Lyman et al. |
| 2024/0148990 A1 | 5/2024 | Lyman et al. |
| 2024/0197653 A1 | 6/2024 | Akasapu et al. |
| 2024/0245856 A1 | 7/2024 | Krishnan et al. |
| 2024/0252489 A1 | 8/2024 | Hoekman et al. |
| 2024/0261227 A1 | 8/2024 | Ogburn et al. |
| 2024/0299680 A1 | 9/2024 | Lyman et al. |
| 2024/0342117 A1 | 10/2024 | Fraser et al. |
| 2024/0366533 A1 | 11/2024 | Howard et al. |
| 2024/0408212 A1 | 12/2024 | Sävmarker et al. |
| 2025/0000792 A1 | 1/2025 | Lyman et al. |
| 2025/0000821 A1 | 1/2025 | Zhang |
| 2025/0009995 A1 | 1/2025 | Walsh et al. |
| 2025/0041243 A1 | 2/2025 | Sävmarker et al. |
| 2025/0041544 A1 | 2/2025 | Haruta |
| 2025/0049862 A1 | 2/2025 | O'Connor |
| 2025/0099374 A1 | 3/2025 | Boyer et al. |
| 2025/0108017 A1 | 4/2025 | Schobel et al. |
| 2025/0114307 A1 | 4/2025 | Eber et al. |
| 2025/0120923 A1 | 4/2025 | Akasapu et al. |
| 2025/0195436 A1 | 6/2025 | Eber et al. |
| 2025/0195470 A1 | 6/2025 | Gandhi et al. |
| 2025/0205224 A1 | 6/2025 | Sävmarker et al. |

FOREIGN PATENT DOCUMENTS

| | | |
|---|---|---|
| EP | 4351517 A1 | 4/2024 |
| GB | 2400565 A | 10/2004 |
| IL | 309122 A | 2/2024 |
| JP | 2024523818 A | 7/2024 |
| KR | 20240036555 A | 3/2024 |
| WO | 2015034822 A1 | 3/2015 |
| WO | 2015035822 | 3/2015 |
| WO | 2019182908 A1 | 9/2019 |
| WO | 2019241401 A1 | 12/2019 |
| WO | 2022261453 A1 | 12/2022 |
| WO | 2023114462 A1 | 6/2023 |

OTHER PUBLICATIONS

Lapidot Intranasal Epinephrine Spray, p. 3047, Jun. 19, 2023.
Nutrition, What is Lactose Monohydrate, and how is it used? Accessed online Dec. 11, 2025 (Year: 2025).
International Search Report and Written Opinion dated Feb. 11, 2026 issued by the US Patent Office as International Searching Authority in connection with International Application No. PCT/US2025/050828 (17 pages).

* cited by examiner

10

12 exposing a delivery aperture of a drug delivery device having a reservoir, an air delivery assembly, and a delivery head defining the delivery aperture, the reservoir containing a dose of the dry powder pharmaceutical composition, the dry powder pharmaceutical composition comprising epinephrine or a pharmaceutically acceptable salt thereof and a carrier, the dry powder pharmaceutical composition having a bulk particle size distribution characterized by a Dv50 of between 5 microns and 30 microns

13 actuating the drug delivery device to produce, via the air delivery assembly, an airflow through the reservoir to deliver a mixture of the airflow and the dose of the dry powder pharmaceutical composition via the delivery aperture, the mixture having an emitted particle size distribution characterized by a Dv50 of between 25 microns and 200 microns and that is greater than the Dv50 of the bulk particle size distribution

20 placing a delivery head of an intranasal device into a nasal passage of a body. The intranasl device has a reservoir and an air delivery assembly, the reservoir containing a dose of the dry powder pharmaceutical composition, the dry powder pharmaceutical composition comprising epinephrine or a pharmaceutically acceptable salt thereof and a carrier, the dry powder pharmaceutical composition having a bulk particle size distribution characterized by a Dv50 of between 5 microns and 30 microns

23 actuating the intranasal device to cause the air delivery assembly to produce an airflow through the reservoir to deliver the dose of the dry powder pharmaceutical composition into the body via a delivery aperture defined by the delivery head

24 wherein the delivered dry powder pharmaceutical composition has an emitted particle size distribution characterized by a Dv50 of between 25 microns and 200 microns and that is greater than the Dv50 of the bulk particle size distribution

FIG. 11

30

32 placing a delivery head of an intranasal device into a nasal passage of a body. The delivery head defines a delivery aperture and the intranasal device further includes a reservoir and an air delivery assembly. The reservoir contains a dose of the dry powder pharmaceutical composition, the dry powder pharmaceutical composition comprising epinephrine or a pharmaceutically acceptable salt thereof and a carrier

33 actuating the intranasal device to cause the air delivery assembly to produce a delivery airflow through the reservoir to deliver the dose of the dry powder pharmaceutical composition into the body via the delivery aperture

34 wherein a target delivery percentage of a total mass of the delivered dry powder pharmaceutical composition to a mass of the delivered dry powder composition that is deposited on a turbinate region and an olfactory region is greater than about 74 percent

35 wherein the target delivery percentage is substantially independent of an orientation of the body and a presence of a respiratory airflow through the nasal passage

42 placing a delivery head of an intranasal device into a nasal passage of a body. The intranasal device includes a reservoir containing a dose of the dry pharmaceutical composition, the dry powder pharmaceutical composition comprising epinephrine or a pharmaceutically acceptable salt thereof and a carrier, wherein the dose contains about 3.5 mg to about 5.5 mg of the epinephrine or the pharmaceutically acceptable salt thereof

43 actuating the intranasal device to deliver the dose of the pharmaceutical composition into the body such that

43A a relative mean maximum epinephrine plasma concentration after the dose is delivered into the body (Cmax) is greater than a Cmax of a first reference dose and less than a Cmax of a second reference dose – OR -

43B a time to reach a maximum epinephrine plasma concentration (Tmax) is greater than a Tmax of the first reference dose and less than a Tmax of the second reference dose

44 wherein the first reference dose contains about 0.3 mg of epinephrine or a pharmaceutically acceptable salt delivered intramuscularly via a manual injection and the second reference dose contains about 0.3 mg of epinephrine or a pharmaceutically acceptable salt delivered intramuscularly via an autoinjector

FIG. 13

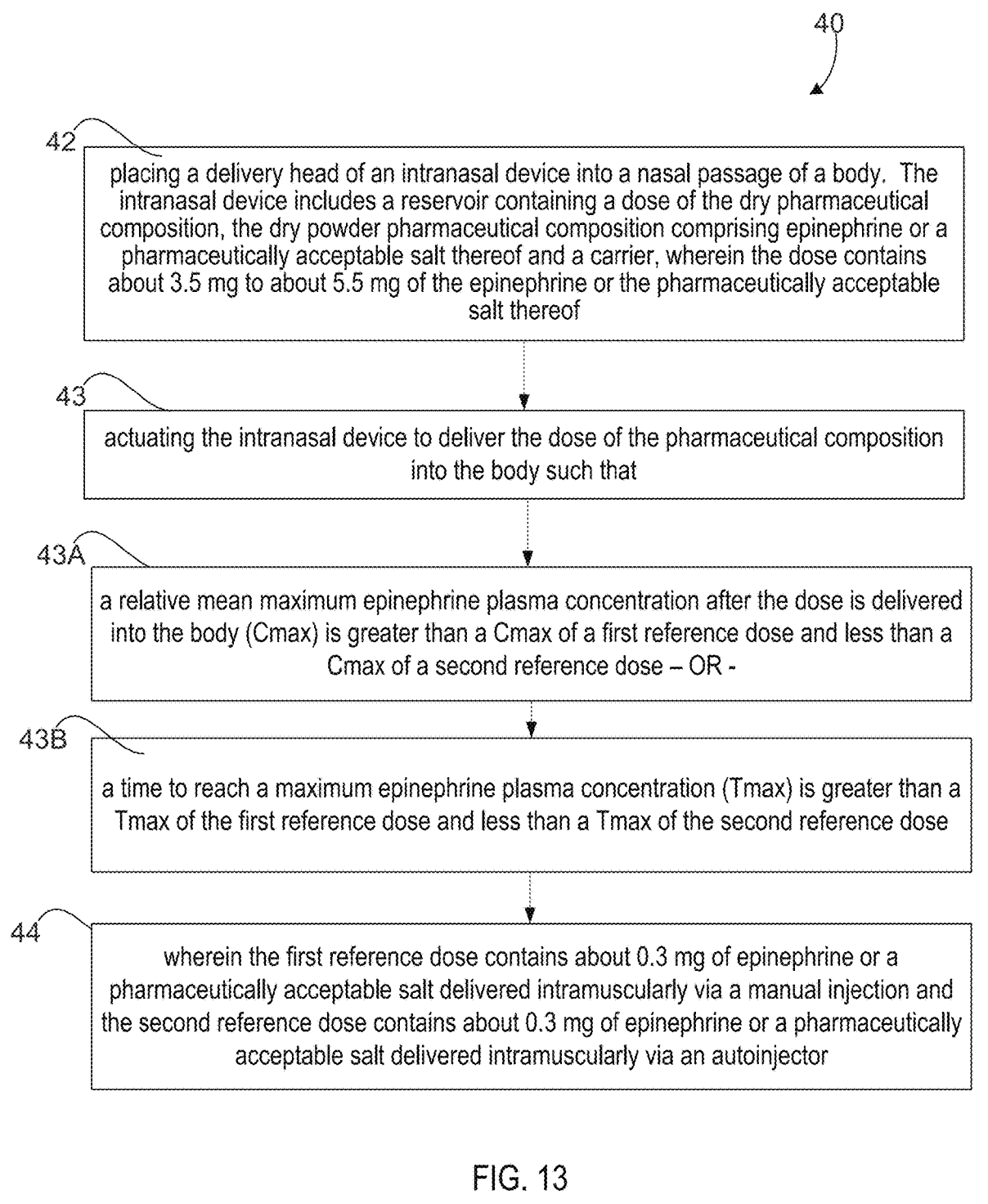

| | Treatment A | Treatment B | Treatment C | Treatment D |
|---|---|---|---|---|
| Drug Name | BBP01 Epinephrine | IM Epinephrine | IM Epinephrine | BBP01 Epinephrine |
| Dosage Form | IN Nasal powder | IM Solution | IM Solution | IN Nasal powder |
| Dose | 3.5 mg | 0.3 mg | 0.5 mg | 5.5 mg |

IN = intranasal, IM = intramuscular

FIG. 20

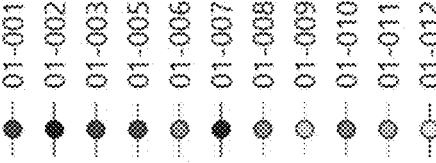
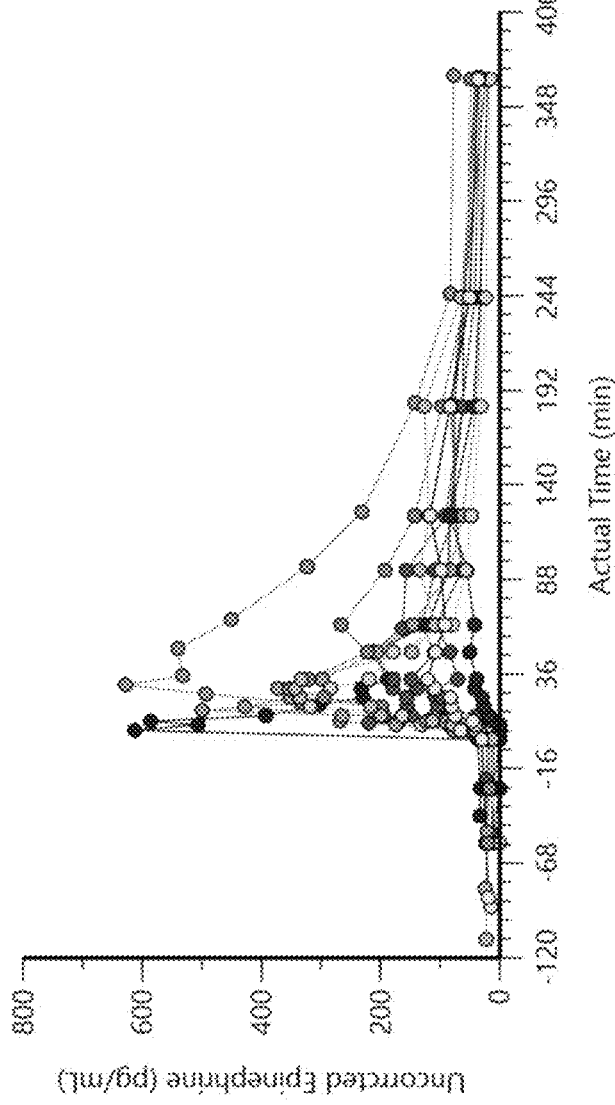
FIG. 25

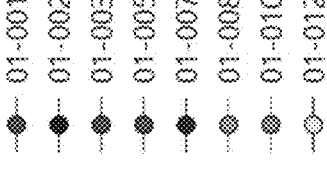
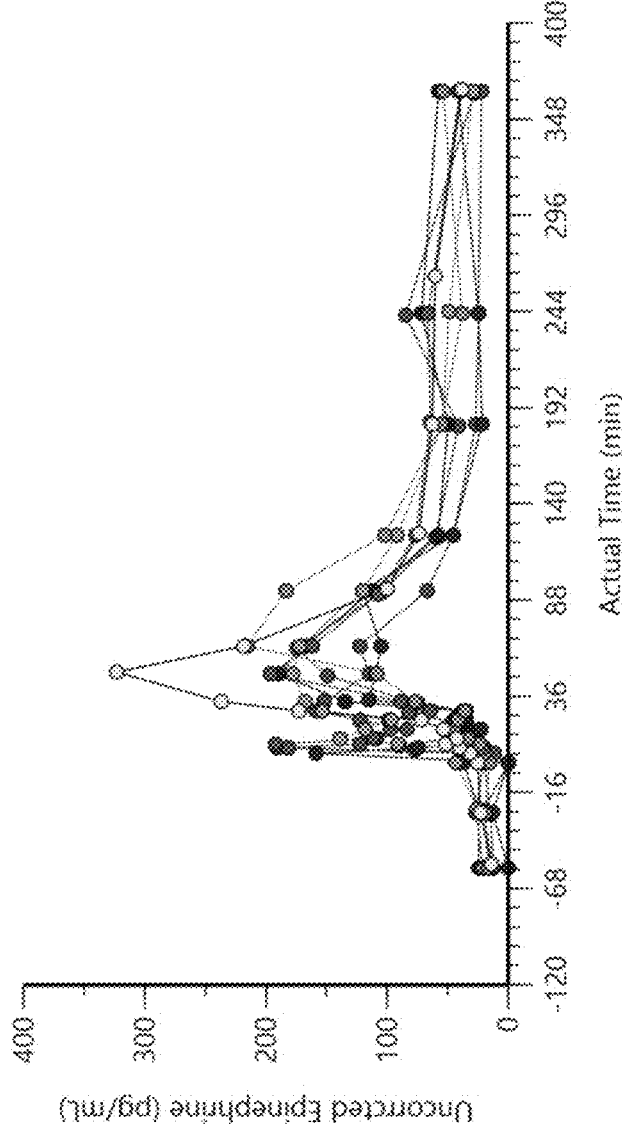
FIG. 26

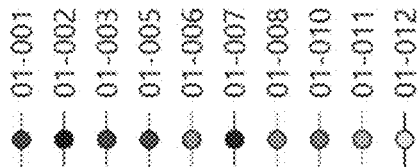
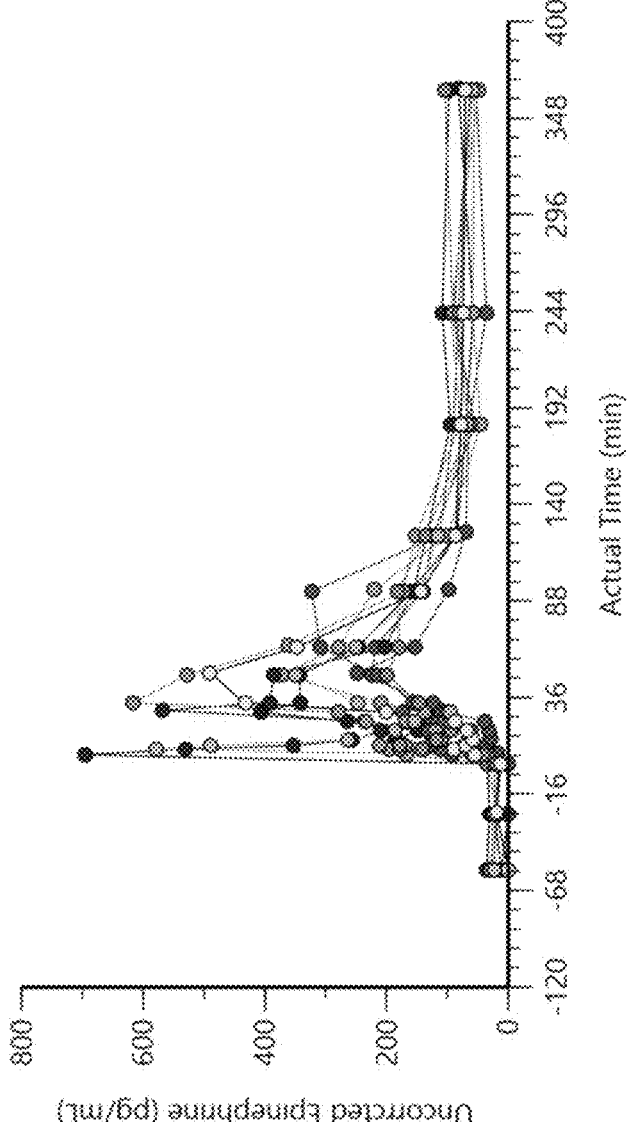
FIG. 27

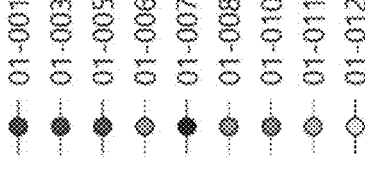
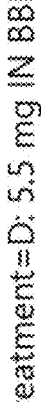
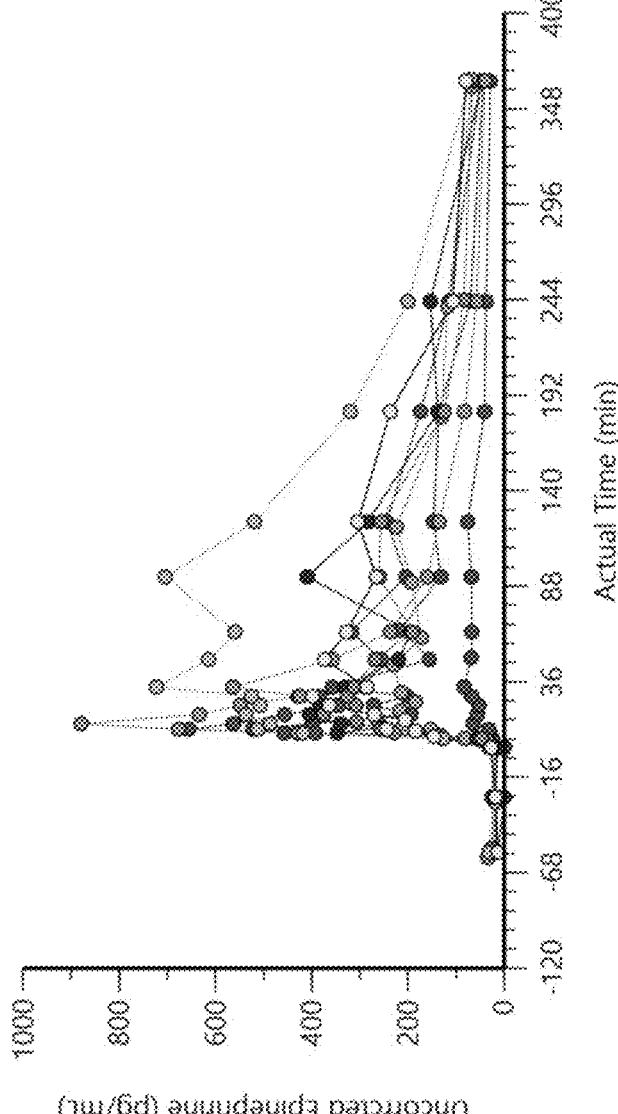
FIG. 28

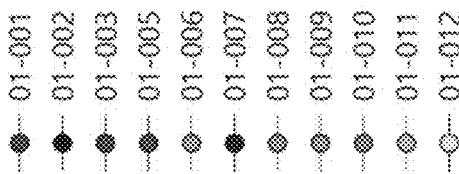
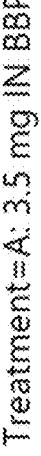
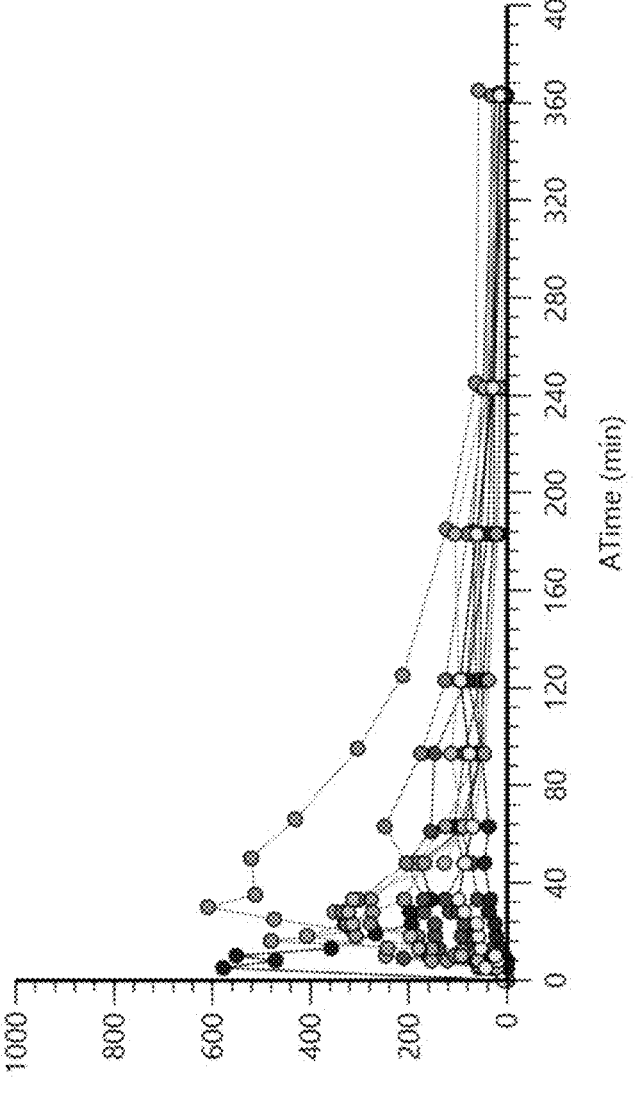
FIG. 29

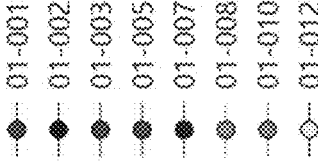
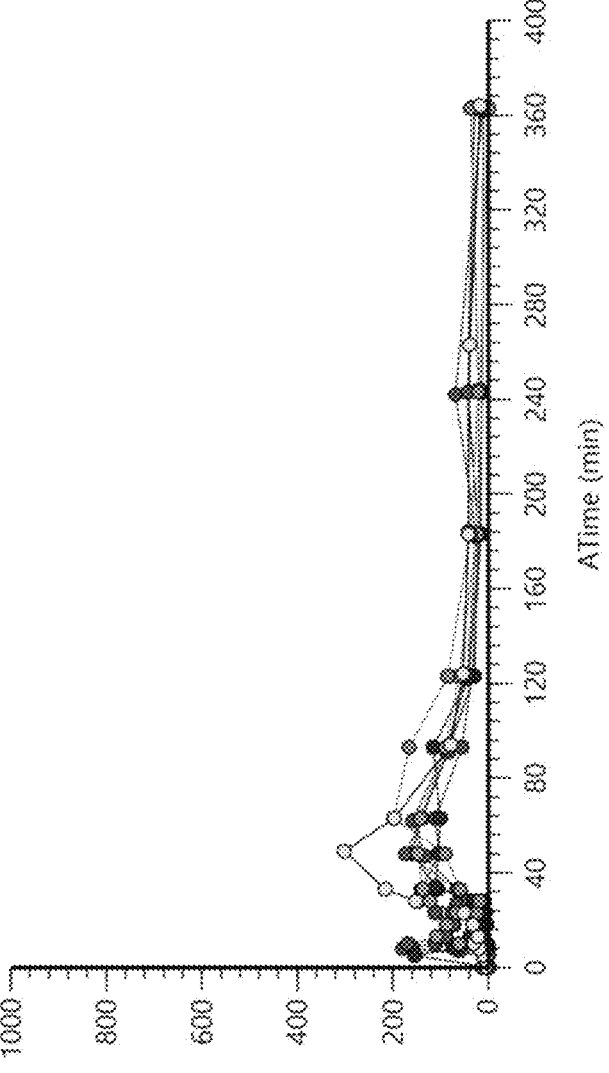
FIG. 30

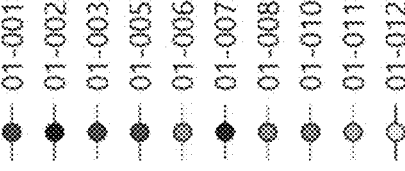
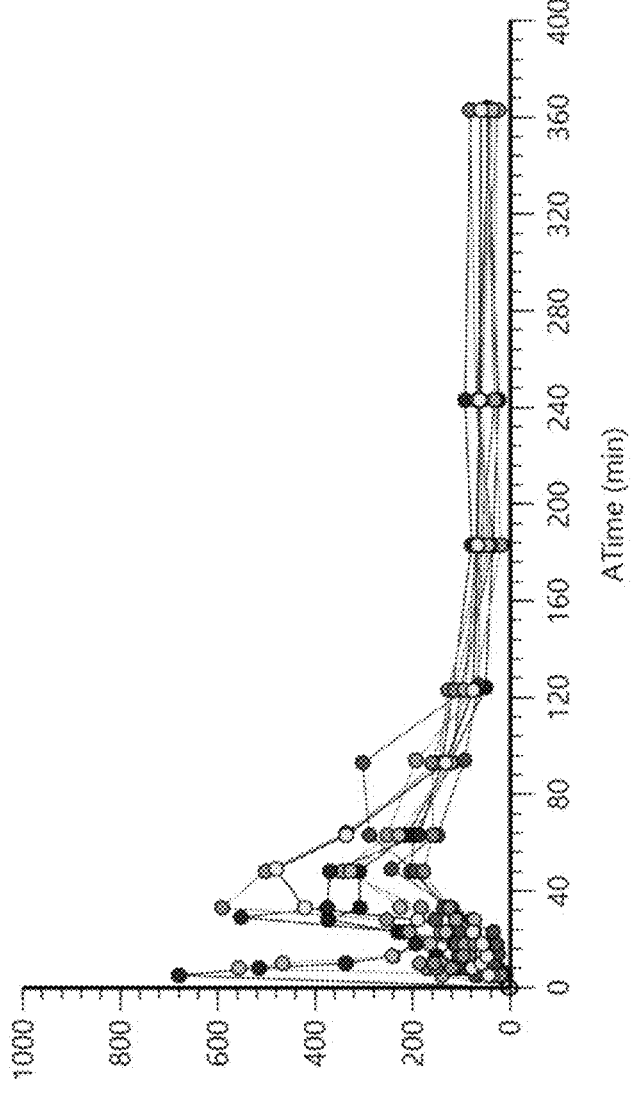
FIG. 31

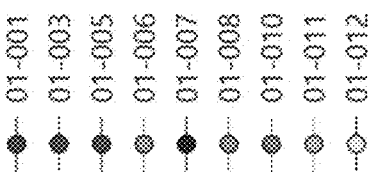
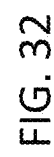
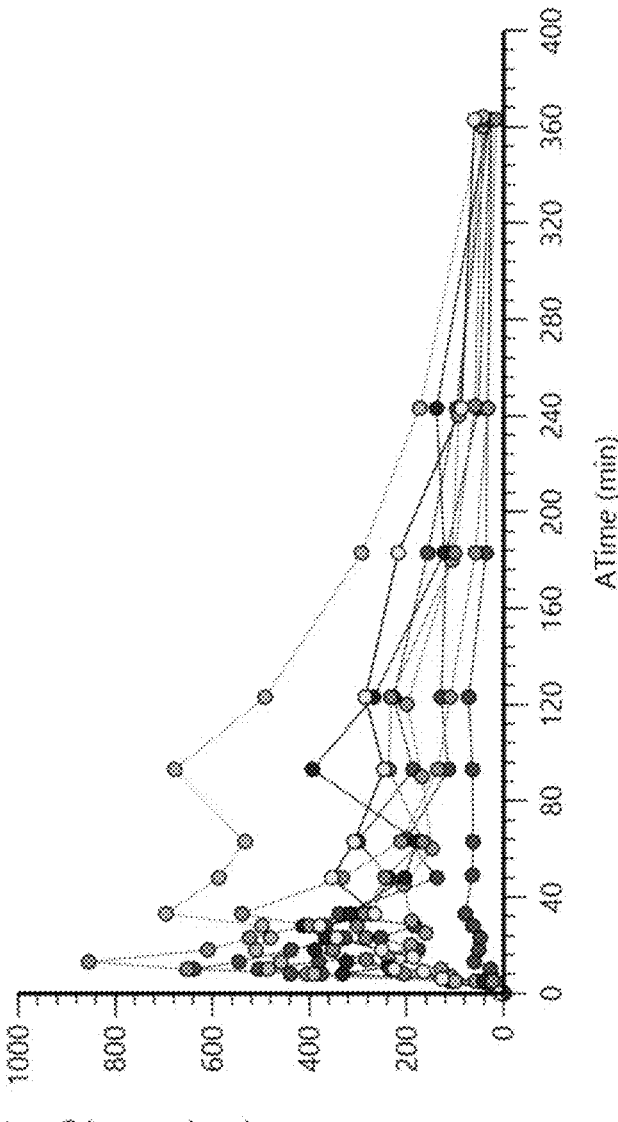
FIG. 32

| Treatment | Subject | Time (min) Epinephrine (pg/mL) | | | | | | | | |
|---|---|---|---|---|---|---|---|---|---|---|
| | | -57 | -27 | 0 | 5 | 8 | 10 | 13 | 18 | 23 |
| A: 3.5 mg IN BBP01 | 01-001 | 23.2 | 22.9 | 20.9 | 52.6 | 85.7 | 113 | 103 | 96.1 | 108 |
| | 01-002 | 33.5 | 32.6 | 37.0 | 613 | 506 | 586 | 393 | 303 | 229 |
| | 01-003 | 11.4 | 10.6 | 10.7 | 35.4 | 33.9 | 40.4 | 38.7 | 104 | 97.7 |
| | 01-005 | 14.0 | 11.4 | 0.00 | 33.1 | 220 | 169 | 149 | 156 | 156 |
| | 01-006 | 21.2 | 20.0 | 20.3 | 77.9 | 175 | 268 | 265 | 428 | 351 |
| | 01-007 | 13.1 | 0.00 | 0.00 | 0.00 | 0.00 | 10.6 | 17.6 | 26.9 | 29.4 |
| | 01-008 | 19.1 | 19.3 | 17.8 | 41.5 | 92.0 | 111 | 500 | 333 | 493 |
| | 01-009 | 0.00 | 14.5 | 14.8 | 67.9 | 132 | 117 | 164 | 318 | 336 |
| | 01-010 | 20.2 | 17.5 | 13.0 | 33.8 | 79.9 | 123 | 195 | 199 | 295 |
| | 01-011 | 22.6 | 24.4 | 12.5 | 41.0 | 79.4 | 113 | 200 | 217 | 335 |
| | 01-012 | 15.0 | 19.4 | 30.2 | 65.7 | 41.4 | 45.6 | 75.0 | 80.6 | 83.1 |
| | N | 11 | 11 | 11 | 11 | 11 | 11 | 11 | 11 | 11 |
| | Mean | 17.6 | 17.5 | 16.1 | 96.5 | 131 | 154 | 191 | 205 | 229 |
| | SD | 8.49 | 8.47 | 11.2 | 173 | 139 | 159 | 148 | 127 | 145 |
| | CV% | 48.3 | 48.4 | 69.4 | 178.8 | 106.1 | 103.0 | 77.5 | 61.7 | 63.4 |
| | Min | 0.00 | 0.00 | 0.00 | 0.00 | 0.00 | 10.6 | 17.6 | 26.9 | 29.4 |
| | Median | 19.1 | 19.3 | 14.8 | 41.5 | 85.7 | 113 | 164 | 199 | 229 |
| | Max | 33.5 | 32.6 | 37.0 | 613 | 506 | 586 | 500 | 428 | 493 |
| | Geometric Mean | NC | NC | NC | NC | NC | 101 | 134 | 162 | 177 |

FIG. 33A

| Treatment | Subject | Time (min) Epinephrine (pg/mL) | | | | | | | | |
|---|---|---|---|---|---|---|---|---|---|---|
| | | 28 | 33 | 48 | 63 | 93 | 123 | 183 | 243 | 363 |
| A: 3.5 mg IN BBP01 | 01-001 | 139 | 149 | 110 | 130 | 109 | 76.7 | 76.2 | 59.8 | 24.1 |
| | 01-002 | 232 | 188 | 212 | 121 | 86.0 | 84.4 | 61.7 | 60.6 | 40.6 |
| | 01-003 | 111 | 71.0 | 83.7 | 106 | 64.2 | 74.0 | 81.4 | 60.6 | 36.1 |
| | 01-005 | 179 | 179 | 213 | 163 | 157 | 90.8 | 62.8 | 42.1 | 32.3 |
| | 01-006 | 372 | 298 | 206 | 146 | 82.9 | 62.7 | 39.1 | 31.4 | 34.0 |
| | 01-007 | 42.0 | 38.9 | 50.5 | 42.3 | 55.2 | 83.5 | 44.1 | 33.4 | 20.1 |
| | 01-008 | 628 | 532 | 540 | 451 | 323 | 231 | 142 | 82.8 | 77.3 |
| | 01-009 | 284 | 219 | 179 | 79.5 | 56.7 | 48.3 | 31.6 | 23.7 | 16.2 |
| | 01-010 | 353 | 321 | 222 | 266 | 192 | 143 | 97.7 | 57.0 | 48.6 |
| | 01-011 | 343 | 333 | 148 | 109 | 134 | 118 | 127 | 65.6 | 34.7 |
| | 01-012 | 109 | 121 | 108 | 92.1 | 98.2 | 117 | 83.4 | 50.6 | 36.1 |
| | N | 11 | 11 | 11 | 11 | 11 | 11 | 11 | 11 | 11 |
| | Mean | 254 | 223 | 188 | 155 | 124 | 103 | 76.9 | 51.6 | 36.4 |
| | SD | 167 | 141 | 131 | 113 | 79.0 | 50.5 | 34.9 | 17.4 | 16.4 |
| | CV% | 65.6 | 63.3 | 69.3 | 73.0 | 63.9 | 49.2 | 45.4 | 33.8 | 45.1 |
| | Min | 42.0 | 38.9 | 50.5 | 42.3 | 55.2 | 48.3 | 31.6 | 23.7 | 16.2 |
| | Median | 232 | 188 | 179 | 121 | 98.2 | 84.4 | 76.2 | 57.0 | 34.7 |
| | Max | 628 | 532 | 540 | 451 | 323 | 231 | 142 | 82.8 | 77.3 |
| | Geometric Mean | 203 | 179 | 158 | 129 | 107 | 93.9 | 69.8 | 48.6 | 33.5 |

FIG. 33B

| Treatment | Subject | Time (min) Epinephrine (pg/mL) | | | | | | | | |
|---|---|---|---|---|---|---|---|---|---|---|
| | | -57 | -27 | 0 | 5 | 8 | 10 | 13 | 18 | 23 |
| B: 0.3 mg IM Epinephrine | 01-001 | 12.5 | 14.6 | 20.0 | 19.4 | 77.3 | 90.3 | 49.3 | 29.4 | 45.9 |
| | 01-002 | 24.7 | 23.9 | 36.9 | 37.8 | 20.1 | 30.3 | 38.2 | 32.3 | 34.7 |
| | 01-003 | 13.0 | 20.6 | 0.00 | 11.7 | 191 | 123 | 109 | 83.6 | 123 |
| | 01-005 | 20.8 | 26.5 | 21.1 | 30.1 | 182 | 192 | 112 | 97.5 | 98.4 |
| | 01-007 | 0.00 | 12.9 | 0.00 | 159 | 74.7 | 42.1 | 43.0 | 22.9 | 42.9 |
| | 01-008 | 21.0 | 25.8 | 43.3 | 28.9 | 35.0 | 91.1 | 139 | 118 | 96.8 |
| | 01-010 | 16.7 | 19.3 | 15.6 | 20.1 | 21.6 | 23.7 | 33.2 | 45.2 | 41.5 |
| | 01-012 | 14.0 | 23.0 | 25.4 | 31.6 | 40.2 | 51.7 | 42.5 | 53.5 | 71.9 |
| | N | 8 | 8 | 8 | 8 | 8 | 8 | 8 | 8 | 8 |
| | Mean | 15.3 | 20.8 | 20.3 | 42.3 | 80.2 | 80.5 | 70.7 | 60.3 | 69.3 |
| | SD | 7.58 | 5.00 | 15.5 | 47.7 | 69.0 | 56.7 | 41.8 | 35.3 | 33.1 |
| | CV% | 49.4 | 24.0 | 76.3 | 112.9 | 86.0 | 70.4 | 59.2 | 58.5 | 47.7 |
| | Min | 0.00 | 12.9 | 0.00 | 11.7 | 20.1 | 23.7 | 33.2 | 22.9 | 34.7 |
| | Median | 15.4 | 21.8 | 20.5 | 29.5 | 57.4 | 71.0 | 46.1 | 49.4 | 58.9 |
| | Max | 24.7 | 26.5 | 43.3 | 159 | 191 | 192 | 139 | 118 | 123 |
| | Geometric Mean | NC | 20.2 | NC | 30.5 | 57.7 | 64.6 | 61.0 | 51.6 | 62.7 |

FIG. 34A

| Treatment | Subject | Time (min) Epinephrine (pg/mL) | | | | | | | | |
|---|---|---|---|---|---|---|---|---|---|---|
| | | 28 | 33 | 48 | 63 | 93 | 123 | 183 | 243 | 363 |
| B: 0.3 mg IM Epinephrine | 01-001 | 81.9 | 74.6 | 149 | 174 | 105 | 59.9 | 41.1 | 84.7 | 28.4 |
| | 01-002 | 37.3 | 135 | 189 | 169 | 111 | 58.0 | 49.6 | 71.6 | 57.6 |
| | 01-003 | 159 | 152 | 115 | 123 | 67.0 | 45.5 | 26.9 | 24.6 | 22.0 |
| | 01-005 | 64.4 | 88.6 | 196 | 162 | 107 | 76.4 | 64.4 | 66.2 | 39.9 |
| | 01-007 | 34.9 | 115 | 109 | 105 | 120 | 45.5 | 21.6 | 24.7 | 41.4 |
| | 01-008 | 153 | 168 | 178 | 172 | 120 | 91.9 | 54.3 | 49.0 | 29.4 |
| | 01-010 | 35.9 | 76.9 | 108 | 216 | 183 | 102 | 55.1 | 38.1 | 54.0 |
| | 01-012 | 173 | 237 | 323 | 218 | 100 | 73.8 | 62.8 | 60.3 | 38.3 |
| | N | 8 | 8 | 8 | 8 | 8 | 8 | 8 | 8 | 8 |
| | Mean | 92.5 | 131 | 171 | 167 | 114 | 69.1 | 47.0 | 52.4 | 38.9 |
| | SD | 59.8 | 55.0 | 71.3 | 39.5 | 32.6 | 20.7 | 15.8 | 22.1 | 12.4 |
| | CV% | 64.7 | 42.1 | 41.7 | 23.6 | 28.5 | 29.9 | 33.8 | 42.2 | 31.8 |
| | Min | 34.9 | 74.6 | 108 | 105 | 67.0 | 45.5 | 21.6 | 24.6 | 22.0 |
| | Median | 73.2 | 125 | 164 | 170 | 109 | 66.9 | 51.9 | 54.7 | 39.1 |
| | Max | 173 | 237 | 323 | 218 | 183 | 102 | 64.4 | 84.7 | 57.6 |
| | Geometric Mean | 75.3 | 122 | 160 | 163 | 110 | 66.5 | 44.1 | 47.8 | 37.1 |

FIG. 34B

| Treatment | Subject | | Time (min) Epinephrine (pg/mL) | | | | | | | | |
|---|---|---|---|---|---|---|---|---|---|---|---|
| | | -57 | -27 | 0 | 5 | 8 | 10 | 13 | 18 | 23 |
| C: 0.5 mg IM Epinephrine | 01-001 | 23.8 | 25.8 | 12.2 | 92.3 | 45.9 | 71.4 | 63.7 | 61.5 | 126 |
| | 01-002 | 35.5 | 31.0 | 34.2 | 53.9 | 141 | 175 | 186 | 149 | 265 |
| | 01-003 | 11.4 | 0.00 | 0.00 | 18.7 | 33.3 | 36.6 | 28.8 | 32.2 | 38.9 |
| | 01-005 | 25.2 | 17.2 | 17.0 | 42.0 | 112 | 126 | 125 | 131 | 150 |
| | 01-006 | 27.1 | 19.6 | 32.9 | 167 | 197 | 169 | 110 | 102 | 168 |
| | 01-007 | 12.0 | 21.9 | 13.4 | 696 | 531 | 353 | 257 | 210 | 236 |
| | 01-008 | 29.6 | 23.3 | 23.0 | 34.6 | 178 | 212 | 111 | 120 | 234 |
| | 01-010 | 20.6 | 24.9 | 18.0 | 40.9 | 141 | 178 | 118 | 94.1 | 95.9 |
| | 01-011 | 23.0 | 23.6 | 18.7 | 59.0 | 579 | 489 | 264 | 186 | 154 |
| | 01-012 | 0.00 | 19.2 | 12.6 | 55.3 | 89.5 | 69.9 | 58.5 | 68.0 | 87.7 |
| | N | 10 | 10 | 10 | 10 | 10 | 10 | 10 | 10 | 10 |
| | Mean | 20.8 | 20.7 | 18.3 | 126 | 205 | 188 | 132 | 115 | 155 |
| | SD | 10.3 | 8.23 | 10.1 | 204 | 192 | 139 | 80.1 | 55.9 | 72.5 |
| | CV% | 49.7 | 39.8 | 55.5 | 162.3 | 93.8 | 73.8 | 60.6 | 48.4 | 46.6 |
| | Min | 0.00 | 0.00 | 0.00 | 18.7 | 33.3 | 36.6 | 28.8 | 32.2 | 38.9 |
| | Median | 23.4 | 22.6 | 17.5 | 54.6 | 141 | 172 | 114 | 111 | 152 |
| | Max | 35.5 | 31.0 | 34.2 | 696 | 579 | 489 | 264 | 210 | 265 |
| | Geometric Mean | NC | NC | NC | 67.9 | 142 | 146 | 109 | 102 | 137 |

FIG. 35A

| Treatment | Subject | Time (min) Epinephrine (pg/mL) | | | | | | | | |
|---|---|---|---|---|---|---|---|---|---|---|
| | | 28 | 33 | 48 | 63 | 93 | 123 | 183 | 243 | 363 |
| C: 0.5 mg IM Epinephrine | 01-001 | 133 | 148 | 224 | 218 | 140 | 124 | 55.3 | 89.4 | 61.6 |
| | 01-002 | 407 | 342 | 343 | 246 | 159 | 84.5 | 69.3 | 57.8 | 81.7 |
| | 01-003 | 112 | 124 | 248 | 154 | 98.1 | 69.9 | 65.1 | 36.0 | 52.5 |
| | 01-005 | 174 | 156 | 214 | 309 | 323 | 113 | 90.0 | 81.3 | 62.8 |
| | 01-006 | 138 | 210 | 373 | 270 | 221 | 99.6 | 45.4 | 58.8 | 56.1 |
| | 01-007 | 569 | 392 | 386 | 203 | 156 | 134 | 95.0 | 109 | 97.3 |
| | 01-008 | 279 | 617 | 528 | 362 | 173 | 153 | 78.9 | 93.9 | 49.2 |
| | 01-010 | 99.9 | 147 | 200 | 180 | 182 | 136 | 62.8 | 91.2 | 105 |
| | 01-011 | 95.4 | 248 | 350 | 251 | 144 | 116 | 68.6 | 80.0 | 58.9 |
| | 01-012 | 201 | 432 | 491 | 347 | 145 | 86.9 | 78.0 | 73.9 | 71.0 |
| | N | 10 | 10 | 10 | 10 | 10 | 10 | 10 | 10 | 10 |
| | Mean | 221 | 282 | 336 | 255 | 174 | 112 | 70.8 | 77.1 | 69.5 |
| | SD | 156 | 161 | 115 | 69.6 | 61.2 | 26.2 | 15.1 | 21.2 | 19.0 |
| | CV% | 70.6 | 57.2 | 34.2 | 27.3 | 35.2 | 23.5 | 21.4 | 27.5 | 27.3 |
| | Min | 95.4 | 124 | 200 | 154 | 98.1 | 69.9 | 45.4 | 36.0 | 49.2 |
| | Median | 156 | 229 | 347 | 248 | 157 | 114 | 69.0 | 80.6 | 62.2 |
| | Max | 569 | 617 | 528 | 362 | 323 | 153 | 95.0 | 109 | 105 |
| | Geometric Mean | 184 | 245 | 318 | 246 | 166 | 109 | 69.3 | 73.9 | 67.4 |

FIG. 35B

| Treatment | Subject | Time (min) | | | | | | | | |
| --- | --- | --- | --- | --- | --- | --- | --- | --- | --- | --- |
| | | -57.0 | -27.0 | 0.00 | 5.00 | 8.00 | 10.0 | 13.0 | 18.0 | 23.0 |
| | | Uncorrected Epinephrine (pg/mL) | | | | | | | | |
| D: 5.5 mg IN BBP01 | 01-001 | 15.1 | 22.5 | 17.0 | 128 | 457 | 523 | 399 | 194 | 272 |
| | 01-003 | 12.8 | 0.00 | 0.00 | 24.7 | 31.6 | 32.3 | 65.0 | 55.9 | 52.7 |
| | 01-005 | 18.7 | 17.3 | 17.0 | 55.3 | 393 | 656 | 563 | 457 | 345 |
| | 01-006 | 34.5 | 18.9 | 20.4 | 46.7 | 81.8 | 135 | 153 | 203 | 217 |
| | 01-007 | 13.3 | 20.1 | 13.0 | 56.8 | 348 | 253 | 340 | 405 | 383 |
| | 01-008 | 26.5 | 16.4 | 31.2 | 35.9 | 430 | 677 | 880 | 634 | 549 |
| | 01-010 | 21.4 | 25.2 | 25.3 | 47.5 | 229 | 256 | 307 | 376 | 309 |
| | 01-011 | 31.6 | 20.7 | 29.3 | 128 | 418 | 513 | 487 | 538 | 507 |
| | 01-012 | 12.9 | 18.2 | 27.4 | 146 | 185 | 245 | 206 | 270 | 364 |
| | N | 9 | 9 | 9 | 9 | 9 | 9 | 9 | 9 | 9 |
| | Mean | 20.7 | 17.7 | 20.1 | 74.4 | 286 | 366 | 378 | 355 | 333 |
| | SD | 8.34 | 7.17 | 9.76 | 46.1 | 159 | 232 | 246 | 179 | 149 |
| | CV% | 40.2 | 40.5 | 48.7 | 62.0 | 55.7 | 63.5 | 65.0 | 50.4 | 44.6 |
| | Min | 12.8 | 0.00 | 0.00 | 24.7 | 31.6 | 32.3 | 65.0 | 55.9 | 52.7 |
| | Median | 18.7 | 18.9 | 20.4 | 55.3 | 348 | 256 | 340 | 376 | 345 |
| | Max | 34.5 | 25.2 | 31.2 | 146 | 457 | 677 | 880 | 634 | 549 |
| | Geometric Mean | 19.4 | NC | NC | 62.6 | 221 | 272 | 302 | 298 | 286 |

FIG. 36A

| Treatment | Subject | Time (min) | | | | | | | | |
| | | Uncorrected Epinephrine (pg/mL) | | | | | | | | |
| | | 28 | 33 | 48 | 63 | 93 | 123 | 183 | 243 | 363 |
| D: 5.5 mg IN BBP01 | 01-001 | 202 | 357 | 156 | 218 | 132 | 147 | 135 | 70.5 | 44.0 |
| | 01-003 | 67.7 | 83.5 | 69.0 | 67.6 | 68.6 | 76.3 | 40.7 | 37.7 | 29.0 |
| | 01-005 | 385 | 290 | 255 | 318 | 205 | 244 | 174 | 115 | 47.8 |
| | 01-006 | 185 | 214 | 231 | 172 | 193 | 224 | 131 | 117 | 67.5 |
| | 01-007 | 429 | 332 | 220 | 194 | 409 | 283 | 138 | 154 | 46.4 |
| | 01-008 | 425 | 564 | 358 | 237 | 160 | 135 | 82.8 | 57.5 | 40.5 |
| | 01-010 | 326 | 312 | 269 | 191 | 260 | 256 | 125 | 83.6 | 66.1 |
| | 01-011 | 526 | 723 | 614 | 560 | 705 | 519 | 320 | 200 | 70.3 |
| | 01-012 | 398 | 286 | 374 | 328 | 266 | 304 | 237 | 107 | 79.7 |
| | N | 9 | 9 | 9 | 9 | 9 | 9 | 9 | 9 | 9 |
| | Mean | 327 | 351 | 283 | 254 | 267 | 243 | 154 | 105 | 54.6 |
| | SD | 146 | 188 | 155 | 139 | 191 | 128 | 82.7 | 50.2 | 16.8 |
| | CV% | 44.7 | 53.6 | 55.0 | 54.6 | 71.5 | 52.5 | 53.8 | 47.9 | 30.8 |
| | Min | 67.7 | 83.5 | 69.0 | 67.6 | 68.6 | 76.3 | 40.7 | 37.7 | 29.0 |
| | Median | 385 | 312 | 255 | 218 | 205 | 244 | 136 | 107 | 47.8 |
| | Max | 526 | 723 | 614 | 560 | 705 | 519 | 320 | 200 | 79.7 |
| | Geometric Mean | 284 | 304 | 244 | 222 | 219 | 214 | 134 | 93.9 | 52.2 |

FIG. 36B

| Treatment | Subject | Time (min) | | | | | | | |
|---|---|---|---|---|---|---|---|---|---|
| | | Baseline-corrected Epinephrine (pg/mL) | | | | | | | |
| | | 0 | 5 | 8 | 10 | 13 | 18 | 23 | 28 |
| A: 3.5 mg IN EPKPX01 | 01-001 | 0.00 | 30.2 | 63.4 | 90.9 | 81.1 | 73.8 | 85.8 | 117 |
| | 01-002 | 2.63 | 578 | 472 | 551 | 359 | 268 | 195 | 198 |
| | 01-003 | 0.00 | 24.5 | 23.0 | 29.5 | 27.8 | 92.9 | 86.8 | 100 |
| | 01-005 | 0.00 | 24.6 | 211 | 161 | 140 | 147 | 148 | 171 |
| | 01-006 | 0.00 | 57.4 | 154 | 247 | 244 | 408 | 331 | 352 |
| | 01-007 | 0.00 | 0.00 | 0.00 | 6.25 | 13.2 | 22.5 | 25.0 | 37.6 |
| | 01-008 | 0.00 | 22.7 | 73.2 | 91.8 | 481 | 314 | 474 | 609 |
| | 01-009 | 5.04 | 58.1 | 122 | 107 | 154 | 308 | 327 | 275 |
| | 01-010 | 0.00 | 16.9 | 63.0 | 107 | 178 | 182 | 278 | 336 |
| | 01-011 | 0.00 | 21.1 | 59.5 | 93.6 | 180 | 197 | 316 | 323 |
| | 01-012 | 8.65 | 44.1 | 19.9 | 24.1 | 53.5 | 59.1 | 61.6 | 87.7 |
| | N | 11 | 11 | 11 | 11 | 11 | 11 | 11 | 11 |
| | Mean | 1.48 | 79.8 | 115 | 137 | 174 | 188 | 212 | 237 |
| | SD | 2.88 | 166 | 134 | 153 | 143 | 124 | 143 | 165 |
| | CV% | 194.1 | 208.2 | 116.7 | 111.4 | 82.4 | 65.7 | 67.7 | 69.5 |
| | Min | 0.00 | 0.00 | 0.00 | 6.25 | 13.2 | 22.5 | 25.0 | 37.6 |
| | Median | 0.00 | 24.6 | 63.4 | 93.6 | 154 | 182 | 195 | 198 |
| | Max | 8.65 | 578 | 472 | 551 | 481 | 408 | 474 | 609 |
| | Geometric Mean | NC | NC | NC | 80.1 | 115 | 143 | 158 | 184 |

FIG. 37A

| Treatment | Subject | Time (min) | | | | | | | |
|---|---|---|---|---|---|---|---|---|---|
| | | 33 | 48 | 63 | 93 | 123 | 183 | 243 | 363 |
| | | Baseline-corrected Epinephrine (pg/mL) | | | | | | | |
| A: 3.5 mg IN BBP01 | 01-001 | 127 | 87.7 | 108 | 87.0 | 54.4 | 53.9 | 37.5 | 1.72 |
| | 01-002 | 154 | 177 | 87.0 | 51.6 | 50.0 | 27.3 | 26.3 | 6.20 |
| | 01-003 | 60.1 | 72.8 | 95.2 | 53.3 | 63.1 | 70.5 | 49.7 | 25.2 |
| | 01-005 | 170 | 204 | 155 | 148 | 82.3 | 54.3 | 33.6 | 23.9 |
| | 01-006 | 278 | 186 | 126 | 62.5 | 42.3 | 18.6 | 10.9 | 13.5 |
| | 01-007 | 34.5 | 46.2 | 38.0 | 50.8 | 79.1 | 39.7 | 29.1 | 15.7 |
| | 01-008 | 513 | 521 | 432 | 304 | 213 | 123 | 64.0 | 58.5 |
| | 01-009 | 210 | 170 | 69.7 | 46.9 | 38.5 | 21.8 | 13.9 | 6.42 |
| | 01-010 | 304 | 205 | 249 | 175 | 126 | 80.8 | 40.1 | 31.7 |
| | 01-011 | 314 | 128 | 89.4 | 114 | 98.2 | 107 | 45.7 | 14.8 |
| | 01-012 | 99.5 | 86.5 | 70.6 | 76.7 | 95.6 | 61.9 | 29.1 | 14.6 |
| | N | 11 | 11 | 11 | 11 | 11 | 11 | 11 | 11 |
| | Mean | 206 | 171 | 138 | 106 | 85.6 | 59.9 | 34.5 | 19.3 |
| | SD | 139 | 129 | 112 | 78.4 | 49.9 | 33.8 | 15.4 | 15.8 |
| | CV% | 67.6 | 75.3 | 81.3 | 73.6 | 58.3 | 56.5 | 44.7 | 81.7 |
| | Min | 34.5 | 46.2 | 38.0 | 46.9 | 38.5 | 18.6 | 10.9 | 1.72 |
| | Median | 170 | 170 | 95.2 | 76.7 | 79.1 | 54.3 | 33.6 | 14.8 |
| | Max | 513 | 521 | 432 | 304 | 213 | 123 | 64.0 | 58.5 |
| | Geometric Mean | 161 | 140 | 111 | 88.1 | 75.5 | 50.9 | 30.9 | 13.8 |

FIG. 37B

| Treatment | Subject | Time (min) | | | | | | | |
| --- | --- | --- | --- | --- | --- | --- | --- | --- | --- |
| | | Baseline-corrected Epinephrine (pg/mL) | | | | | | | |
| | | 0 | 5 | 8 | 10 | 13 | 18 | 23 | 28 |
| B: 0.3 mg IM Epinephrine | 01-001 | 4.31 | 3.67 | 61.6 | 74.6 | 33.6 | 13.7 | 30.2 | 66.2 |
| | 01-002 | 8.42 | 9.32 | 0.00 | 1.80 | 9.67 | 3.82 | 6.19 | 8.79 |
| | 01-003 | 0.00 | 0.483 | 180 | 111 | 97.5 | 72.5 | 111 | 148 |
| | 01-005 | 0.00 | 7.29 | 159 | 169 | 88.7 | 74.7 | 75.6 | 41.6 |
| | 01-007 | 0.00 | 154 | 70.3 | 37.7 | 38.7 | 18.6 | 38.6 | 30.5 |
| | 01-008 | 13.3 | 0.00 | 4.99 | 61.1 | 109 | 88.3 | 66.7 | 123 |
| | 01-010 | 0.00 | 2.92 | 4.42 | 6.50 | 16.0 | 28.0 | 24.3 | 18.7 |
| | 01-012 | 4.58 | 10.8 | 19.4 | 30.9 | 21.7 | 32.7 | 51.1 | 152 |
| | N | 8 | 8 | 8 | 8 | 8 | 8 | 8 | 8 |
| | Mean | 3.82 | 23.6 | 62.4 | 61.7 | 51.8 | 41.5 | 50.5 | 73.6 |
| | SD | 4.93 | 52.9 | 71.3 | 56.5 | 40.0 | 32.1 | 33.4 | 58.9 |
| | CV% | 128.8 | 224.4 | 114.2 | 91.7 | 77.1 | 77.4 | 66.1 | 80.0 |
| | Min | 0.00 | 0.00 | 0.00 | 1.80 | 9.67 | 3.82 | 6.19 | 8.79 |
| | Median | 2.16 | 5.48 | 40.5 | 49.4 | 36.1 | 30.4 | 44.9 | 53.9 |
| | Max | 13.3 | 154 | 180 | 169 | 109 | 88.3 | 111 | 152 |
| | Geometric Mean | NC | NC | NC | 32.3 | 37.7 | 28.4 | 38.7 | 49.9 |

FIG. 38A

| Treatment | Subject | Time (min) | | | | | | | |
|---|---|---|---|---|---|---|---|---|---|
| | | Baseline-corrected Epinephrine (pg/mL) | | | | | | | |
| | | 33 | 48 | 63 | 93 | 123 | 183 | 243 | 363 |
| B: 0.3 mg IM Epinephrine | 01-001 | 59.0 | 133 | 159 | 89.3 | 44.2 | 25.4 | 69.0 | 12.7 |
| | 01-002 | 106 | 161 | 140 | 82.8 | 29.5 | 21.1 | 43.1 | 29.1 |
| | 01-003 | 141 | 104 | 111 | 55.8 | 34.3 | 15.7 | 13.4 | 10.9 |
| | 01-005 | 65.8 | 173 | 139 | 84.5 | 53.6 | 41.6 | 43.4 | 17.1 |
| | 01-007 | 111 | 105 | 101 | 116 | 41.2 | 17.3 | 20.4 | 37.0 |
| | 01-008 | 138 | 148 | 142 | 89.9 | 61.8 | 24.2 | 19.0 | 0.00 |
| | 01-010 | 59.7 | 91.1 | 198 | 166 | 84.8 | 37.9 | 20.9 | 36.8 |
| | 01-012 | 216 | 302 | 198 | 79.2 | 53.0 | 42.0 | 39.5 | 17.5 |
| | N | 8 | 8 | 8 | 8 | 8 | 8 | 8 | 8 |
| | Mean | 112 | 152 | 149 | 95.4 | 50.3 | 28.1 | 33.6 | 20.1 |
| | SD | 53.6 | 67.4 | 35.5 | 33.0 | 17.5 | 10.8 | 18.6 | 13.1 |
| | CV% | 47.8 | 44.3 | 23.9 | 34.5 | 34.8 | 38.3 | 55.5 | 65.2 |
| | Min | 59.0 | 91.1 | 101 | 55.8 | 29.5 | 15.7 | 13.4 | 0.00 |
| | Median | 109 | 141 | 141 | 86.9 | 48.6 | 24.8 | 30.2 | 17.3 |
| | Max | 216 | 302 | 198 | 166 | 84.8 | 42.0 | 69.0 | 37.0 |
| | Geometric Mean | 102 | 142 | 145 | 91.2 | 47.9 | 26.4 | 29.4 | NC |

FIG. 38B

| Treatment | Subject | Time (min) Baseline-corrected Epinephrine (pg/mL) | | | | | | | |
| --- | --- | --- | --- | --- | --- | --- | --- | --- | --- |
| | | 0 | 5 | 8 | 10 | 13 | 18 | 23 | 28 |
| C: 0.5 mg IM Epinephrine | 01-001 | 0.00 | 71.7 | 25.2 | 50.7 | 43.1 | 40.9 | 105 | 112 |
| | 01-002 | 0.680 | 20.4 | 108 | 141 | 152 | 115 | 231 | 374 |
| | 01-003 | 0.00 | 14.9 | 29.5 | 32.8 | 25.0 | 28.4 | 35.1 | 109 |
| | 01-005 | 0.00 | 22.2 | 92.0 | 107 | 105 | 112 | 130 | 154 |
| | 01-006 | 6.36 | 141 | 170 | 142 | 83.9 | 75.9 | 142 | 111 |
| | 01-007 | 0.00 | 680 | 515 | 338 | 241 | 194 | 220 | 553 |
| | 01-008 | 0.00 | 9.08 | 153 | 186 | 85.2 | 94.5 | 208 | 254 |
| | 01-010 | 0.00 | 19.7 | 120 | 157 | 96.9 | 73.0 | 74.8 | 78.7 |
| | 01-011 | 0.00 | 37.2 | 557 | 467 | 242 | 165 | 132 | 73.6 |
| | 01-012 | 1.99 | 44.7 | 78.9 | 59.3 | 47.9 | 57.4 | 77.1 | 190 |
| | N | 10 | 10 | 10 | 10 | 10 | 10 | 10 | 10 |
| | Mean | 0.904 | 106 | 185 | 168 | 112 | 95.6 | 136 | 201 |
| | SD | 2.02 | 205 | 191 | 137 | 77.0 | 52.7 | 66.4 | 154 |
| | CV% | 223.6 | 193.7 | 103.3 | 81.2 | 68.6 | 55.2 | 49.0 | 76.8 |
| | Min | 0.00 | 9.08 | 25.2 | 32.8 | 25.0 | 28.4 | 35.1 | 73.6 |
| | Median | 0.00 | 29.7 | 114 | 142 | 91.0 | 85.2 | 131 | 133 |
| | Max | 6.36 | 680 | 557 | 467 | 242 | 194 | 231 | 553 |
| | Geometric Mean | NC | 41.1 | 118 | 126 | 89.6 | 82.3 | 119 | 161 |

FIG. 39A

| Treatment | Subject | Time (min) Baseline-corrected Epinephrine (pg/mL) | | | | | | | |
| | | 33 | 48 | 63 | 93 | 123 | 183 | 243 | 363 |
|---|---|---|---|---|---|---|---|---|---|
| C: 0.5 mg IM Epinephrine | 01-001 | 128 | 204 | 198 | 120 | 103 | 34.7 | 68.8 | 40.9 |
| | 01-002 | 308 | 310 | 212 | 126 | 50.9 | 35.8 | 24.2 | 48.1 |
| | 01-003 | 120 | 245 | 150 | 94.3 | 66.1 | 61.4 | 32.2 | 48.7 |
| | 01-005 | 137 | 194 | 289 | 303 | 92.8 | 70.2 | 61.5 | 43.0 |
| | 01-006 | 183 | 346 | 252 | 194 | 73.1 | 18.9 | 32.3 | 29.5 |
| | 01-007 | 376 | 370 | 187 | 140 | 119 | 79.3 | 92.8 | 81.5 |
| | 01-008 | 592 | 503 | 336 | 147 | 127 | 53.4 | 68.4 | 23.7 |
| | 01-010 | 126 | 179 | 159 | 161 | 115 | 41.6 | 70.1 | 83.4 |
| | 01-011 | 226 | 328 | 229 | 122 | 94.1 | 46.8 | 58.2 | 37.1 |
| | 01-012 | 422 | 481 | 337 | 133 | 76.3 | 67.4 | 63.3 | 60.4 |
| | N | 10 | 10 | 10 | 10 | 10 | 10 | 10 | 10 |
| | Mean | 262 | 316 | 235 | 154 | 91.7 | 50.9 | 57.2 | 49.6 |
| | SD | 160 | 114 | 67.7 | 58.8 | 24.8 | 18.8 | 21.3 | 20.1 |
| | CV% | 61.0 | 36.1 | 28.8 | 38.2 | 27.1 | 36.9 | 37.3 | 40.4 |
| | Min | 120 | 179 | 150 | 94.3 | 50.9 | 18.9 | 24.2 | 23.7 |
| | Median | 205 | 319 | 221 | 136 | 93.4 | 50.1 | 62.4 | 45.6 |
| | Max | 592 | 503 | 337 | 303 | 127 | 79.3 | 92.8 | 83.4 |
| | Geometric Mean | 224 | 298 | 226 | 146 | 88.4 | 47.3 | 53.0 | 46.2 |

FIG. 39B

| Treatment | Subject | Time (min) | | | | | | | |
| | | 0 | 5 | 8 | 10 | 13 | 18 | 23 | 28 |
| | | Baseline-corrected Epinephrine (pg/mL) | | | | | | | |
| D: 5.5 mg IN BBP01 | 01-001 | 0.00 | 110 | 439 | 505 | 381 | 176 | 254 | 184 |
| | 01-003 | 0.00 | 20.4 | 27.4 | 28.0 | 60.7 | 51.6 | 48.4 | 63.5 |
| | 01-005 | 0.00 | 37.6 | 375 | 638 | 546 | 439 | 328 | 367 |
| | 01-006 | 0.00 | 22.1 | 57.2 | 111 | 128 | 239 | 192 | 160 |
| | 01-007 | 0.00 | 41.3 | 332 | 237 | 324 | 389 | 367 | 413 |
| | 01-008 | 6.53 | 11.2 | 406 | 652 | 855 | 609 | 524 | 400 |
| | 01-010 | 1.35 | 23.5 | 205 | 232 | 283 | 352 | 285 | 302 |
| | 01-011 | 2.09 | 101 | 391 | 485 | 460 | 511 | 480 | 499 |
| | 01-012 | 7.92 | 127 | 165 | 225 | 187 | 251 | 344 | 379 |
| | N | 9 | 9 | 9 | 9 | 9 | 9 | 9 | 9 |
| | Mean | 1.99 | 54.9 | 267 | 346 | 358 | 335 | 314 | 308 |
| | SD | 3.08 | 44.6 | 156 | 229 | 242 | 174 | 144 | 142 |
| | CV% | 155.1 | 81.3 | 58.7 | 66.2 | 67.7 | 51.9 | 45.9 | 46.2 |
| | Min | 0.00 | 11.2 | 27.4 | 28.0 | 60.7 | 51.6 | 48.4 | 63.5 |
| | Median | 0.00 | 37.6 | 332 | 237 | 324 | 352 | 328 | 367 |
| | Max | 7.92 | 127 | 439 | 652 | 855 | 609 | 524 | 499 |
| | Geometric Mean | NC | 40.0 | 198 | 251 | 281 | 279 | 267 | 265 |

FIG. 40A

| Treatment | Subject | Time (min) — Baseline-corrected Epinephrine (pg/mL) | | | | | | | |
|---|---|---|---|---|---|---|---|---|---|
| | | 33 | 48 | 63 | 93 | 123 | 183 | 243 | 363 |
| D: 5.5 mg IN BBP01 | 01-001 | 339 | 138 | 200 | 114 | 129 | 118 | 52.3 | 25.8 |
| | 01-003 | 79.2 | 64.7 | 63.3 | 64.3 | 72.0 | 36.5 | 33.4 | 24.7 |
| | 01-005 | 273 | 237 | 300 | 187 | 227 | 156 | 97.1 | 30.1 |
| | 01-006 | 190 | 206 | 148 | 169 | 200 | 107 | 92.7 | 42.9 |
| | 01-007 | 317 | 204 | 179 | 394 | 268 | 122 | 138 | 30.9 |
| | 01-008 | 540 | 333 | 212 | 135 | 110 | 58.1 | 32.8 | 15.8 |
| | 01-010 | 288 | 245 | 167 | 236 | 232 | 101 | 59.6 | 42.1 |
| | 01-011 | 696 | 587 | 533 | 678 | 492 | 203 | 173 | 43.2 |
| | 01-012 | 266 | 354 | 308 | 247 | 285 | 217 | 87.3 | 60.2 |
| | N | 9 | 9 | 9 | 9 | 9 | 9 | 9 | 9 |
| | Mean | 332 | 263 | 234 | 247 | 224 | 134 | 85.2 | 35.1 |
| | SD | 184 | 150 | 135 | 187 | 124 | 79.2 | 47.3 | 13.3 |
| | CV% | 55.3 | 57.2 | 57.4 | 75.8 | 55.4 | 59.0 | 55.5 | 37.9 |
| | Min | 79.2 | 64.7 | 63.3 | 64.3 | 72.0 | 36.5 | 32.8 | 15.8 |
| | Median | 288 | 237 | 200 | 187 | 227 | 118 | 87.3 | 30.9 |
| | Max | 696 | 587 | 533 | 678 | 492 | 293 | 173 | 60.2 |
| | Geometric Mean | 286 | 225 | 203 | 199 | 195 | 114 | 73.7 | 32.8 |

FIG. 40B

| Treatment | Subject | Cmax (pg/mL) | Tmax (min) | AUClast (min*pg/mL) |
|---|---|---|---|---|
| A: 3.5 mg IN BBP01 | 01-001 | 149 | 33.0 | 26700 |
| | 01-002 | 613 | 5.0 | 36180 |
| | 01-003 | 111 | 28.0 | 23960 |
| | 01-005 | 220 | 8.0 | 30870 |
| | 01-006 | 428 | 18.0 | 29920 |
| | 01-007 | 83.5 | 123.0 | 14750 |
| | 01-008 | 628 | 28.0 | 73650 |
| | 01-009 | 336 | 23.0 | 21610 |
| | 01-010 | 353 | 28.0 | 43970 |
| | 01-011 | 343 | 28.0 | 38280 |
| | 01-012 | 121 | 33.0 | 26860 |
| | N | 11 | 11 | 11 |
| | Mean | 308 | 32.3 | 33340 |
| | SD | 193 | 31.5 | 15640 |
| | CV% | 62.6 | 97.6 | 46.9 |
| | Min | 83.5 | 5.00 | 14750 |
| | Median | 336 | 28.0 | 29920 |
| | Max | 628 | 123 | 73650 |
| | Geometric Mean | 250.8 | 23.8 | 30680 |

FIG. 43

| Treatment | Subject | Cmax (pg/mL) | Tmax (min) | AUClast (min*pg/mL) |
|---|---|---|---|---|
| B: 0.3 mg IM Epinephrine | 01-001 | 174 | 63.0 | 25270 |
| | 01-002 | 189 | 48.0 | 27660 |
| | 01-003 | 191 | 8.0 | 18110 |
| | 01-005 | 196 | 48.0 | 28950 |
| | 01-007 | 159 | 5.0 | 18120 |
| | 01-008 | 178 | 48.0 | 28050 |
| | 01-010 | 216 | 63.0 | 27970 |
| | 01-012 | 323 | 48.0 | 31620 |
| | N | 8 | 8 | 8 |
| | Mean | 203.3 | 41.3 | 25720 |
| | SD | 51.27 | 22.5 | 5004 |
| | CV% | 25.2 | 54.4 | 19.5 |
| | Min | 158.6 | 5.0 | 18110 |
| | Median | 190.1 | 48.0 | 27820 |
| | Max | 323.2 | 63.0 | 31620 |
| | Geometric Mean | 198.7 | 30.9 | 25240 |

FIG. 44

| Treatment | Subject | Cmax (pg/mL) | Tmax (min) | AUClast (min*pg/mL) |
|---|---|---|---|---|
| C: 0.5 mg IM Epinephrine | 01-001 | 224 | 48.0 | 36660 |
| | 01-002 | 407 | 28.0 | 42580 |
| | 01-003 | 248 | 48.0 | 25850 |
| | 01-005 | 323 | 93.0 | 45920 |
| | 01-006 | 373 | 48.0 | 40070 |
| | 01-007 | 696 | 5.0 | 57110 |
| | 01-008 | 617 | 33.0 | 54200 |
| | 01-010 | 200 | 48.0 | 40930 |
| | 01-011 | 579 | 8.0 | 43490 |
| | 01-012 | 491 | 48.0 | 45390 |
| | N | 10 | 10 | 10 |
| | Mean | 415.8 | 40.7 | 43220 |
| | SD | 174.1 | 24.9 | 8729 |
| | CV% | 41.9 | 61.1 | 20.2 |
| | Min | 199.8 | 5.0 | 25850 |
| | Median | 389.9 | 48.0 | 43040 |
| | Max | 695.6 | 93.0 | 57110 |
| | Geometric Mean | 382.3 | 31.2 | 42350 |

FIG. 45

| Treatment | Subject | Cmax (pg/mL) | Tmax (min) | AUClast (min*pg/mL) |
|---|---|---|---|---|
| D: 5.5 mg IN BBP01 | 01-001 | 523 | 10.0 | 45750 |
| | 01-003 | 83.5 | 33.0 | 17710 |
| | 01-005 | 656 | 10.0 | 64740 |
| | 01-006 | 263 | 18.0 | 51990 |
| | 01-007 | 429 | 28.0 | 68130 |
| | 01-008 | 880 | 13.0 | 53780 |
| | 01-010 | 376 | 18.0 | 56880 |
| | 01-011 | 723 | 33.0 | 125400 |
| | 01-012 | 398 | 28.0 | 73120 |
| | N | 9 | 9 | 9 |
| | Mean | 481 | 21.2 | 61950 |
| | SD | 244 | 9.42 | 28750 |
| | CV% | 50.7 | 44.4 | 46.4 |
| | Min | 83.5 | 10.0 | 17710 |
| | Median | 429 | 18.0 | 56880 |
| | Max | 880 | 33.0 | 125400 |
| | Geometric Mean | 407.2 | 19.2 | 55760 |

FIG. 46

| Treatment | Subject | Cmax (pg/mL) | Tmax (min) | AUClast (min*pg/mL) | t½ (min) | AUCinf (min*pg/mL) |
|---|---|---|---|---|---|---|
| A: 3.5 mg IN BEPX01 | 01-001 | 127 | 33.0 | 17930 | 34.5 | 18020 |
| | 01-002 | 578 | 5.0 | 23430 | 86.3 | 24200 |
| | 01-003 | 100 | 28.0 | 19950 | 121 | 24360 |
| | 01-005 | 211 | 8.0 | 27780 | 102 | 31280 |
| | 01-006 | 408 | 18.0 | 22400 | 63.3 | 23640 |
| | 01-007 | 79.1 | 123.0 | 13180 | 134 | 16220 |
| | 01-008 | 609 | 28.0 | 66770 | 91.9 | 74520 |
| | 01-009 | 327 | 23.0 | 18000 | 103 | 18950 |
| | 01-010 | 336 | 28.0 | 37780 | 96.5 | 42200 |
| | 01-011 | 323 | 28.0 | 30880 | 64.5 | 32240 |
| | 01-012 | 99.5 | 33.0 | 16940 | 86.6 | 20760 |
| | N | 11 | 11 | 11 | 11 | 11 |
| | Mean | 291 | 32.3 | 27000 | 89.5 | 29670 |
| | SD | 188 | 31.5 | 14890 | 27.9 | 16680 |
| | CV% | 64.6 | 97.6 | 55.1 | 31.2 | 56.2 |
| | Min | 79.1 | 5.00 | 13180 | 34.5 | 16220 |
| | Median | 323 | 28.0 | 22400 | 91.9 | 24200 |
| | Max | 609 | 123 | 66770 | 134 | 74520 |
| | Geometric Mean | 233 | 23.8 | 24400 | 84.6 | 26780 |

FIG. 47

| Treatment | Subject | Cmax (pg/mL) | Tmax (min) | AUClast (min*pg/mL) |
|---|---|---|---|---|
| B: 0.3 mg IM Epinephrine | 01-001 | 159 | 63.0 | 19200 |
| | 01-002 | 161 | 48.0 | 17200 |
| | 01-003 | 180 | 8.0 | 14000 |
| | 01-005 | 173 | 48.0 | 20500 |
| | 01-007 | 154 | 5.0 | 16500 |
| | 01-008 | 148 | 48.0 | 16100 |
| | 01-010 | 198 | 63.0 | 21700 |
| | 01-012 | 302 | 48.0 | 23900 |
| | N | 8 | 8 | 8 |
| | Mean | 184 | 41.4 | 18700 |
| | SD | 50.3 | 22.5 | 3280 |
| | CV% | 27.3 | 54.4 | 17.6 |
| | Min | 148 | 5.00 | 14000 |
| | Median | 167 | 48.0 | 18200 |
| | Max | 302 | 63.0 | 23900 |
| | Geometric Mean | 180 | 31.0 | 18400 |

FIG. 48

| Treatment | Subject | Cmax (pg/mL) | Tmax (min) | AUClast (min*pg/mL) |
|---|---|---|---|---|
| C: 0.5 mg IM Epinephrine | 01-001 | 204 | 48.0 | 29000 |
| | 01-002 | 374 | 28.0 | 30300 |
| | 01-003 | 245 | 48.0 | 24500 |
| | 01-005 | 303 | 93.0 | 38700 |
| | 01-006 | 346 | 48.0 | 30200 |
| | 01-007 | 680 | 5.00 | 51400 |
| | 01-008 | 592 | 33.0 | 44700 |
| | 01-010 | 179 | 48.0 | 33200 |
| | 01-011 | 557 | 8.0 | 35500 |
| | 01-012 | 481 | 48.00 | 41500 |
| | N | 10 | 10 | 10 |
| | Mean | 396 | 40.7 | 35900 |
| | SD | 173 | 24.9 | 8190 |
| | CV% | 43.8 | 61.1 | 22.8 |
| | Min | 179 | 5.00 | 24500 |
| | Median | 360 | 48.0 | 34300 |
| | Max | 680 | 93.0 | 51400 |
| | Geometric Mean | 361 | 31.2 | 35100 |

FIG. 49

| Treatment | Subject | Cmax (pg/mL) | Tmax (min) | AUClast (min*pg/mL) | t½ (min) | AUCinf (min*pg/mL) |
|---|---|---|---|---|---|---|
| D: 5.5 mg IN BBP01 | 01-001 | 505 | 10.0 | 39010 | 96.3 | 42590 |
| | 01-003 | 79.2 | 33.0 | 16160 | 313 | 27290 |
| | 01-005 | 638 | 10.0 | 58090 | 75.0 | 61350 |
| | 01-006 | 239 | 18.0 | 42920 | 114 | 50000 |
| | 01-007 | 413 | 28.0 | 62170 | 78.9 | 65680 |
| | 01-008 | 855 | 13.0 | 44660 | 84.9 | 46600 |
| | 01-010 | 352 | 18.0 | 48050 | 115 | 55010 |
| | 01-011 | 696 | 33.0 | 115100 | 68.9 | 119400 |
| | 01-012 | 379 | 28.0 | 65940 | 119 | 76320 |
| | N | 9 | 9 | 9 | 9 | 9 |
| | Mean | 462 | 21.2 | 54680 | 118 | 60470 |
| | SD | 240 | 9.42 | 27050 | 75.2 | 26230 |
| | CV% | 51.9 | 44.4 | 49.5 | 63.6 | 43.4 |
| | Min | 79.2 | 10.0 | 16160 | 68.9 | 27290 |
| | Median | 413 | 18.0 | 48050 | 96.3 | 55010 |
| | Max | 855 | 33.0 | 115100 | 313 | 119400 |
| | Geometric Mean | 388 | 19.2 | 48870 | 106 | 56060 |

FIG. 50

| Treatment | Subject | AUC0-23 (min*pg/mL) | AUC0-33 (min*pg/mL) | AUC0-48 (min*pg/mL) | AUC0-243 (min*pg/mL) | AUC0-363 (min*pg/mL) |
|---|---|---|---|---|---|---|
| A: 3.5 mg IN BRP01 | 01-001 | 1414 | 2530 | 4119 | 16540 | 17930 |
| | 01-002 | 8095 | 9953 | 12440 | 21760 | 23430 |
| | 01-003 | 1022 | 1882 | 2878 | 15630 | 19950 |
| | 01-005 | 2690 | 4338 | 7146 | 24860 | 27780 |
| | 01-006 | 5070 | 8344 | 11780 | 20940 | 22400 |
| | 01-007 | 243.5 | 580.3 | 1185 | 10570 | 13180 |
| | 01-008 | 5153 | 10660 | 18420 | 59420 | 66770 |
| | 01-009 | 3792 | 6494 | 9329 | 16840 | 18800 |
| | 01-010 | 2808 | 5941 | 9710 | 33490 | 37780 |
| | 01-011 | 2961 | 6150 | 9256 | 27570 | 30860 |
| | 01-012 | 966.9 | 1808 | 3201 | 16420 | 18940 |
| | N | 11 | 11 | 11 | 11 | 11 |
| | Mean | 3110 | 5335 | 8133 | 23960 | 27000 |
| | SD | 2317 | 3420 | 5101 | 13370 | 14890 |
| | CV% | 74.5 | 64.1 | 62.7 | 55.8 | 55.1 |
| | Min | 243.5 | 580.3 | 1185 | 10570 | 13180 |
| | Median | 2808 | 5941 | 9256 | 20940 | 22400 |
| | Max | 8095 | 10660 | 18420 | 59420 | 66770 |
| | Geometric Mean | 2209 | 4030 | 6392 | 21530 | 24400 |

FIG. 57

| Treatment | Subject | AUC0-23 (min*pg/mL) | AUC0-33 (min*pg/mL) | AUC0-48 (min*pg/mL) | AUC0-243 (min*pg/mL) | AUC0-363 (min*pg/mL) |
|---|---|---|---|---|---|---|
| B: 0.3 mg IM Epinephrine | 01-001 | 628.4 | 1182 | 2624 | 15230 | 19220 |
| | 01-002 | 133.9 | 459.0 | 2462 | 12960 | 17240 |
| | 01-003 | 1752 | 3121 | 4939 | 12580 | 14030 |
| | 01-005 | 1754 | 2307 | 4101 | 17150 | 20540 |
| | 01-007 | 1205 | 1731 | 3350 | 13090 | 16540 |
| | 01-008 | 1238 | 2366 | 4508 | 16060 | 17190 |
| | 01-010 | 303.8 | 606.8 | 1738 | 18190 | 21650 |
| | 01-012 | 557.7 | 1987 | 5877 | 20690 | 23940 |
| | N | 8 | 8 | 8 | 8 | 8 |
| | Mean | 946.5 | 1720 | 3700 | 15750 | 18790 |
| | SD | 629.9 | 919.2 | 1402 | 2868 | 3176 |
| | CV% | 66.5 | 53.4 | 37.9 | 18.2 | 16.9 |
| | Min | 133.9 | 459.0 | 1738 | 12580 | 14030 |
| | Median | 916.9 | 1859 | 3725 | 15640 | 18230 |
| | Max | 1754 | 3121 | 5877 | 20690 | 23940 |
| | Geometric Mean | 711.0 | 1448 | 3452 | 15520 | 18560 |

FIG. 58

| Treatment | Subject | AUC0-23 (min*pg/mL) | AUC0-33 (min*pg/mL) | AUC0-48 (min*pg/mL) | AUC0-243 (min*pg/mL) | AUC0-363 (min*pg/mL) |
|---|---|---|---|---|---|---|
| C: 0.5 mg IM Epinephrine | 01-001 | 1104 | 2246 | 4733 | 22610 | 29050 |
| | 01-002 | 2463 | 5675 | 10310 | 25970 | 30310 |
| | 01-003 | 544.4 | 1476 | 4211 | 19620 | 24480 |
| | 01-005 | 1890 | 3328 | 5810 | 32450 | 38660 |
| | 01-006 | 2421 | 3789 | 7759 | 26520 | 30230 |
| | 01-007 | 7300 | 11520 | 17120 | 40910 | 51360 |
| | 01-008 | 2199 | 5467 | 13060 | 39590 | 44650 |
| | 01-010 | 1701 | 2596 | 4881 | 23860 | 33170 |
| | 01-011 | 4776 | 6025 | 10180 | 29860 | 35490 |
| | 01-012 | 1199 | 3397 | 10160 | 34080 | 41510 |
| | N | 10 | 10 | 10 | 10 | 10 |
| | Mean | 2560 | 4552 | 8882 | 29560 | 35890 |
| | SD | 2021 | 2885 | 4239 | 7141 | 8186 |
| | CV% | 79.0 | 63.4 | 47.7 | 24.2 | 22.8 |
| | Min | 544.4 | 1476 | 4211 | 19620 | 24480 |
| | Median | 2045 | 3593 | 8962 | 28190 | 34330 |
| | Max | 7300 | 11520 | 17120 | 40910 | 51360 |
| | Geometric Mean | 2007 | 3890 | 8015 | 28790 | 35080 |

FIG. 59

| Treatment | Subject | AUC0-23 (min*pg/mL) | AUC0-33 (min*pg/mL) | AUC0-48 (min*pg/mL) | AUC0-243 (min*pg/mL) | AUC0-303 (min*pg/mL) |
|---|---|---|---|---|---|---|
| Dr 5.5 mg IN BBP01 | 01-001 | 5765 | 8158 | 11510 | 34510 | 39010 |
| | 01-003 | 8413 | 1478 | 2553 | 12700 | 16160 |
| | 01-005 | 7855 | 11180 | 15000 | 51220 | 58090 |
| | 01-006 | 2092 | 4446 | 7413 | 35170 | 42920 |
| | 01-007 | 5745 | 9510 | 13350 | 53570 | 62170 |
| | 01-008 | 10440 | 15090 | 21510 | 41870 | 44660 |
| | 01-010 | 4780 | 7731 | 11720 | 42010 | 48050 |
| | 01-011 | 8190 | 13820 | 23220 | 103900 | 115100 |
| | 01-012 | 4365 | 7770 | 12420 | 57190 | 65940 |
| | N | 9 | 9 | 9 | 9 | 9 |
| | Mean | 5632 | 8776 | 13190 | 48010 | 54680 |
| | SD | 2928 | 4245 | 6376 | 24780 | 27050 |
| | CV% | 52.0 | 48.4 | 48.3 | 51.6 | 49.5 |
| | Min | 8413 | 1478 | 2553 | 12700 | 16160 |
| | Median | 5745 | 8158 | 12420 | 42010 | 48050 |
| | Max | 10440 | 15090 | 23220 | 103900 | 115100 |
| | Geometric Mean | 4669 | 7446 | 11370 | 42390 | 48870 |

FIG. 60

| Test | Reference | Dependent Variable | Test LSM | Ref LSM | Ratio %Ref | CI 90% Lower | CI 90% Upper |
|------|-----------|--------------------|----------|---------|------------|--------------|--------------|
| A: 3.5 mg IN BBP01 | B: 0.3 mg IM Epi | Ln(AUC0-23) | 7.86 | 7.16 | 201.91 | 115.28 | 353.65 |
| | | Ln(AUC0-33) | 8.43 | 7.70 | 207.87 | 125.85 | 343.35 |
| | | Ln(AUC0-48) | 8.89 | 8.42 | 159.88 | 104.34 | 244.99 |
| | | Ln(AUC0-243) | 10.15 | 9.92 | 126.58 | 97.75 | 163.92 |
| | | Ln(AUC0-363) | 10.33 | 10.15 | 120.47 | 94.16 | 154.12 |
| | | Ln(Cmax) | 5.52 | 5.32 | 122.72 | 81.30 | 185.23 |

FIG. 61

| Test | Reference | Dependent Variable | Test LSM | Ref LSM | Ratio %Ref | CI 90% Lower | CI 90% Upper |
|------|-----------|--------------------|----------|---------|------------|--------------|--------------|
| D: 5.5 mg IN BBP01 | B: 0.3 mg IM Epi | Ln(AUC0-23) | 8.55 | 7.16 | 401.14 | 223.16 | 721.07 |
| | | Ln(AUC0-33) | 9.01 | 7.70 | 368.46 | 217.95 | 622.89 |
| | | Ln(AUC0-49) | 9.43 | 8.42 | 276.22 | 176.75 | 431.68 |
| | | Ln(AUC0-243) | 10.75 | 9.92 | 230.16 | 175.67 | 301.55 |
| | | Ln(AUC0-363) | 10.92 | 10.15 | 217.52 | 168.13 | 281.41 |
| | | Ln(Cmax) | 6.03 | 5.32 | 202.96 | 131.92 | 312.24 |

3.5 mg BBP01 and 0.3 mg IM Epinephrine

| Subject | Cmax BBP01 pg/mL | Cmax IM Epi pg/mL | AUC0-363 BBP-01 min*pg/mL | AUC0-363 IM Epi min*pg/mL | Cmax Frel A/B | AUC Frel A/B |
|---|---|---|---|---|---|---|
| 01-001 | 149.0 | 174.3 | 26700 | 25270 | 7.3% | 9.2% |
| 01-002 | 612.7 | 189.3 | 36181 | 27663 | 27.7% | 11.4% |
| 01-003 | 111.2 | 190.9 | 23960 | 18113 | 5.0% | 11.6% |
| 01-005 | 219.8 | 196.2 | 30866 | 28952 | 9.6% | 9.3% |
| 01-007 | 83.5 | 158.6 | 14749 | 18121 | 4.5% | 7.1% |
| 01-008 | 628.1 | 178.0 | 73646 | 28049 | 30.2% | 23.0% |
| 01-010 | 353.0 | 215.5 | 43967 | 27974 | 14.0% | 13.8% |
| 01-012 | 121.0 | 323.2 | 26865 | 31615 | 3.2% | 7.4% |
| | | | | Mean Frel = | 13.5% | 11.9% |

FIG. 63B

5.5 mg BBP01 and 0.3 mg IM Epinephrine

| Subject | Cmax BBP01 pg/mL | Cmax IM Epi pg/mL | AUC0-363 BBP-01 min*pg/mL | AUC0-363 IM Epi min*pg/mL | Cmax Frel D/B | AUC Frel D/B |
|---|---|---|---|---|---|---|
| 01-001 | 523.0 | 174.3 | 45754 | 25270 | 25.7% | 15.8% |
| 01-003 | 83.5 | 190.9 | 17714 | 18113 | 3.7% | 8.6% |
| 01-005 | 656.0 | 196.2 | 64736 | 28952 | 28.7% | 19.6% |
| 01-007 | 428.7 | 158.6 | 68128 | 18121 | 23.2% | 32.9% |
| 01-008 | 879.8 | 178.0 | 53780 | 28049 | 42.4% | 16.8% |
| 01-010 | 375.9 | 215.5 | 56877 | 27974 | 14.9% | 17.8% |
| 01-012 | 398.5 | 323.2 | 73118 | 31615 | 10.6% | 20.2% |
| | | | | Mean Frel = | 21.3% | 18.8% |

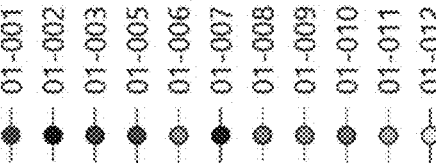
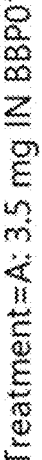
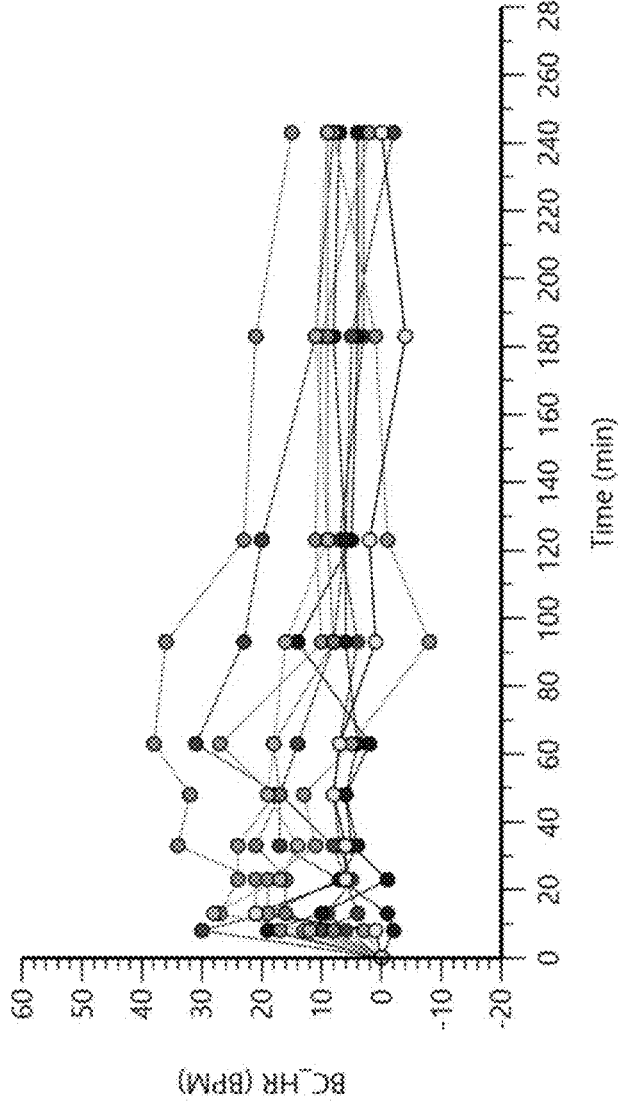
FIG. 68

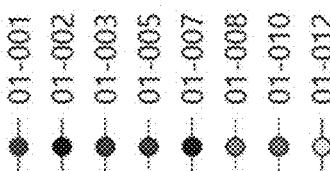
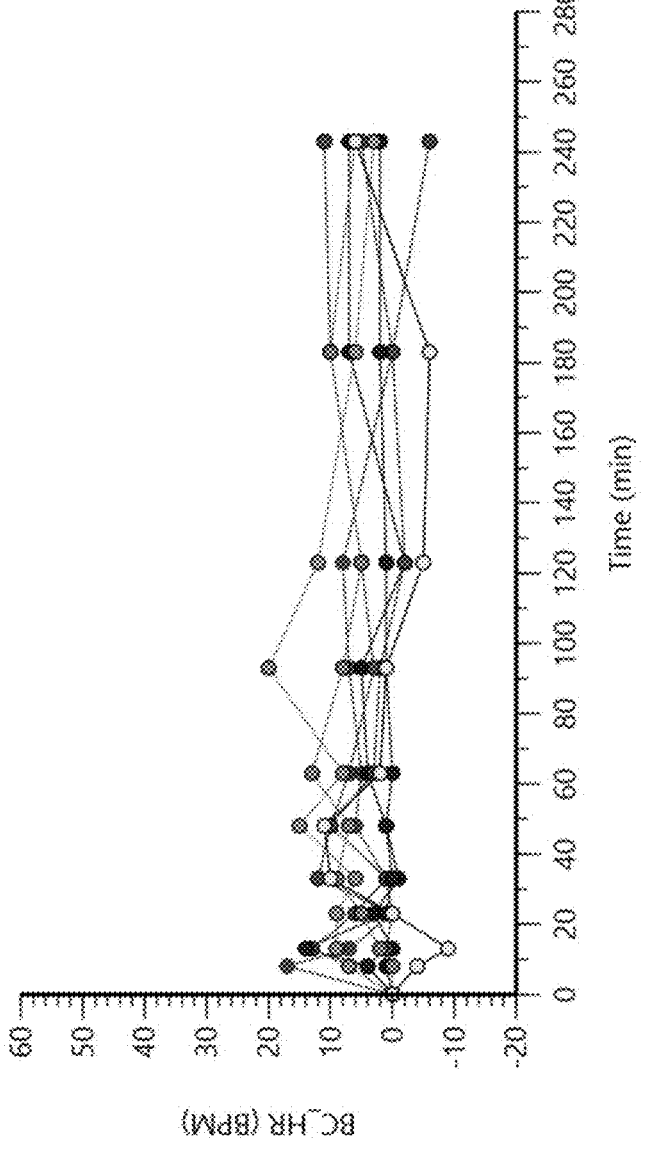
FIG. 69

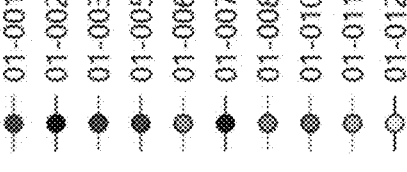
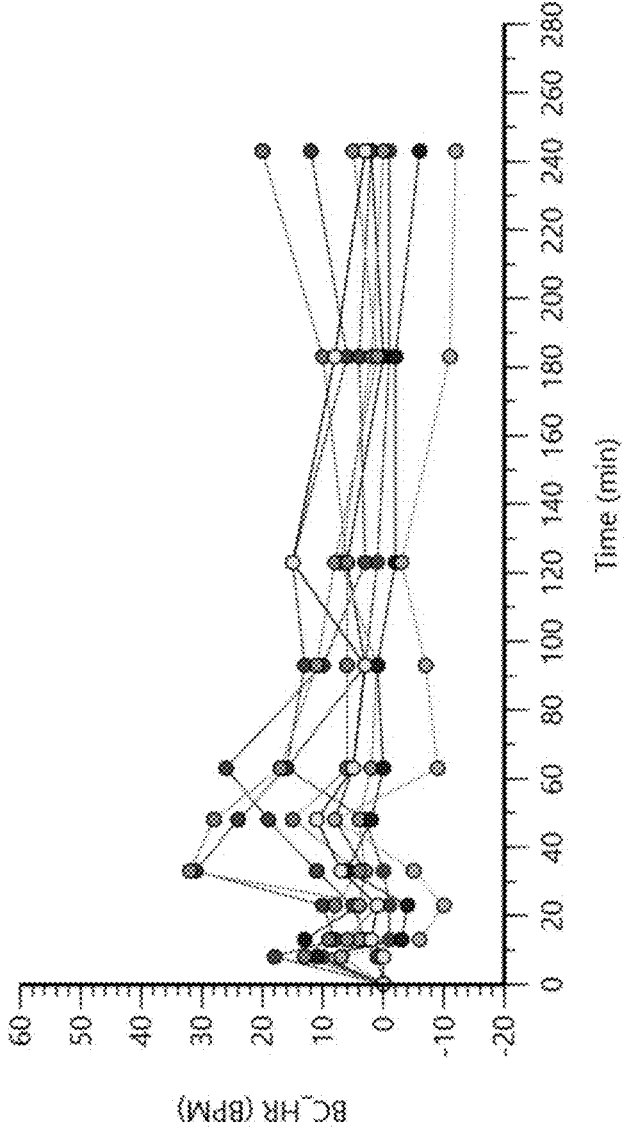
FIG. 70

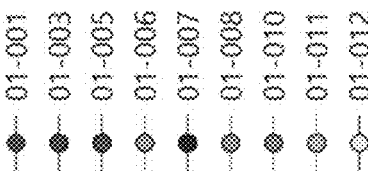
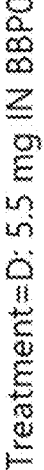
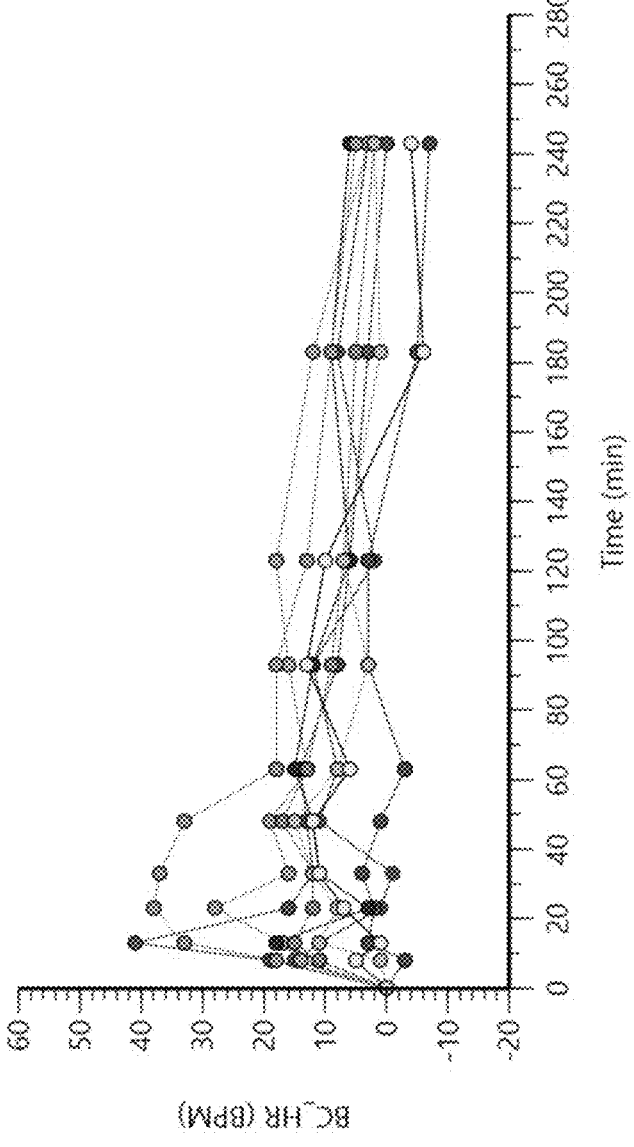
FIG. 71

| Time Point | Condition | XRPD (n=1) | % Moisture Content (SD, n=3) |
|---|---|---|---|
| T0 | 30% RH | Amorphous | 6.1 (0.1) |
| 2 weeks | 40°C/75% | Amorphous | 5.5 (0.1) |
| 4 weeks | 25°C/60% | Amorphous | 5.7 (0.0) |
|  | 40°C/75% | Amorphous | 4.9 (0.2) |
| 8 weeks | 25°C/60% | Amorphous | 6.3 (0.1) |
|  | 40°C/75% | Amorphous | 4.8 (0.2) |
| 12 weeks | 25°C/60% | Amorphous | 5.6 (0.1) |
|  | 40°C/75% | Amorphous | 4.0 (0.2) |

FIG. 73

| Time Point | Condition | ePSD Dv10 μm (mean, n=5) | ePSD Dv50 μm (mean, n=5) | ePSD Dv90 μm (mean, n=5) | SP Dmax mm² (mean, n=5) | SP Dmin mm² (mean, n=5) | AF Kg (max, n=5) | DDU % (mean, n=5) |
|---|---|---|---|---|---|---|---|---|
| T0 | | 10 | 38 | 516 | 43 | 28 | 5.4 | 94 |
| 2 weeks | 40°C/75% | 10 | 38 | 568 | 43 | 25 | 5.9 | 94 |
| | 25°C/60% | 9 | 36 | 472 | 45 | 28 | 5.6 | 94 |
| 4 weeks | 40°C/75% | 11 | 40 | 471 | 38 | 27 | 6.0 | 93 |
| | 25°C/60% | 11 | 41 | 515 | 45 | 28 | 5.9 | 91 |
| 8 weeks | 40°C/75% | 12 | 54 | 503 | 49 | 29 | 5.9 | 93 |
| | 50°C | 18 | 64 | 527 | NT | NT | 5.8 | NT |
| 12 weeks | 25°C/60% | 9 | 36 | 507 | 45 | 28 | 6.0 | 94 |
| | 40°C/75% | 10 | 37 | 486 | 45 | 31 | 6.2 | 95 |
| | 50°C | 18 | 49 | 438 | NT | NT | 6.0 | NT |

NT: Not tested

FIG. 74

Study 101 and 102 PK (Unadjusted GeoMean)

Legend:
- 0.3 mg EAI (Group B)
- 4.5 mg IN (Group A)
- 5.5 mg IN (Group C)
- 4.5 mg IN NAC (Group D)
- 5.5 mg IN
- 3.5 mg IN
- 0.5 mg IM
- 0.3 mg IM Plasma Epinephrine (pg/mL)

Minute (Protocol)

COMPOSITIONS, DEVICES, AND METHODS FOR INTRANASAL DELIVERY OF DRY POWDER EPINEPHRINE

CROSS REFERENCES TO RELATED APPLICATIONS

This application is related to and claims priority from the following U.S. patents and patent applications. This application claims priority to and the benefit of U.S. Provisional Patent Application No. 63/709,741, filed Oct. 21, 2024, which is incorporated herein by reference in its entirety.

BACKGROUND OF THE INVENTION

1. Field of the Invention

The present invention relates to dry powder epinephrine compositions and more specifically to drug products for the intranasal delivery of epinephrine.

2. Description of the Prior Art

It is generally known in the prior art to provide epinephrine for the treatment of various health emergencies, including anaphylaxis, severe allergic reaction, major adverse cardiac events (MACE), bronchospasms, organophosphate poisoning, and more. Existing epinephrine compositions are aqueous compositions, delivered via intravenous injection, or by subcutaneous or intra-muscular injection. These injections are most commonly delivered via an auto-injector, though medically trained personnel are capable of delivering epinephrine parenterally using a needle and syringe. Alternative epinephrine compositions and intranasal delivery of dry powders have been explored in the prior art.

Prior art patent documents include the following:

US Patent Publication No. 2024/0408212 for Pharmaceutical composition comprising biopharmaceutical drug compounds by inventors Savmarker, et al., filed May 21, 2024, and published Dec. 12, 2024, is directed to a which composition is in the form of an amorphous, mono-particulate powder comprising a mixture of: (a) a pharmacologically-effective dosage amount of at least one biopharmaceutical drug compound; and (b) a pharmaceutically-acceptable carrier material, which carrier material comprises a combination of a disaccharide and a polymeric material. Preferred pharmaceutically-acceptable carriers in this regard include lactose or trehalose and dextrins (e.g. maltodextrins). Compositions may further comprise one or more alkyl saccharides. Preferred alkyl saccharides include sucrose esters, such as sucrose monolaurate. Powder compositions may be produced by spray-drying the various components together in combination.

US Patent Publication No. 2025/0041243 for Pharmaceutical composition comprising adrenaline by inventors Savmarker, et al., filed Mar. 1, 2024, and published Feb. 6, 2025, is directed to a pharmaceutically-acceptable composition in the form of a solid, amorphous, mono-particulate powder comprising a mixture of: a pharmacologically-effective dosage amount of an adrenergic receptor modulator, or a pharmaceutically-acceptable salt thereof; and a pharmaceutically-acceptable carrier material, which carrier material comprises a maltodextrin with a dextrose equivalent (DE) that is above 15. Compositions are suitable for transmucosal drug delivery, including nasal delivery, by which said compositions may be loaded into a single-use nasal applicator. Compositions are preferably made by way of spray drying and may further include a disaccharide, such as lactose or trehalose which, along with the active ingredient and maltodextrin, may be spray-dried together in combination. Compositions may further comprise one or more alkyl saccharides. Preferred alkyl saccharides include sucrose esters, such as sucrose monolaurate. Preferred adrenergic receptor modulators include epinephrine (adrenaline). The compositions are thus particularly useful in the treatment of allergic reactions, including anaphylaxis.

U.S. Pat. No. 11,957,647 for Pharmaceutical composition comprising adrenaline by inventors Savmarker et al., filed May 24, 2023 and issued Apr. 16, 2024 is directed to a pharmaceutically-acceptable composition in the form of a solid, amorphous, mono-particulate powder comprising a mixture of: (a) a pharmacologically-effective dosage amount of an adrenergic receptor modulator, or a pharmaceutically-acceptable salt thereof; and (b) a pharmaceutically-acceptable carrier material, which carrier material comprises a maltodextrin with a dextrose equivalent (DE) that is above 15. Compositions are suitable for transmucosal drug delivery, including nasal delivery, by which said compositions may be loaded into a single-use nasal applicator. Compositions are preferably made by way of spray drying and may further include a disaccharide, such as lactose or trehalose which, along with the active ingredient and maltodextrin, may be spray-dried together in combination. Compositions may further comprise one or more alkyl saccharides. Preferred alkyl saccharides include sucrose esters, such as sucrose monolaurate. Preferred adrenergic receptor modulators include epinephrine (adrenaline). The compositions are thus particularly useful in the treatment of allergic reactions, including anaphylaxis.

U.S. Pat. No. 11,737,980 for Pharmaceutical composition for drug delivery by inventors Savmarker et al., filed Dec. 2, 2021 and issued Aug. 29, 2023 is directed to a pharmaceutically-acceptable composition which is preferably in the form of a spray-dried powder comprising a mixture of: (a) a pharmacologically-effective dosage amount of at least one pharmaceutically-active compound; and (b) a pharmaceutically-acceptable carrier material, which carrier material comprises a combination of a disaccharide and a polymeric material. Compositions are suitable for, for example, transmucosal drug delivery, including sublingual and nasal delivery. In the case of nasal delivery, said compositions may be loaded into single- or multiple-use nasal applicators. Preferred pharmaceutically-acceptable carriers in this regard include lactose or trehalose and dextrins (e.g. cyclodextrins or maltodextrins), which may be spray-dried together in combination. Compositions may further comprise one or more alkyl saccharides. Preferred alkyl saccharides include sucrose esters, such as sucrose monolaurate.

U.S. Pat. No. 12,029,709 for Inhalable Epinephrine Formulation by inventors Fraser, et al., filed Aug. 11, 2022, and issued Jul. 9, 2024, is directed to an inhalable formulation, suitable for use in a dry powder inhaler, for the delivery of epinephrine, or a pharmaceutically acceptable salt or derivative thereof. The inhalable formulation further comprises a solid carrier and results in a stable formulation with useful physical properties for delivery to the lungs of a subject in need of epinephrine.

U.S. Patent Pub. No. 2023/0105615 for Treatment with powdered intranasal epinephrine by inventors Temtsin-Krayz and Kazhdan, filed Sep. 14, 2022, and published Apr. 6, 2023, is directed to a pharmaceutical composition in dry powder form for intranasal administration, comprising an anti-anaphylactic adrenergic receptor agonist in the form of dry powder for intranasal administration, the composition comprising solid particles of the active agent in combination with at least one functional additive, and solid particles of an inert carrier.

U.S. Patent Pub. No. 2020/0085765 for Safer and more effective methods of transmucosal, including intranasal, delivery for raising blood pressure and stimulating the body by inventor Rubin, filed Sep. 20, 2019 and published Mar. 19, 2020, is directed to methods of mimicking epinephrine plasma pharmacokinetic parameters/plasma epinephrine levels of an at least one 1-epinephrine injection in humans with an at least one dosage of an intranasal and/or sublingual 1-epinephrine formulation. Methods of maintaining constant elevated plasma epinephrine level(s) by the consecutive dosing of intranasal and/or sublingual 1-epinephrine are also provided. These methods may be helpful when 1-epinephrine injection is not available or not possible. These methods allow formulations for intranasal administration of 1-epinephrine and/or small, 1-epinephrine sublingual tablets to be conveniently carried by soldiers and others, such as in a remote location or battlefield, and such as when emergency medical services are not readily available or accessible. The methods may be able to sustain life and restore proper blood perfusion when someone is having cardiopulmonary difficulty until medical help or transport can arrive.

U.S. Pat. No. 11,918,655 for Intranasal epinephrine formulations and methods for the treatment of disease by inventors Lowenthal, et al, filed Jun. 7, 2023, and issued Mar. 5, 2024, is directed to drug products adapted for nasal delivery comprising formulations with epinephrine and devices comprising such formulations are provided. Methods of treating anaphylaxis with epinephrine products are also provided.

U.S. Pat. No. 9,789,071 for Intranasal formulation of epinephrine for the treatment of anaphylaxis by inventor Fleming, filed Jun. 27, 2013, and issued Oct. 17, 2017, is directed to pharmaceutical compositions of epinephrine for delivery to the nasal mucosa and methods of treating a subject in acute severe anaphylaxis, bronchospasm or during cardiopulmonary resuscitation (CPR). The composition further comprising agents, that either prevent localized degradation of epinephrine or enhance its absorption in the nasal mucosa to counter anaphylactic effects, symptoms or complications in a subject.

U.S. Pat. No. 8,747,813 for Inhalable epinephrine by inventors Batycky, et al., filed Mar. 6, 2013, and issued Jun. 10, 2014, is directed to particles for delivery of epinephrine to the respiratory system and methods for treating a patient in need of epinephrine. The particles and respirable compositions comprising the particles comprise the bioactive agent epinephrine, or a salt thereof, as a therapeutic agent. The particles are preferably formed by spray drying. Preferably, the particles and the respirable compositions are substantially dry and are substantially free of propellants. The patent discloses that the particles have aerodynamic characteristics that permit targeted delivery of epinephrine to the site(s) of action.

U.S. Pat. No. 8,415,397 for Inhalable epinephrine by inventors Batycky, et al., filed Apr. 8, 2011, and issued Apr. 9, 2013, is directed to particles for delivery of epinephrine to the respiratory system and methods for treating a patient in need of epinephrine. The particles and respirable compositions comprising the particles comprise the bioactive agent epinephrine, or a salt thereof, as a therapeutic agent. The particles are preferably formed by spray drying. Preferably, the particles and the respirable compositions are substantially dry and are substantially free of propellants.

The patent discloses that the particles have aerodynamic characteristics that permit targeted delivery of epinephrine to the site(s) of action.

U.S. Pat. No. 7,954,491 for Low dose pharmaceutical powders for inhalations by inventor Hrkrach, filed Jun. 14, 2004 and issued Jun. 7, 2011, is directed to a method of delivering an agent to the pulmonary system of a compromised patient, in a single breath-activated step, comprising administering a particle mass comprising an agent from an inhaler containing less than 5 milligrams of the mass, wherein at least about 50% of the mass in the receptacle is delivered to the pulmonary system of a patient. The patent also discloses receptacles containing the particle mass and the inhaler for use therein.

U.S. Pat. No. 7,947,742 for Inhalable epinephrine by inventors Batycky, et al., filed Jun. 26, 2003, and issued May 24, 2011, is directed to particles for delivery of epinephrine to the respiratory system and methods for treating a patient in need of epinephrine. The particles and respirable compositions comprising the particles comprise the bioactive agent epinephrine, or a salt thereof, as a therapeutic agent. The particles are preferably formed by spray drying. Preferably, the particles and the respirable compositions are substantially dry and are substantially free of propellants. The patent discloses that the particles have aerodynamic characteristics that permit targeted delivery of epinephrine to the site(s) of action.

U.S. Pat. No. 10,688,044 for Epinephrine Spray Formulations by inventors Hartman et al., filed Mar. 15, 2019, and issued Jun. 23, 2020, is directed to epinephrine spray formulations. Also provided are methods of treating anaphylaxis by administering epinephrine spray formulations to subjects in need of such treatment.

U.S. Pat. No. 11,013,691 for Heat-Stable Dry Powder Pharmaceutical Compositions and Methods by inventors Fabio et al., filed Aug. 1, 2019, and issued May 25, 2021, is directed to heat-stable dry powders which include peptides or protein such as oxytocin for use as a pharmaceutical composition. The composition is highly stable at increased temperatures and relatively high humid environments, and are intended for storage at room temperature with an improved shelf-life. In particular, the dry powders are intended for inhalation, however, other routes of administration can be used when reconstituted in solution.

US Patent Pub. No. 2021/0205238 for Stabilized Injectable Pharmaceutical Composition of L-epinephrine by inventors Augustin et al., filed Apr. 10, 2020 and published Jul. 8, 2021, is directed to injectable pharmaceutical compositions comprising epinephrine, an antioxidant selected from the group consisting of sodium metabisulfite, sodium sulfite and sodium bisulfite, tartrate, a tonicity regulating agent, EDTA or Na2EDTA*2H2O and pH 3.0-4.5.

U.S. Pat. No. 10,806,709 for Intranasal Formulation of Epinephrine for the Treatment of Anaphylaxis by inventor Fleming, filed Jun. 27, 2013, and issued Oct. 17, 2017, is directed to pharmaceutical compositions of epinephrine for delivery to the nasal mucosa and methods of treating a subject in acute severe anaphylaxis, bronchospasm or during cardiopulmonary resuscitation (CPR). The composition further comprising agents, that either prevent localized degradation of epinephrine or enhance its absorption in the nasal mucosa to counter anaphylactic effects, symptoms or complications in a subject.

US Patent Pub. No. 2016/0220489 for Intranasal Formulation for the Treatment of Cardiopulmonary Resuscitation (CPR), Cardiac Life Support (CLS), Anaphylaxis and/or Anaphylactoid Reactions by inventors Fleming et al., filed Mar. 2, 2016 and published Aug. 4, 2016, is directed to dry powder compositions and unit doses that comprise vasoactive agents, and/or anti-anaphylactic and/or anti-anaphylactoid agents suitable for intranasal administration, methods of making the compositions, and methods of using the compositions to treat disorders, for example anaphylaxis, anaphylactoid reactions, bronchospasm, cardiac arrest, hypotensive shock, or other situations requiring the need to implement cardiopulmonary resuscitation (CPR) and/or basic or advanced cardiac life support (ACLS).

US Patent Pub. No. 2008/0269347 for Epinephrine Formulations by inventors Bruss et al., filed Sep. 28, 2007, and published Oct. 30, 2008, is directed to an epinephrine formulation that has enhanced stability. In particular embodiments, the formulation is an injectable formulation. In specific aspects, the formulation comprises epinephrine, EDTA, and one or more of an antioxidant such as cysteine, citric acid, acetylcysteine, or thioglycerol. The formulations are suitable for any medical condition that is in need of epinephrine, although in specific embodiments the medical condition is anaphylaxis, asthma, or cardiac arrest.

U.S. Pat. No. 11,400,045 for Treatment with Powdered Intranasal Epinephrine by inventors Temtsin-Krayz et al., filed Dec. 28, 2020 and issued Aug. 2, 2022, is directed to a pharmaceutical composition in dry powder form for intranasal administration, having an anti-anaphylactic adrenergic receptor agonist in the form of dry powder for intranasal administration, the composition having solid particles of the active agent in combination with at least one functional additive, and solid particles of an inert carrier.

US Patent Pub. No. 2017/0304459 for Methods and Compositions for Inhalation Delivery of Conjugated Oligonucleotide by inventors Jadhav et al., filed Apr. 7, 2017 and published Oct. 26, 2017, is directed to an inhalable formulation comprising a ligand conjugated oligonucleotide and particles of a physiologically acceptable pharmacologically-inert carrier.

SUMMARY OF THE INVENTION

The present invention relates to dry powder epinephrine compositions and more specifically to drug products for the intranasal delivery of epinephrine.

It is an object of this invention to provide epinephrine compositions that are shelf stable and operable to be delivered in an emergency setting by a layperson without medical training. The epinephrine compositions disclosed herein are dry powder compositions configured to be absorbed via the nasal passage, thereby eliminating the problems that arise with the epinephrine delivery systems and methods of the prior art.

In one embodiment, the present invention includes an apparatus for delivery of a dry powder pharmaceutical composition, the apparatus including a reservoir containing a dose of the dry powder pharmaceutical composition, wherein the dry powder pharmaceutical composition comprises epinephrine or a pharmaceutically acceptable salt thereof and a carrier, wherein the dry powder pharmaceutical composition has a bulk particle size distribution characterized by a Dv50 of between 5 microns and 30 microns, an air delivery assembly configured to be placed in fluid communication with the reservoir, and a delivery head operatively coupled to the reservoir, wherein the delivery head defines a delivery aperture, and wherein upon actuation of the apparatus, the air delivery assembly is configured to produce an airflow through the reservoir to deliver a mixture of the airflow and the dose of the dry powder pharmaceutical composition via the delivery aperture, wherein the mixture has an emitted particle size distribution characterized by a Dv50 of between 15 microns and 200 microns and that is greater than the Dv50 of the bulk particle size distribution.

In another embodiment, the present invention includes an apparatus for delivery of a dry powder pharmaceutical composition, the apparatus including, a reservoir containing a dose of the dry powder pharmaceutical composition, wherein the dry powder pharmaceutical composition comprises epinephrine or a pharmaceutically acceptable salt thereof, wherein the dry powder pharmaceutical composition has a bulk particle size distribution characterized by a Dv50 of between 5 microns and 18 microns, an air delivery assembly configured to be placed in fluid communication with the reservoir, and a delivery head operatively coupled to the reservoir, the delivery head defining a delivery aperture, and wherein upon actuation of the apparatus, the air delivery assembly is configured to produce an airflow through the reservoir to deliver a mixture of the airflow and the dose of the dry powder pharmaceutical composition via the delivery aperture, wherein the mixture has an emitted particle size distribution characterized by a Dv50 of between 20 microns and 185 microns and that is greater than the Dv50 of the bulk particle size distribution.

In yet another embodiment, the present invention includes a dry powder pharmaceutical composition, including, epinephrine or a pharmaceutically acceptable salt thereof, and a carrier, wherein a single dose of the dry powder pharmaceutical composition contains about 3.5 mg to about 5.5 mg of epinephrine or the pharmaceutically acceptable salt thereof, wherein the dry powder pharmaceutical composition has a bulk particle size distribution characterized by a Dv50 of between 5 microns and 30 microns, and wherein the dry powder pharmaceutical composition is formulated such that delivery of the dose of the dry powder pharmaceutical composition produces a spray having an emitted particle size distribution characterized by a Dv50 of between 15 microns and 200 microns and that is greater than the Dv50 of the bulk particle size distribution.

These and other aspects of the present invention will become apparent to those skilled in the art after a reading of the following description of the preferred embodiment when considered with the drawings, as they support the claimed invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 10 is a flow chart of a method of delivering a dry powder pharmaceutical composition, according to an embodiment.

FIG. 11 is a flow chart of a method of delivering a dry powder pharmaceutical composition intranasally, according to an embodiment.

FIG. 12 is a flow chart of a method of delivering a dry powder pharmaceutical composition intranasally, according to an embodiment.

FIG. 13 is a flow chart of a method of producing delivering a dry powder pharmaceutical composition intranasally, according to an embodiment.

FIG. 20 illustrates the study treatments for the Phase I human clinical trial.

FIG. 25 illustrates a graph of uncorrected epinephrine concentration-time for individual human subjects in Treatment A.

FIG. 26 illustrates a graph of uncorrected epinephrine concentration-time for individual human subjects in Treatment B.

FIG. 27 illustrates a graph of uncorrected epinephrine concentration-time for individual human subjects in Treatment C.

FIG. 28 illustrates a graph of uncorrected epinephrine concentration-time for individual human subjects in Treatment D.

FIG. 29 illustrates a graph of baseline-corrected epinephrine concentration-time for individual human subjects in Treatment A.

FIG. 30 illustrates a graph of baseline-corrected epinephrine concentration-time for individual human subjects in Treatment B.

FIG. 31 illustrates a graph of baseline-corrected epinephrine concentration-time for individual human subjects in Treatment C.

FIG. 32 illustrates a graph of baseline-corrected epinephrine concentration-time for individual human subjects in Treatment D.

FIG. 33A illustrates a table of individual human subject uncorrected plasma epinephrine concentrations with summary statistics in Treatment A.

FIG. 33B illustrates a table of individual human subject uncorrected plasma epinephrine concentrations with summary statistics in Treatment A.

FIG. 34A illustrates a table of individual human subject uncorrected plasma epinephrine concentrations with summary statistics in Treatment B.

FIG. 34B illustrates a table of individual human subject uncorrected plasma epinephrine concentrations with summary statistics in Treatment B.

FIG. 35A illustrates a table of individual human subject uncorrected plasma epinephrine concentrations with summary statistics in Treatment C.

FIG. 35B illustrates a table of individual human subject uncorrected plasma epinephrine concentrations with summary statistics in Treatment C.

FIG. 36A illustrates a table of individual human subject uncorrected plasma epinephrine concentrations with summary statistics in Treatment D.

FIG. 36B illustrates a table of individual human subject uncorrected plasma epinephrine concentrations with summary statistics in Treatment D.

FIG. 37A illustrates a table of individual subject baseline-corrected plasma epinephrine concentrations with summary statistics in Treatment A.

FIG. 37B illustrates a table of individual human subject baseline-corrected plasma epinephrine concentrations with summary statistics in Treatment A.

FIG. 38A illustrates a table of individual human subject baseline-corrected plasma epinephrine concentrations with summary statistics in Treatment B.

FIG. 38B illustrates a table of individual human subject baseline-corrected plasma epinephrine concentrations with summary statistics in Treatment B.

FIG. 39A illustrates a table of individual human subject baseline-corrected plasma epinephrine concentrations with summary statistics in Treatment C.

FIG. 39B illustrates a table of individual human subject baseline-corrected plasma epinephrine concentrations with summary statistics in Treatment C.

FIG. 40A illustrates a table of individual human subject baseline-corrected plasma epinephrine concentrations with summary statistics in Treatment D.

FIG. 40B illustrates a table of individual human subject baseline-corrected plasma epinephrine concentrations with summary statistics in Treatment D.

FIG. 43 illustrates a summary table of noncompartmental pharmacokinetic parameters for uncorrected plasma epinephrine for Treatment A in humans.

FIG. 44 illustrates a summary table of noncompartmental pharmacokinetic parameters for uncorrected plasma epinephrine for Treatment B in humans.

FIG. 45 illustrates a summary table of noncompartmental pharmacokinetic parameters for uncorrected plasma epinephrine for Treatment C in humans.

FIG. 46 illustrates a summary table of noncompartmental pharmacokinetic parameters for uncorrected plasma epinephrine for Treatment D in humans.

FIG. 47 illustrates a summary table of noncompartmental pharmacokinetic parameters for baseline-corrected plasma epinephrine for Treatment A in humans.

FIG. 48 illustrates a summary table of noncompartmental pharmacokinetic parameters for baseline-corrected plasma epinephrine for Treatment B in humans.

FIG. 49 illustrates a summary table of noncompartmental pharmacokinetic parameters for baseline-corrected plasma epinephrine for Treatment C in humans.

FIG. 50 illustrates a summary table of noncompartmental pharmacokinetic parameters for baseline-corrected plasma epinephrine for Treatment D in humans.

FIG. 57 illustrates a summary table of partial AUCs for baseline-corrected plasma epinephrine for Treatment A in humans.

FIG. 58 illustrates a summary table of partial AUCs for baseline-corrected plasma epinephrine for Treatment B in humans.

FIG. 59 illustrates a summary table of partial AUCs for baseline-corrected plasma epinephrine for Treatment C in humans.

FIG. 60 illustrates a summary table of partial AUCs for baseline-corrected plasma epinephrine for Treatment D in humans.

FIG. 61 illustrates a table of bioequivalence calculation results in humans, with Treatment A as the test and Treatment B as the reference.

FIG. 62 illustrates a table of bioequivalence calculation results in humans, with Treatment D as the test and Treatment B as the reference.

FIG. 63A illustrates a table of relative bioavailability calculation results in humans.

FIG. 63B illustrates a table of relative bioavailability calculation results in humans.

FIG. 68 illustrates a graph of baseline-corrected heart rate data of individual human subjects in Treatment A.

FIG. 69 illustrates a graph of baseline-corrected heart rate data of individual human subjects in Treatment B.

FIG. 70 illustrates a graph of baseline-corrected heart rate data of individual human subjects in Treatment C.

FIG. 71 illustrates a graph of baseline-corrected heart rate data of individual human subjects in Treatment D.

FIG. 73 illustrates the solid-state characterization of the dry powder epinephrine composition during the stability study.

FIG. 74 illustrates the product performance characterization during the stability study.

DETAILED DESCRIPTION

Figures 1, 2:
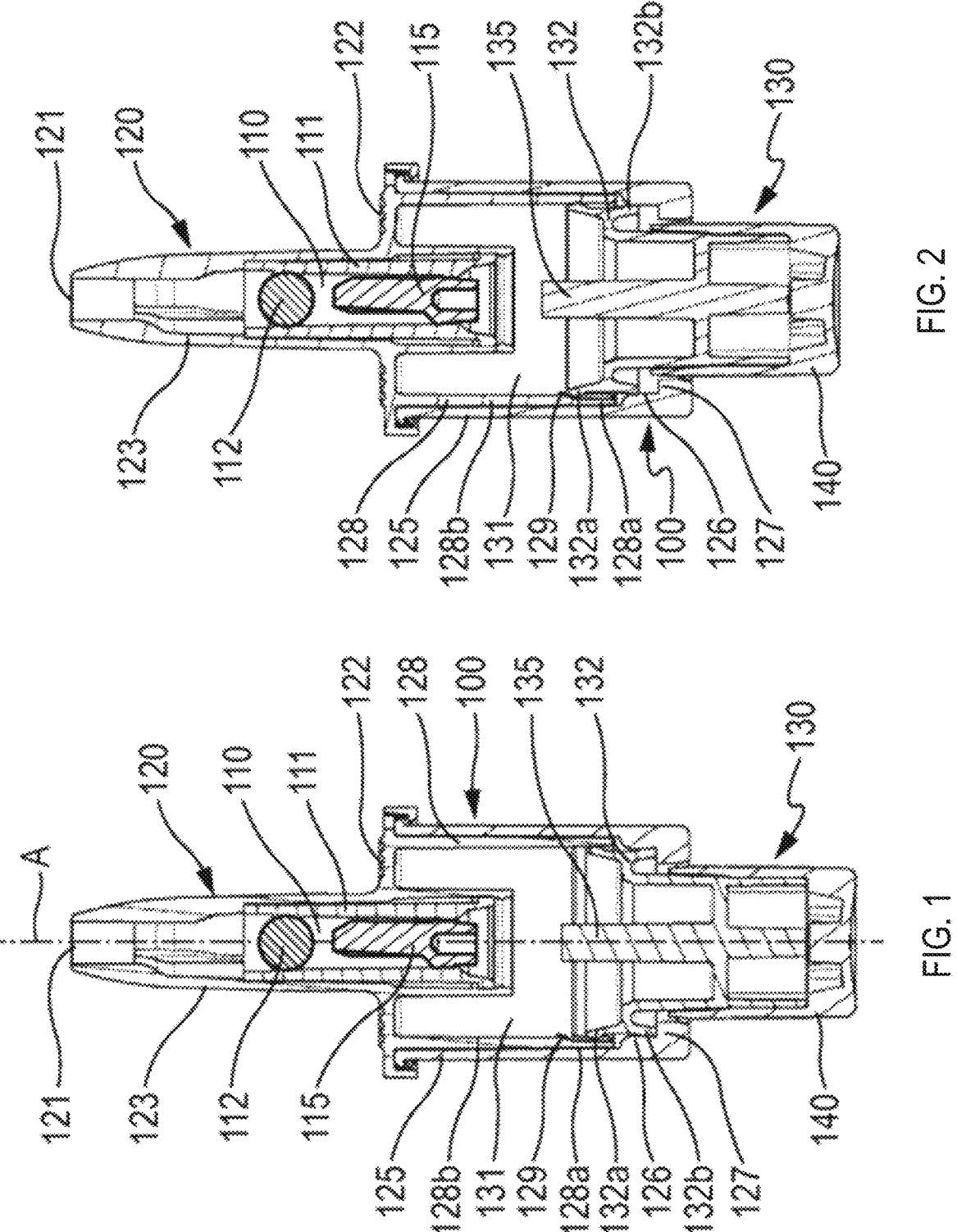
FIGS. 1 and 2 are cross-sectional views of an intranasal delivery device containing a dry powder composition according to an embodiment, in a lower transport configuration (FIG. 1) and an upper transport configuration (FIG. 2).
Figures 3, 4:
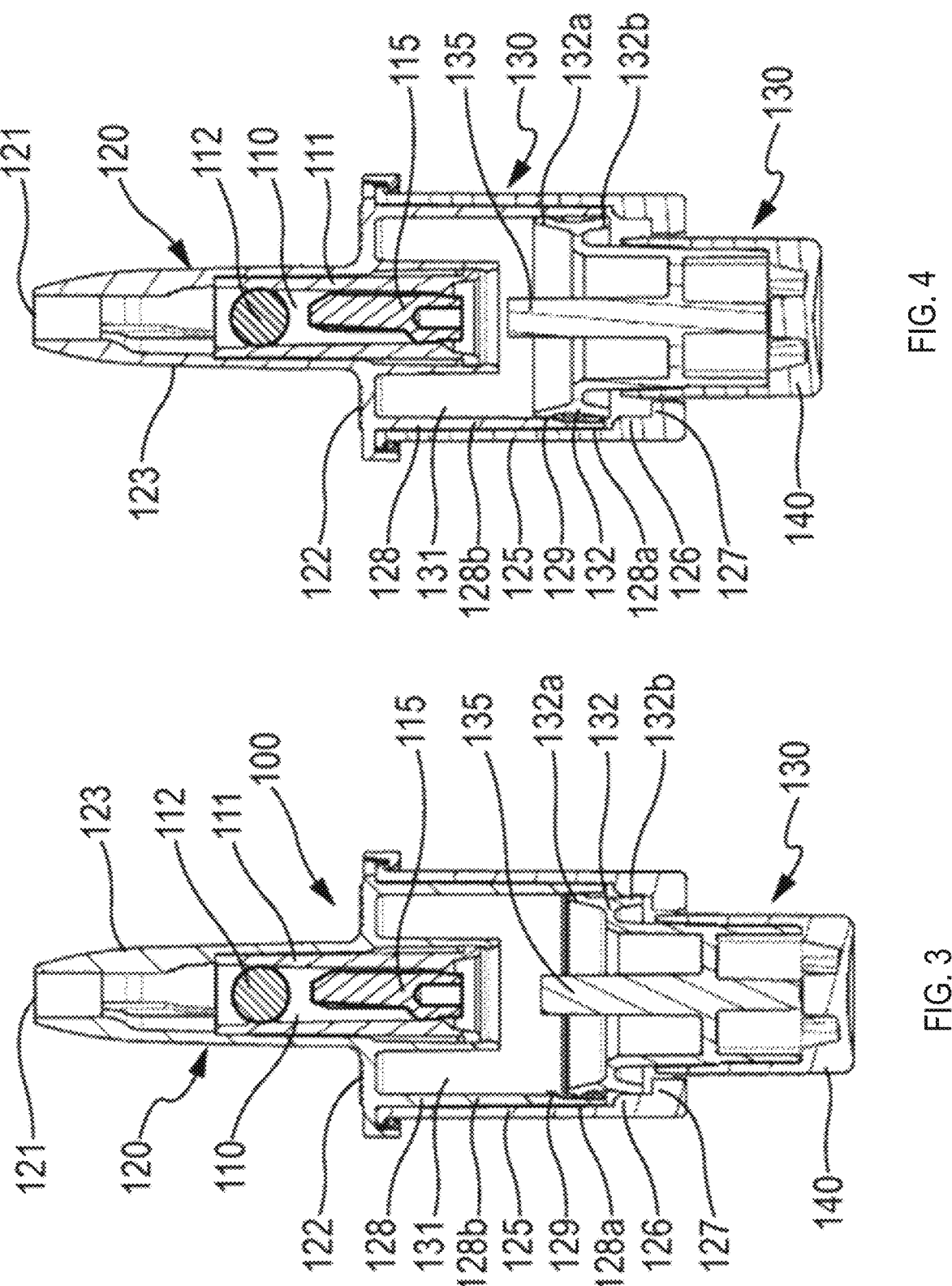
FIG. 3 is a cross-sectional view of the intranasal delivery device of FIGS. 1 and 2 before actuation.
FIG. 4 is a cross-sectional view of the intranasal delivery device of FIGS. 1 and 2 at the start of actuation.
Figures 5, 6:
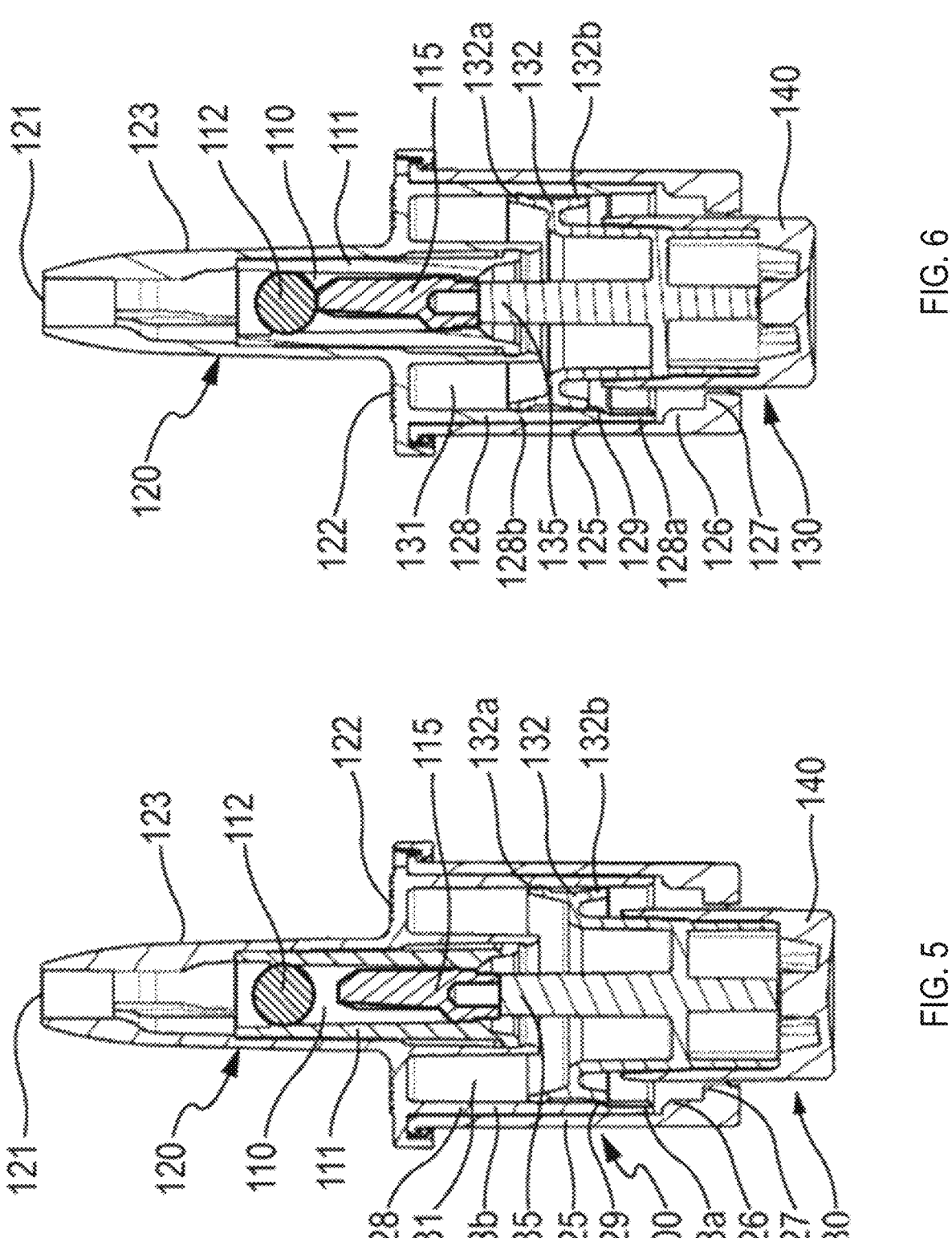
FIGS. 5-7 are cross-sectional views of the intranasal delivery device of FIGS. 1 and 2 showing different positions of the piston during actuation.
Figure 8:
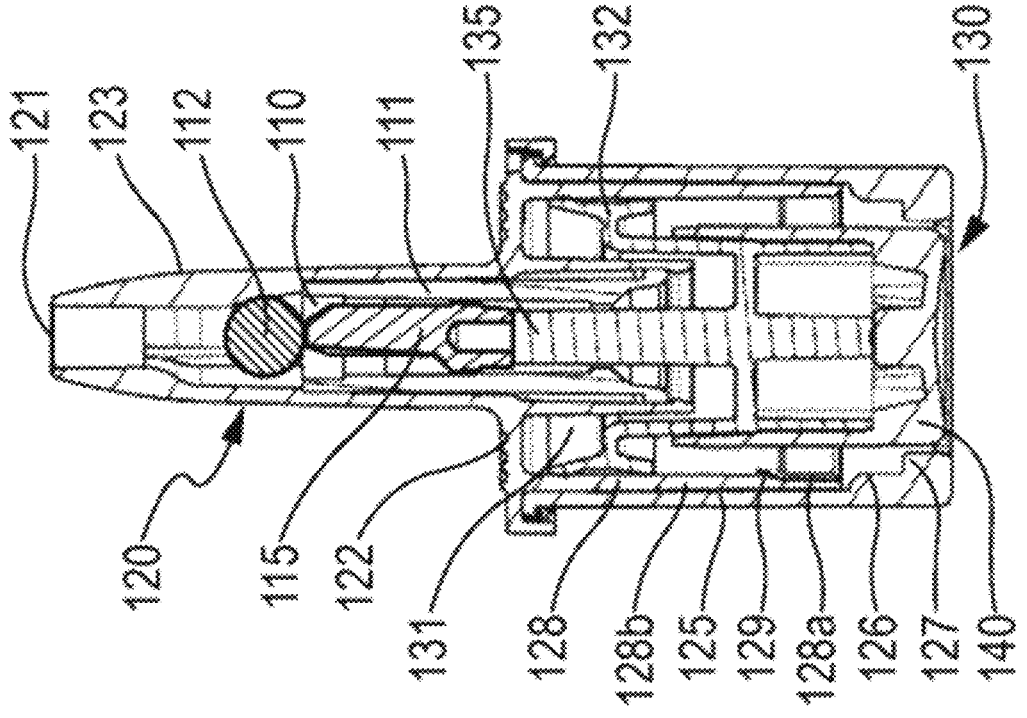
FIG. 8 is a cross-sectional view of the intranasal delivery device of FIGS. 1 and 2 at the end of actuation.
Figure 7:
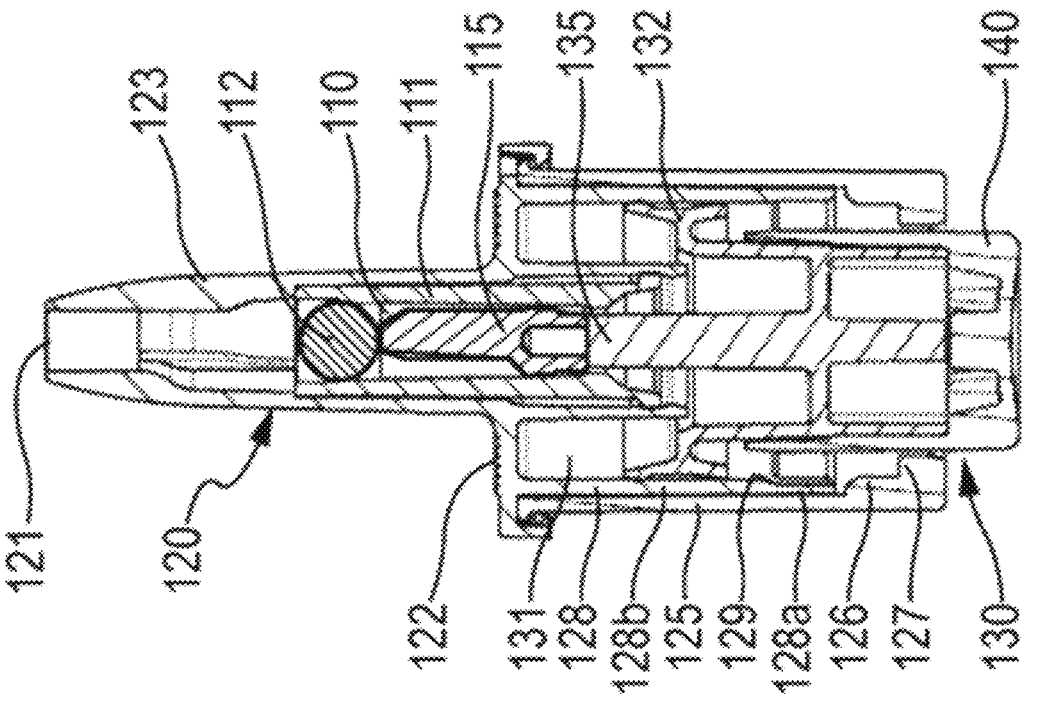

The present invention is generally directed to dry powder epinephrine compositions and more specifically to drug products for the intranasal delivery of epinephrine.

In one embodiment, the present invention includes an apparatus for delivery of a dry powder pharmaceutical composition, the apparatus including a reservoir containing a dose of the dry powder pharmaceutical composition, wherein the dry powder pharmaceutical composition comprises epinephrine or a pharmaceutically acceptable salt thereof and a carrier, wherein the dry powder pharmaceutical composition has a bulk particle size distribution characterized by a Dv50 of between 5 microns and 30 microns, an air delivery assembly configured to be placed in fluid communication with the reservoir, and a delivery head operatively coupled to the reservoir, wherein the delivery head defines a delivery aperture, and wherein upon actuation of the apparatus, the air delivery assembly is configured to produce an airflow through the reservoir to deliver a mixture of the airflow and the dose of the dry powder pharmaceutical composition via the delivery aperture, wherein the mixture has an emitted particle size distribution characterized by a Dv50 of between 15 microns and 200 microns and that is greater than the Dv50 of the bulk particle size distribution, wherein the bulk particle size distribution is characterized by a Dv10 of between 1.5 microns and 5 microns, wherein the emitted particle size distribution is characterized by a Dv10 of between 5 microns and 10 microns and is greater than the Dv10 of the bulk particle size distribution, wherein the bulk particle size distribution is characterized by a Dv90 of between 13 microns and 50 microns, wherein the emitted particle size distribution is characterized by a Dv90 of between 475 microns and 625 microns, wherein the Dv50 of the bulk particle size distribution is between 5 microns and 18 microns and wherein the Dv50 of the emitted particle size distribution is between 20 microns and 185 microns, wherein the dry powder pharmaceutical composition has a moisture content of between 3% and 6%, wherein the dose contains between about 3.5 mg and about 5.5 mg of the epinephrine or the pharmaceutically acceptable salt, wherein the dry powder pharmaceutical composition further comprises a dispersing agent, wherein the air delivery assembly includes an air chamber and a piston configured to be moved within the air chamber to produce the airflow through the reservoir, wherein the apparatus is configured to be manually actuated by moving the piston within the air chamber, and wherein the dry powder pharmaceutical composition does not include an alpha-adrenergic blocker.

In another embodiment, the present invention includes an apparatus for delivery of a dry powder pharmaceutical composition, the apparatus including, a reservoir containing a dose of the dry powder pharmaceutical composition, wherein the dry powder pharmaceutical composition comprises epinephrine or a pharmaceutically acceptable salt thereof, wherein the dry powder pharmaceutical composition has a bulk particle size distribution characterized by a Dv50 of between 5 microns and 18 microns, an air delivery assembly configured to be placed in fluid communication with the reservoir, and a delivery head operatively coupled to the reservoir, the delivery head defining a delivery aperture, and wherein upon actuation of the apparatus, the air delivery assembly is configured to produce an airflow through the reservoir to deliver a mixture of the airflow and the dose of the dry powder pharmaceutical composition via the delivery aperture, wherein the mixture has an emitted particle size distribution characterized by a Dv50 of between 20 microns and 185 microns and that is greater than the Dv50 of the bulk particle size distribution, wherein the dry powder composition further includes a carrier, wherein the dry powder pharmaceutical composition does not include an alpha-adrenergic blocker, wherein the bulk particle size distribution is characterized by a Dv10 of between 1.5 microns and 5 microns, wherein the emitted particle size distribution is characterized by a Dv10 of between 5 microns and 10 microns and is greater than the Dv10 of the bulk particle size distribution, wherein the bulk particle size distribution is characterized by a Dv90 of between 13 microns and 50 microns, wherein the emitted particle size distribution is characterized by a Dv90 of between 475 microns and 625 microns, wherein the dose contains between about 3.5 mg and about 5.5 mg of the epinephrine or the pharmaceutically acceptable salt, and wherein the carrier is lactose monohydrate.

In yet another embodiment, the present invention includes a dry powder pharmaceutical composition, including, epinephrine or a pharmaceutically acceptable salt thereof, and a carrier, wherein a single dose of the dry powder pharmaceutical composition contains about 3.5 mg to about 5.5 mg of epinephrine or the pharmaceutically acceptable salt thereof, wherein the dry powder pharmaceutical composition has a bulk particle size distribution characterized by a Dv50 of between 5 microns and 30 microns, and wherein the dry powder pharmaceutical composition is formulated such that delivery of the dose of the dry powder pharmaceutical composition produces a spray having an emitted particle size distribution characterized by a Dv50 of between 15 microns and 200 microns and that is greater than the Dv50 of the bulk particle size distribution, wherein the dry powder pharmaceutical composition does not include an alpha-adrenergic blocker, and wherein the carrier includes any of mannitol, a cyclodextrin, citric acid, lactose, or sodium carboxymethylcellulose.

None of the prior art discloses a dry powder epinephrine composition, methods of delivery, and drug product for intranasal delivery of epinephrine, wherein the dry powder epinephrine composition is operable to be successfully delivered by the nasal route and which does not contain vasodilating ingredients in the alpha blocker drug class. None of the prior art discloses a dry powder epinephrine composition operable to maintain its integrity when exposed to high temperature conditions. None of the prior art discloses a dry powder epinephrine composition with a consistent particle size that does not enter the lung.

Anaphylaxis is a severe, life-threatening reaction that can occur rapidly after a person is exposed to certain substances, such as peanuts, shellfish, or bee venom. Anaphylaxis is a systemic reaction involving multiple organ systems. The exposure to allergens stimulates the release of immune system mediators, which stimulates vasodilation, increases vascular permeability, heart rate, and cardiac contraction, and induces bronchoconstriction, pulmonary and coronary vasoconstriction, and peripheral vasodilation. Accordingly, the onset of anaphylaxis can cause a sharp drop in blood pressure, hives, and/or severe airway constriction. To treat anaphylaxis, a person is administered epinephrine (i.e., adrenaline), which often provides substantial and/or complete relief of the symptoms. Epinephrine is also administered in response to a variety of medical conditions, including septic shock, respiratory conditions including bronchospasms, hemodynamic collapse, including hypotension, cardiopulmonary arrest, and other life-threatening conditions. Because emergency medical facilities are not always available when a person is suffering from anaphylaxis and/or medical conditions with similar symptoms, many people that are susceptible to such conditions carry an auto-injector to rapidly self-administer epinephrine in response to the onset of anaphylaxis.

Many known auto-injectors include aqueous epinephrine compositions that are delivered intramuscularly via a needle. Moreover, another less common, but known method of delivery includes manual injection by a syringe, which include either a prefilled syringe or the process of withdrawing the solution from a vial. Many users have a fear of needle-based injections and are therefore reluctant to use an auto-injector or manual injector. Additionally, liquid epinephrine is sensitive to light and variations in temperature, which can compromise the efficacy of the auto-injector. For example, the instructions for some known auto-injectors indicate that it should be stored at room temperature without exposure to light. Because of the potential for degradation, the shelf-life of some known auto-injectors is 24 months. Moreover, obesity can present a confounding factor for the delivery of epinephrine via auto-injectors. Many patients using auto-injectors do not receive the recommended dose via an intramuscular (IM) injection. One U.S. study estimated that thirty percent (30%) of both adults and children would not receive an IM injection from an auto-injection of epinephrine. While subcutaneous (SQ) delivery is operable to occur in such situations, the SQ injection of epinephrine generally results in a substantially lower plasma drug level and delayed delivery.

Other known delivery devices include inhalers and intranasal delivery devices. Some known intranasal delivery devices include an aqueous solution of epinephrine and produce an aerosolized mist of the epinephrine. The aqueous epinephrine formulations in such known intranasal devices, however, are also subject to degradation in high temperatures and experience decreased bioavailability over time. Additionally, known aqueous epinephrine formulations often contain preservatives to extend the shelf-life of the composition. These preservatives, such as sodium bisulfite, are operable to induce an allergic reaction in many individuals. Additionally, when aqueous epinephrine formulations are delivered to the nasal passages, a significant portion of the drug volume may be lost due to the formulation running down the back of the throat or back out the front of the nose when the device is removed.

Although intranasal delivery of dry powder compositions for certain drugs has been explored, some known dry powder formulations for epinephrine incorporate complex drug components that limit their effectiveness. For example, some known dry powder compositions may include and be dependent on the use of an alpha-adrenergic blocker as a vasodilator, which causes the widening of blood vessels to enable the uptake of epinephrine. The use of alpha-adrenergic antagonists, however, can be problematic because the primary therapeutic goal of administering epinephrine during adverse health events is to counteract the drop in peripheral circulatory blood pressure. Alpha-adrenergic antagonists act to widen the blood vessels in smooth muscle, thereby counteracting the intended therapeutic action of epinephrine. Furthermore, some known dry powder epinephrine compositions promote the administration of two active adrenergic receptor agents (i.e., drugs) versus just one drug. Administering more than one drug at a time may pose additional risks, as the pharmacodynamic interactions of the active adrenergic receptor agents may have adverse effects and, further, may present medical complications due to the varying physiology of users.

Moreover, some known intranasal delivery devices may not effectively deliver the powder with the desired particle size distribution to the targeted portions of the anatomy (e.g., the turbinates and olfactory region). For example, if the formulation has a very small particle size distribution, device filling and handling can be difficult. If the delivered particles are too small, there is also an increased likelihood that the small particles will flow past the targeted portions of the anatomy and be conveyed into the lungs (which is not the desired route of administration). If, however, the particle size distribution is too large, issues may arise with efficient deposition and dissolution.

Additionally, some known dry powder delivery devices are susceptible to inconsistent performance resulting from variations in how users interact with the device. For example, some known dry powder delivery devices can be susceptible to variations in performance based on any one or all the following: tilting of the device (before or during use), the angle of entry of the delivery member into the patient's nostril, and whether the patient is sitting upright or laying in a horizontal position.

Thus, a need exists for an improved dry powder epinephrine composition, methods of intranasal delivery, and drug products for the intranasal delivery of epinephrine. Additionally, there is a long-standing, unmet need for a dry powder formulation of epinephrine that is operable to be successfully delivered by the nasal route and which does not contain vasodilating ingredients in the alpha blocker drug class. Further, there is a long-standing, unmet need for a dry powder formulation of epinephrine to maintain its integrity when exposed to high temperature conditions. Further still, there is also a long-standing, unmet need for a dry powder formulation of epinephrine with a consistent particle size that does not enter the lung.

Referring now to the drawings in general, the illustrations are for the purpose of describing one or more preferred embodiments of the invention and are not intended to limit the invention thereto.

In some embodiments, the present invention includes an apparatus for delivery of a dry powder pharmaceutical composition, the apparatus including a reservoir containing a dose of the dry powder pharmaceutical composition, the dry powder pharmaceutical composition comprising epinephrine or a pharmaceutically acceptable salt thereof and a carrier, the dry powder pharmaceutical composition having a bulk particle size distribution characterized by a Dv50 of between 5 microns and 30 microns, an air delivery assembly configured to be placed in fluid communication with the reservoir, a delivery head operatively coupled to the reservoir, the delivery head defining a delivery aperture, and wherein upon actuation of the apparatus, the air delivery assembly is configured to produce an airflow through the reservoir to deliver a mixture of the airflow and the dose of the dry powder pharmaceutical composition via the delivery aperture, the mixture having an emitted particle size distribution characterized by a Dv50 of between 15 microns and 200 microns and that is greater than the Dv50 of the bulk particle size distribution.

In some embodiments, a drug product for delivery of a dry powder pharmaceutical composition includes a reservoir containing a dose of the dry powder pharmaceutical composition, an air delivery assembly, and a delivery head. The dry powder pharmaceutical composition comprises epinephrine or a pharmaceutically acceptable salt thereof and a carrier. The dry powder pharmaceutical composition has a bulk particle size distribution characterized by a Dv50 of between 5 microns and 30 microns. The air delivery assembly is configured to be placed in fluid communication with the reservoir. The delivery head is operatively coupled to the reservoir and defines a delivery aperture. Upon actuation, the air delivery assembly is configured to produce an airflow through the reservoir to deliver a mixture of the airflow and the dose of the dry powder pharmaceutical composition via the delivery aperture. The mixture has an emitted particle size distribution characterized by a Dv50 of between 25 microns and 200 microns and that is greater than the Dv50 of the bulk particle size distribution.

In some embodiments, a method of delivering a dry powder pharmaceutical composition includes placing a delivery head of an intranasal device into a nasal passage of a body. The intranasal device has a reservoir and an air delivery assembly. The reservoir contains a dose of the dry powder pharmaceutical composition. The dry powder pharmaceutical composition comprises epinephrine or a pharmaceutically acceptable salt thereof and a carrier. The dry powder pharmaceutical composition has a bulk particle size distribution characterized by a Dv50 of between 5 microns and 30 microns. The method includes actuating the intranasal device to cause the air delivery assembly to produce an airflow through the reservoir to deliver the dose of the dry powder pharmaceutical composition into the body via a delivery aperture defined by the delivery head. The delivered dry powder pharmaceutical composition has an emitted particle size distribution characterized by a Dv50 of between 25 microns and 200 microns and that is greater than the Dv50 of the bulk particle size distribution.

In some embodiments, a method of delivering a dry powder pharmaceutical composition includes placing a delivery head of an intranasal device into a nasal passage of a body. The delivery head defines a delivery aperture. The intranasal device further includes a reservoir and an air delivery assembly. The reservoir contains a dose of the dry powder pharmaceutical composition, which comprises epinephrine or a pharmaceutically acceptable salt thereof and a carrier. The intranasal device is actuated to cause the air delivery assembly to produce a delivery airflow through the reservoir to deliver the dose of the dry powder pharmaceutical composition into the body via the delivery aperture. A target delivery percentage of a total mass of the delivered dry powder pharmaceutical composition to a mass of the delivered dry powder composition that is deposited on a turbinate region and an olfactory region is greater than about 74%. The target delivery percentage is substantially independent of an orientation of the body and a presence of a respiratory airflow through the nasal passage.

In some embodiments, a method of delivering a dry powder pharmaceutical composition includes placing a delivery head of an intranasal device into a nasal passage of a body. The intranasal device includes a reservoir containing a dose of the dry pharmaceutical composition. The dry powder pharmaceutical composition comprises epinephrine or a pharmaceutically acceptable salt thereof and a carrier. The dose contains about 3.5 mg to about 5.5 mg of the epinephrine or the pharmaceutically acceptable salt thereof. The intranasal device is actuated to deliver the dose of the pharmaceutical composition into the body such that at least one of: (A) a relative mean maximum epinephrine plasma concentration after the dose is delivered into the body (Cmax) is greater than a Cmax of a first reference dose and less than a Cmax of a second reference dose OR (B) a time to reach a maximum epinephrine plasma concentration (Tmax) is greater than a Tmax of the first reference dose and less than a Tmax of the second reference dose. The first reference dose contains about 0.3 mg of epinephrine or a pharmaceutically acceptable salt that is delivered intramuscularly via a manual injection and the second reference dose contains about 0.3 mg of epinephrine or a pharmaceutically acceptable salt that is delivered intramuscularly via an autoinjector.

In some embodiments, the present invention includes an intranasal device for administration of a dry powder pharmaceutical composition, including a reservoir containing a dose of the dry powder pharmaceutical composition, the dry powder pharmaceutical composition comprising epinephrine or a pharmaceutically acceptable salt thereof and a carrier, wherein the dose contains between about 3.5 mg and about 5.5 mg of the epinephrine or the pharmaceutically acceptable salt thereof, a delivery head defining a delivery aperture, wherein the intranasal device is configured to deliver the dose of the dry powder pharmaceutical composition into a body via the delivery aperture to produce at least one of: (A) a relative mean maximum epinephrine plasma concentration after the dose is delivered into the body (Cmax) that is greater than a Cmax of a first reference dose and less than a Cmax of a second reference dose, or (B) a time to reach a maximum epinephrine plasma concentration (Tmax) that is greater than a Tmax of the first reference dose and less than a Tmax of the second reference dose, and wherein the first reference dose contains about 0.3 mg of epinephrine or a pharmaceutically acceptable salt that is delivered intramuscularly via a manual injection and the second reference dose contains about 0.3 mg of epinephrine or a pharmaceutically acceptable salt that is delivered intramuscularly via an autoinjector.

In some embodiments, the present invention includes a method for intranasal administration of a pharmaceutical composition includes intranasally administering to a human with anaphylaxis a single dose of a dry powder pharmaceutical composition comprising about 3.5 mg to about 5.5 mg of epinephrine or a pharmaceutically acceptable salt thereof, wherein the intranasal administration of the single dose produces plasma epinephrine concentrations in the human with a time to reach a maximum epinephrine plasma concentration (Tmax) between about 15 minutes and about 30 minutes.

In some embodiments, the present invention includes a method for intranasal administration of a pharmaceutical composition includes intranasally administering to a human with anaphylaxis a single dose of a dry powder pharmaceutical composition comprising about 3.5 mg to about 5.5 mg of epinephrine or a pharmaceutically acceptable salt thereof, wherein the intranasal administration of the single dose produces at least one physiological change in the human selected from the group consisting of an increase in systolic blood pressure by at least 10 mm Hg for a duration of up to 50 minutes after administration of the single dose and an increased heart rate of at least 10 beats per minute for a duration of up to 50 minutes after administration of the single dose.

Dry powder epinephrine compositions, methods of intranasal delivery, and drug products for the intranasal delivery of epinephrine are described herein. The dry powder epinephrine compositions comprise epinephrine, a dry powder stabilizing agent, and a dry powder carrier that have optimized systemic delivery of epinephrine through the nasal passages. In some instances, the formulations include 0.25% to 10% w/w epinephrine. In some embodiments, the formulations include a salt of epinephrine. In some embodiments, the salt is epinephrine hydrochloride. Alternatively, the salt is epinephrine acetate, epinephrine tartrate, epinephrine bitartrate, epinephrine hydrogen tartrate, or epinephrine borate. In some instances, the formulations include 0.1% to 20% w/w of the at least one enabling agent. In some embodiments, the intranasal dry powder formulations are spray-dried powder formulations.

The formulations of the present invention are configured to deliver a dosage of epinephrine to the nasal passage of a user. In some embodiments, a single dose of epinephrine is at least about: 2.0 mg, 2.5 mg, 3.0 mg, 3.5 mg, 4.0 mg, 4.5 mg, 5.0 mg, 5.5 mg, 6.0 mg, 6.5 mg, or 7.0 mg in the formulation. In some embodiments, the epinephrine present in the formulation is about: 0.1 mg to 15.0 mg, 1 mg to 15.0 mg, 1 mg to 7 mg, 1.5 mg to 7.0 mg, 3.0 to 6.0 mg, 3.5 mg to 5.5 mg, or 1 mg to 20.0 mg. In one embodiment, a single dose of epinephrine is about 3.5 mg. In one embodiment, a single dose of epinephrine is about 5.5 mg. In another instance, a single dose of epinephrine is about 3.0 mg. In another embodiment, a single dose of epinephrine is about 4.5 mg. In another embodiment, a single dose of epinephrine is about 15 mg. In another embodiment, a single dose of epinephrine is about 18 mg. In another embodiment, a single dose of epinephrine is about 20.0 mg.

In some embodiments, the epinephrine is about 0.1% to about 15% w/w of the weight of the formulation, for example about: 0.1%, 0.25%, 0.5%, 1%, 2%, 3%, 4%, 5%, 6%, 7%, 7.5%, 8%, 9%, 10%, 11%, 12%, 13%, 14%, or 15% w/w, based on the weight of the formulations and/or dosage units. For example, the epinephrine is about 0.25%, about 7.5%, or about 10% w/w of the weight of the formulation. In one embodiment, the epinephrine is about 0.1% to about 15% w/w of the weight of the formulation. In one embodiment, epinephrine is present in an amount of about 0.25% w/w in a bulk solution of epinephrine prior to spray drying, and about 10% w/w based on the total weight of the formulations and/or dosage units after spray drying.

The disclosed dry powder compositions can be included within any of the intranasal delivery devices described herein, and are formulated such that, upon actuation of the device, the desired particle size distribution is produced. Specifically, as described herein, the dry powder pharmaceutical composition can have a bulk particle size (i.e., the particle size of the composition that is filled or loaded into the device) that is within a desired range, to reduce the amount of undesired dust or clumping of particles, which facilitates efficient filing of the intranasal delivery device. Additionally, the intranasal delivery device and the dry powder composition can be configured such that the resulting drug product produces an emitted particle size (i.e., the particle size of the composition that is emitted from the device) within a desired range, to facilitate delivery to and deposition on the target anatomy, while limiting the amount of the composition delivered to the lungs. For example, in some embodiments, any of the carriers of the composition, the dispersing agents of the composition, the moisture content of the composition, the flow rate and/or pressure of the airflow produced by the intranasal delivery device, or the size of the delivery aperture of the intranasal delivery device can be formulated or configured to produce an emitted particle size distribution within the desired range. For example, in some embodiments, the emitted particle size distribution is greater than the bulk size particle distribution. Said another way, the overall size of the particles emitted is greater than that of the dry powder composition filled into the device. In some embodiments, the intranasal delivery device can produce an emitted particle size distribution characterized by a volumetric median particle size (Dv50 or D50) of between 15 microns and 200 microns. In some embodiments, the intranasal delivery device can produce an emitted particle size distribution characterized by a Dv50 of between 20 microns and 185 microns, of between 20 microns and 50 microns, of between 20 microns and 30 microns, of about 20 microns, or of about 25 microns.

Additionally, the dry powder compositions and the intranasal delivery devices described herein can produce the desired range of emitted particle size distribution from a wide range of bulk particle size distributions. Said another way, one of the surprising results of the compositions described herein includes the particle size distribution output by the intranasal delivery device, and more particularly the Dv50, which is not overly sensitive to the bulk particle size distribution of the composition.

Moreover, the dry powder compositions and the intranasal delivery devices described herein can deliver an effective amount of the dry powder composition for deposition on the target anatomy of the body in a variety of different orientations (e.g., with the patient's head in a vertical position or a horizontal position). Said another way, there is limited variation in the delivery of the dry powder composition to the target anatomy whether the patient is lying down or in a seated or upright orientation. In this manner, the drug products disclosed herein can deliver an effective amount of epinephrine to the target anatomy substantially independent of the patient's orientation. For example, in some embodiments, the delivery percentage of a total mass of the delivered dry powder composition to a mass of the dry powder composition that is deposited on a turbinate region and an olfactory region is greater than about 65%, is greater than about 74%, or is between about 74% and 85%.

The dry powder epinephrine compositions, methods of intranasal delivery, and drug products for intranasal delivery of epinephrine disclosed herein are formulated and/or configured to produce the desired pharmacokinetics (PK) of the epinephrine composition. In some embodiments, the dry powder formulations provided herein, when administered to a patient, produce a maximal plasma concentration (Cmax) of epinephrine that is at least about: 2- to 3-fold, 3- to 5-fold, 5- to 7-fold, or 7- to 10-fold more than the baseline level of epinephrine in the patient. One of ordinary skill in the art will appreciate that the baseline level of circulating plasma epinephrine concentration ranges from 25 to 50 pg/mL. In some embodiments, the dry powder formulations provided herein, when administered to a patient, produce a maximal blood concentration (Cmax) of epinephrine at least 2-, 3-, 4-, 5-, 6-, 7-, 8-, 9-, 10-fold more than the baseline level of epinephrine in the patient. In one embodiment, the dry powder formulations provided herein, when administered to a patient, produce a maximal blood concentration (Cmax) of epinephrine at least 2-fold more than the baseline level of the epinephrine in the patient. In one embodiment, the formulations provided herein, when administered to a patient, increase the blood concentration of epinephrine by about 10 to 400 pg/mL).

In other embodiments, one or more pharmacokinetic parameters of the epinephrine composition are greater than that from the intramuscular delivery of a corresponding dose of an epinephrine composition via a manually actuated syringe and less than that from the intramuscular delivery of the corresponding dose of the epinephrine composition via an autoinjector. Said another way, the pharmacokinetics of the epinephrine drug products described herein can be bracketed between that for a first reference dose (i.e., intramuscular injection via a manual syringe) and a second reference dose (i.e., intramuscular injection via an autoinjector).

Further, in some embodiments, the drug products described herein can rapidly reach a desired blood plasma epinephrine level to effectively treat anaphylaxis. Specifically, in some embodiments, the dry powder compositions and the intranasal delivery devices described herein can deliver a dose of epinephrine that produces plasma epinephrine concentrations within a time to reach a maximum epinephrine plasma concentration (Tmax) of between about 15 minutes and about 30 minutes. In some embodiments, the mean baseline-corrected epinephrine present is at least 100 pg/mL within less than about 10 minutes, less than about 7 minutes, or less than about 5 minutes after delivery of the single dose. Said another way, the T100 (the time to reach a plasma epinephrine concentration of 100 pg/mL) is within about 5 minutes. Thus, the embodiments described herein produce a rapid and effective rise in blood plasma epinephrine levels.

In some embodiments, the blood concentration of epinephrine is increased by about at least 80, 85, 90, 95, 100, 105, 110, 115, or 120 pg/mL within less than about 15 minutes of administration of a single dose, within less than about 10 minutes of administration of a single dose, within less than about 8 minutes of administration of a single dose, or within less than about 5 minutes of administration of a single dose. Advantageously, the present invention provides for providing a rapid change in baseline of at least approximately 100 pg/mL. The change in baseline of at least approximately 100 pg/mL is sufficient to treat anaphylaxis in a human being. However, the present invention is operable to provide higher changes in the baseline, and is operable to provide changes of 140, 150, 190, 200, 210, 230, 240, 270, 300, 340, 350, or 400 pg/mL. In some embodiments, the dry powder formulations provided herein, when administered to a patient, produce a maximum plasma concentration (Cmax) of epinephrine that is at least 10%, 20%, 30%, 40%, or 50% more compared to the maximum plasma concentration (Cmax) of a corresponding epinephrine composition injected IV, IM, or SQ.

In some embodiments, the dry powder formulations provided herein, when administered to a patient, reach a maximal blood concentration of epinephrine in less than about 30 minutes (Tmax) after administration. In some embodiments, the dry powder formulations provided herein, when administered to a patient, reach a maximal blood concentration of epinephrine in less than about 10 minutes (Tmax) after administration. In some embodiments, the dry powder formulations provided herein, when administered to a patient, reach a maximal blood concentration of epinephrine in less than about 15 minutes (Tmax) after administration. In some embodiments, the dry powder formulations provided herein, when administered to a patient, reach a maximal blood concentration of epinephrine in less than about 25 minutes (Tmax) after administration. In some embodiments, the dry powder formulations provided herein, when administered to a patient, reach a maximal blood concentration (Tmax) of epinephrine in less than about 60, 50, 40, 30, 20, 15, 10, or 5 minute(s) (Tmax) after administration. In some embodiments, the dry powder formulation provided herein, when administered to a patient, reach a maximal blood concentration of epinephrine in at least 10%, 20%, 30%, 40%, 50%, 60%, or 70% less time (Tmax) than a corresponding epinephrine composition injected IV, IM, or SQ.

In some embodiments, the dry powder formulations provided herein, when administered to a patient, reach a mean area under the curve (AUC) over a time period before administration to a time of a last detectable concentration of the delivered dose of the dry powder (0-t) (e.g., 0-45 minutes, 0-60 minutes, 0-360 minutes) of epinephrine that is at least 80%, 85%, 90%, 95%, 100%, 105%, 110%, 115%, 120%, or 125% of the mean AUC over the time period of an IV, IM, or SQ injected epinephrine. In some embodiments, the dry powder formulations provided herein, when administered to a patient, reach a mean area under the curve (AUC) over a time period (0-t) (e.g., 0-45 minutes, 0-60 minutes, 0-360 minutes) of epinephrine that is at least about 80% to 120% of the mean AUC over the time period of an IV, IM, or SQ injected epinephrine. In some embodiments, the dry powder formulations provided herein, when administered to a patient, reach a mean AUC over a time period before administration extrapolated to infinity (0-00) of epinephrine that is at least 80%, 85%, 90%, 95%, 100%, 105%, 110%, 115%, 120%, or 125% of the mean AUC over the time period of an IV, IM, or SQ injected epinephrine, or IN aqueous epinephrine. In some embodiments, the dry powder formulations provided herein, when administered to a patient, reach a mean AUC over a time period (0-0) of epinephrine that is at least about 80% to 120% of the mean AUC over the time period of an IV, IM, or SQ injected epinephrine, or IN aqueous epinephrine. In some embodiments, the IV, IM, or SQ injected epinephrine or IN aqueous epinephrine contains 0.10 mg, 0.15 mg, 0.20 mg, 0.25 mg, 0.30 mg, 0.40 mg, 0.50 mg, 0.75 mg, 0.90 mg, 0.95 mg, or 1.0 mg, 1.25 mg, 1.50 mg, 1.75 mg, 2.0 mg, 2.25 mg, 2.50 mg, 2.75 mg, 3.0 mg, 3.25 mg, 3.50 mg, 3.75 mg, 4.0 mg, 4.25 mg, 4.50 mg, 4.75 mg, 5.0 mg, 5.25 mg, or 5.50 mg of epinephrine.

In one embodiment, the dry powder formulations provided herein, when administered to a patient, reach a mean AUC over a time period (0-t) (e.g., 0-45 minutes, 0-60 minutes, 0-360 minutes) of epinephrine that is at least 80% of the mean AUC over the time period of a 0.3 mg IM injected epinephrine. In one embodiment, the dry powder formulations provided herein, when administered to a patient, reach a mean AUC over a time period (e.g., 0-∞) of epinephrine that is at least 80% of the mean AUC over the time period of a 0.3 mg IM injected epinephrine. In one embodiment, the dry powder formulations provided herein, when administered to a patient, reach a mean AUC over a time period (0-t) of epinephrine that is at least 80% of the mean AUC over the time period of 0.5 mg IM injected epinephrine. In one embodiment, the dry powder formulations provided herein, when administered to a patient, reach a mean AUC over a time period (e.g., 0-∞) of epinephrine that is at least 80% of the mean AUC over the time period of a 0.5 mg IM injected epinephrine. In one embodiment, the dry powder formulations provided herein, when administered to a patient, reach a mean AUC over a time period (0-t) (e.g., 0-45 minutes, 0-60 minutes, 0-360 minutes) of epinephrine that is at least 80% of the mean AUC over the time period of a 2 mg IN aqueous epinephrine treatment. In one embodiment, the dry powder formulations provided herein, when administered to a patient, reach a mean AUC over a time period (e.g., 0-∞) of epinephrine that is at least 80% of the mean AUC over the time period of a 2 mg IN aqueous epinephrine treatment.

The dry powder epinephrine compositions, methods of intranasal delivery, and drug products for the intranasal delivery of epinephrine disclosed herein can also produce advantageous pharmacodynamic (PD) results. Specifically, the pharmacodynamic response to intranasal delivery of the dry powder epinephrine compositions described herein show a desired increase in blood pressure and/or heart rate, while also maintaining these parameters with a desired range. For example, in some embodiments, the intranasal administration of a dose of epinephrine produces at least one of an increase in systolic blood pressure by at least 10 mm Hg for a duration of up to 50 minutes after administration of the single dose or an increased heart rate of at least 10 beats per minute for a duration of up to 50 minutes after administration of the single dose.

Additionally, the compositions and intranasal delivery devices described herein reduce the susceptibility of the epinephrine product to heat-related degradation and extends the product's shelf life. This advantageously allows for the epinephrine formulation to be stored in emergency response kits used by emergency medical services or deployed for public access without the concern for degradation. The drug products described herein include dry powder formulations for delivery to the nasal passages by means of a nasal delivery device that is handheld, portable, and easy-to-use, for non-medically trained personnel.

In some embodiments, the dry powder compositions can include constituents of and/or be used within any of the intranasal delivery devices shown and described in U.S. Patent Publication No. 2024/0148990, entitled "Dry Powder Formulations of Epinephrine and Associated Methods," filed on Jan. 19, 2024, which is incorporated herein by reference in its entirety.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the words "proximal" and "distal" refer to direction closer to and away from, respectively, an operator of the medical device. Thus, for example, the end of an intranasal delivery device contacting the patient's body would be the distal end of the device, while the end opposite the distal end would be the proximal end of the intranasal delivery device.

The term "about" when used in connection with a referenced numeric indication means the referenced numeric indication plus or minus up to 10 percent of that referenced numeric indication. For example, "about 100" means from 90 to 110.

While numerical ranges are provided for certain quantities, it is to be understood that these ranges can include all subranges therein. Thus, the range "from 50 to 80" includes all possible ranges therein (e.g., 51-79, 52-78, 53-77, 54-76, 55-75, 70-70, etc.). Furthermore, all values within a given range may be an endpoint for the range encompassed thereby (e.g., the range 50-80 includes the ranges with endpoints such as 55-80, 50-75, etc.).

As used herein, $AUC_{(0-\infty)}$ is the area under the plasma concentration-time curve from pre-dose (time 0) extrapolated to infinity.

As used herein, $AUC_{(0-t)}$ is the area under the plasma concentration-time curve from pre-dose (time 0) to the time of the last quantifiable concentration ($T_{last}$).

As used herein, Cmax is the maximum plasma naloxone concentration determined directly from the plasma concentration-time profile.

As used herein, Tmax is the time of maximum plasma naloxone concentration determined directly from the plasma concentration-time profile.

As used herein, the term "pharmacokinetic" (PK) refers generally to the characteristic interactions of a drug and the body in terms of the absorption, distribution, metabolism, and excretion of the drug. By way of example, the terms "pharmacokinetic parameter" or "pharmacokinetic parameters" can include, but are not limited to parameters such as Cmax. Tmax. $AUC_{(0-t)}$, and $AUC_{(0-\infty)}$.

As used herein, the term "pharmacodynamic" (PD) refers generally to the relationship between the drug concentration at the site of action and the resulting physiological effects, such as the effects on the patient's heart rate or blood pressure.

Intranasal Delivery Devices

FIGS. 1-8 show various views of an intranasal delivery device 100 according to one embodiment in various different configurations (or stages of operation). The device 100 includes a drug reservoir (or container) 110 coupled to a nasal delivery head 120, an actuator 140, and an air delivery assembly 130. As described herein, upon actuation, the air delivery assembly 130 produces a flow of compressed air to deliver the dose of the dry powder composition contained in the drug reservoir 110. The drug reservoir 110 is formed by a hollow tube 111 which is open at its two axial ends and is closed at its distal end by a closing element 112 (e.g., a ball), and is closed at its proximal end by an insert 115. The insert 115 comprises an axial extension forming a rod, and can, upon actuation, slide distally (i.e., towards the patient) in the hollow tube 111 to move the closing element 112 outside of its closing position. The piston 132 of the air delivery assembly 130 includes, or is rigidly connected to, an axial projection 135 which extends distally. Accordingly, during actuation, the axial projection 135 will move together with the piston 132 during the compression of the air contained in the air chamber 131. When the projection 135 of the piston 132 contacts the insert 115 of the reservoir 110, continued movement of the piston 132 will cause movement of the insert 115 within the hollow tube 111 outside of its closing position. Thus, the insert 115 will, on the one hand, open the passage between the air delivery assembly 130 and the reservoir 110 and, on the other hand, cause the expulsion of the closing element 112. Thus, the air compressed in the air chamber 131 will flow into the reservoir and convey the dose of powder out of the drug reservoir 110 in the direction of said delivery aperture 121.

The drug reservoir 110 can include any of the dry powder epinephrine compositions described herein. For example, in some embodiments, the drug reservoir 110 can include a dry powder pharmaceutical composition comprising epinephrine or a pharmaceutically acceptable salt thereof and a carrier, wherein the dry powder pharmaceutical composition has a bulk particle size distribution characterized by a Dv50 of between 5 microns and 30 microns. In some embodiments, the dry powder pharmaceutical composition has a moisture content of less than 6 percent. In some embodiments, the moisture content of the dry powder composition is between about 3.5 percent and 6 percent, between about 4 percent and 5.5 percent, or about 5 percent.

The nasal delivery head 120 is coupled to the reservoir 110 and is configured to be inserted in a nostril of a user. The nasal delivery head comprises a delivery aperture 121 through which the mixture of the airflow and the dose of the dry powder pharmaceutical composition is delivered. The delivery head 120 includes a finger rest 122 extending radially to facilitate the actuation. A hollow sleeve 123 extends axially upwards from the finger rest 122 and ends at the delivery aperture 121. In some embodiments, the hollow sleeve 123 is of reduced radial dimension to facilitate insertion into a nostril at the time of the actuation. On the opposite side of the finger rest 122, a skirt 125 extends axially downwards from said finger rest 122. The skirt 125 comprises, in the vicinity of its axially lower end, a lower flange 127, which radially projects inwards.

The air delivery assembly 130 is configured to produce a flow of compressed air to deliver the dose of the dry powder composition from the reservoir 110 and into the nostril through the delivery aperture 121. The air delivery assembly comprises an air chamber 131 and a piston 132 sealingly and slidably coupled within the air chamber 131. Movement of the piston 132 compresses the air contained in the air chamber 131 and thus produces the flow of compressed air. The piston 132 comprises an upper lip 132a and a lower lip 132b. The air chamber 131 is formed by a hollow axial cylinder 128 which is rigidly connected to the finger rest 122 of the delivery head 120. The lower side of the hollow cylinder 128 is open and receives therein the piston 132. The skirt 125 is arranged around the hollow cylinder 128 and can, in particular, be formed by a hollow sleeve fixed in the finger rest 122 of the delivery head 120. The lower flange 127 of the skirt 125 forms a lower abutment for the piston 132, in particular, for its lower lip 132b (see, e.g., FIG. 1).

The piston 132 is coupled to the actuation member 140, which can be pressed by the user to actuate the device 100 and move the piston 132 in the air chamber 131. Movement of the piston 132, however, is resisted until the actuation member 140 is pressed with a force that exceeds a predetermined threshold. Specifically, the hollow axial cylinder 128 that forms the air chamber 131 comprises a radial shoulder 129. The radial shoulder 129 defines within the side wall of said cylinder 128 a profile that the piston 132 (and in particular the upper lip 132a) must overcome at the start of actuation. The radial shoulder 129 therefore forms a resistance to actuation that the user must overcome at the start of actuation. This arrangement reduces the likelihood of accidental actuation of the device.

The radial shoulder 129 connects a first cylinder portion 128a of larger diameter and a second cylinder portion 128b of smaller diameter. Before actuation, the piston 132 is arranged at the first cylinder portion 128a, such that it does not necessarily sealingly cooperate with the cylinder 128. Thus, at rest, the air chamber 131 is open to the atmosphere. Upon actuation, the piston 132 sealingly cooperates with the second (smaller diameter) cylinder portion 128b, to compress the air contained in the air chamber 131 and thus produce the flow of compressed air.

As can be seen in FIGS. 1 and 2, the piston 132 can, before actuation, move between two non-actuated positions, a lower transport position (see FIG. 1) and an upper transport position (see FIG. 2). In the lower transport position, the lower lip 132b of the piston 132 is abutted against the lower flange 127 of the skirt 125. In the upper transport position, the upper lip 132a of the piston 132 is abutted against the radial shoulder 129 of the cylinder 128. Thus, at rest, the piston 132 is in any position located between the two transport positions, and in case of accidental fall, the device is therefore not static, as would be the case if the piston were fixed to the skirt by breakable bridges.

The lower portion of the side wall of the skirt 125, in the vicinity of the lower flange 127, comprises at least one profile which radially projects inwards 126. These profiles 126 can advantageously be formed by one or more axial ridges, for example three or four ridges distributed over the periphery of the skirt 125. The profiles 126 cooperate with the lower lip 132b of the piston 132 before actuation, i.e., when the piston 132 is located between its lower and upper transport positions, which can be seen in FIGS. 1-3. This is only at the start of the actuation, which can be seen in FIG. 4, that the lower lip 132b is released from said profiles 126. The presence of these profiles 126 reinforces the cooperation by friction between the piston 132 and the skirt 125 and therefore limits the likelihood of accidental actuation.

Figures 9A, 9B, 9C, 9D:
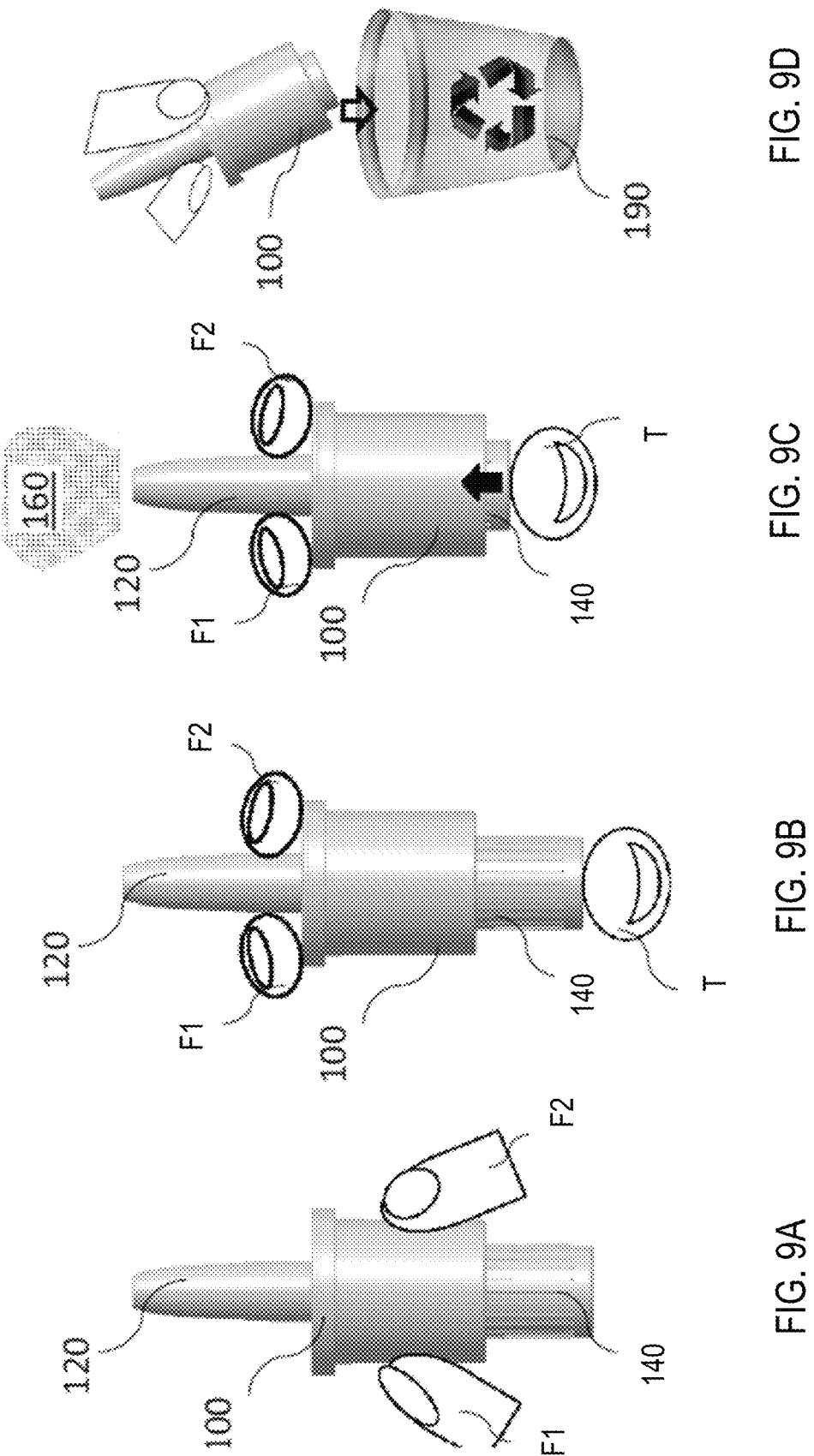
FIG. 9A illustrates a nasal delivery device at rest according to one embodiment of the present invention.
FIG. 9B illustrates positioning of fingers and a thumb on the nasal delivery device of FIG. 9A.
FIG. 9C illustrates discharge of the nasal delivery device of FIG. 9A.
FIG. 9D illustrates disposal of the nasal delivery device following use according to one embodiment of the present invention.

FIGS. 9A-9D illustrate a method of using the nasal delivery device 100 according to the present invention. FIG. 9A illustrates the nasal delivery device 100 at rest. FIG. 5B illustrates positioning of a first finger F1 and a second finger F2 on the nasal delivery device 100. A thumb Tis positioned on the push button actuator 140 of the nasal delivery device 100. To discharge the nasal delivery device 100, the thumb T presses up on the push button 140 of the nasal delivery device 100 as shown in FIG. 5C. Thus, this arrangement allows the device to be manually actuated. Actuation of the nasal delivery device 100 causes the air delivery assembly 130 to produce an airflow through the reservoir 110 to deliver a mixture of the airflow and the dose of the dry powder pharmaceutical composition 160 via the delivery aperture 121. As described herein, the aperture 121 can be placed with a nasal passage for intranasal delivery of the aerosolized particles 160. The intranasal delivery device 100 can then be disposed of (e.g., in a recycling can 190) following use, as shown in FIG. 9D.

In some embodiments, the actuating of the nasal delivery device 100 includes manually moving the piston 132 within the air chamber 131 to produce a pressure of between about 1 atmosphere and 2 atmospheres within the air chamber 131. In this manner, the nasal delivery device 100 can produce the desired airflow through the reservoir 110 to deliver a mixture of the airflow and the dose of the dry powder pharmaceutical composition via the delivery aperture 121. In some embodiments, the dry powder composition and the nasal delivery device 100 are collectively configured to produce an emitted particle size (i.e., the particle size of the composition that is emitted from the device) within a desired range to facilitate delivery to and deposition on the target anatomy while limiting the amount of the composition delivered to the lung. Specifically, the composition and characteristics of the dry powder composition used to fill the nasal delivery device 100 (or any other devices described herein) is suitable such that the airflow produced by the nasal delivery device 100 (i.e., the airflow rate and pressure of the air), the characteristics of the drug reservoir 110 and the characteristics of the delivery head 120 and aperture 121 (e.g., the aperture size) produces the desired emitted particle size distribution 160 (see FIG. 9C; the emitted particle size distribution is also referred to as the ePSD). For example, any of the carrier of the composition, the dispersing agent of the composition, and/or the moisture content of the composition can influence the ePSD. Additionally, although the bulk particle size distribution (i.e., the particle size distribution of the dry powder composition used to fill the device; also referred to as bPSD) can impact the ePSD, one of the surprising results of the testing disclosed herein is that the bPSD has limited influence on the ePSD (as compared to other factors, such moisture and composition). The testing further showed that for the compositions and devices described herein, the ePSD increased in size as compared to the bPSD. Thus, the drug products described herein had limited agglomeration.

In some embodiments, the nasal delivery device 100 is filled with the dry powder composition comprising epinephrine or a pharmaceutically acceptable salt thereof and a carrier. The dry powder pharmaceutical composition has a bPSD characterized by a Dv50 of between 5 microns and 30 microns. Upon actuation of the nasal delivery device 100, the air delivery assembly 130 produces an airflow through the reservoir 110 to deliver a mixture of the airflow and the dose of the dry powder pharmaceutical composition having an ePSD characterized by a Dv50 of between 15 microns and 200 microns and that is greater than the Dv50 of the bPSD. In other embodiments, the Dv50 of the bPSD is between 5 microns and 18 microns and the Dv50 of the ePSD is between 20 microns and 185 microns. In other embodiments, the Dv50 of the bPSD is between 15 microns and 25 microns and the Dv50 of the ePSD is between 20 microns and 50 microns. In some embodiments, the dry powder pharmaceutical composition has a bPSD characterized by a Dv50 of about 20 microns and the ePSD is characterized by a Dv50 of between 25 microns and 40 microns.

In some embodiments, the bPSD is characterized by a size below which there is 10% of the volume of the sample (Dv10) of between 1.5 microns and 5 microns and the ePSD characterized by a Dv10 of between 5 microns and 10 microns and is greater than the Dv10 of the bPSD. In some embodiments, the bPSD is characterized by a size below which there is 90% of the volume of the sample (Dv90) of between 13 microns and 50 microns and the ePSD is characterized by a Dv90 of between 475 microns and 625 microns.

In some embodiments, the dose of the dry powder composition emitted contains between about 3.5 mg and about 5.5 mg of the epinephrine or the pharmaceutically acceptable salt, and the carrier is lactose monohydrate. In some embodiments, the dry powder composition has a moisture content of between 3.5% and 6%, between 4% and 5.5%, or between 4.5% and 5%.

Compositions

Any of the dry powder compositions described herein can be produced by spray drying, as described in U.S. Patent Publication No. 2024/0148990, entitled "Dry Powder Formulations of Epinephrine and Associated Methods," filed on Jan. 19, 2024, which is incorporated herein by reference in its entirety. Specifically, the formulation can be prepared as a solution in a mixture of water and ethanol (EtOH). The solution can be pumped into a heated inlet and then aspirated through a sonicated nozzle with compressed air into a heated spray cylinder where it dries. The resultant powder can then be collected through a cyclone and into a collection vessel. By controlling the concentration of the formulation within the feed solution, the spray dryer pump rate, inlet temperature, aspirator power, nozzle power, and other process parameters, the average particle size, and yield can be adjusted to achieve the values described herein. Of course, it will be appreciated that the moisture content is, at least in part, dictated by the formulation and is controlled by the process conditions employed, e.g., inlet temperature, feed concentration, pump rate, and blowing agent type, concentration and/or post processing or drying.

In one embodiment, the intranasal dry powder compositions and/or unit doses include at least one stabilizing agent. One of ordinary skill in the art will appreciate that stabilizing agents (i.e., "stabilizers") are substances added to a product to maintain its physical and chemical properties over time. In the pharmaceutical industry, stabilizers are used to improve the stability and efficacy of drug compositions, protect against degradation, improve solubility and bioavailability, and control the release of pharmaceutical compositions over time. In one embodiment, the stabilizing agent of the present composition is an ingredient that includes both buffering (i.e., maintaining the pH of the composition) and antioxidizing (i.e., neutralizing the production of free radicals by inhibiting oxidation of the composition) characteristics.

In one embodiment, the at least one stabilizing agent is a non-sulfite stabilizer (e.g., ascorbic acid, sodium citrate). In one embodiment, the at least one stabilizing agent is a buffering acid, or a pharmaceutically acceptable salt derived therefrom. In one embodiment, the at least one stabilizing agent is ascorbic acid, sodium ascorbate, calcium ascorbate, potassium ascorbate, citric acid, sodium citrate (e.g., monosodium citrate, disodium citrate, trisodium citrate), potassium citrate (e.g., monopotassium citrate, tripotassium citrate), phosphoric acid, sodium phosphate (e.g., monosodium phosphate, disodium phosphate, trisodium phosphate), potassium phosphate (e.g., monopotassium phosphate, dipotassium phosphate, tripotassium phosphate), tartaric acid, sodium tartrate (e.g., monosodium tartrate, disodium tartrate), potassium tartrate (e.g., monopotassium tartrate, dipotassium tartrate), sodium potassium tartrate, acetic acid, sodium acetate, sodium diacetate, potassium acetate, potassium diacetate, alginic acid, sodium alginate, potassium alginate, succinic acid, sodium succinate, potassium succinate, malic acid, sodium malate (e.g., monosodium malate, disodium malate), benzoic acid, sodium benzoate, potassium benzoate, lactic acid, sodium lactate, potassium lactate, histidine, glycine, arginine, ammonium chloride, sodium chloride, potassium chloride, zinc chloride, calcium chloride, sodium acetate trihydrate, and/or triethanolamine. In one embodiment, the at least one stabilizing agent is about 1% to about 25% w/w of the weight of the composition, for example about: 1%, 5%, 7%, 8%, 9%, 10%, 11%, 12%, 13%, 14%, 15%, 16%, 17%, 18%, 19%, 20%, 21%, 22%, 23%, 24%, or 25% w/w based on the weight of the compositions and/or unit doses. In one embodiment, the at least one stabilizing agent is about 1% to 5%, 5% to 20%, 5% to 30%, 10% to 20%, or 10% to 30% w/w based on the weight of the compositions and/or unit doses.

In one embodiment, the intranasal dry powder composition is stable at higher temperatures than prior art compositions.

In some embodiments, the dry powder composition further includes at least one carrier and/or excipient. In one embodiment, the carrier and/or excipient is a pharmaceutically acceptable carrier or excipient. In one embodiment, the at least one carrier and/or excipient includes, but is not limited to, lactose (e.g., D-lactose, lactose monohydrate), sucrose, glucose, dextrose, trehalose, sodium carboxymethylcellulose (CMC), mannitol, sorbitol, malitol, xylitol, maltose, cellulose and derivatives, starch and derivatives, microcrystalline cellulose, sodium starch glycolate, and/or a mixture of mannitol and hydroxypropyl methylcellulose (HPMC). In one embodiment, the at least one carrier and/or excipient includes at least one carbohydrate. In one embodiment, the at least one carbohydrate includes at least one monosaccharide, at least one disaccharide, at least one cyclodextrin, at least one polysaccharide, at least one starch, and/or at least one cellulose. In one embodiment, the at least one carrier and/or excipient includes a sucrose ester, a sugar ether, and/or an alkyl glycoside. In another embodiment, the at least one carrier and/or excipient does not include a sucrose ester, a sugar ether, and/or an alkyl glycoside.

In some embodiments, the at least one carrier and/or excipient includes a first cellulose and/or a second cellulose. In some embodiments, the first cellulose is a crystalline cellulose. In some embodiments, the first cellulose is a microcrystalline cellulose. In some embodiments, the first cellulose has an average particle diameter of about 100 μm or less, for example about: 90 to 100 μm, 80 to 90 μm, 70 to 80 μm, 60 to 70 μm, 50 to 60 μm, 40 to 50 μm, 30 to 40 μm, 20 to 30 μm, or 10 to 20 μm. In some embodiments, the first cellulose has an average particle diameter of less than about 100 μm, 90 μm, 80 μm, 70 μm, 60 μm, 50 μm, 40 μm, 30 μm, 20 μm, 10 μm, or 5 μm. In some embodiments, the first cellulose has an average particle diameter of about 30

μm or less. In some embodiments, the at least one carrier and/or excipient includes a second cellulose. In some embodiments, the second cellulose is a crystalline cellulose. In some embodiments, the second cellulose is a microcrystalline cellulose. In some embodiments, the at least one carrier and/or excipient further includes a starch. In some embodiments, the at least one carrier and/or excipient includes a second cellulose and starch. In some embodiments, the second cellulose and/or starch have an average particle diameter of about 30 to about 100 μm, for example about: 30-40 μm, 30-50 μm, 30-60 μm, 30-70 μm, 30-80 μm, or 30-90 μm. In some embodiments, the second cellulose and/or starch have an average particle diameter of less than about 100 μm, 90 μm, 80 μm, 70 μm, 60 μm, 50 μm, 40 μm, 30 μm, 20 μm, 10 μm, or 5 μm. In some embodiments, the second cellulose, the starch, or the second cellulose and starch each individually has an average particle diameter of about 30 to about 100 μm.

In one embodiment, the at least one carrier and/or excipient present in the intranasal dry powder compositions is a mixture of a first microcrystalline cellulose, a second microcrystalline cellulose, a starch, and/or tribasic calcium phosphate. In one embodiment, the at least one carrier and/or excipient includes: i) a first crystalline cellulose with an average particle diameter of about 30 μm or less, for example about: 30-10 μm, 30-15 μm, 30-20 μm, or 30-25 μm; ii) tribasic calcium phosphate; and iii) a second crystalline cellulose, or starch, with an average particle diameter of about 30 to about 100 μm, for example about: 30-40 μm, 30-50 μm, 30-60 μm, 30-70 μm, 30-80 μm, or 30-90 μm. See, e.g., U.S. Pat. No. 8,337,817, which is incorporated herein by reference in its entirety.

In one embodiment, the at least one carrier and/or excipient includes particles having an average diameter of 1 μm to 100 μm. This is applicable to unimodal or multimodal compositions. In a preferred embodiment, the at least one carrier and/or excipient includes particles having an average diameter of at least 15 μm. Advantageously, an average diameter greater than 15 μm prevents particles from entering the lungs. In a preferred embodiment, the at least one carrier and/or excipient includes particles having an average diameter of about 50 μm. In one embodiment, the at least one carrier and/or excipient includes particles having an average diameter of about 25 μm to about 75 μm.

In one embodiment, an average particle diameter of a dry powder composition is determined using a laser-diffraction particle size distribution analyzer. In some embodiments, an average particle diameter of a dry powder composition is determined using sieve sorting.

In one embodiment, the at least one carrier and/or excipient is about 40% to about 90% w/w of the weight of the composition, for example about: 40%, 43%, 45%, 48%, 51%, 53%, 55%, 57%, 60%, 63%, 66%, 69%, 75%, 80%, 85%, 88%, or 90% w/w based on the weight of the compositions and/or unit doses. In one embodiment, the carrier is about 20% to about 70% w/w of the weight of the composition, for example about: 20%, 25%, 30%, 35%, 40%, 45%, 48%, 49%, 50%, 51%, 52%, 55%, 60%, 65%, 70%, or % w/w based on the weight of the compositions and/or unit doses. In one embodiment, the at least one carrier and/or excipient is about 45% to 65% w/w based on the weight of the compositions and/or unit doses. In one embodiment, the at least one carrier and/or excipient is about 40% to 60%, 45% to 55%, or 48% to 53% w/w based on the weight of the compositions and/or unit doses.

The compositions of the present invention preferably do not include any liquid carriers (e.g., water, alcohol, and/or propylene glycol). Liquid carriers often require additional preservatives to improve stability. Advantageously, dry powder compositions do not require a preservative, which reduces the risk for allergic reactions.

Further, the formulations of the present invention preferably do not include a surfactant. Some liquid formulations of epinephrine require a surfactant to prevent aggregation of the active ingredient. Advantageously, dry powder formulations do not require a surfactant.

The epinephrine and other enabling agents are operable to be individually substantially amorphous or crystalline. In some embodiments, the formulations and/or unit doses provided herein are in the form of particles, and the shapes of the particles are operable to be individually, e.g., cylindrical, discoidal, spherical, tabular, ellipsoidal, angular, and/ or irregular. In one embodiment the epinephrine, carrier and stabilizing agent are combined in solution and spray dried to produce a homogenous amorphous powder.

In some embodiments, the average particle diameter of the epinephrine, enabling agent, and/or carrier (i.e., the bulk particle diameter of the powder being filled into the device) are, individually, up to 100 μm, up to 50 μm, or up to 30 μm. In a preferred embodiment, the average particle diameter of the epinephrine, enabling agent, and/or carrier are, individually, less than or equal to 50 μm. In one embodiment, the average particle diameter of the epinephrine, enabling agent, and/or carrier are, individually, about: 10-20, 20-30, 30-40, 40-50, 50-60, 60-70, 70-80, 80-90, or 90-100 μm. In another embodiment, the average particle diameter of the epinephrine, enabling agent, and/or carrier are, individually, about: 10, 15, 20, 25, 30, 35, 40, 45, 50, 55, 60, 65, 70, 75, 80, 85, 90, 95, or 100 μm.

In some embodiments, the median particle diameter of the epinephrine powder (i.e., the bulk median diameter of the powder being filled into the device) herein is about 30 μm (e.g., 28.7 μm). In some embodiments, the median particle diameter of the epinephrine powder herein is about: 10-50, 20-40, or 25-35 μm. In one embodiment, 90% of the epinephrine particles herein have a particle diameter under about 50 μm (e.g., about 45.5 μm). In another embodiment, 90% of the epinephrine particles herein have a particle diameter under about: 40, 45, 35, 30, 25, or 20 μm. In yet another embodiment, about 10% of the epinephrine particles herein have a particle diameter under about 20 μm (e.g., about 17.3 μm). In still another embodiment, about 10% of the epinephrine particles herein have a particle diameter under about: 19, 18, 17, 16, 15, 14, 13, 12, 11, or 10 μm.

In a preferred embodiment, the average particle size, and/or the mean particle size of the dry powder composition being filled into the device is greater than 15 μm. Advantageously, an average particle size and/or a mean particle size greater than 15 μm avoids any entry of the particles into the lungs. In a preferred embodiment, the average particle size and/or the mean particle size is about 50 μm. In one embodiment, the average particle size and/or the mean particle size is between about 25 μm and about 75 μm. In one embodiment, the composition undergoes an agglomeration step before being deposited into the reservoir of the device of the present invention. In one embodiment, the particle size of the epinephrine contained within the dispensing device is between about 100 μm and about 1000 μm. In one embodiment, the particle size of the epinephrine contained within a dispensing device is between about 100 μm and about 500 μm or between about 200 μm and about 600 μm. In one embodiment, the dispensation of the particles via the device mechanically breaks up the particles of the composition such that the particle delivered to the nasal passage has a median diameter (i.e., D50 for the particle) of about 25 μm. In one embodiment, the dispensation of the particles via the device mechanically breaks up the particles of the composition such that the particle delivered to the nasal passage has a median diameter of at least 15 μm. In one embodiment, the dispensation of the particles via the device mechanically breaks up the particles of the composition such that the particle delivered to the nasal passage has a median diameter of between about 15 μm and about 75 μm.

In one embodiment, the formulations or dosage units herein are not or do not include spray-dried particles. In some embodiments, the formulations herein do not possess a fine particle fraction of less than 5.6 microns of at least about 45 percent. In some embodiments, the formulations herein do not include particles including: (a) about 11 to about 21 weight percent epinephrine bitartrate; (b) about 62 to about 82 weight percent leucine; and/or (c) about 7 to about 17 weight percent sodium tartrate.

Methods of Treatment

Any of the dry powder compositions, nasal delivery devices and drug products described herein can be used to treat a patient experiencing any condition treated by the administration of epinephrine. In some embodiments, the patient being treated is experiencing the symptoms of at least one of an anaphylactic reaction, an anaphylactoid reaction, cardiac arrest, exposure to a toxic synthetic organophosphorus compound, or exposure to cyanide or hydrogen sulfide. In some embodiments, the patient is experiencing one or more of bronchoconstriction (bronchospasm), hypotension (low blood pressure), hypotensive shock, and/or cardiac arrest (e.g., including minimal or no cardiac activity). In some instances, the patient in need of treatment is experiencing cardiac arrest and/or bronchospasm. In some embodiments, the patient is experiencing bronchoconstriction. In some embodiments, the patient is experiencing hemodynamic collapse. In some embodiments, the patient has hypotension. In some embodiments, the patient is experiencing hypotensive shock. In some embodiments, the patient is experiencing cardiac arrest. In some embodiments, the dry powder formulation is administered to a patient in a unit dose form as disclosed herein. In some embodiments, the dry powder formulation is administered to a patient by using a delivery device or product as disclosed herein. In some embodiments, as discussed above, the dry powder formulation provided herein provides a fast onset time.

In some embodiments, any of the drug delivery devices (e.g., the nasal drug delivery device 100 described herein) can be used to deliver a dry powder pharmaceutical composition such that the emitted particles have the desired particle size distribution. For example, FIG. 10 is a flow chart of a method 10 of delivering a dry powder pharmaceutical composition from a drug delivery device. The drug delivery device can be, for example, the device 100 or any other suitable intranasal drug delivery device. The device has a reservoir, an air delivery assembly, and a delivery head defining a delivery aperture. The reservoir containing a dose of the dry powder pharmaceutical composition. The dry powder pharmaceutical composition comprising epinephrine or a pharmaceutically acceptable salt thereof and a carrier. The dry powder pharmaceutical composition having a bulk particle size distribution characterized by a Dv50 of between 5 microns and 30 microns. The method includes exposing the delivery aperture, at 12. In some embodiments, the delivery aperture can be exposed by removing the device from a protective case or pouch followed by removing a protective cap from about the delivery aperture. The drug delivery device is then actuated, at 13, to produce, via the air delivery assembly, an airflow through the reservoir to deliver a mixture of the airflow and the dose of the dry powder pharmaceutical composition via the delivery aperture. The delivered mixture has an emitted particle size distribution characterized by a Dv50 of between 25 microns and 200 microns and that is greater than the Dv50 of the bulk particle size distribution.

In some embodiments, the air delivery assembly includes an air chamber, and a piston movably disposed within the air chamber. The actuating includes manually moving the piston within the air chamber to produce the airflow through the reservoir. For example, in some embodiments, the piston can be manually moved by squeezing the device between the user's fingers and thumb, as shown in FIGS. 9A-9C. In some embodiments, the actuating includes manually moving the piston within the air chamber to produce a pressure of between about 1 atmosphere and 2 atmospheres within the air chamber. In this manner, the composition and the device can cooperatively function to produce the desired emitted particle size distribution.

In some embodiments, the dose contains between about 3.5 mg and about 5.5 mg of the epinephrine or the pharmaceutically acceptable salt and the carrier is lactose monohydrate. In some embodiments, the dry powder pharmaceutical composition has a moisture content of between 3.5% and 6%, or any other suitable range as described herein.

FIG. 11 is a flow chart of a method 20 of delivering a dry powder pharmaceutical composition. The method 20 includes placing a delivery head of an intranasal device into a nasal passage of a body, at 22. The intranasal device can be, for example, the device 100. The device has a reservoir and an air delivery assembly. The reservoir contains a dose of the dry powder pharmaceutical composition. The dry powder pharmaceutical composition comprises epinephrine or a pharmaceutically acceptable salt thereof and a carrier. The dry powder pharmaceutical composition has a bulk particle size distribution characterized by a Dv50 of between 5 microns and 30 microns. The method includes actuating the intranasal device to cause the air delivery assembly to produce an airflow through the reservoir to deliver the dose of the dry powder pharmaceutical composition into the body via a delivery aperture defined by the delivery head, at 22. The delivered dry powder pharmaceutical composition has an emitted particle size distribution characterized by a Dv50 of between 25 microns and 200 microns and that is greater than the Dv50 of the bulk particle size distribution, at 23.

In some embodiments, the air delivery assembly includes an air chamber, and a piston movably disposed within the air chamber. The actuating includes manually moving the piston within the air chamber to produce the airflow through the reservoir. For example, in some embodiments, the piston can be manually moved by squeezing the device between the user's fingers and thumb, as shown in FIGS. 9A-9C. In some embodiments, the actuating includes manually moving the piston within the air chamber to produce a pressure of between about 1 atmosphere and 2 atmospheres within the air chamber. In this manner, the composition and the device can cooperatively function to produce the desired emitted particle size distribution.

In some embodiments, the dose contains between about 3.5 mg and about 5.5 mg of the epinephrine or the pharmaceutically acceptable salt and the carrier is lactose monohydrate. In some embodiments, the dry powder pharmaceutical composition has a moisture content of between 3.5% and 6%, or any other suitable range as described herein.

In some embodiments, a percentage of a total mass of the delivered dry powder pharmaceutical composition to a mass of the delivered dry powder composition that is deposited on a turbinate region and an olfactory region is greater than about 65 percent. In some embodiments, a percentage of the total mass of the delivered dry powder pharmaceutical composition to a mass of the delivered dry powder composition that is deposited downstream of a nasopharynx is less than 5 percent. Thus, the method of delivery provides the dry powder composition to the desired target regions of the patient to produce the desired result.

In some embodiments, the percentage of the total mass of the delivered dry powder pharmaceutical composition to the mass of the delivered dry powder composition that is deposited on the turbinate region and the olfactory region is between 74 percent and 85 percent.

As described herein, the dry powder compositions and intranasal devices cooperate to deliver an effective amount of the dry powder composition for deposition on the target anatomy of the body, when the body is in a variety of different orientations (e.g., with the patient's head in a vertical position or a horizontal position). Said another way, there is limited variation in the delivery of the dry powder composition to the target anatomy whether the patient is lying down or in a seated or upright orientation. In this manner, the drug products disclosed herein can deliver an effective amount of epinephrine to the target anatomy substantially independent of the patient's orientation. FIG. 12 is a flow chart of a method 30 of delivering a dry powder pharmaceutical composition. The method 30 includes placing a delivery head of an intranasal device into a nasal passage of a body, at 32. The delivery head defines a delivery aperture. The intranasal device further includes a reservoir and an air delivery assembly. The reservoir contains a dose of the dry powder pharmaceutical composition, which comprises epinephrine or a pharmaceutically acceptable salt thereof and a carrier.

The intranasal device is actuated, at 33, to cause the air delivery assembly to produce a delivery airflow through the reservoir to deliver the dose of the dry powder pharmaceutical composition into the body via the delivery aperture. A target delivery percentage of a total mass of the delivered dry powder pharmaceutical composition to a mass of the delivered dry powder composition that is deposited on a turbinate region and an olfactory region is greater than about 74 percent, at 34. The target delivery percentage is substantially independent of an orientation of the body and a presence of a respiratory airflow through the nasal passage.

In some embodiments, a downstream percentage of the total mass of the delivered dry powder pharmaceutical composition to a mass of the delivered dry powder composition that is deposited downstream of a nasopharynx is less than 5 percent. In some embodiments, the downstream percentage is substantially independent of the orientation of the body and the presence of the respiratory airflow through the nasal passage.

In some embodiments, the orientation of the body ranges from a vertical orientation to a horizontal orientation. In some embodiments, the target delivery percentage is substantially independent of a presence of a mucus coating on the turbinate region and olfactory region.

In some embodiments, the delivered dry powder pharmaceutical composition has an emitted particle size distribution characterized by a Dv50 of between 25 microns and 200 microns, of between 20 microns and 185 microns, of between 20 microns and 50 microns, of between 20 microns and 30 microns, of about 20 microns, or of about 25 microns.

In some embodiments, the dose contains between about 3.5 mg and about 5.5 mg of the epinephrine or the pharmaceutically acceptable salt and the carrier is lactose monohydrate.

In some embodiments, the dry powder pharmaceutical composition has a moisture content of between 3.5% and 6%.

In some embodiments a drug product for intranasal delivery of epinephrine can deliver a dose of the epinephrine composition into a body such that one or more pharmacokinetic parameters of the epinephrine composition are greater than that from the intramuscular delivery of a corresponding dose of an epinephrine composition via a manually actuated syringe and less than that from the intramuscular delivery of the corresponding dose of the epinephrine composition via an autoinjector. Said another way, the pharmacokinetics of an epinephrine drug product can be bracketed between that for a first reference dose (i.e., intramuscular injection via a manual syringe) and a second reference dose (i.e., intramuscular injection via an autoinjector). FIG. 13 is a flow chart of a method 30 of delivering a dry powder pharmaceutical composition. The method 40 includes placing a delivery head of an intranasal device into a nasal passage of a body, at 42. The intranasal device includes a reservoir containing a dose of the dry pharmaceutical composition. The dry powder pharmaceutical composition comprises epinephrine or a pharmaceutically acceptable salt thereof and a carrier. The dose contains about 3.5 mg to about 5.5 mg of the epinephrine or the pharmaceutically acceptable salt thereof.

The intranasal device is actuated at 43 to deliver the dose of the pharmaceutical composition into the body such that at least one of: (A) a relative mean maximum epinephrine plasma concentration after the dose is delivered into the body (Cmax) is greater than a Cmax of a first reference dose and less than a Cmax of a second reference dose, at 43A OR (B) a time to reach a maximum epinephrine plasma concentration (Tmax) is greater than a Tmax of the first reference dose and less than a Tmax of the second reference dose, at 43B. The first reference dose contains about 0.3 mg of epinephrine, or a pharmaceutically acceptable salt delivered intramuscularly via a manual injection and the second reference dose contains about 0.3 mg of epinephrine or a pharmaceutically acceptable salt delivered intramuscularly via an autoinjector. The autoinjector can be an EPIPEN® auto-injector of 0.3 mg dose for adult patients.

In some embodiments, the intranasal device includes an air delivery assembly having an air chamber and a piston movably disposed within the air chamber. The actuating includes manually moving the piston within the air chamber to produce the airflow through the reservoir. For example, in some embodiments, the piston can be manually moved by squeezing the device between the user's fingers and thumb, as shown in FIGS. 9A-9C.

In some embodiments, a baseline-corrected epinephrine present in the body is at least 100 pg/mL after about 5 minutes after delivery of the dose.

In some embodiments, the dry powder pharmaceutical composition is formulated such that delivery of the dose of the dry powder pharmaceutical composition via the delivery aperture produces a spray having an emitted particle size distribution characterized by a Dv50 of between 25 microns and 200 microns.

In some embodiments, the dry powder pharmaceutical composition is formulated to have a moisture content of between 3.5% and 6%.

Nasal Cast and Particle Size Studies—Part 1

To evaluate the particle size and deposition performance of the dry powder compositions, devices, and methods described herein, in vitro nasal cast deposition tests simulating real-life conditions were completed. The tests were conducted using a unit dose powder device similar to the device 100 described above, filled with 30 mg of a dry powder epinephrine composition. Specifically, the dry powder epinephrine composition for this test is provided in Table 1 below:

TABLE 1

| Dry powder epinephrine composition tested. | | |
|---|---|---|
| | SD1 | SD2 |
| Epinephrine (freebase) (w/w %) | 20% | 15% |
| Epinephrine Bitartrate (w/w %) | 35.1% | 27.3% |
| Lactose Monohydrate-Carrier (w/w %) | 50.9% | 50.9% |
| Trisodium Citrate, anhydrous-Buffering agent (w/w %) | 14.0% | 21.8% |

The particle size of the emitted dose was evaluated with two different techniques: emitted particle size distribution (ePSD) with laser diffraction and aerodynamic particle size distribution (APSD). The emitted particle size distribution (ePSD) was characterized by evaluating the particle size distribution of the particles emitted from the device using a Spraytec® (Malvern Panalytical, Worcestershire, UK) equipped with a 300-mm lens. Five devices were actuated by an actuation mechanism that moved the actuator at a rate of 70 mm/s, with the device exit being 4 cm from the laser. The percentage of particles lower than 10 μm was reported.

Aerodynamic particle size distribution (APSD) analysis was performed using a next generation impactor (NGI, Copley Scientific, UK) with coated cups (5% Tween 20 in Methanol % v/v) and attached to a glass expansion chamber at 15 L/min. The analysis was performed in triplicate with three UDS powder devices per NGI. The cumulative deposition (%) on stage 2 to 8, which corresponds to a cut-off of 14.10 μm, was reported.

Figure 14:
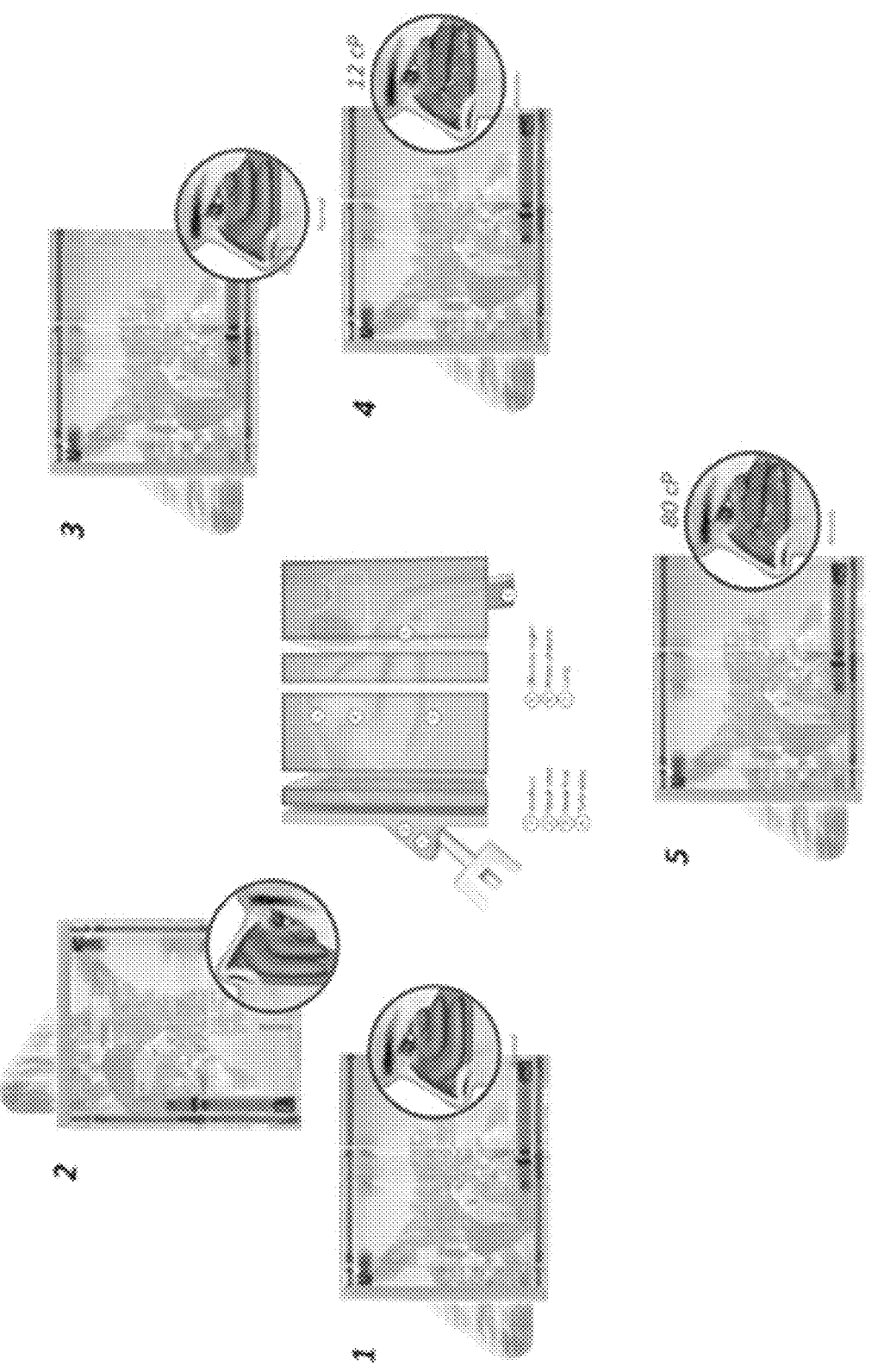
FIG. 14 is an illustration of the five nasal cast configurations tested.

The in vitro deposition was characterized in an adult male nasal cast (Aeronose™) with high performance liquid chromatography (HPLC) quantification. The nasal cast model used was designed from computed tomography images of a plastinated head model, which was previously validated as a predictive model for nasal aerosol deposition. FIG. 14 and Table 2 show and described the five different configurations that were evaluated with the nasal cast model. One device was manually actuated into both nostrils of the nasal cast with an accurately defined insertion depth of 10 mm, a delivery angle (horizontal plane) of 45° and a fixed angle from the center wall of 5°. For test configurations 1-3, which were not coated with different viscosity formulations, the nasal cast was humidified with water with a nebuliser (AMGH, DTF, France) for 10 min at 3 L/min (nebuliser output) to prevent powder bouncing. For test configurations 4 and 5, the nasal cast was coated with a mixture of glycerol/water at two different levels of viscosity to cover a wide range of nasal mucus viscosities (12 and 80 cP) by adding 50 mL of this mixture into the nasal cast; rotating in all directions for 5 min and draining any excess of liquid. The different regions of interest (vestibule and nasal valve, olfactory region, turbinates, and nasal floor, rhinopharynx and "lungs") were rinsed with different volumes of diluent. The analysis was performed in triplicate per configuration. Both NGI and nasal cast samples were then quantified by HPLC with a compendial method.

TABLE 2

| Nasal cast configurations tested. | | |
|---|---|---|
| Configuration | Simulated use | Laboratory Testing |
| Configuration 1 | Standard | Vertical nasal cast position without airflow |
| Configuration 2 | Patient lying on the floor | Horizontal nasal cast position without airflow |
| Configuration 3 | Inhalation | Vertical nasal cast position with 15 L/min |
| Configuration 4 | Rhinorrhea | Vertical nasal cast position coated with 12 cP solution |
| Configuration 5 | Rhinorrhea | Vertical nasal cast position coated with 80 cP solution |

Table 3 presents a comparison of the fraction of the smaller particles that could go into the lower respiratory tract with different techniques. When comparing ePSD and APSD, a 9% difference between the averages is observed. This difference can be attributed to intrinsic differences between both techniques, particularly regarding the different type of particle size that is evaluated for ePSD (geometric) and APSD (aerodynamic). When evaluating the nasal cast deposition, the percentage of epinephrine expected to reach the lower respiratory tract was on average between 0-1% without airflow (four different configurations) and 5% on average with 15 L/min.

TABLE 3

| Comparison of lower respiratory fraction with three different methods: ePSD, APSD and nasal cast configuration 3. | | |
|---|---|---|
| ePSD % of particles < 10 μm | APSD % of epinephrine < 14.10 μm | Nasal Cast % of epinephrine "lung" deposition |
| 10.3 ± 1.2% | 1.3 ± 0% | 5.4 ± 2% |

Figure 15:
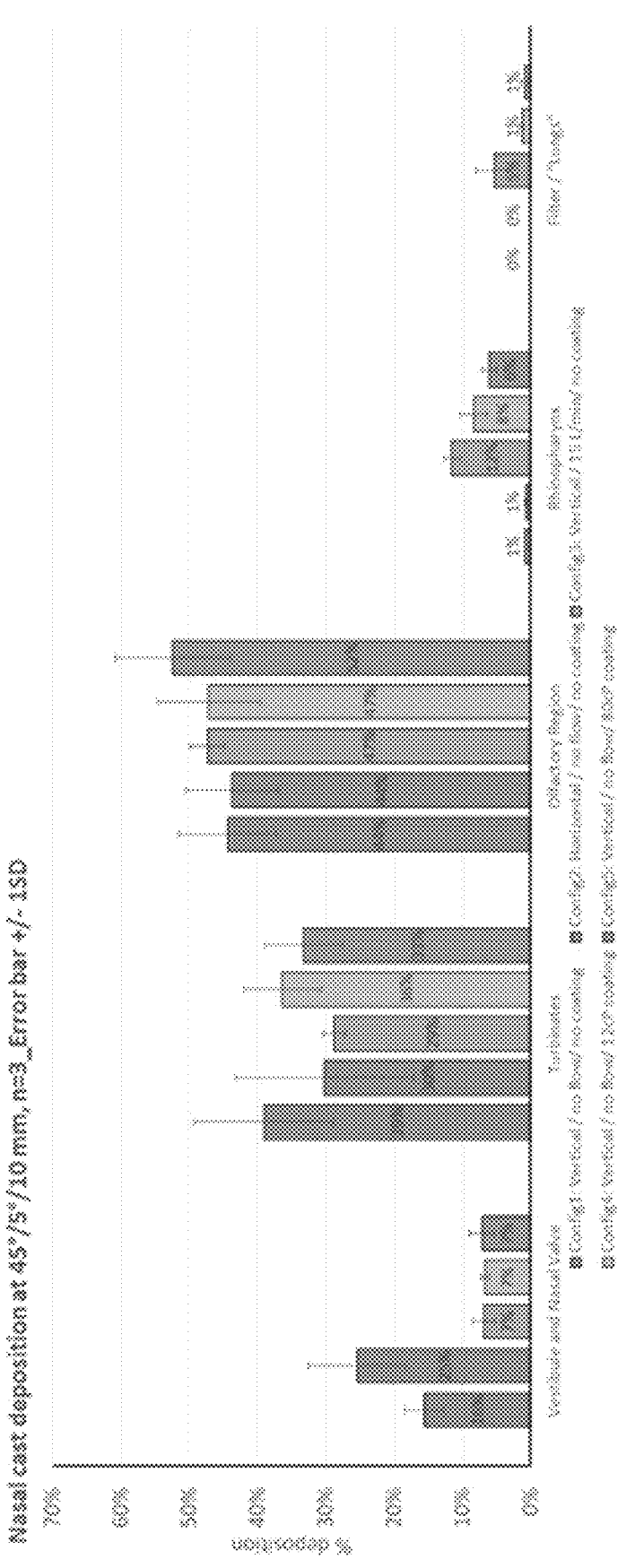
FIG. 15 is a plot showing nasal cast deposition percentage for testing performed with a nasal delivery device including a dry powder composition according to embodiment.

The simulated use in vitro nasal cast deposition data is presented in FIG. 15. When evaluating all the configurations, a stable deposition (74-84% on average) is observed for the main region of interest of systemic delivery, which corresponds to the upper, middle and lower turbinates (represented below as turbinates and olfactory region). The position (configuration 1 and 2) has limited impact on the regional deposition. When applying airflow or coating with different viscosity liquids, a slight reduction of deposition in the vestibule and nasal valve and an increase on deposition in the rhinopharynx and "lungs" is observed. Specifically, the percentage of epinephrine expected to reach the lower respiratory tract was on average between 0-1% without airflow (four different configurations) and 5% on average with 15 L/min (simulated respiratory airflow). The deposition in the lower respiratory tract remains negligible for all configurations. Thus, this study shows that regional deposition is not expected to be greatly impacted by factors such as position (vertical vs horizontal), airflow, and variations in mucus simulants viscosity simulating rhinitis.

Nasal Cast and Particle Size Studies—Part 2

An additional study was performed to evaluate the performance of two epinephrine formulations to determine if their differences in bulk particle size distribution (bPSD) would impact the emitted particle size distribution (ePSD), as well to evaluate the deposition pattern in an Alberta Idealized Nasal Inlet (AINI) model. Secondarily, the effect of drum vacuum pressure used during device filling on ePSD was also assessed.

The tests were conducted using a unit dose powder device similar to the device 100 described above, filled with 17.5 mg of a dry powder epinephrine composition. Specifically, the dry powder epinephrine compositions for this test are provided in Table 4 below:

TABLE 4

| Dry powder epinephrine compositions tested. | | |
|---|---|---|
| | SD1 | SD2 |
| Epinephrine (freebase) (w/w %) | 20% | 15% |
| Epinephrine Bitartrate (w/w %) | 35.1% | 27.3% |
| Lactose Monohydrate-Carrier (w/w %) | 50.9% | 50.9% |
| Trisodium Citrate, anhydrous-Buffering agent (w/w %) | 14.0% | 21.8% |
| Moisture (w/w %) | 5.7% | 5.3% |
| bPSD (laser diffraction) | | |
| Dv(10) (μm) | 1.8 | 4.6 |
| Dv(50) (μm) | 5.3 | 17.9 |
| Dv(90) (μm) | 13.4 | 42.1 |

Various methods were evaluated for the filling of the devices. Namely, SD1 was filled using the Mettler Toledo Quantos Filler, equipped with QH012-LNMP dosing head and target fill weight of 17.5 mg±3%. SD-2 powder was filled using a tabletop drum filler (Harro Hoefliger, Allmersbach im Tal, Germany) equipped with a 15 mm3 pore size drum at blowout pressure of 400 mbar and vacuum pressure of 200 mbar (low vacuum) or 600 mbar (high vacuum).

Emitted particle size distribution (ePSD) was measured upon actuation of the devices. The analysis was performed using the Malvern Spraytec laser diffraction system (Malvern Panalytical, Malvern, UK). Parameters for analysis included 150.0 ms rapid measurement at a 1 kHz acquisition rate. Transmission (%), Dv10 (μm), Dv50 (μm), Dv90 (μm), %<10 μm (%), and Span were measured. The Proveris NSx (Proveris Scientific, Hudson, MA, USA) was utilized as an automatic actuation station. Each actuation consisted of a 12 mm stroke length, 70 mm/sec velocity, 5000 mm/sec^2 acceleration, and a symmetric actuation profile.

For the AINI nasal cast, a coating solution was prepared by combining 60 g of Brij-35 and 400 mL of ethanol. The solution was mixed until completely dissolved. 100 g of glycerol was added to the Brij-35 solution and then was mixed until a clear solution was obtained. The surfaces of the individual stages of the AINI were coated using a transfer pipet. Excess solution was drained off into waste. The AINI model was assembled, and 25 mL of coating solution was poured into the assembly. Both ends of the AINI were covered with parafilm and the AINI was gently rocked to coat the interior surfaces. The parafilm was removed and excess coating solution was drained from the AINI. The disassembled stages of the AINI were allowed to dry under ambient conditions. The AINI was re-assembled for testing.

The nasal stage deposition of SD1 and SD2 by AINI was performed in triplicate. Briefly, the coated AINI in vertical position was placed on a fast-screening impactor (FSI) (MSP, MN, USA) which is composed of a pre-separator and glass fiber filter. The nozzle of the device was positioned approximately 1 cm into the nostril at a 45° angle. A continuous flow rate of 7.5 L/min using a TPK flow controller and vacuum source was utilized for drug product testing. Extraction of the nostril, olfactory and turbinates sections of the AINI was performed using 10 mL of diluent. The nasopharynx was extracted with 10 mL of diluent via inverted shaking due to parafilmed ends. The pre-separator section of the FSI was extracted with 10 mL of diluent, while the filter of the FSI was extracted with 5 mL of diluent in a petri dish via orbital shaking (120 rpm, 3 minutes). The extracted drug product solution was vialed and analyzed for epinephrine content via HPLC.

Figure 16:
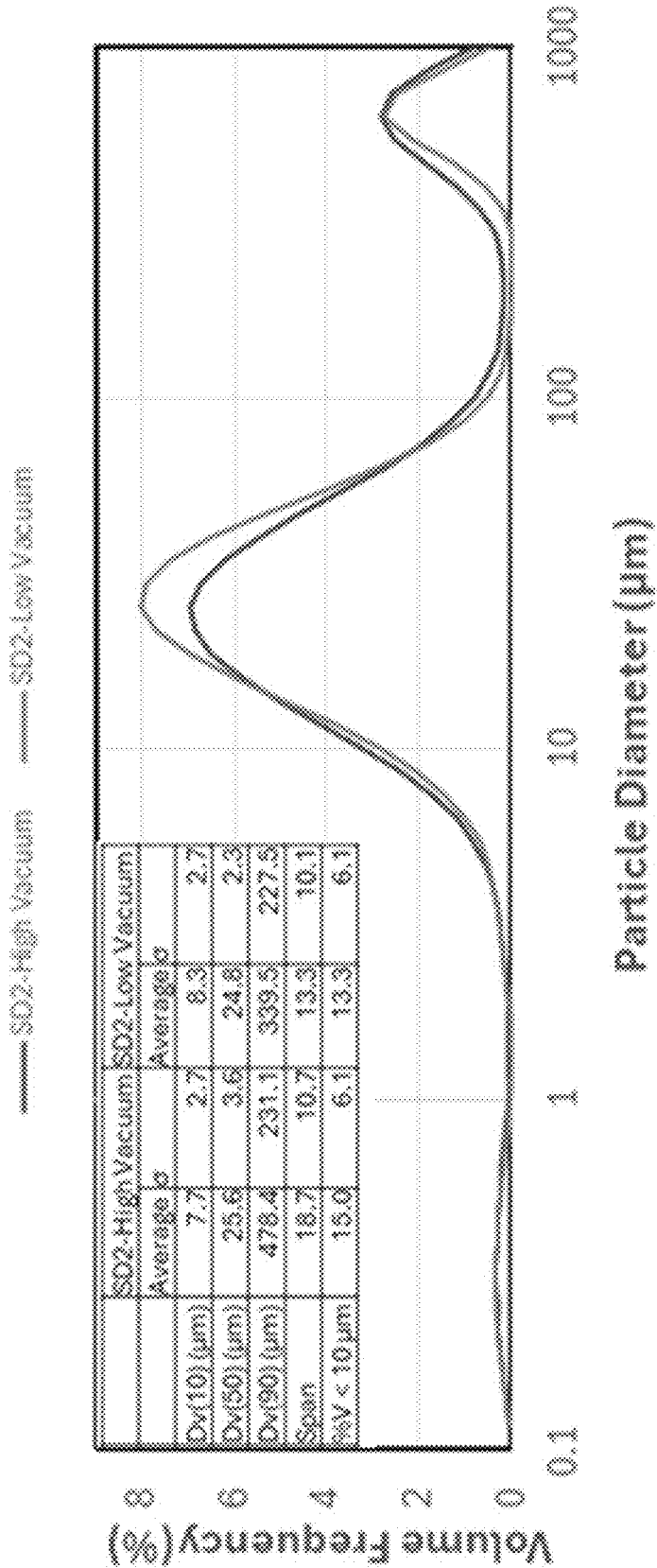
FIG. 16 is a plot showing the mean particle size distribution (n=3) of emitted SD2 powders, under low and high vacuum drum filling, emitted from a nasal delivery device according to an embodiment.

To assess the effect on device filling parameters, namely the vacuum level during drum filling, two vacuum levels were applied. These are represented as SD2-Low Vacuum and SD2-High Vacuum. Drum vacuum is necessary to control the filling weight during a drum filling unit operation, however, it is feasible that this vacuum could result in powder compression and changes in aerosol performance. In theory, a higher vacuum could lead to larger ePSD due to powder compaction. This was tested experimentally using laser diffraction to determine the emitted particle size distribution as seen in FIG. 16. The vacuum level does seem to moderately, although not statistically (p value >0.05), affect the emitted particle size distribution, as revealed by the increase in Dv50 and Dv90 by ~1.03 and 1.41-fold. These results verify the assumption that higher vacuum level during the filling operation increases the aggregation tendencies of the powder post-actuation.

Figure 17:
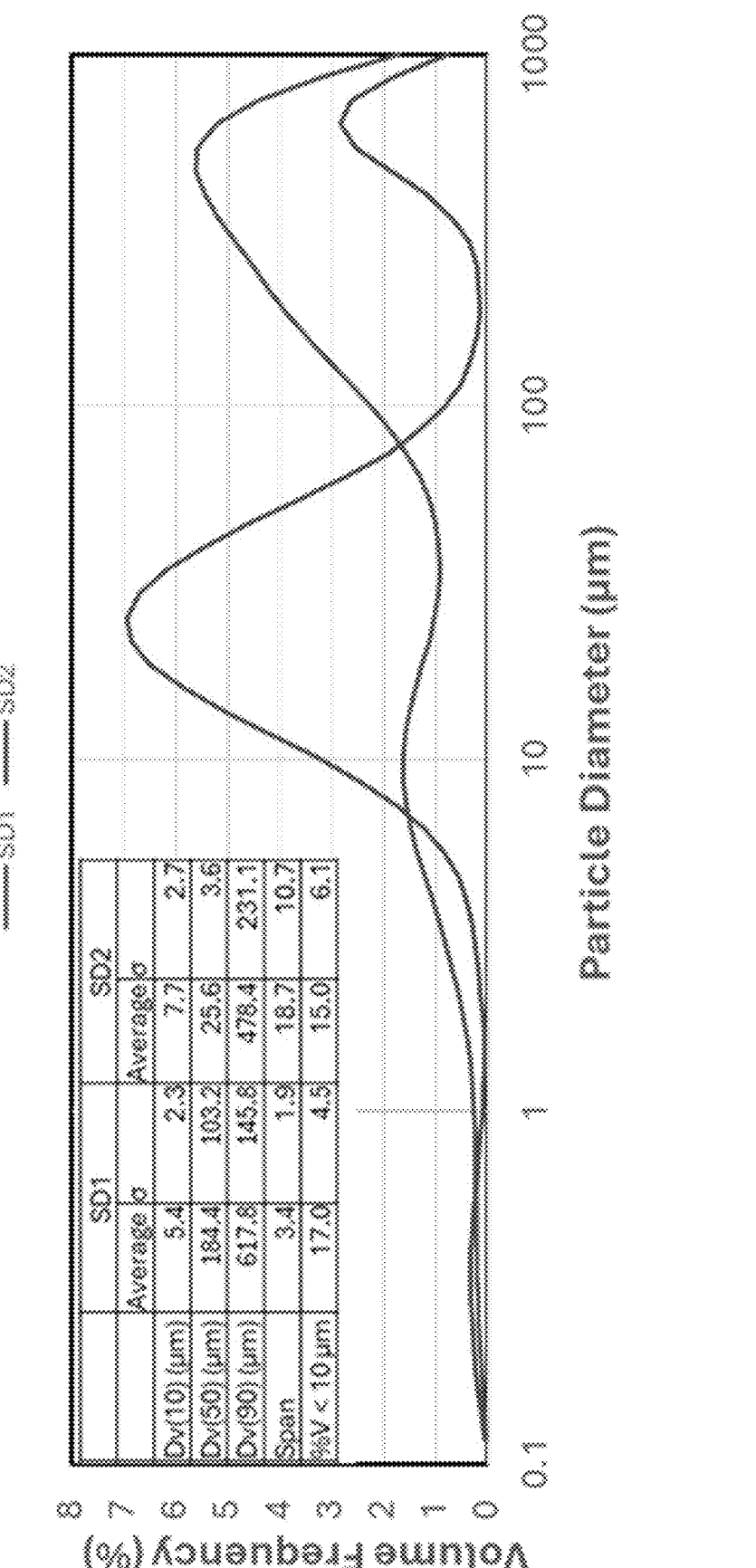
FIG. 17 is a plot showing the mean particle size distribution (n=3) of emitted powder (SD1 and SD2) from a nasal delivery device according to an embodiment.

FIG. 17 shows results of laser diffraction performed to assess the effect of different bPSD of SD1 and SD2 on ePSD. A statistical difference (p<0.05) was observed in the ePSD of the two formulations. Specifically, bulk PSD Dv50 of SD2 is more than 3-fold larger than that of SD1. However, following actuation the emitted PSD Dv50 of SD1 is 7.2-fold larger than SD2.

Figure 18:
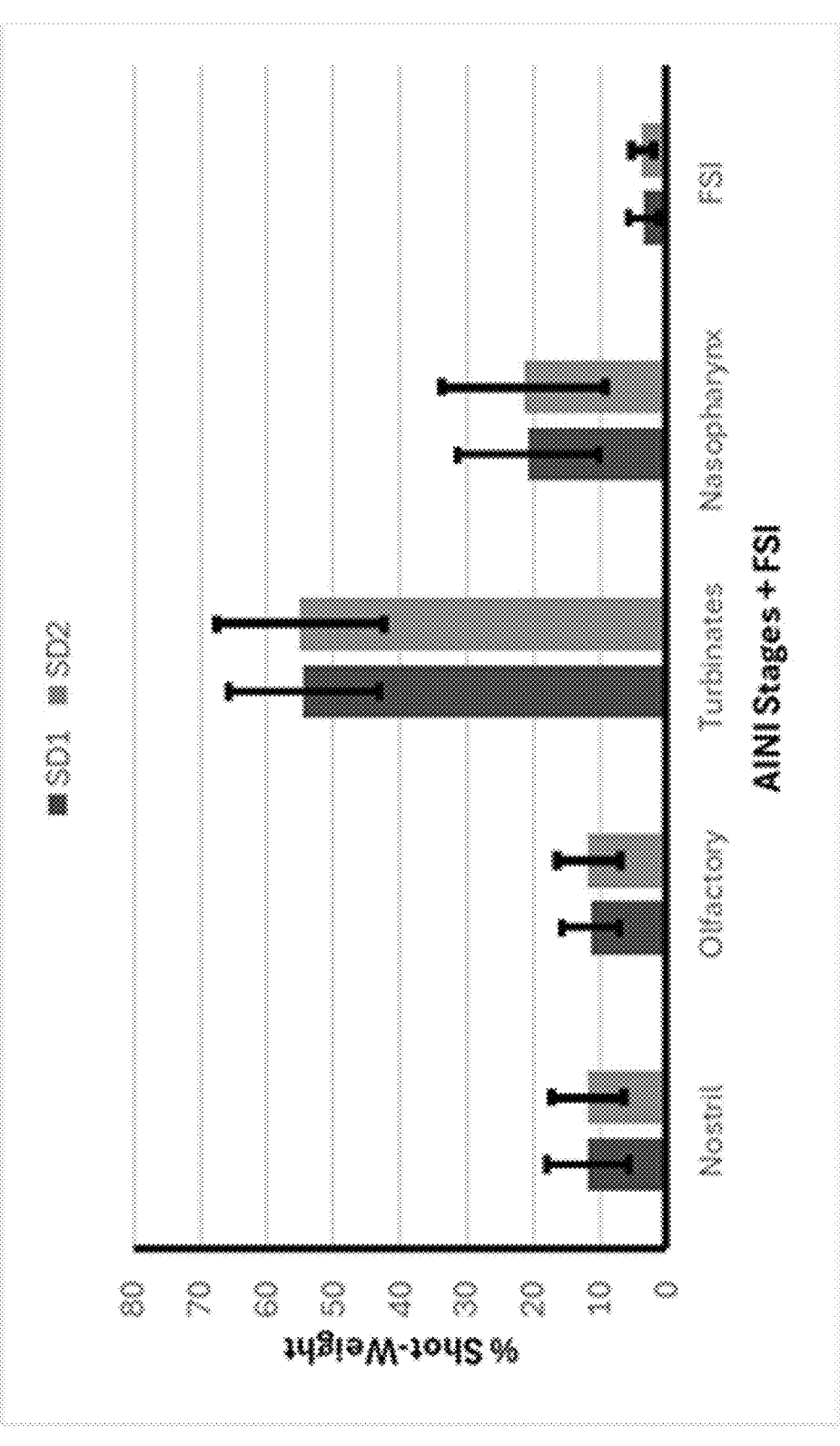
FIG. 18 is a plot showing deposition comparison in the Alberta Idealized Nasal Inlet for two dry powder compositions (SD1 and SD2), according to an embodiment.

As shown in FIG. 18, however, despite distinctly different profiles post-actuation, AINI stage deposition was surprisingly similar. FIG. 18 shows the AINI stages including the FSI plotted as a function of % of Shot Weight. As shown, the nasal deposition is statistically insignificant (p>0.05) across each assessment stage for SD1 and SD2. These results reveal that even though the bPSD and the ePSD is different, the AINI deposition is quite similar with few particles navigating past the nasopharynx. Additionally, while emitted powders of both formations have large fractions less than 10 μm in size (17 and 15% for SD1 and SD2 respectively), this did not translate into high levels of FSI deposition. For the powders tested, the deposition was limited to <5%, which indicates minimal deposition into the lungs.

Human Phase 1 Results

The pharmacokinetics (PK), relative and comparative bioavailability, safety, and tolerability of dry powder formulations of epinephrine at two different doses were determined during a Phase 1 clinical study. Epinephrine administered by the intramuscular (IM) route was used as a comparator. The dose formulation, designated as BBP01 in the study, was a combination of epinephrine, lactose as the carrier, and trisodium citrate as the stabilizing agent. Twelve human subjects participated in the open-label, single sequence crossover study. The subjects received all treatments in order, with a washout period of at least 72 hours between each treatment dose, wherein Treatment A was the 3.5 mg intranasal (IN) epinephrine formulation, Treatment B was the 0.3 mg epinephrine IM formulation, Treatment C was the 0.5 mg epinephrine IM formulation, and Treatment D was the 5.5 mg intranasal epinephrine formulation. The subjects returned for a safety follow up visit 3 to 5 days after the final treatment. One subject was excluded from the analysis set as a result of the subject having significantly higher maximum observed concentration (Cmax) values in comparison to the other subjects in Treatment B and C. Nor did the subject participate in Treatment D.

Figure 19:
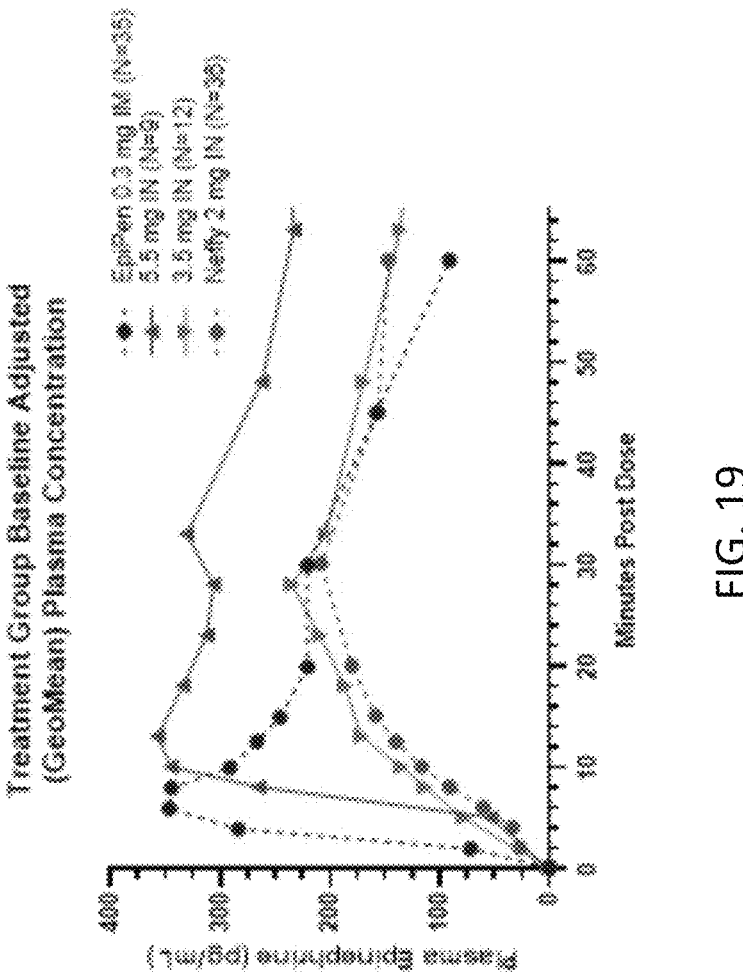
FIG. 19 illustrates cross-study comparisons of mean baseline adjusted plasma epinephrine concentrations.

FIG. 19 illustrates cross-study comparisons of mean baseline adjusted plasma epinephrine concentrations, wherein the pharmacokinetics of the epinephrine drug products described herein, 3.5 mg IN and 5.5 mg IN, are bracketed between a first reference dose, 0.3 mg IM (i.e., intramuscular injection via a manual syringe) and a second reference dose, EpiPen 0.3 mg (i.e., intramuscular injection via an autoinjector).

FIG. 20 is a table summarizing the four treatment dosages in humans.

The dry powder formulation was administered via intranasal instillation once using a nasal device (APTAR). The IM solution and materials were supplied by the study site and prepared according to the local procedures. The study drug was administered at approximately the same time on each treatment day. There was a washout period of 20 days between the nasal doses administered as treatment A and treatment D. The subjects were admitted to the clinical site the day before each treatment administration and remained on site until at least 8 hours post-dose, or when applicable, until 24 hours post-dose of the specific treatment period. The study drug was administered after at least a 10 hour fast. A standardized meal was provided approximately 4 hours after dosing.

Blood samples were collected prior to dosing at 60, 30, and 0 minutes before dosing, and after dosing at 2, 5, 7, 10, 15, 20, 25, 30, 45, 60, 90, 120, 180, 240, and 360 minutes. Vital signs, ECGs, and cardiac telemetry were obtained throughout the treatment period. Blood samples were analyzed in 8 runs with between run accuracy of −3.66% to 4.02% and precision of 1.30% to 9.94%. The calibration curve range of the bioanalytical method was from 10 to 10000 pg/mL. Recovery was >75% and freeze-thaw, short-term and long-term stability (584 days) were all shown to be acceptable; the analyte was stable under all conditions tested.

The performance of the analytical method was successfully demonstrated during the validation and study sample analyses. Reported values for the study samples were determined to be reliable.

Noncompartmental analysis was performed on individual human subject plasma concentration-time data using nominal doses and actual blood sampling times. Uncorrected plasma epinephrine concentration-time data and/or baseline-corrected data were used. Baseline correction was accomplished using the average of the measured concentrations at nominal times of −60, −30, and 0 minutes before dosing.

Pharmacokinetic analyses were performed using the standard PK analysis software package PHOENIX® WinNonlin version 8.4.

Heart rate and blood pressure measurements were made at the following times: at approximately 57 minutes pre-dose, and at 8, 13, 23, 33, 48, 63, 93, 123, 183, 243, and 363 minutes after dosing. The results at 363 minutes after dosing were deemed unreliable since subjects were not restricted to activities at that time. Analysis was conducted using change from baseline values for each individual subject.

Statistical analysis of comparative bioavailability data was conducted using a standard bioequivalence approach to determine 90% confidence intervals for the ratio of the test to reference formulations.

The PK population consists of all human subjects who provided sufficient PK samples for a given treatment to allow for adequate determination of PK parameters of interest.

Figure 21:
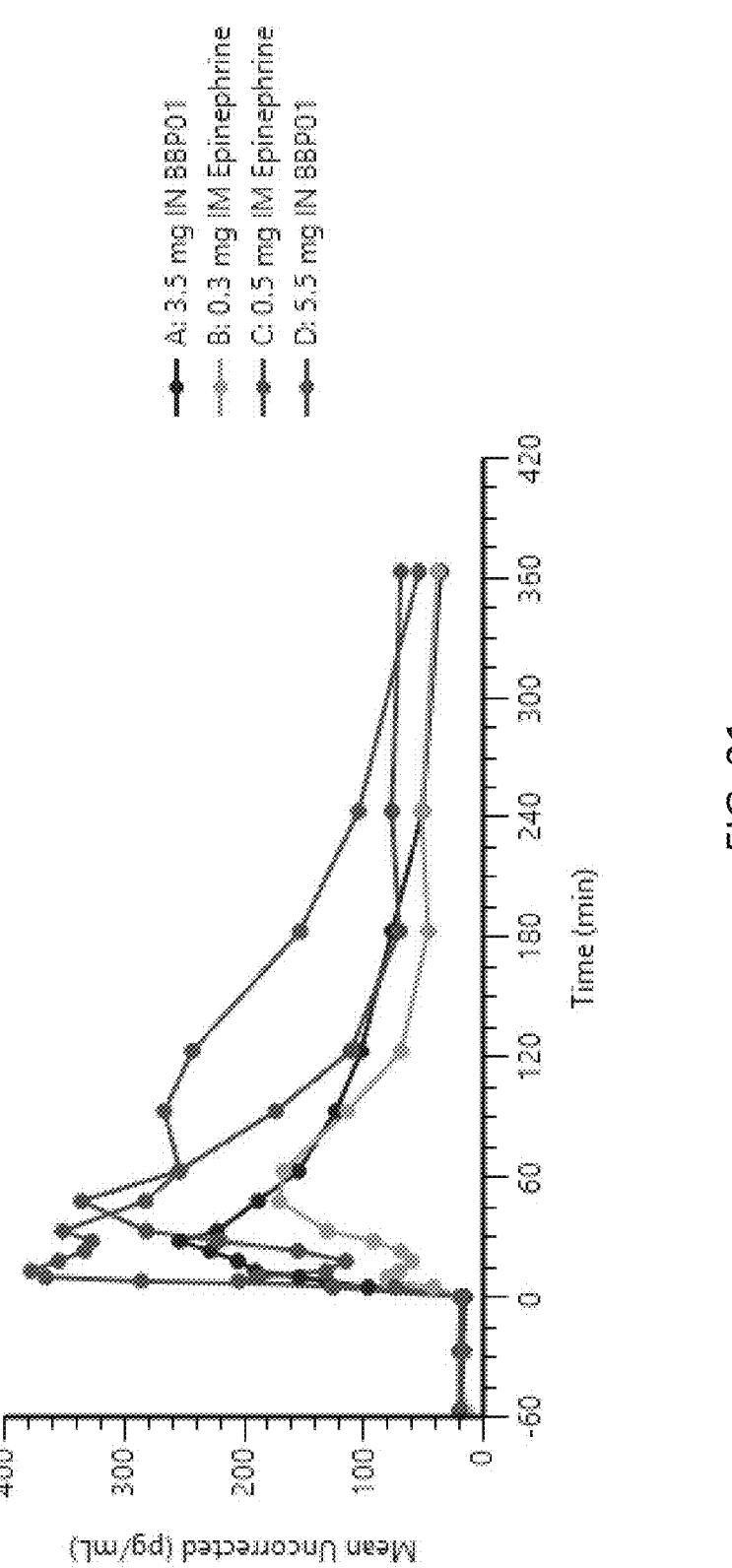
FIG. 21 illustrates a graph of mean uncorrected epinephrine concentration-time data in humans by treatment with linear axes.

FIG. 21 illustrates a graph of mean uncorrected epinephrine concentration-time data in humans by treatment with linear axes.

Figure 22:
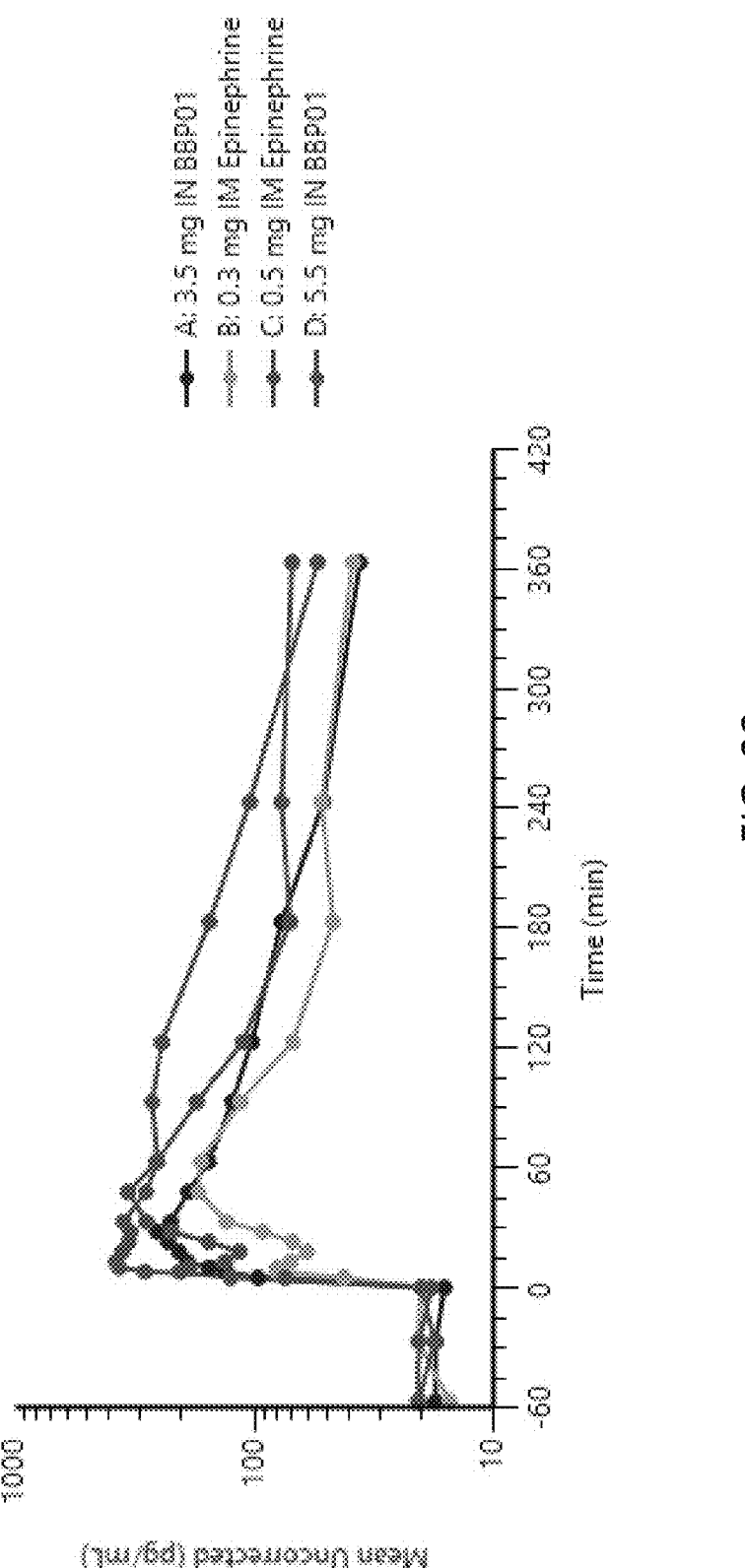
FIG. 22 illustrates a graph of mean uncorrected epinephrine concentration-time data in humans by treatment with log-linear axes.

FIG. 22 illustrates a graph of mean uncorrected epinephrine concentration-time data in humans by treatment with log-linear axes.

Figure 23:
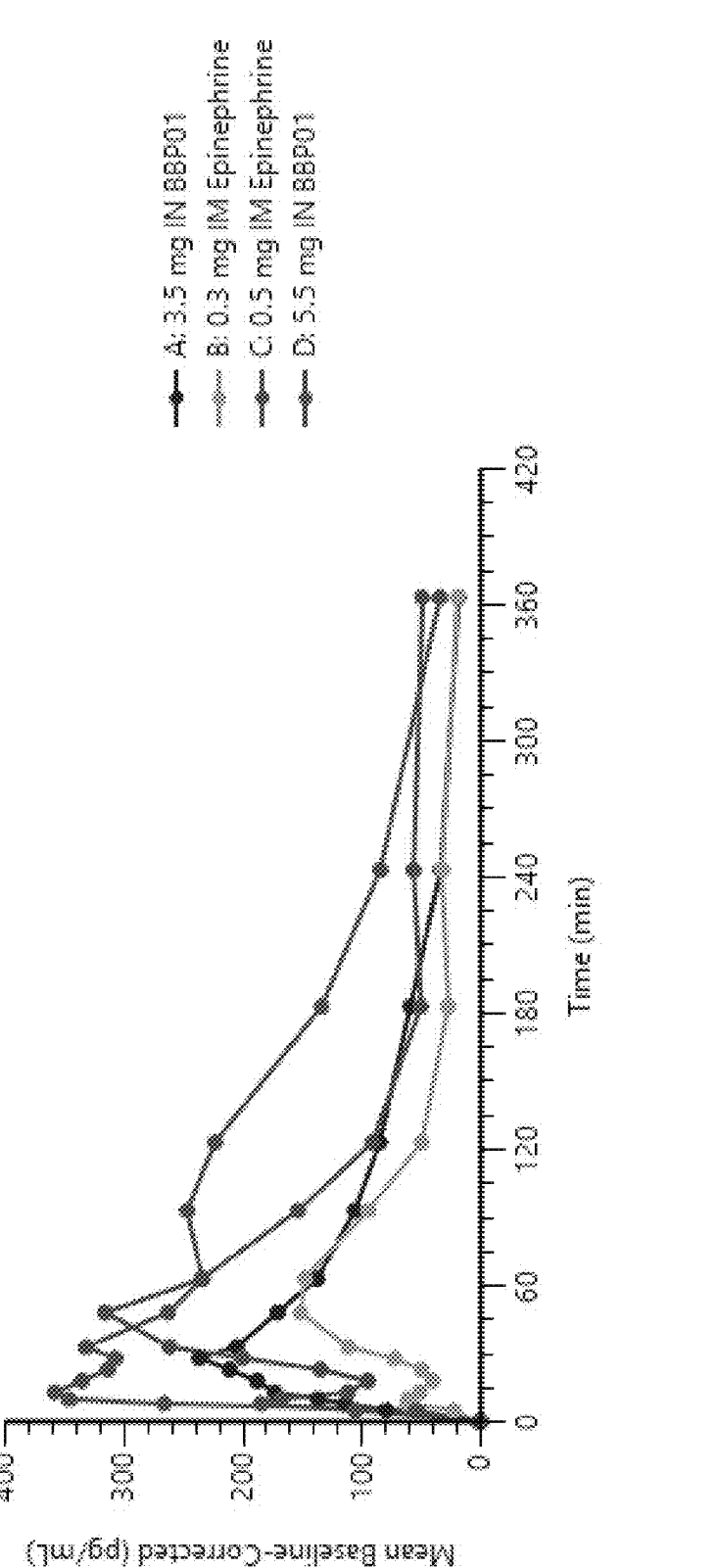
FIG. 23 illustrates a graph of mean baseline-corrected epinephrine concentration-time data in humans by treatment with linear axes.

FIG. 23 illustrates a graph of mean baseline-corrected epinephrine concentration-time data in humans by treatment with linear axes.

Figure 24:
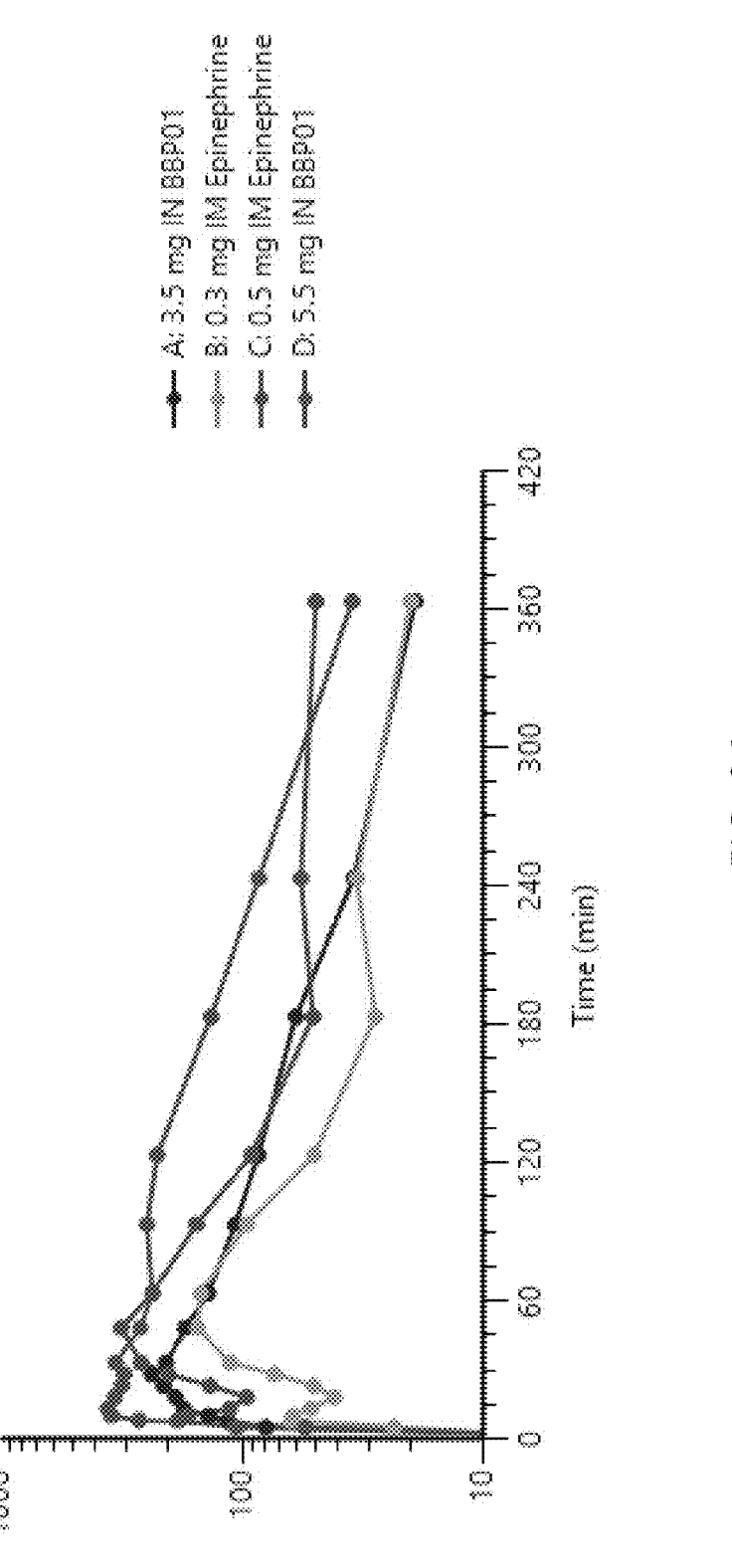
FIG. 24 illustrates a graph of mean baseline-corrected epinephrine concentration-time data in humans by treatment with log-linear axes.

FIG. 24 illustrates a graph of mean baseline-corrected epinephrine concentration-time data in humans by treatment with log-linear axes.

When data from both IN and IM administration was compared, a single peak following IN (mean Cmax) occurred at approximately the same time as the first observed peak from IM administration. This pattern is present in both uncorrected and baseline-corrected concentration-time data. However, the magnitude of the IN Cmax far exceeded the first IM Cmax. On average, the second IM Cmax occurred approximately 45 minutes after dosing and was greater than the first IM peak, but lower than the single IN BBP01 Cmax.

Cmax values for both the IN and IM formulations increased when the dose increased, but in both cases, the mean Cmax was greater for IN BBP01. The mean baseline corrected Cmax values for 3.5 mg and 5.5 mg IN BBP01 were 291 and 462 pg/mL, respectively. For 0.3 mg and 0.5 mg IM epinephrine, the mean baseline-corrected Cmax values were 184 and 396 pg/mL, respectively.

Graphs of the uncorrected epinephrine concentration-time data for individual subjects are depicted in FIGS. 25-28, and graphs of the baseline-corrected epinephrine concentration-time data for the individual subjects are depicted in FIGS. 29-32.

FIG. 33A is a table of individual subject uncorrected plasma epinephrine concentrations with summary statistics in Treatment A from −57-23 minutes. FIG. 33B is a table of individual subject uncorrected plasma epinephrine concentrations with summary statistics in Treatment A from 28-363 minutes.

FIG. 34A is a table of individual subject uncorrected plasma epinephrine concentrations with summary statistics in Treatment B from −57-23 minutes. FIG. 34B is a table of individual subject uncorrected plasma epinephrine concentrations with summary statistics in Treatment B from 28-363 minutes.

FIG. 35A is a table of individual subject uncorrected plasma epinephrine concentrations with summary statistics in Treatment C from −57-23 minutes. FIG. 35B is a table of individual subject uncorrected plasma epinephrine concentrations with summary statistics in Treatment C from 28-363 minutes.

FIG. 36A is a table of individual subject uncorrected plasma epinephrine concentrations with summary statistics in Treatment D from −57-23 minutes. FIG. 36B is a table of individual subject uncorrected plasma epinephrine concentrations with summary statistics in Treatment D from 28-363 minutes.

FIG. 37A is a table of individual subject baseline-corrected plasma epinephrine concentrations with summary statistics in Treatment A from 0-28 minutes. FIG. 37B is a table of individual subject baseline-corrected plasma epinephrine concentrations with summary statistics in Treatment A from 33-363 minutes.

FIG. 38A is a table of individual subject baseline-corrected plasma epinephrine concentrations with summary statistics in Treatment B from 0-28 minutes. FIG. 38B is a table of individual subject baseline-corrected plasma epinephrine concentrations with summary statistics in Treatment B from 33-363 minutes.

FIG. 39A is a table of individual subject baseline-corrected plasma epinephrine concentrations with summary statistics in Treatment C from 0-28 minutes. FIG. 39B is a table of individual subject baseline-corrected plasma epinephrine concentrations with summary statistics in Treatment C from 33-363 minutes.

FIG. 40A is a table of individual subject baseline-corrected plasma epinephrine concentrations with summary statistics in Treatment D from 0-28 minutes. FIG. 40B is a table of individual subject baseline-corrected plasma epinephrine concentrations with summary statistics in Treatment D from 33-363 minutes.

To account for endogenous concentrations of epinephrine, baseline-corrected epinephrine concentrations were calculated by averaging the 3 pre-dose concentrations at −72, −27, and 0 minutes. As shown in FIGS. 156A-163B, this approach was substantiated with the data as the mean baseline concentrations were very stable between pre-dose blood sampling times and treatments. Circulating epinephrine concentrations display a diurnal pattern and can be affected by external stimuli such as phobia of needles. Because circulating epinephrine is highly variable both intra and intersubject, the between-subject variability (CV %) in epinephrine plasma concentrations was typically greater than 40%, especially at early sampling times soon after dosing.

Figure 41:
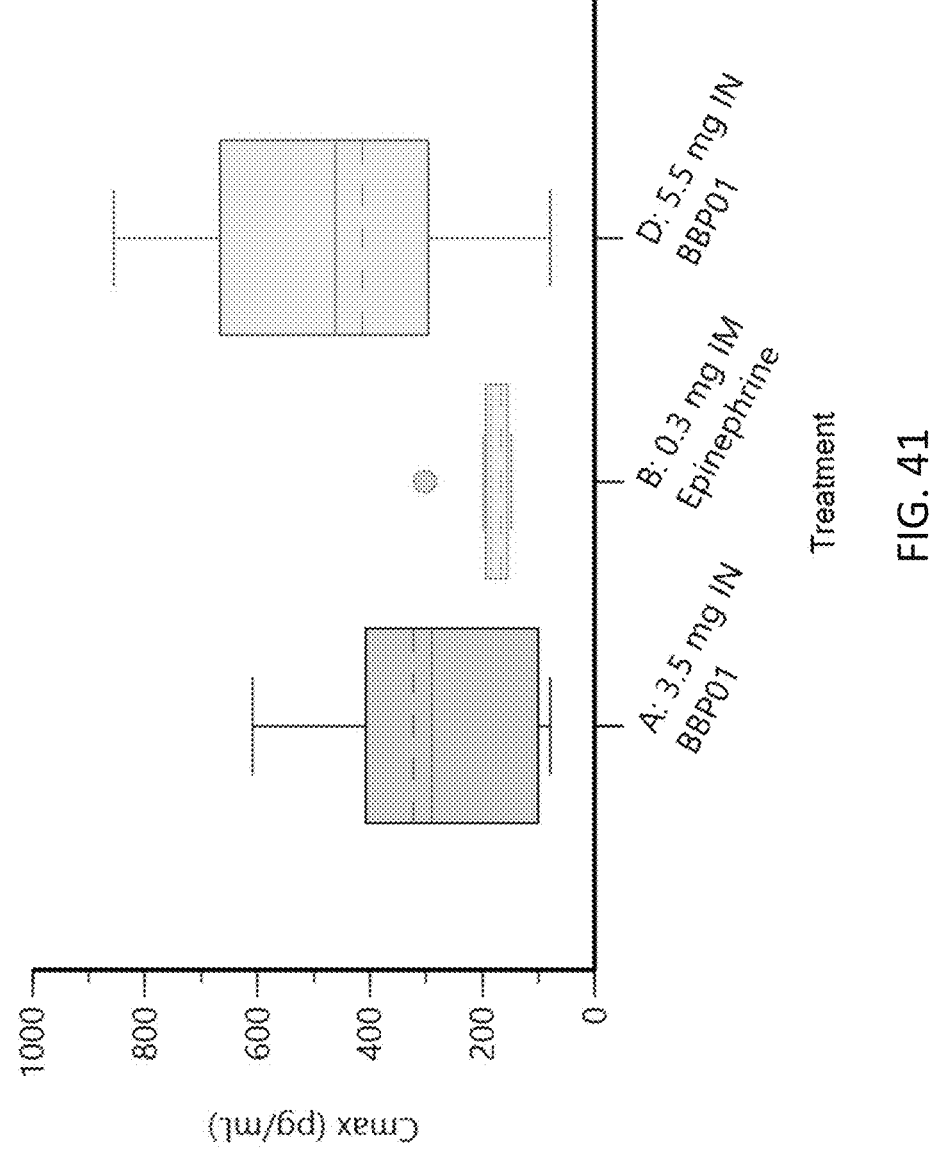
FIG. 41 illustrates a box plot of Cmax values by treatment in humans.

FIG. 41 is a box plot of Cmax values by treatment.

Figure 42:
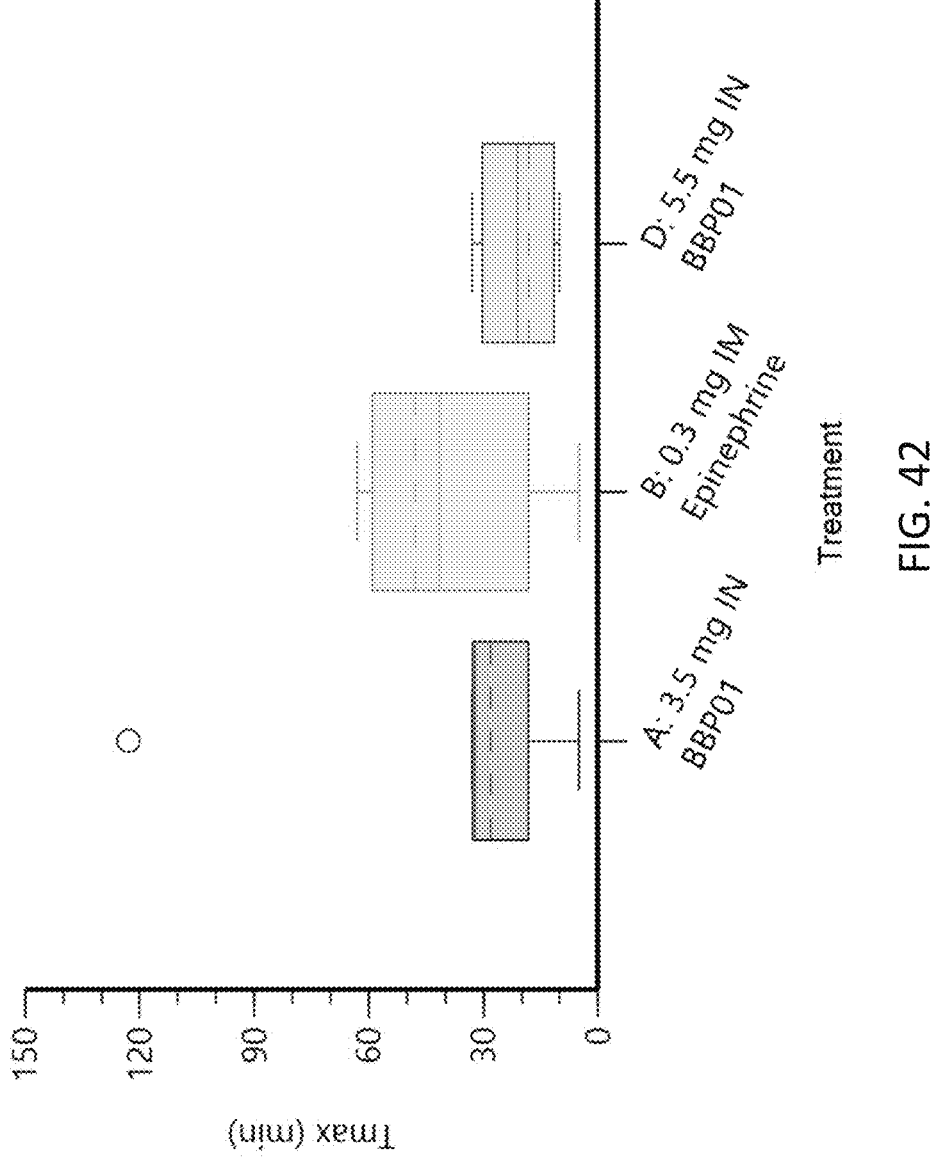
FIG. 42 illustrates a box plot of Tmax values by treatment in humans.

FIG. 42 is a box plot of Tmax values by treatment.

The median Tmax values were 28 and 18 minutes for IN BBP01 and 48 and 48 minutes for IM epinephrine.

The mean terminal phase half-life (t½) following 3.5 mg IN BBP01 administration was 89.5 minutes and for 5.5 IN BBP01, the t½ averaged 118 minutes. Due to the protracted absorption of epinephrine from the IM injection site, there was no true terminal phase for the disposition of the drug, consequently half-lives could not be reliably estimated.

FIGS. 43-46 are summary tables of noncompartmental pharmacokinetic parameters for uncorrected plasma epinephrine for each treatment.

FIGS. 47-50 are summary tables of noncompartmental pharmacokinetic parameters for baseline-corrected plasma epinephrine for each treatment.

Figure 51:
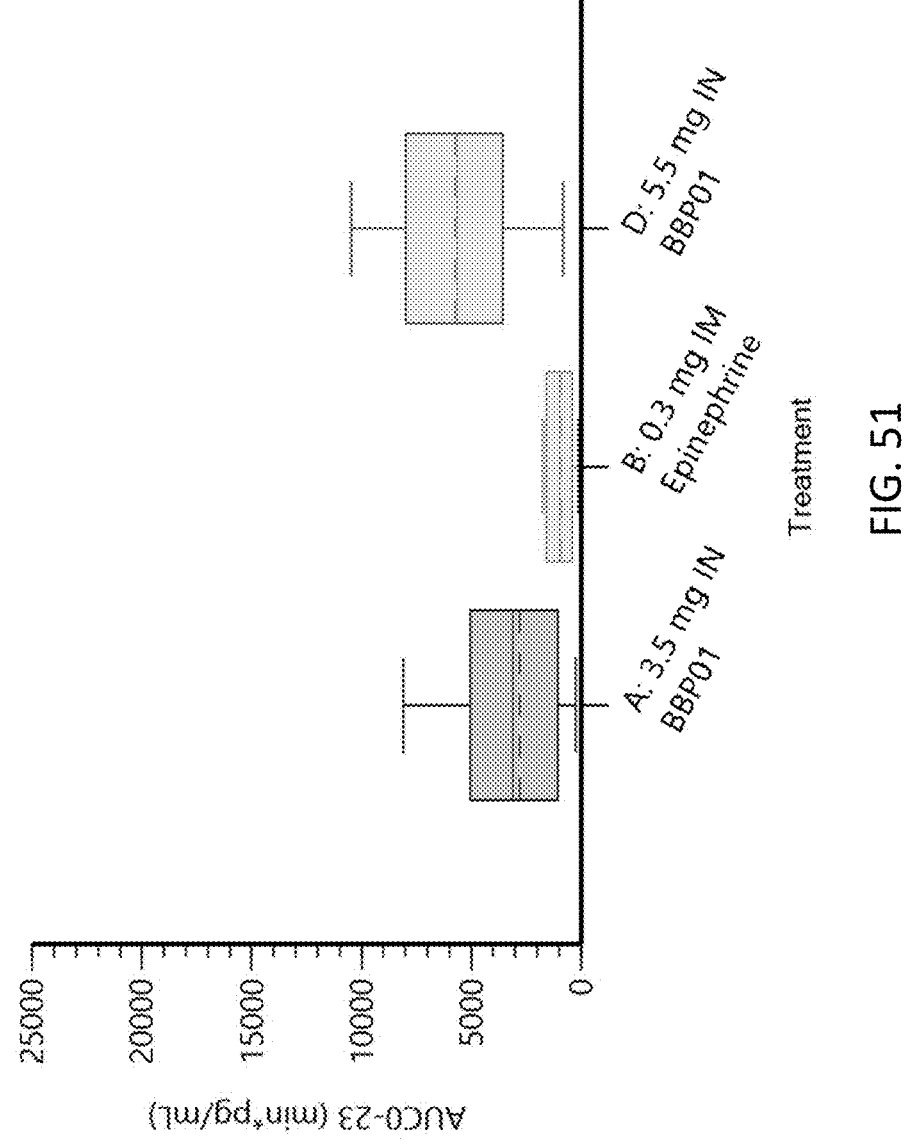
FIG. 51 illustrates a box plot of AUC0-23 values by treatment in humans.
Figure 52:
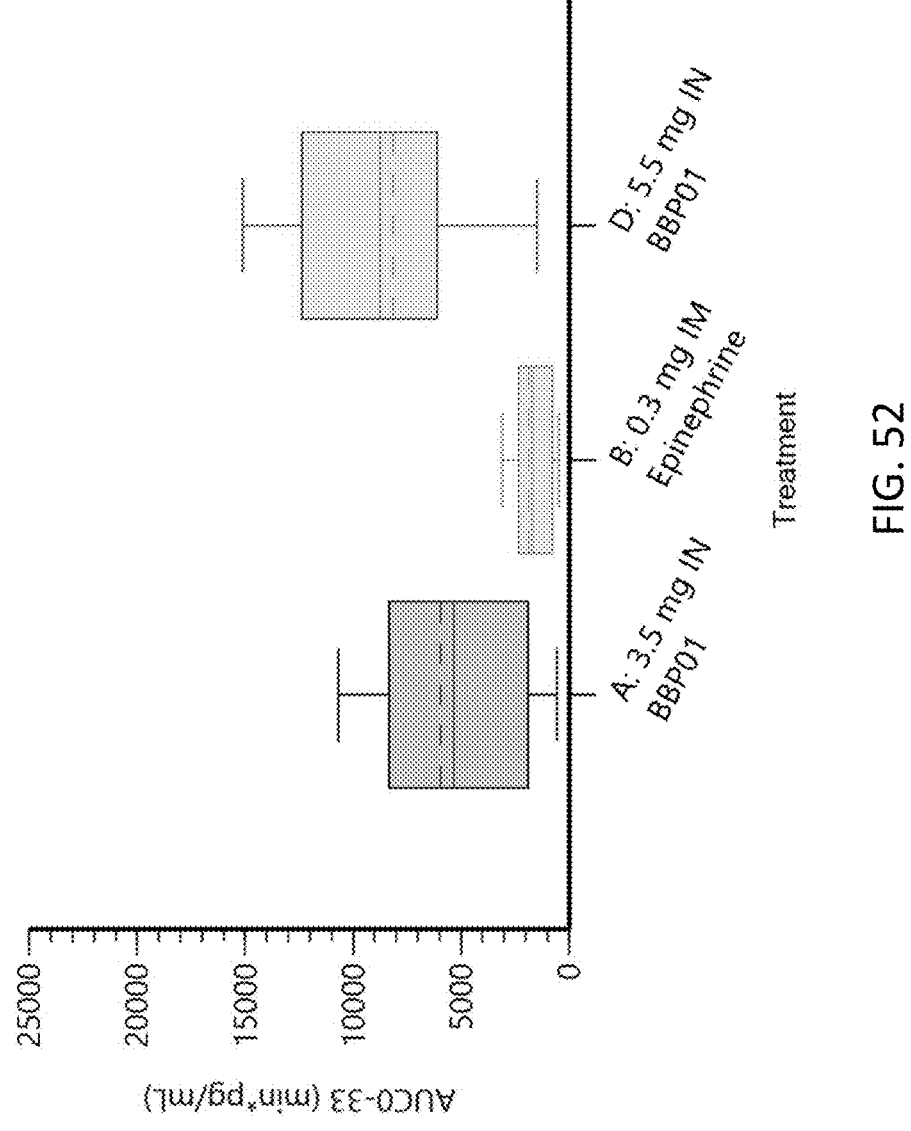
FIG. 52 illustrates a box plot of AUC0-33 values by treatment in humans.
Figure 53:
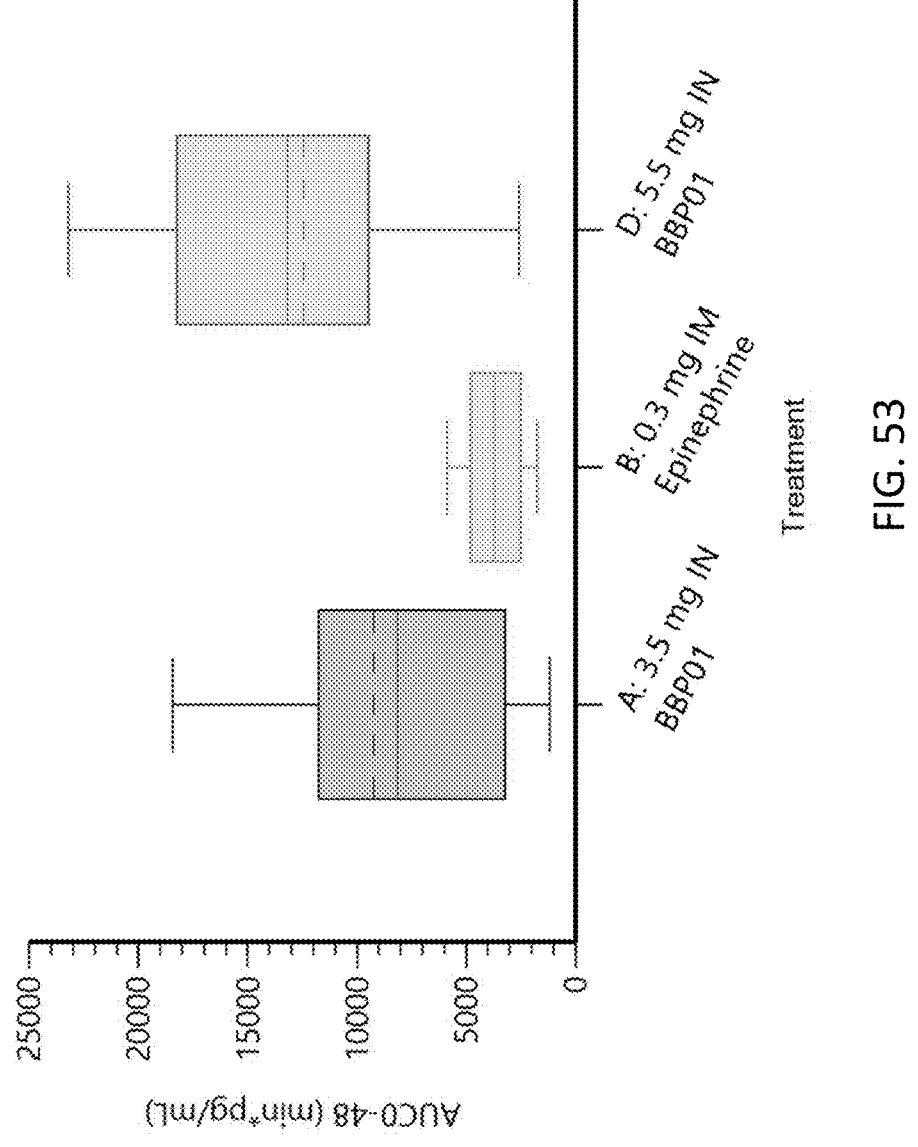
FIG. 53 illustrates a box plot of AUC0-48 values by treatment in humans.
Figure 54:
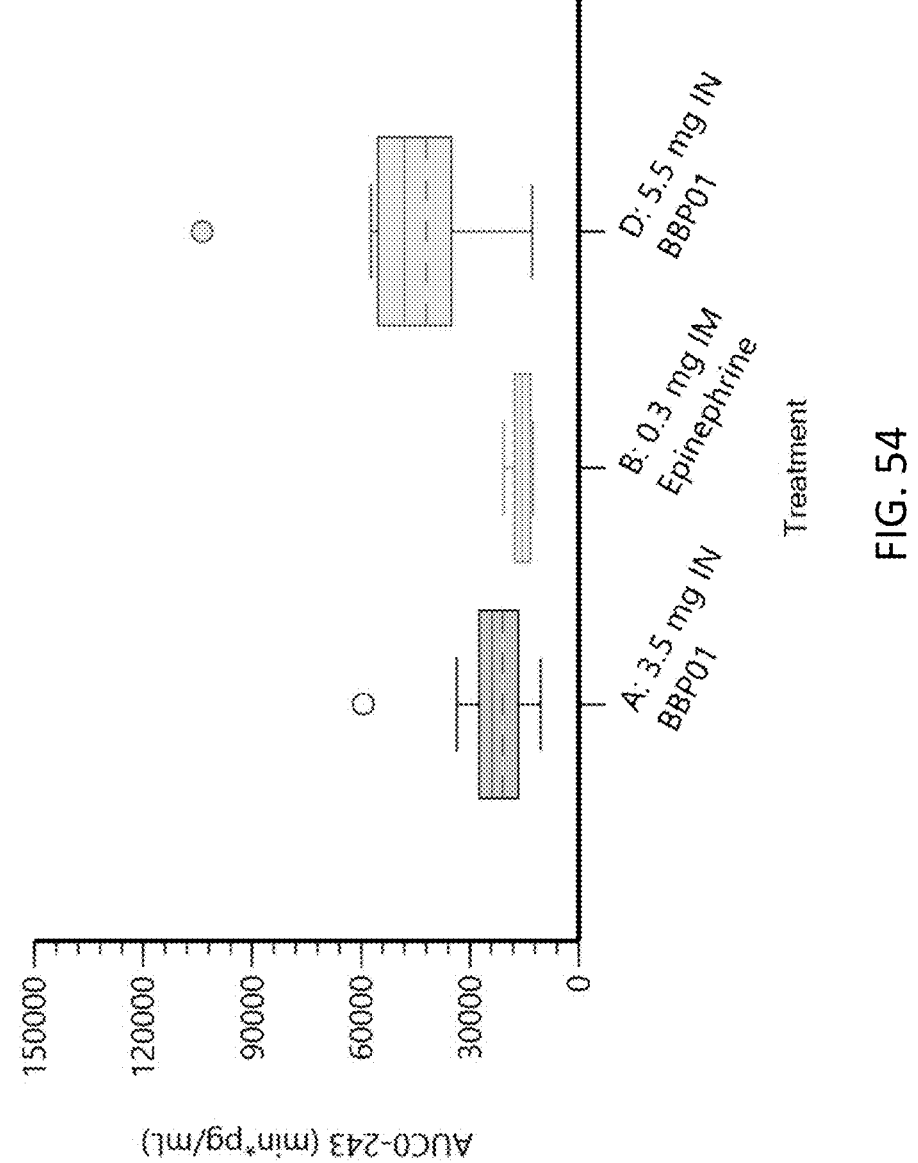
FIG. 54 illustrates a box plot of AUC0-243 values by treatment in humans.
Figure 55:
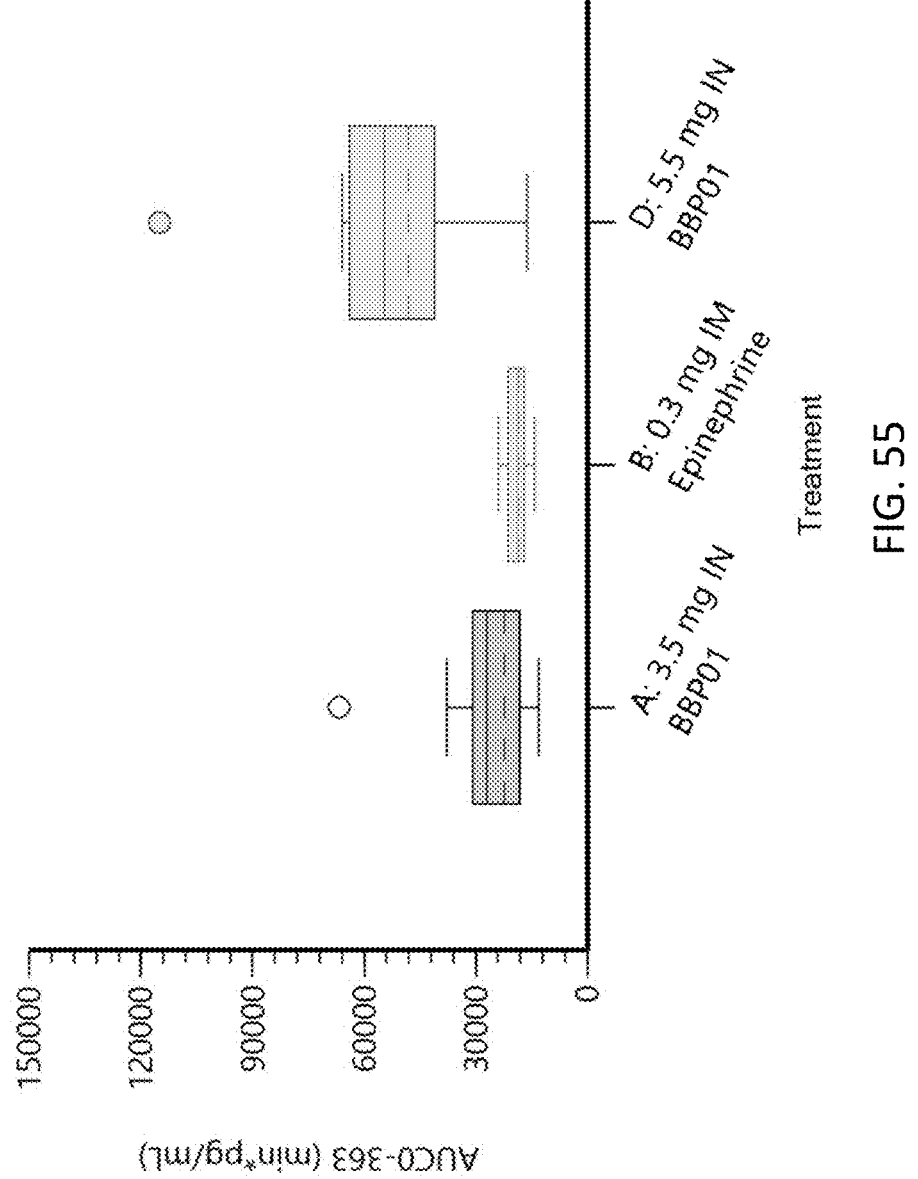
FIG. 55 illustrates a box plot of AUC0-363 values by treatment in humans.

FIG. 51 is a box plot of AUC0-23 values by treatment. FIG. 52 is a box plot of AUC0-33 values by treatment. FIG. 53 is a box plot of AUC0-48 values by treatment. FIG. 54 is a box plot of AUC0-243 values by treatment. FIG. 55 is a box plot of AUC0-363 values by treatment.

With IM administration, the body experiences protracted absorption of epinephrine, thus no true terminal phase for the disposition of the drug can be seen. This physiological phenomenon results in difficulty in estimating half-life times of the drug for IM administration. Furthermore, due to the lack of reliable $t\frac{1}{2}$ for IM administration, a comparison of AUC values could only be made using AUClast (AUC0-363). The mean AUC0-363 values for 3.5 mg and 5.5 mg IN BBP01 were 27000 and 54680 min*pg/mL. AUC0-363 values were lower for both 0.3 and 0.5 mg IM epinephrine, averaging 18790 and 35890 min*pg/mL, respectively. Other important times for partial AUC analysis include 23, 33, 48, and 243 minutes; these time points are most useful to assess the rapidity of the onset of pharmacological effects. Comparison of AUCs between IN and IM administration shows a substantially larger AUC from the IN at early times after dosing, wherein this demonstrates surprising results of the length of time BBP01 remained in the subjects' body and did not decay as expected.

Figure 56:
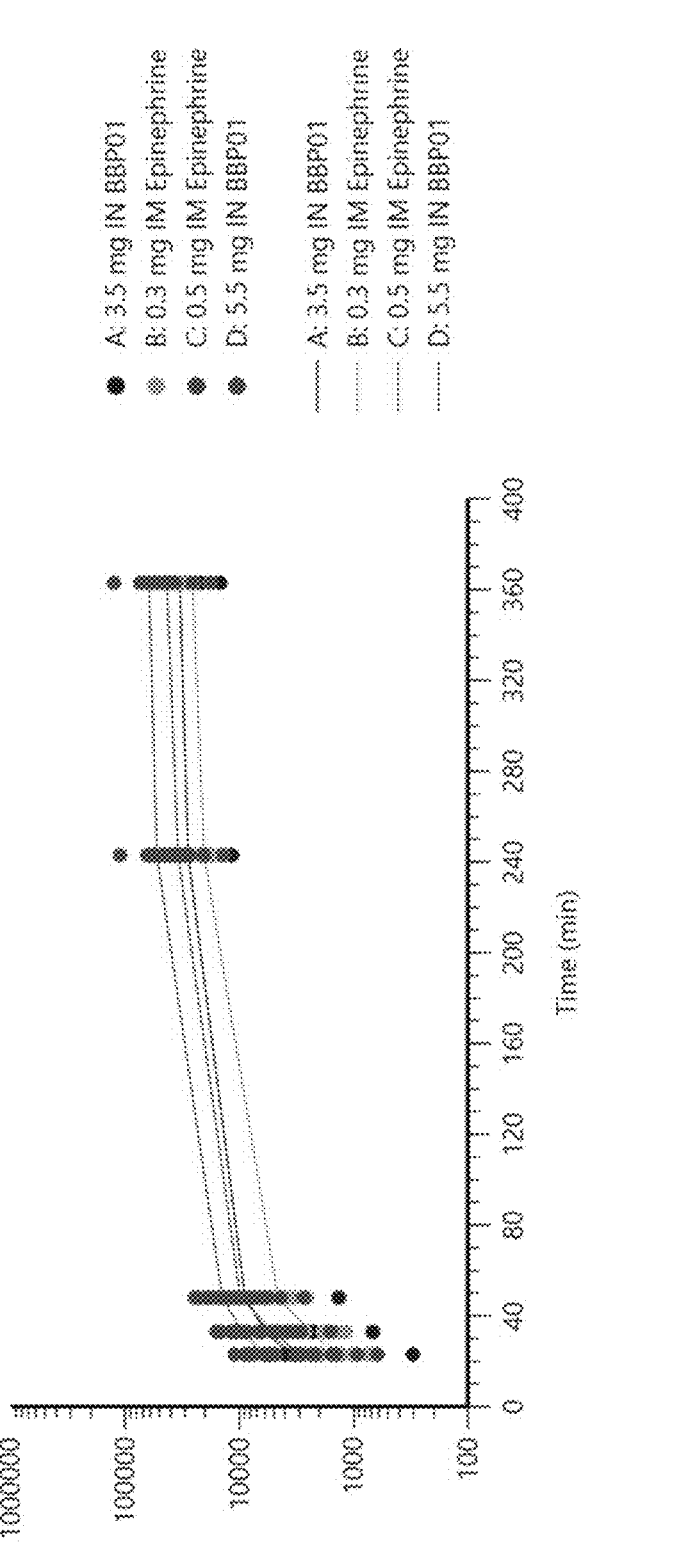
FIG. 56 illustrates a graph of partial and cumulative AUCs by treatment in humans.

FIG. 56 is a graph of partial and cumulative AUCs by treatment in humans.

FIGS. 57-60 are summary tables of partial AUCs for baseline-corrected plasma epinephrine for each treatment.

FIG. 61 is a table of bioequivalence calculation results, with Treatment A as the test and Treatment B as the reference. The ratios (expressed as a percentage) of the LSMs for Cmax and AUC0-363 were closest to 100% for the 3.5 mg IN BBP01 treatment at 122.72 and 120.47, respectively. The lower 90% CI was <100%, and the upper 90% CI exceeded 100%.

FIG. 62 is a table of bioequivalence calculation results, with Treatment D as the test and Treatment B as the reference. The ratios for the 5.5 mg IN were 202.96 and 217.52 for Cmax and AUC0-393, respectively. The lower 90% CI was >100%, and the upper 90% CI exceeded 100%.

Comparative bioavailability was performed using the standard bioequivalence analysis method. While establishing bioequivalence was not a primary objective of this exploratory study, the results can be used to identify a potential IN BBP01 dose for future studies. Finally, the width of the CIs is influenced not only on the variability of epinephrine pharmacokinetics but also the relatively small study sample size of 12 subjects.

FIGS. 63A-B are tables of relative bioavailability calculation results, comparing Treatments A and D against Treatment B as the reference. Relative bioavailability was estimated by comparing dose adjusted Cmax and AUC0-363 values using baseline-corrected epinephrine concentration-time data. The relative bioavailability for the 3.5 mg IN BBP01 formulation versus 0.3 mg IM epinephrine averaged 13.5% based on Cmax and 11.9% based on AUC0-363. The relative bioavailability was about 7% greater for the 5.5 mg IN BBP01 formulation averaging 21.3% based on Cmax and 18.8% based on AUC0-363.

Figure 64:
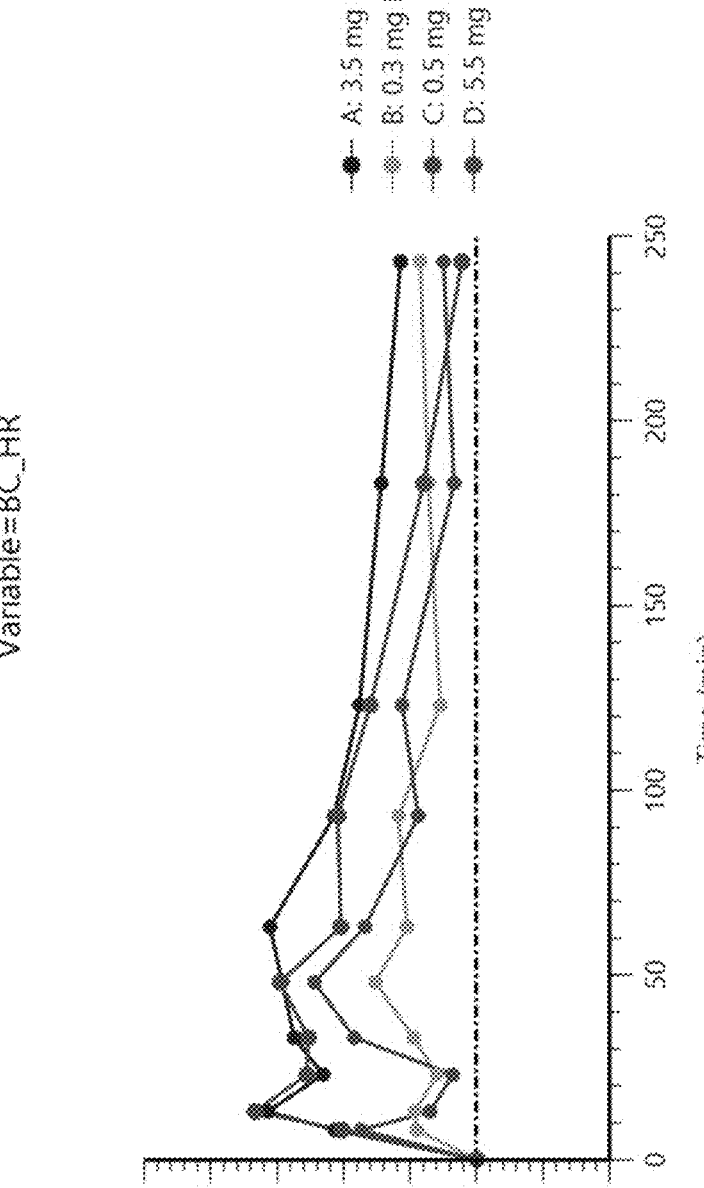
FIG. 64 illustrates a graph of the mean baseline-corrected heart rate by treatment in humans.

FIG. 64 is a graph of the mean baseline-corrected heart rate by treatment in humans.

Figure 65:
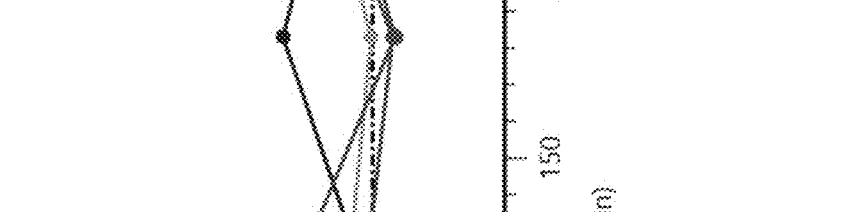
FIG. 65 illustrates a graph of the mean baseline-corrected systolic blood pressure by treatment in humans.
Figure 66:
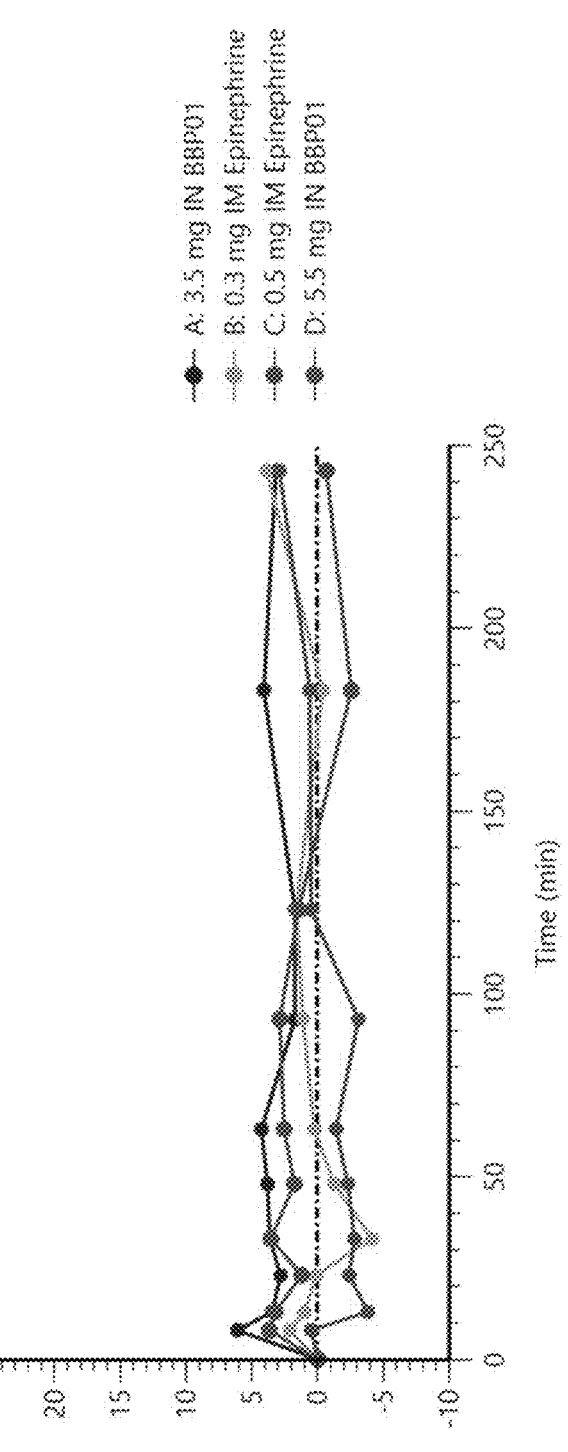
FIG. 66 illustrates a graph of the mean baseline-corrected diastolic blood pressure by treatment in humans.
Figure 67:
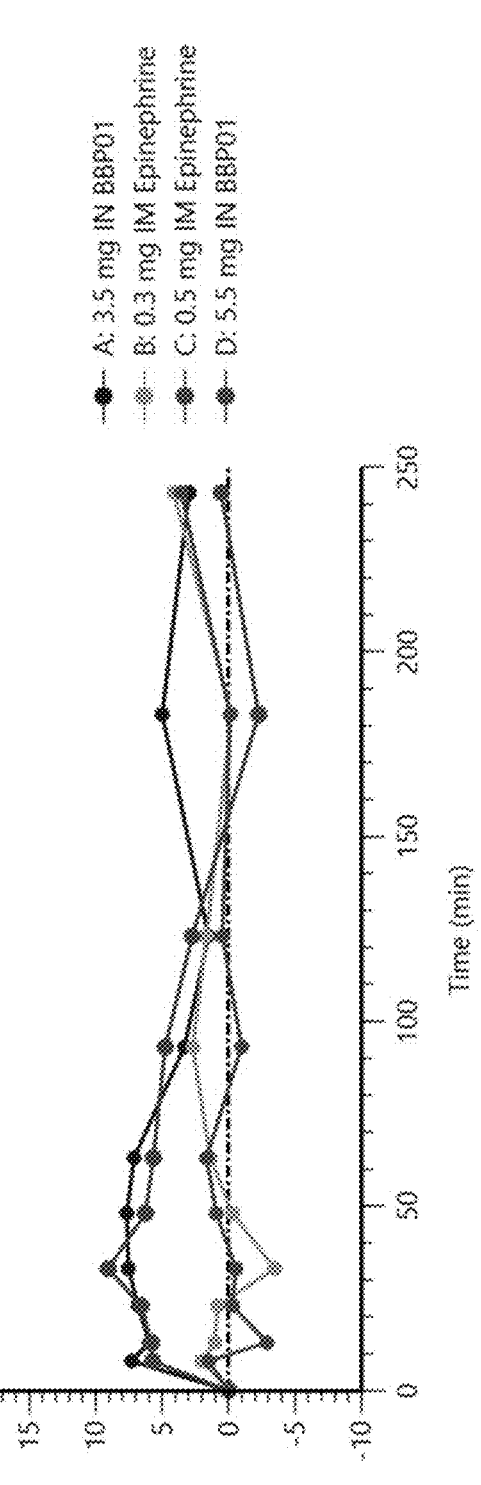
FIG. 67 illustrates a graph of the mean baseline-corrected mean arterial blood pressure by treatment in humans.

FIG. 65 is a graph of the mean baseline-corrected systolic blood pressure by treatment. FIG. 66 is a graph of the mean baseline-corrected diastolic blood pressure by treatment. FIG. 67 is a graph of the mean baseline-corrected mean arterial blood pressure by treatment.

Heart rate and blood pressure analysis was conducted using change from baseline values for each individual subject. All treatments had effects on increasing heart rate, systolic blood pressure, and mean arterial pressure (MAP) with minimal effects on diastolic blood pressure. Greater effects were observed on heart rate and blood pressure for IN versus IM dosing, suggesting IN BBP01 may provide greater efficacy at concentrations that are not much higher than IM dosing.

FIGS. 68-71 are graphs of baseline-corrected heart rate data of individual subjects with respect to each treatment.

Stability Study

To evaluate the stability, including chemical, physical, and product performance of the dry powder epinephrine composition, a 12-week study was conducted, assessing the dry powder epinephrine composition at 25° C./60% relative humidity (RH), 40° C./75% RH, and 50° C./uncontrolled RH.

The dry powder epinephrine composition was manually filled in the laboratory into a unit dose powder device, with 30 mg per device, packaged into an ACTIV-VIAL™, and placed into stability chambers for 12 weeks at 25° C./60% RH, 40° C./75% RH, and 50° C./uncontrolled RH.

X-ray powder diffraction (XRPD) and moisture content analysis were performed after the powder was stored in the device and packaging at different time points. XRPD was performed using a Miniflex 600 HR with a single analysis. Moisture content analysis was performed in triplicate using a Karl Fischer coulometer (Metrohm Ti-Touch 917) by adding 10 mg of formulation into HYDRANAL™ Coulomat AG.

Performance of the device and formulation was evaluated by emitted particle size (ePSD) with laser diffraction, spray pattern (SP), actuation force (AF), and delivered dose uniformity (DDU). SP was determined by using a SPRAY-VIEW (Proveris Scientific, USA). DDU analysis was performed on five devices per time point, wherein samples were then quantified by high performance liquid chromatography (HPLC) quantification.

Emitted particle size distribution (ePSD) was measured upon actuation of the device, using a SPRAYTEC® (Malvern Panalytical, UK) equipped with a 300-mm lens. Actuation force measurements were carried out at the same time as the ePSD with a VEREOR NSx actuator (Proveris Scientific, USA). Five devices were actuated at 70 mm/s at 4 cm from the laser. The actuation force was measured during the ePSD testing.

Figure 72:
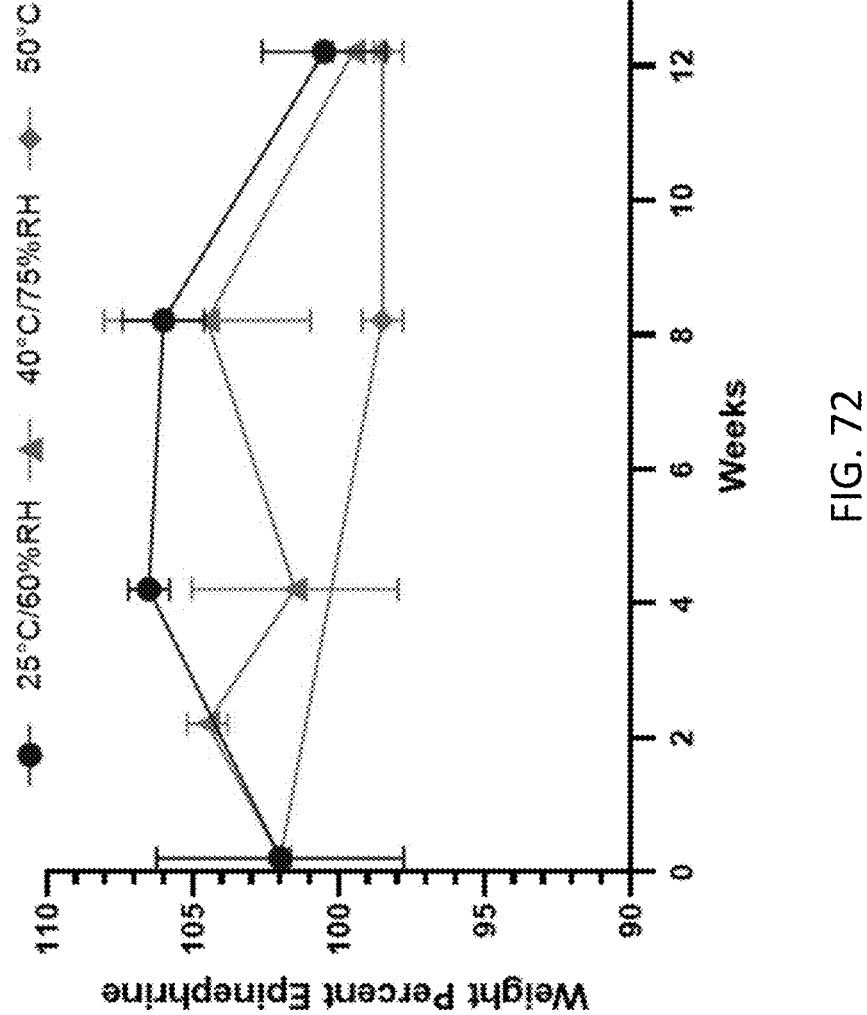
FIG. 72 illustrates the chemical stability of the dry powder epinephrine composition at different conditions over 12 weeks.

FIG. 72 illustrates the chemical stability of the dry powder epinephrine composition at different conditions over 12 weeks. FIG. 73 illustrates the solid-state characterization of the dry powder epinephrine composition during the stability study.

Product performance was analyzed for ePSD, SP, AF, and DDU, all of which remained stable after 12 weeks. Additionally, the emitted Dv10 and Dv50 were within the expected range for nasal drug delivery. FIG. 74 illustrates the product performance characterization during the stability study.

Chemical stability of the dry powder epinephrine composition was determined by assay of 20 mg of powder after opening the device with a HPCL compendial method. After 12 weeks, the dry powder epinephrine composition experienced no moisture ingress or crystallization. The assay was greater than or equal to 99% with no morphic change at all studied conditions. The device performance also remained consistent at all timepoints. Thus, this study suggest that the dry powder epinephrine composition described herein provides greater stability to environmental conditions and a longer shelf life than the known compositions in the prior art.

Study 101

A pilot study, designated as Study 101, was conducted with 12 patients, comparing the physiological and pharmacokinetic effects of intramuscular epinephrine treatments with different doses of the intranasal treatment method and composition of the present invention. Each patient was provided each treatment of the trial with 72-hour washout periods between each treatment, beginning with a 3.5 mg intranasal dose, followed by a 0.3 mg intramuscular dose, followed by a 0.5 mg intramuscular dose, and concluding with a 5.5 mg intranasal dose, with a safety follow-up performed 3 to 5 days after the final dose was administered. The primary endpoints of the study were pharmacokinetic measurements and assessments of comparative bioavailability, while the secondary endpoints were safety concerns and pharmacodynamic assessments. Details of the study are provided in Table 5 below.

TABLE 5

| Study 101 Treatment Regimen | | | | | | | |
|---|---|---|---|---|---|---|---|
| Treatment A | Wash-out | Treatment B | Wash-out | Treatment C | Wash-out | Treatment D | Safety Follow-up |
| BBP01 IN 3.5 mg | ≥72 hours | Epinephrine IM 0.3 mg | ≥72 hours | Epinephrine IM 0.5 mg | ≥72 hours | BBP01 IN 5.5 mg | 3 to 5 days post last dose |

Figure 75:
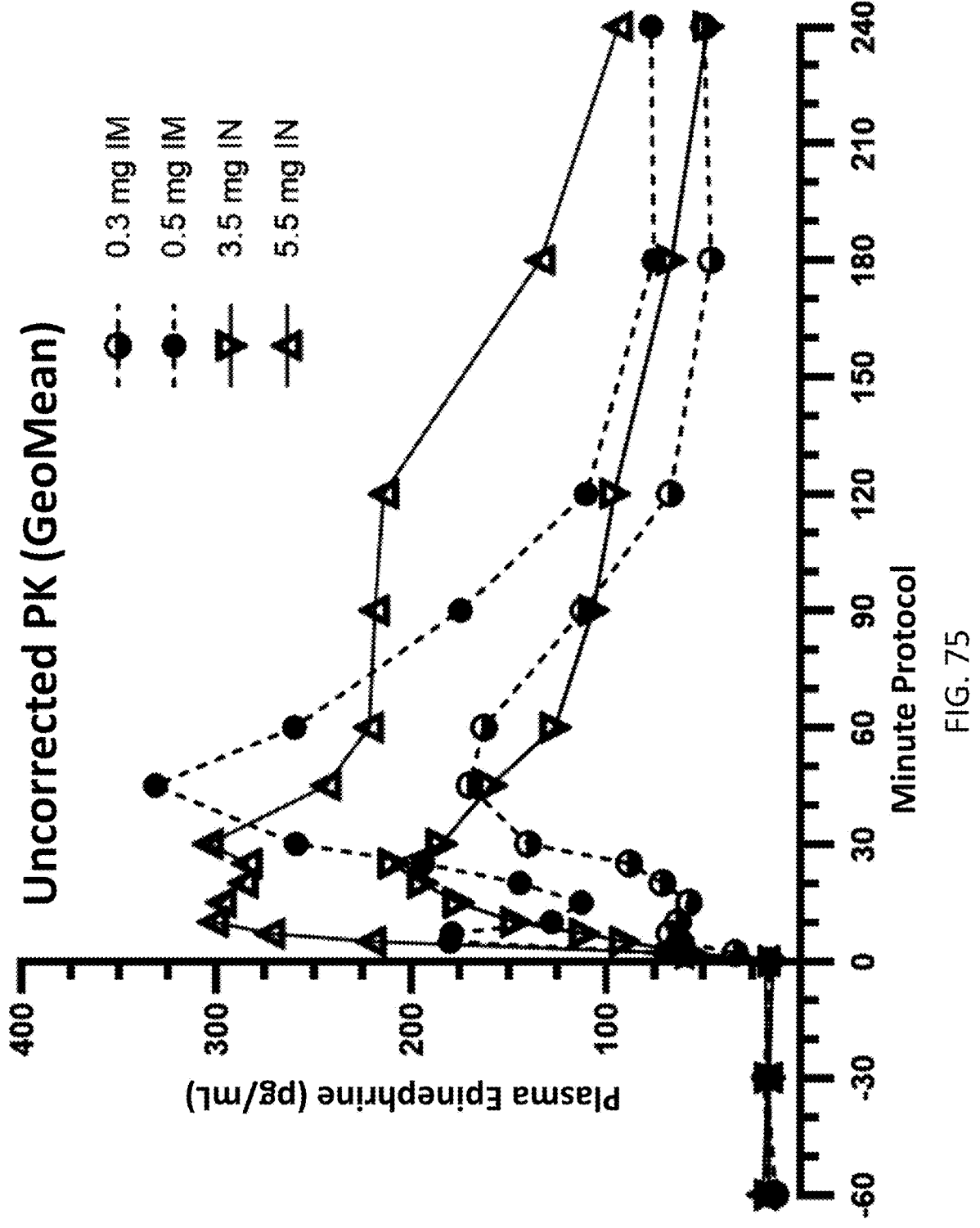
FIG. 75 is a graph of mean uncorrected plasma epinephrine concentration relative to time of dose administration in humans after treatment with both intramuscular doses and intranasal doses of the composition of the present invention.
Figure 76:
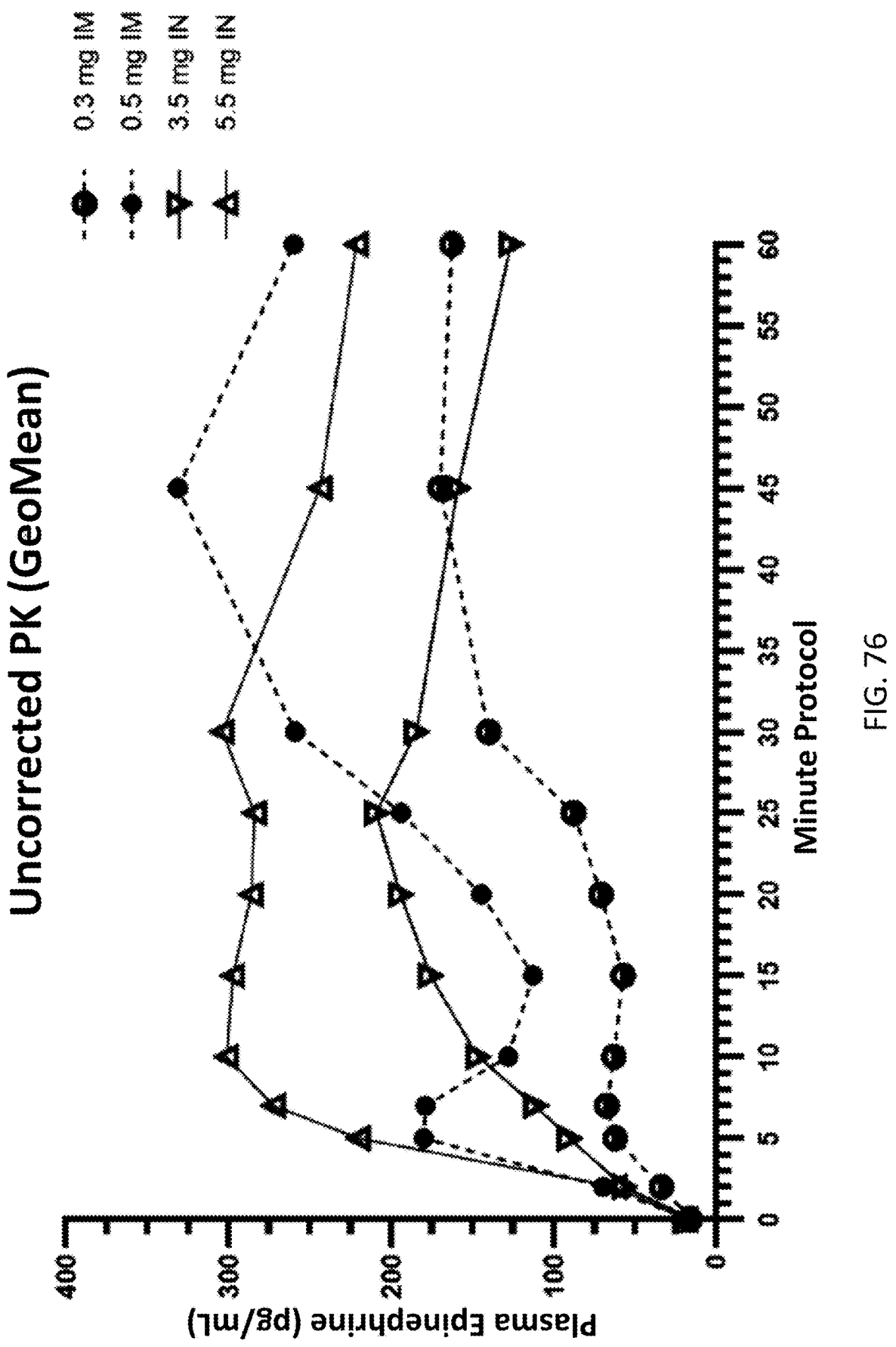
FIG. 76 is a graph of mean uncorrected plasma epinephrine concentration relative to time of dose administration in humans focusing in particular on the first hour after treatment with both intramuscular doses and intranasal doses of the composition of the present invention.
Figure 77:
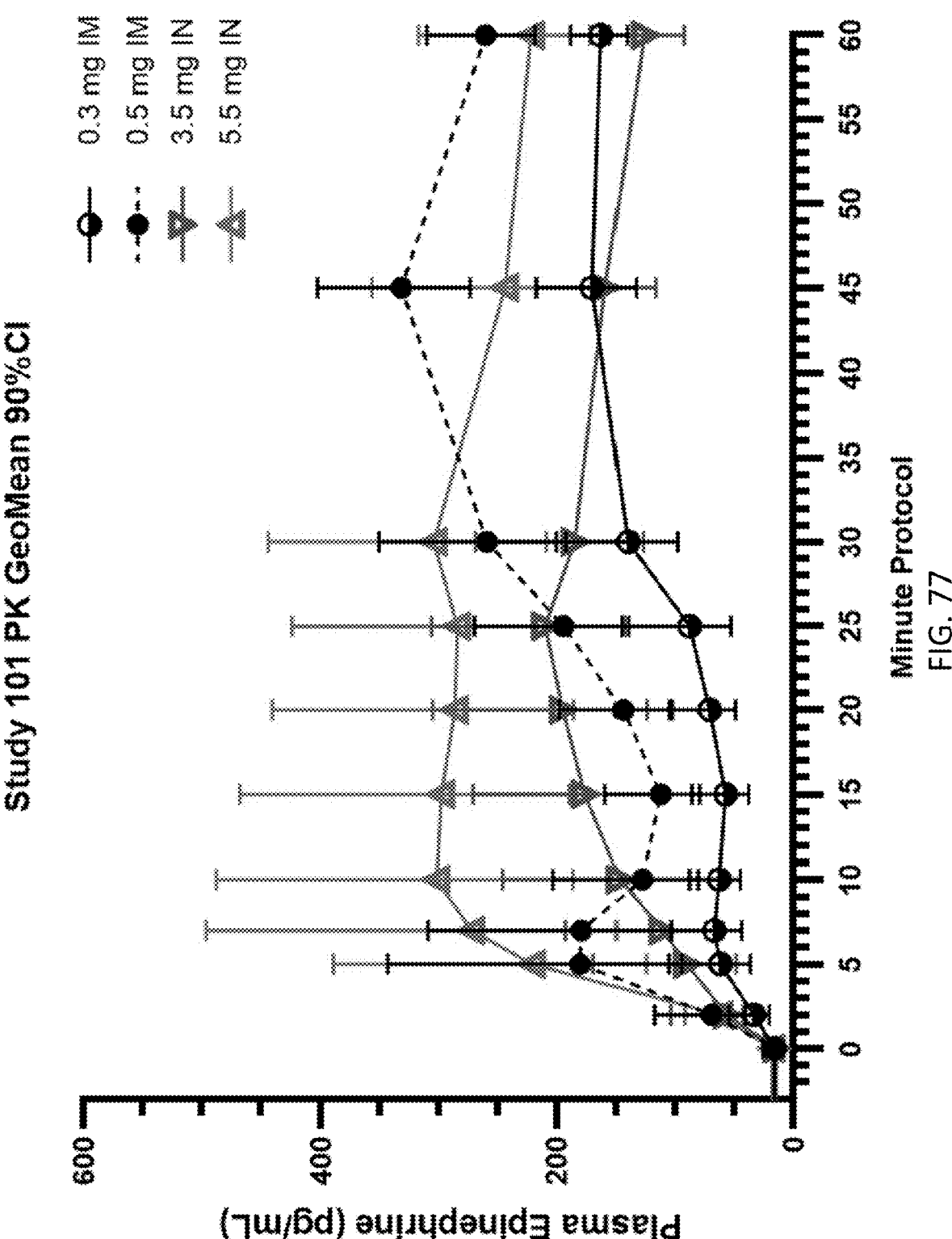
FIG. 77 is a graph of mean uncorrected plasma epinephrine concentration, including 90% confidence intervals, relative to time of dose administration in humans after treatment with both intramuscular doses and intranasal doses of the composition of the present invention.

FIGS. 75 and 76 are graphs of mean uncorrected plasma epinephrine concentration relative to time of dose administration in humans after treatment with both intramuscular doses and intranasal doses of the composition of the present invention. As shown in FIGS. 75 and 76, the 5.5 mg intranasal dose provided an earlier Tmax (18 minutes vs. 48 minutes) value relative to the higher dose (0.5 mg) delivered intramuscularly. Furthermore, the intranasal dose Cmax was comparable to or higher than the Cmax value for the higher dose (0.5 mg) delivered intramuscularly. The 3.5 mg dose provided comparable results when compared to the lower dose (0.3 mg) delivered intramuscularly. FIG. 77 shows 90% confidence intervals for the measurements for each dose. Both the intramuscular and intranasal doses showed variance in the concentration levels at each time point.

TABLE 6

| Comparison of pharmacokinetic data for intramuscular and intranasal doses | | | | |
|---|---|---|---|---|
| | 3.5 mg IN | 5.5 mg IN | 0.3 mg IM | 0.5 mg IM |
| Cmax (GeoMean) | 250.8 | 407.3 | 198.7 | 382.3 |
| Geometric SD | 2.016 | 2.014 | 1.241 | 1.553 |
| Cmax (CV %, GeoMean) | 48.8% | 48.7% | 14.3% | 29.6% |
| Tmax (Median) | 28.0 | 18.0 | 48.0 | 48.0 |
| Tmax (Median 90% LCI) | 18 | 10 | 8 | 8 |
| Tmax (Median 90% UCI) | 33 | 33 | 62 | 49 |
| Tmax (Mean) | 32.5 | 20.9 | 41.4 | 40.9 |
| Tmax (CV %, Mean) | 96.5% | 46.0% | 54.2% | 61.0% |

Figure 78:
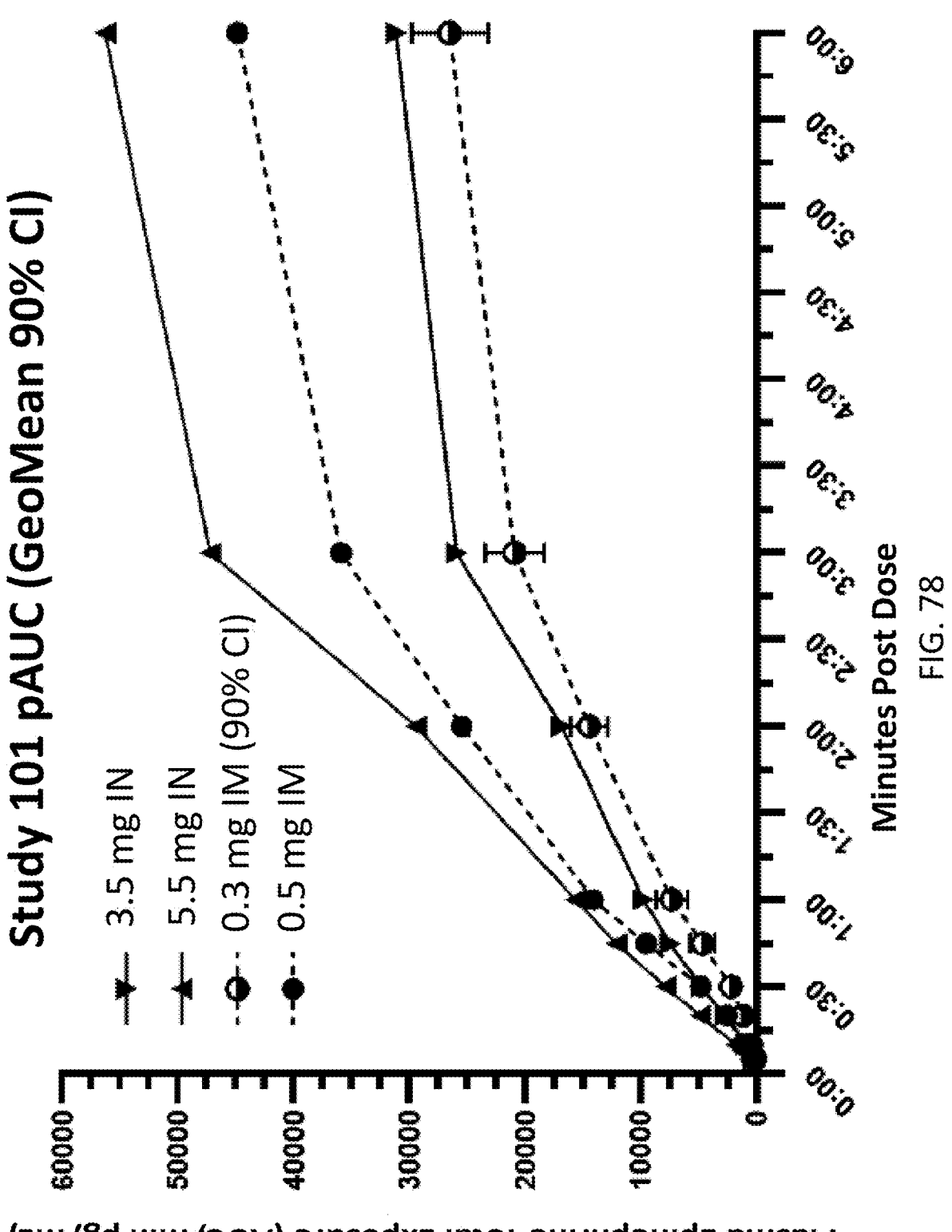
FIG. 78 is a graph comparing partial area under the curve for plasma epinephrine for both intramuscular doses and intranasal doses of the composition of the present invention.

FIG. 78 is a graph comparing partial area under the curve for plasma epinephrine for both intramuscular doses and intranasal doses of the composition of the present invention. As shown in FIG. 78, the higher (5.5 mg) intranasal dose provided greater area under the curve measurements of plasma epinephrine for the first hour after administering the dose when compared to the higher (0.5 mg) intramuscular dose. Increased area under the curve means that not only did the intranasal dose of the present invention provide at least comparable pharmacokinetic effects as the existing intramuscular dosing system, but the intranasal dose actually provided increased plasma epinephrine, providing for additional protection against breakthrough, secondary attacks initiated post-delivery. While such breakthrough attacks are rare, the intranasal doses of the present invention show a profile that suggests benefits in addressing such incidents. Data including average partial area under the curve values and confidence interval boundaries are provided in Table 7 below.

TABLE 7

| Partial Area Under the Curve Plasma Epinephrine Data for Intranasal and Intramuscular Doses | | | | |
|---|---|---|---|---|
| | N | | | |
| AUC | 12 3.5 mg IN | 10 5.5 mg IN | 9 0.3 mg IM | 11 0.5 mg IM |
| 0-5 min | 231 | 445 | 163 | 415 |
| SE | 74 | 108 | 34 | 128 |
| % CV | 111 | 77 | 63 | 102 |
| UCI | 353 | 623 | 219 | 626 |
| LCI | 109 | 267 | 107 | 204 |
| 0-10 min | 852 | 1826 | 511 | 1261 |
| SE | 249 | 486 | 98 | 368 |
| % CV | 101 | 84 | 58 | 97 |
| UCI | 1262 | 2625 | 672 | 1866 |
| LCI | 442 | 1027 | 350 | 656 |
| 0-20 min | 2672 | 4881 | 1174 | 2590 |
| SE | 672 | 1148 | 198 | 630 |
| % CV | 87 | 74 | 51 | 81 |
| UCI | 3777 | 6769 | 1500 | 3626 |
| LCI | 1567 | 2993 | 848 | 1554 |
| 0-30 min | 4762 | 7854 | 2228 | 4840 |
| SE | 1093 | 1718 | 378 | 920 |
| % CV | 80 | 69 | 51 | 63 |
| UCI | 6560 | 10680 | 2850 | 6353 |
| LCI | 2964 | 5028 | 1606 | 3327 |
| 0-45 min | 7462 | 12093 | 4681 | 9539 |
| SE | 1547 | 2464 | 665 | 1429 |
| % CV | 72 | 64 | 43 | 50 |
| UCI | 10007 | 16146 | 5775 | 11890 |
| LCI | 4917 | 8040 | 3587 | 7188 |
| 0-60 min | 9751 | 15697 | 7319 | 14141 |
| SE | 1862 | 3080 | 821 | 1807 |
| % CV | 66 | 62 | 34 | 42 |
| UCI | 12814 | 20764 | 8670 | 17114 |
| LCI | 6688 | 10630 | 5968 | 11168 |
| 0-120 min | 16878 | 29410 | 14450 | 25459 |
| SE | 2516 | 5407 | 993 | 2477 |
| % CV | 52 | 58 | 21 | 32 |
| UCI | 21017 | 38305 | 16083 | 29534 |
| LCI | 12739 | 20515 | 12817 | 21384 |
| 0-240 min | 25935 | 47214 | 20922 | 35922 |
| SE | 3029 | 8203 | 1561 | 3109 |
| % CV | 40 | 55 | 22 | 29 |
| UCI | 30918 | 60708 | 23490 | 41036 |
| LCI | 20952 | 33720 | 18354 | 30808 |
| 0-360 min | 31149 | 56339 | 26535 | 44856 |
| SE | 3421 | 9243 | 2001 | 3505 |
| % CV | 38 | 52 | 23 | 26 |
| UCI | 36777 | 71544 | 29827 | 50622 |
| LCI | 25521 | 41134 | 23243 | 39090 |

Figure 79:
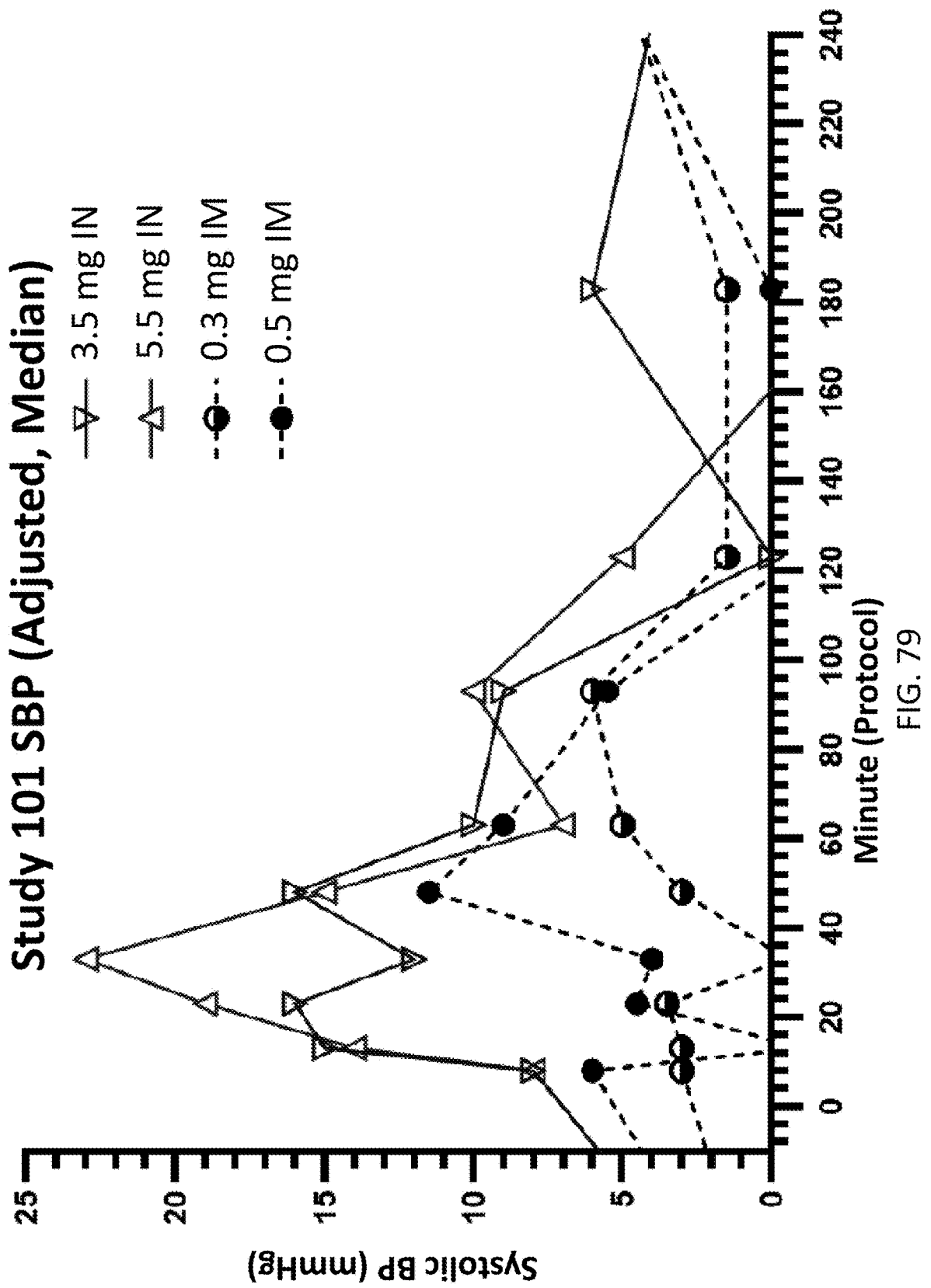
FIG. 79 is a graph comparing systolic blood pressure of patients over time after treatment with both intramuscular doses and intranasal doses of the composition of the present invention.
Figure 80:
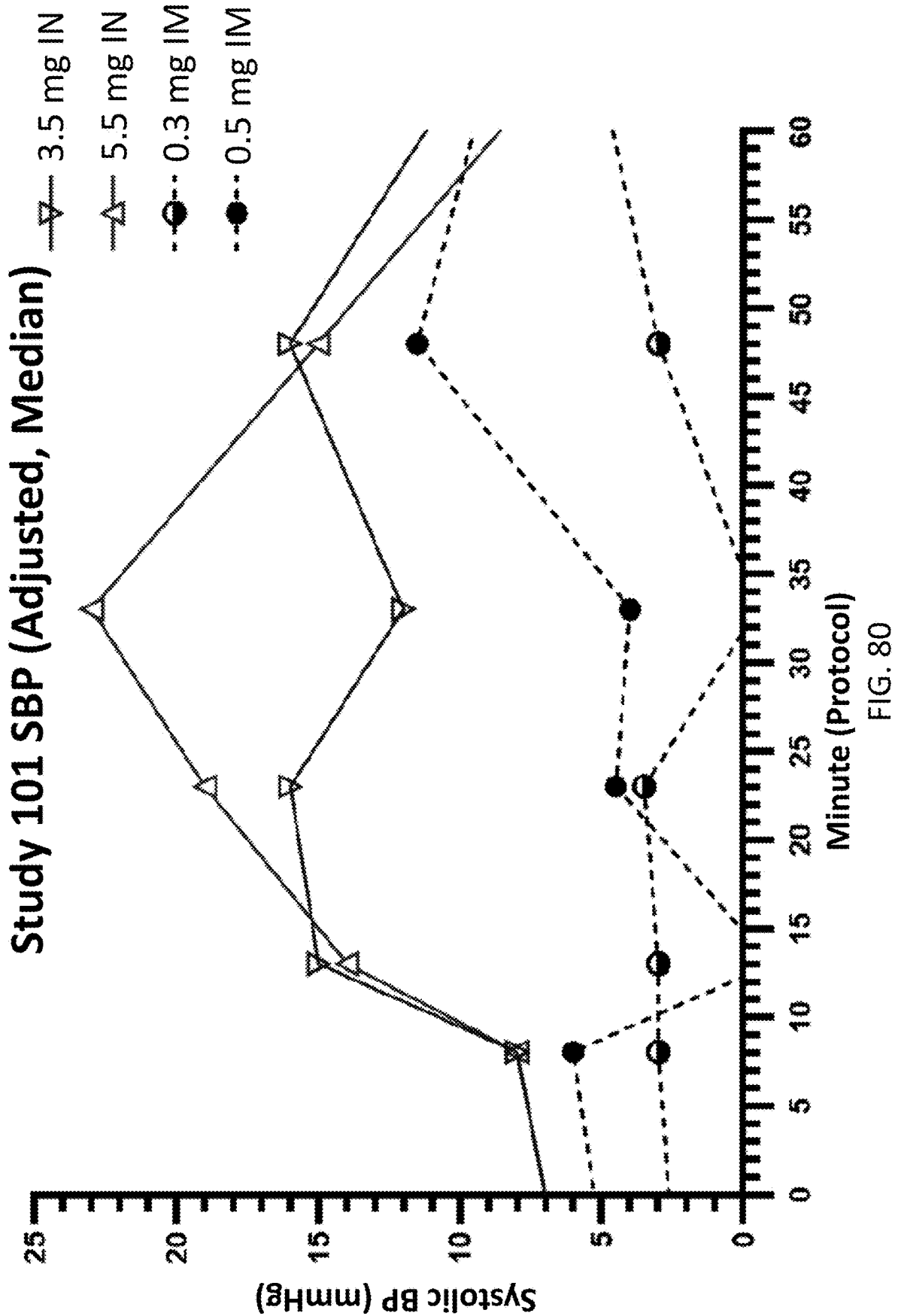
FIG. 80 is a graph comparing systolic blood pressure of patients over time focusing on the first hour after treatment with both intramuscular doses and intranasal doses of the composition of the present invention.

FIGS. 79 and 80 show comparisons of systolic blood pressure of patients over time after treatment with both intramuscular doses and intranasal doses of the composition of the present invention. As shown in FIGS. 79 and 80, both the high and low intranasal doses according to the present invention caused a more pronounced and earlier onset increase in systolic blood pressure compared to either intramuscular dose, while still being within a safe range of physiological effects. Additionally, both the high and low intranasal doses according to the present invention cause a sustained increase in systolic blood pressure compared to either intramuscular dose. A low or no dose response was observed between both the high and low intranasal doses according to the present invention. These results indicate that the intranasal doses act faster and longer in providing relief than comparable intramuscular doses.

Figure 81:
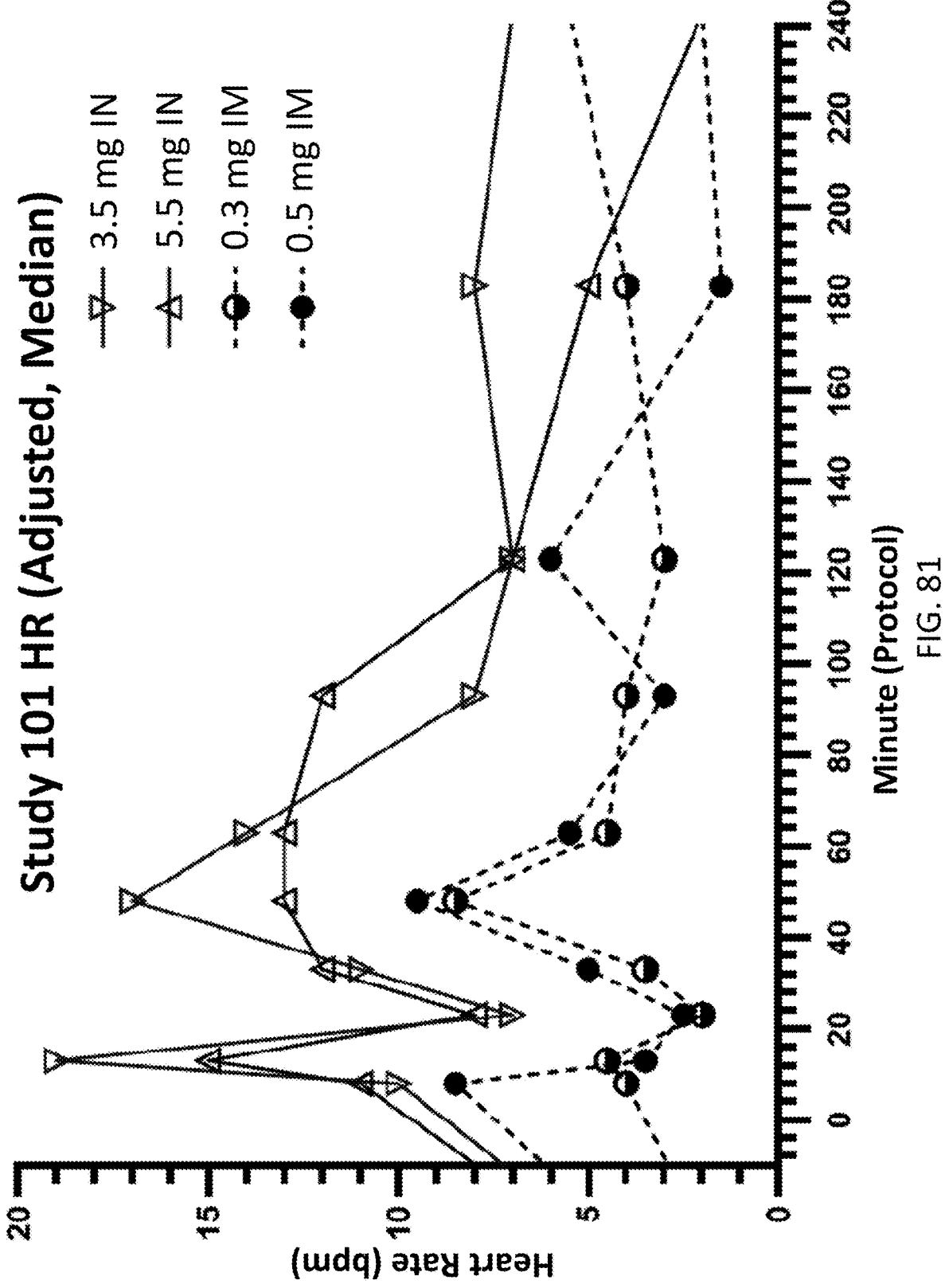
FIG. 81 is a graph comparing heart rate of patients over time after treatment with both intramuscular doses and intranasal doses of the composition of the present invention.
Figure 82:
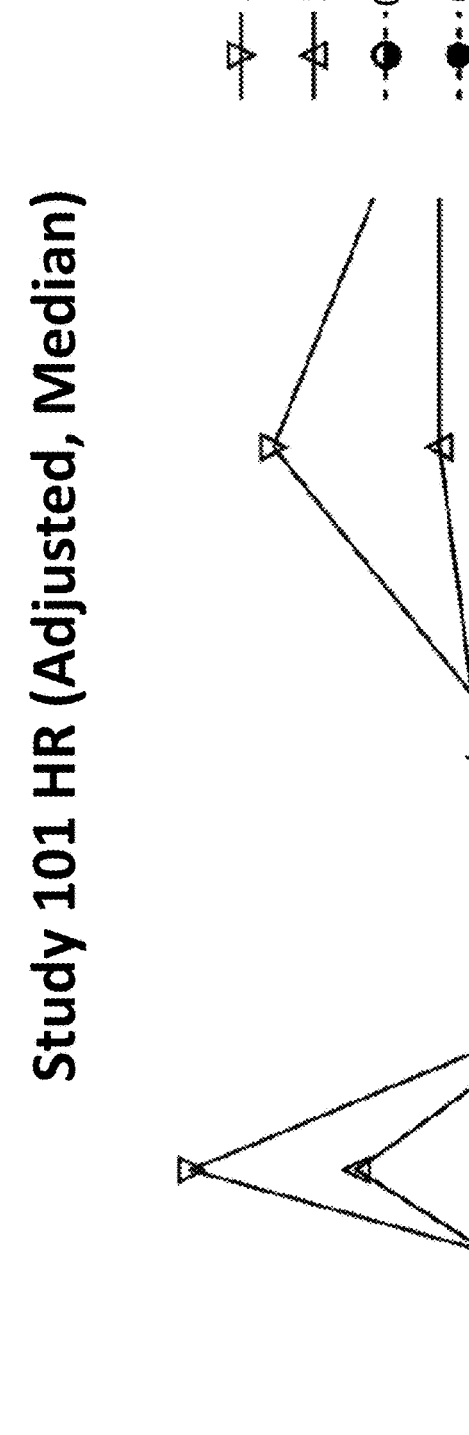
FIG. 82 is a graph comparing heart rate of patients over time focusing on the first hour after treatment with both intramuscular doses and intranasal doses of the composition of the present invention.

FIGS. 81 and 82 show comparisons of heart rate of patients over time after treatment with both intramuscular doses and intranasal doses of the composition of the present invention. Similar to the effects on systolic blood pressure, the intranasal doses produced a more pronounced increase in heart rate in patients relative to the intramuscular doses, while still being within a safe range of physiological effects. However, the timing of the peak heart rate effects of the intranasal doses appears to be comparable to the timing of the peak heart rate effects of the intramuscular doses. Additionally, both the high and low intranasal doses according to the present invention cause a sustained increase in heart rate compared to either intramuscular dose. A low or no dose response was observed between both the high and low intranasal doses according to the present invention.

Figure 83:
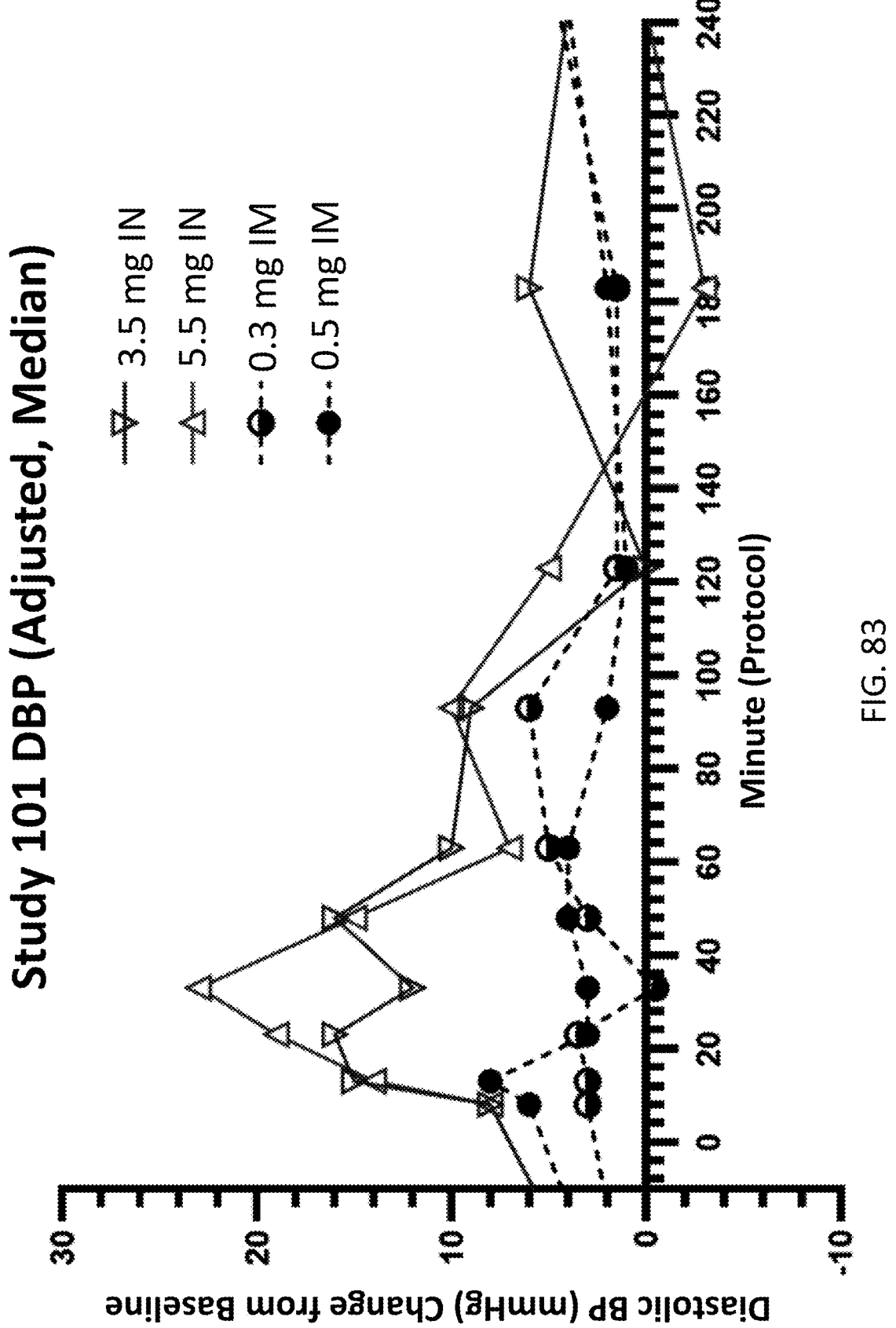
FIG. 83 is a graph comparing diastolic blood pressure of patients over time after treatment with both intramuscular doses and intranasal doses of the composition of the present invention.
Figure 84:
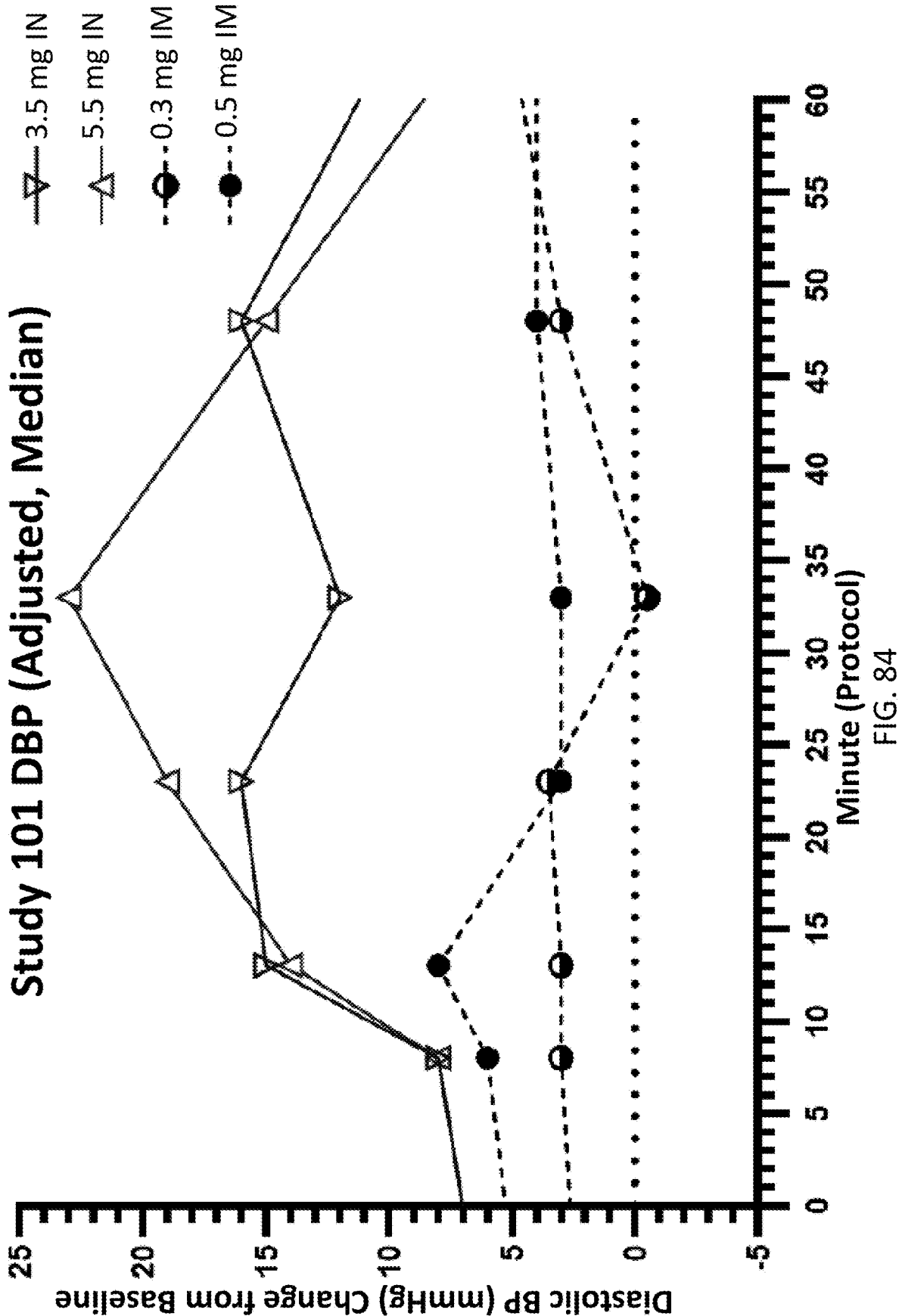
FIG. 84 is a graph comparing diastolic blood pressure of patients over time focusing on the first hour after treatment with both intramuscular doses and intranasal doses of the composition of the present invention.

FIGS. 83 and 84 show comparisons of diastolic blood pressure of patients over time after treatment with both intramuscular doses and intranasal doses of the composition of the present invention. As shown in FIGS. 83 and 84, both the high and low intranasal doses according to the present invention caused a more pronounced and earlier onset increase in diastolic blood pressure compared to either intramuscular dose, while still being within a safe range of physiological effects. Additionally, both the high and low intranasal doses according to the present invention cause a sustained increase in mean arterial pressure compared to either intramuscular dose. A low or no dose response was observed between both the high and low intranasal doses according to the present invention.

Figure 87:
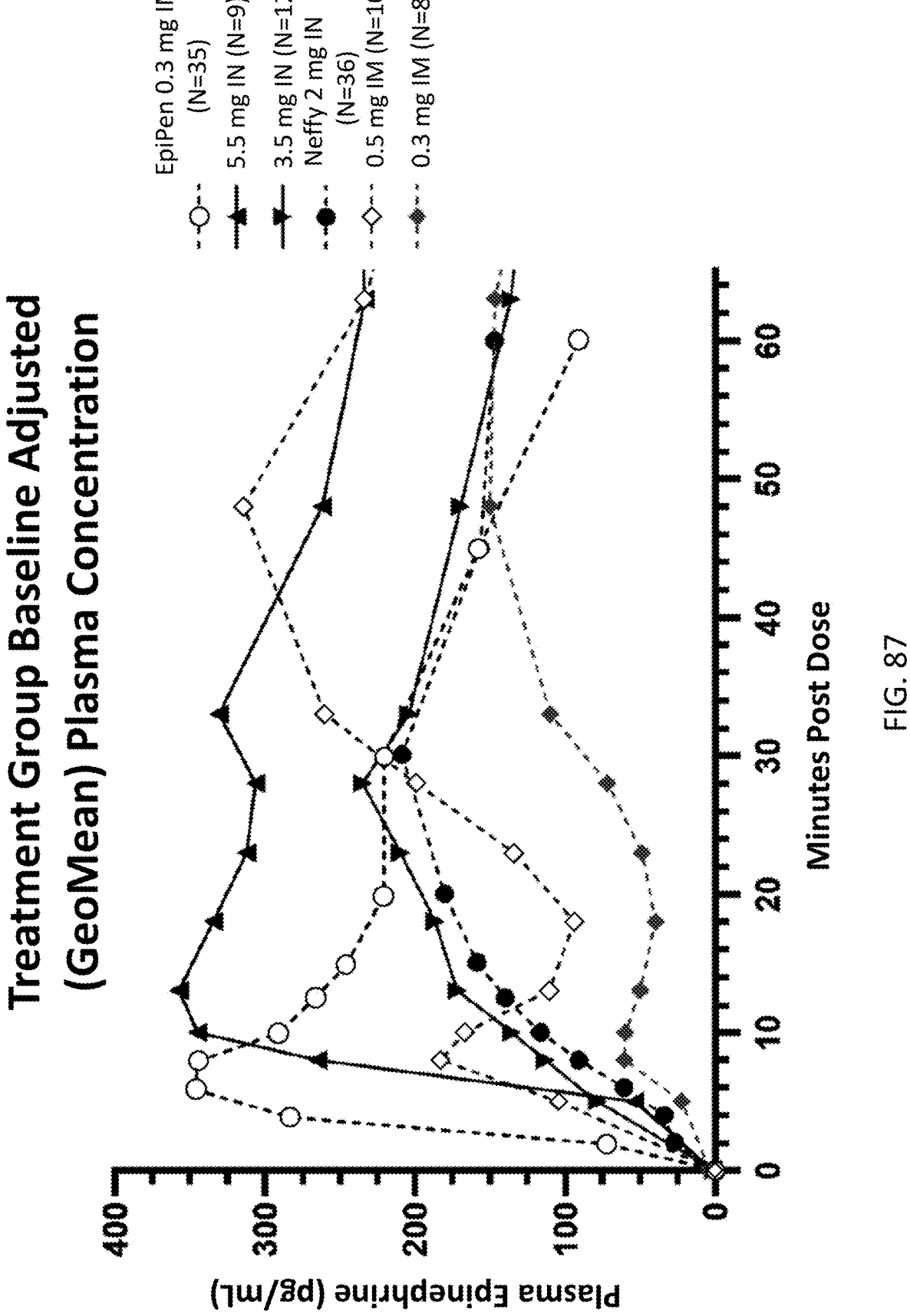
FIG. 87 is a graph of mean adjusted plasma epinephrine concentration relative to time of dose administration in humans after treatment with intramuscular doses, epinephrine autoinjector doses, intranasal doses of the composition of the present invention, and other intranasal dosing systems.

FIG. 87 is a graph of plasma epinephrine concentration relative to time post dose administration in humans after treatment with intramuscular manual doses, an intramuscular autoinjector (EpiPen) dose, an intranasal liquid spray (Neffy) dose, and intranasal doses of the composition of the present invention. As shown in FIG. 87, the 3.5 mg intranasal dose of the composition of the present invention provides comparable exposure to the intranasal liquid Neffy spray. Additionally, as shown in FIG. 87, the 5.5 mg intranasal dose of the composition of the present invention provides comparable exposure to the EpiPen intramuscular autoinjector dose.

Study 102

A second, confirmation study to the pilot study, designated as Study 102, was conducted with 12 patients, comparing the physiological and pharmacokinetic effects of intramuscular epinephrine treatments with different doses of the intranasal treatment method and composition of the present invention. Each patient was provided each treatment of the trial with 6 day washout periods after the first (Treatment A) and second (Treatment B) doses, and a 12-day washout period after the third dose (Treatment C), beginning with a 4.5 mg intranasal dose (Treatment A), followed by a 0.3 mg intramuscular dose (Treatment B), followed by a 5.5 mg intranasal dose (Treatment C), and concluding with a 4.5 mg intranasal dose after nasal allergen administration (Treatment D), with a safety follow-up performed 3 to 5 days after the final dose was administered. The primary endpoints of the study were pharmacokinetic measurements and assessments of comparative bioavailability, while the secondary endpoints were safety concerns and pharmacodynamic assessments. Details of the study are provided in Table 8 below.

TABLE 8

| Study 102 Treatment Regimen | | | | | | | |
|---|---|---|---|---|---|---|---|
| Treatment A | Wash-out | Treatment B | Wash-out | Treatment C | Wash-out | Treatment D | Safety Follow-up |
| 4.5 mg IN BBP01 | ≥6 days | 0.3 mg IM Autoinjector Epinephrine, EpiPen | ≥6 days | 5.5 mg IN BBP01 | ≥12 days | 4.5 mg IN BBP01, after nasal allergen administration | 3 to 5 days post last dose | physiological effects. Additionally, both the high and low intranasal doses according to the present invention cause a sustained increase in diastolic blood pressure compared to either intramuscular dose. These results indicate that the intranasal doses act faster and longer in providing relief than comparable intramuscular doses. A low or no dose response was observed between both the high and low intranasal doses according to the present invention.

Figure 85:
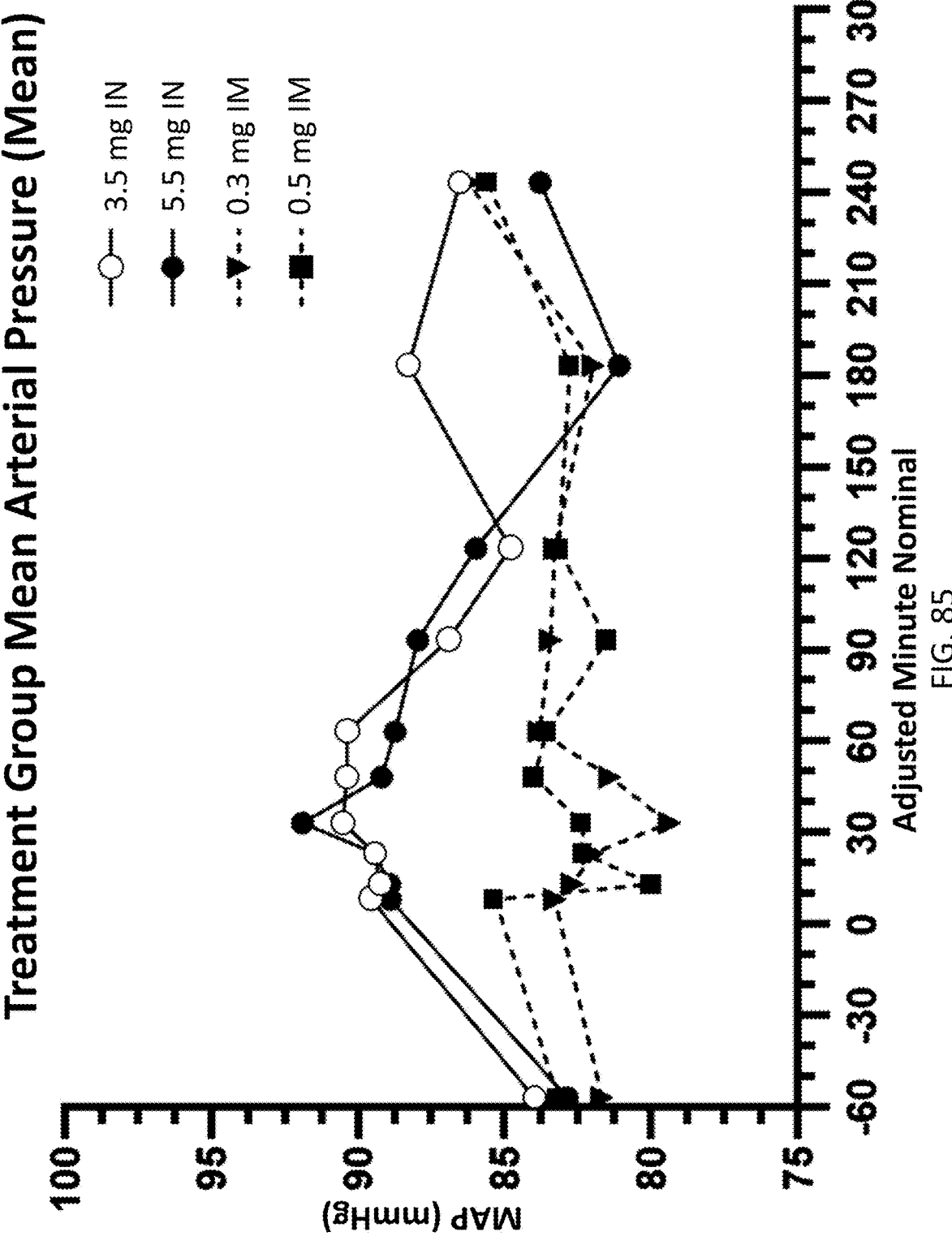
FIG. 85 is a graph comparing mean arterial pressure of patients over time after treatment with both intramuscular doses and intranasal doses of the composition of the present invention.
Figure 86:
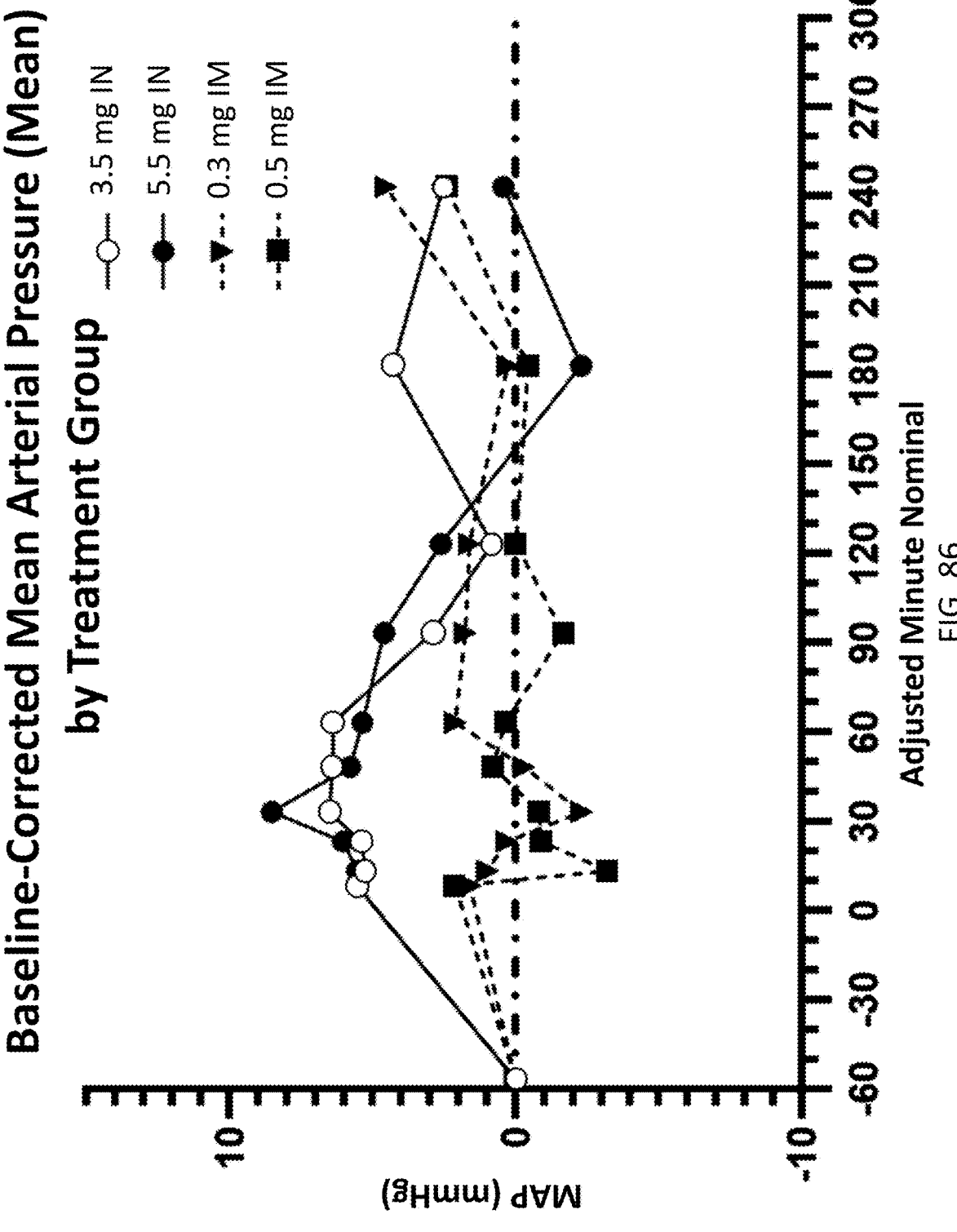
FIG. 86 is a graph comparing mean arterial pressure of patients over time focusing on the first hour after treatment with both intramuscular doses and intranasal doses of the composition of the present invention.
Figure 88:
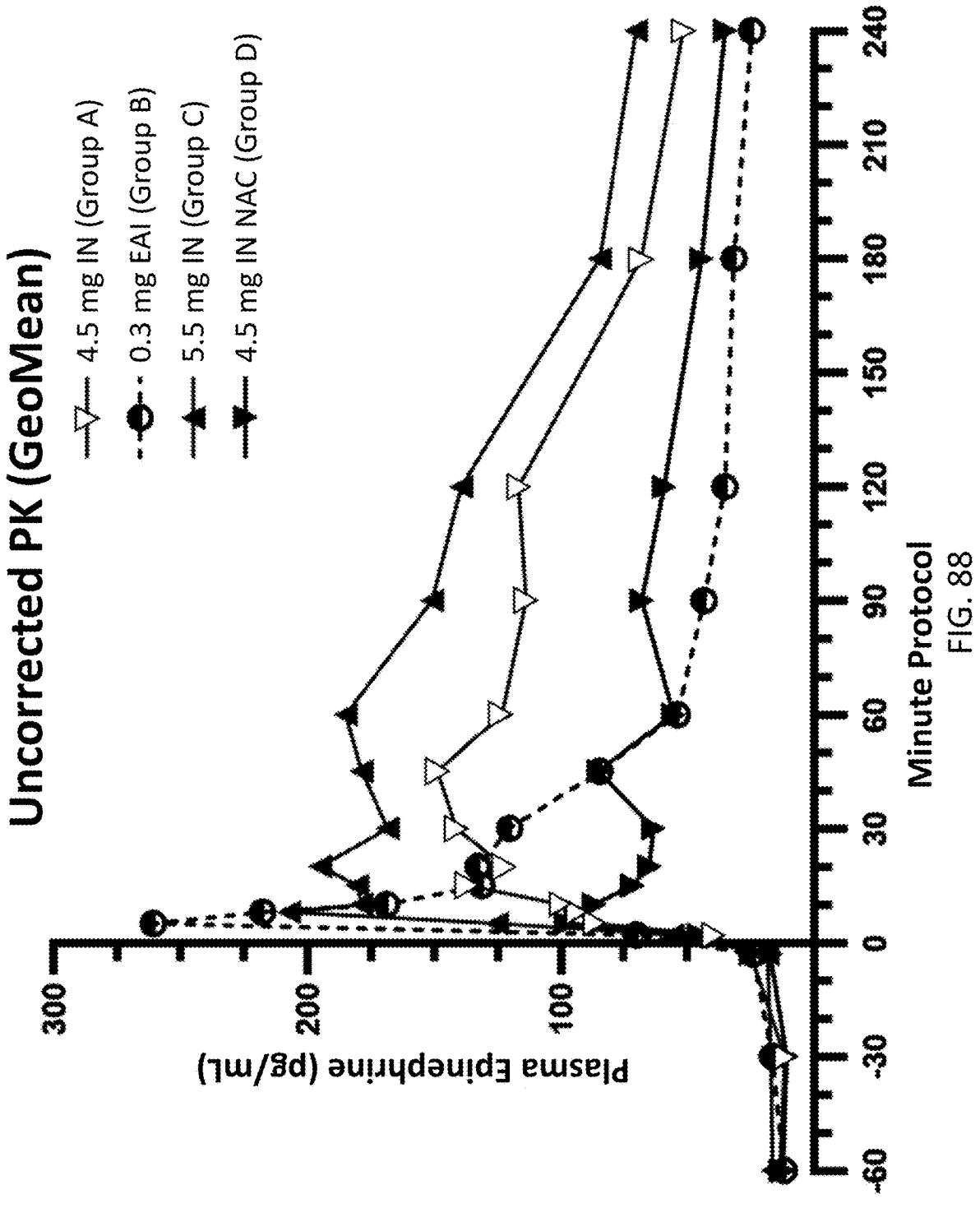
FIG. 88 is a graph of mean uncorrected plasma epinephrine concentration relative to time of dose administration in humans after treatment with autoinjector doses and various intranasal doses of epinephrine.
Figure 89:
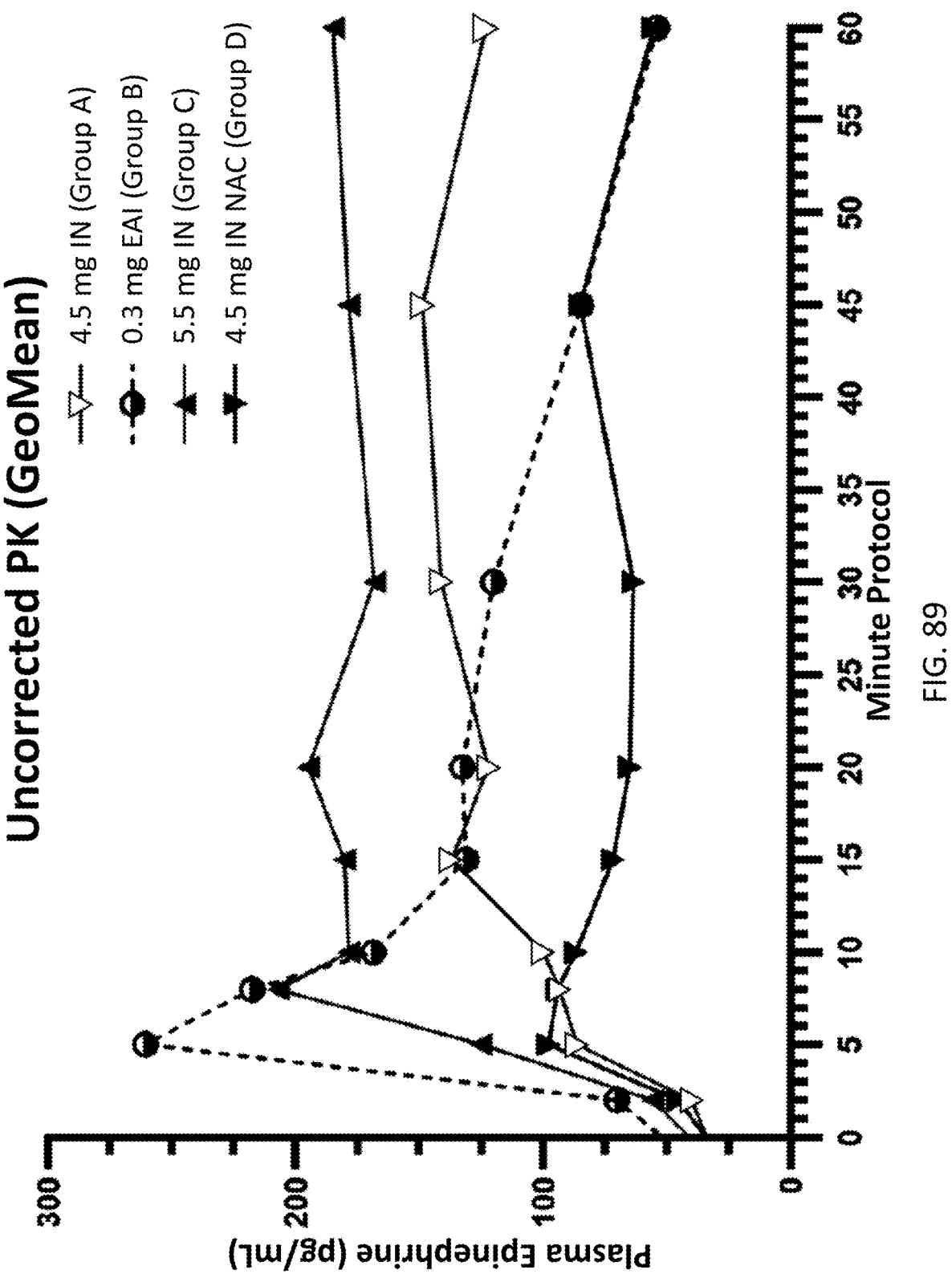
FIG. 89 is a graph of mean uncorrected plasma epinephrine concentration relative to time of dose administration in humans focusing in particular on the first hour after treatment with autoinjector doses and various intranasal doses of epinephrine.
Figure 90:
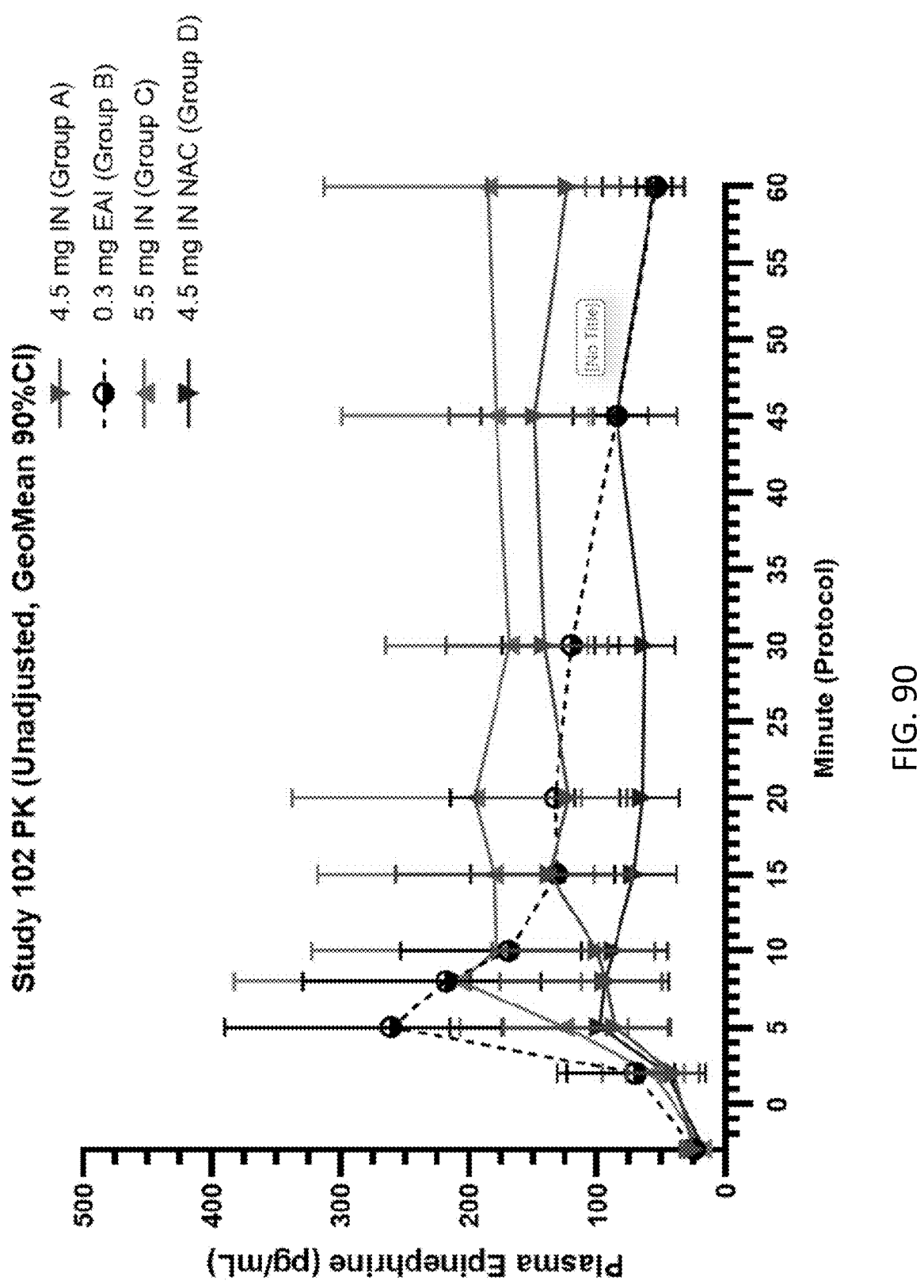
FIG. 90 is a graph of mean uncorrected plasma epinephrine concentration, including 90% confidence intervals, relative to time of dose administration in humans after treatment with autoinjector doses and various intranasal doses of epinephrine.

FIGS. 85 and 86 show comparisons of mean arterial pressure (MAP) of patients over time after treatment with both intramuscular doses and intranasal doses of the composition of the present invention. As shown in FIGS. 85 and 86, both the high and low intranasal doses according to the present invention caused a more pronounced and earlier onset increase in mean arterial pressure compared to either intramuscular dose, while still being within a safe range of FIGS. 88 and 89 are graphs of mean uncorrected plasma epinephrine concentration relative to time of dose administration in humans after treatment with the intramuscular autoinjector dose (EpiPen) and the intranasal doses of the composition of the present invention, including an intranasal dose after nasal allergen administration. As shown in FIGS. 88 and 89, the intranasal doses provide a lower Cmax value relative to the autoinjector dose (EpiPen) delivered intramuscularly. Further, the intranasal dose given after nasal allergen administration decreases exposure, providing an even lower Cmax value relative to the autoinjector dose (EpiPen) delivered intramuscularly. FIG. 90 shows 90% confidence intervals for the measurements for each dose. Both the intramuscular and intranasal doses showed variance in the concentration levels at each time point. Additionally, the Cmax of the intranasal doses does not exceed the Cmax of the autoinjector dose (EpiPen) delivered intramuscularly.

TABLE 9

Comparison of pharmacokinetic data for intramuscular and intranasal doses

|  | 4.5 mg IN | 0.3 mg EAI | 5.5 mg IN | 4.5 mg IN NAC |
|---|---|---|---|---|
| Cmax (GeoMean) | 264.2 | 319.4 | 309.3 | 233.7 |
| Geometric SD | 2.285 | 1.854 | 2.221 | 4.058 |
| Cmax (CV %, GeoMean) | 58.8% | 42.4% | 56.4% | 116.0% |
| Tmax (Median) | 25.0 | 5.0 | 15.0 | 10.0 |
| Tmax (Median 90% LCI) | 8 | 5 | 8 | 5 |
| Tmax (Median 90% UCI) | 90 | 8 | 90 | 45 |
| Tmax (Mean) | 45.3 | 7.0 | 37.7 | 28.7 |
| Tmax (CV %, Mean) | 118.3% | 71.1% | 112.0% | 132.5% |

Figure 91:
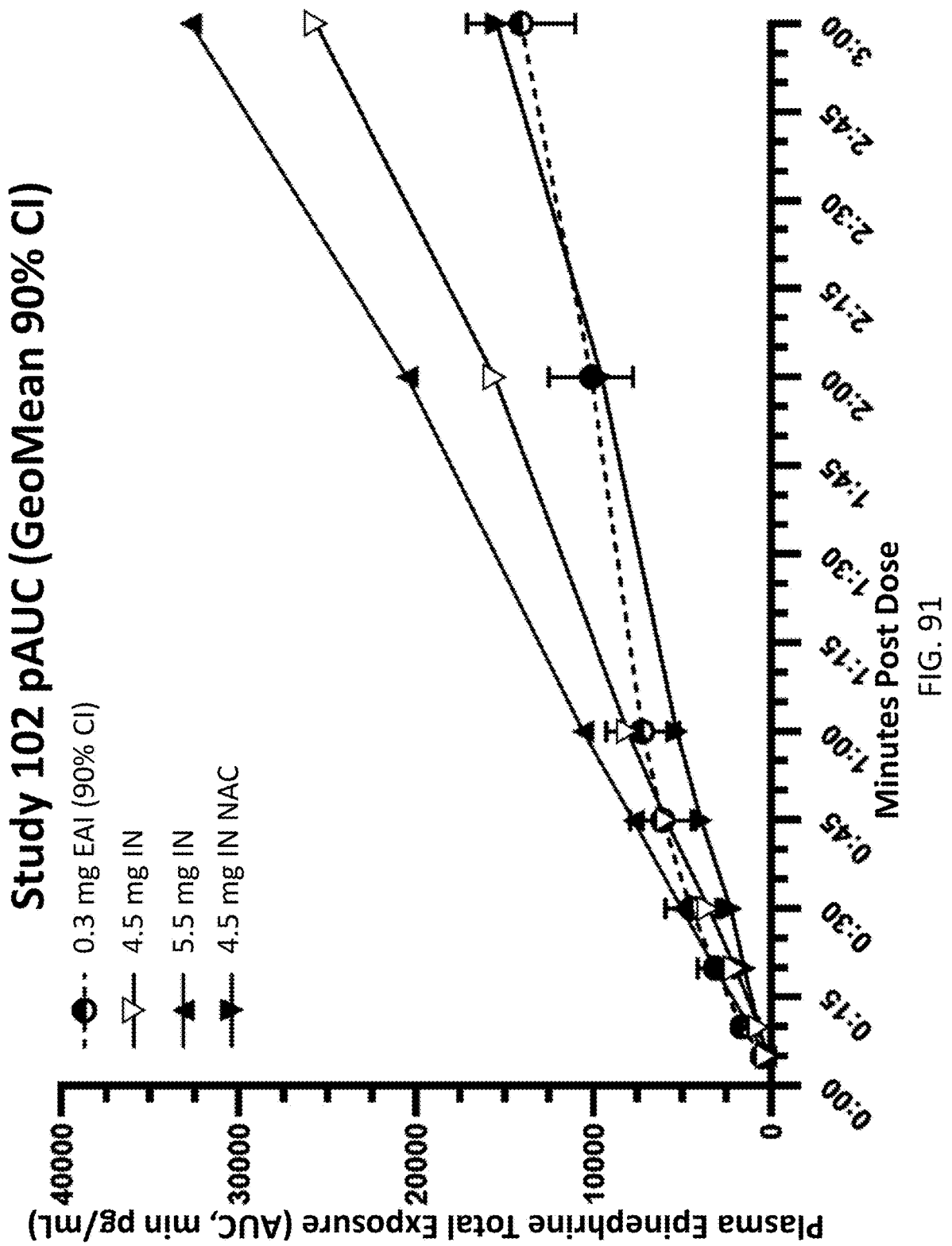
FIG. 91 is a graph comparing partial area under the curve for plasma epinephrine for autoinjector doses and various intranasal doses of epinephrine.

FIG. 91 is a graph comparing partial area under the curve for plasma epinephrine for both intramuscular doses and intranasal doses of the composition of the present invention. As shown in FIG. 91, the lower (4.5 mg) intranasal dose, with and without the nasal allergen administration, provides comparable exposure to the autoinjector dose (EpiPen) delivered intramuscularly. Data including average partial area under the curve values and confidence interval boundaries are provided in Table 10 below.

TABLE 10

Partial Area Under the Curve Plasma Epinephrine Data for Intranasal and Intramuscular Doses

| | N | | | |
|---|---|---|---|---|
| AUC | 10 4.5 mg IN | 9 0.3 mg EAI | 9 5.5 mg IN | 9 NAC 4.5 mg IN |
| 0-5 min | 201 | 519 | 283 | 228 |
| SE | 67 | 105 | 71 | 103 |
| % CV | 105 | 61 | 75 | 136 |
| UCI | 311 | 692 | 400 | 397 |
| LCI | 91 | 346 | 166 | 59 |
| 0-10 min | 677 | 1650 | 1214 | 722 |
| SE | 222 | 326 | 337 | 289 |
| % CV | 104 | 59 | 83 | 120 |
| UCI | 1042 | 2186 | 1768 | 1197 |
| LCI | 312 | 1114 | 660 | 247 |
| 0-20 min | 2031 | 3155 | 3134 | 1533 |
| SE | 620 | 609 | 852 | 542 |
| % CV | 97 | 58 | 82 | 106 |
| UCI | 3051 | 4157 | 4536 | 2425 |
| LCI | 1011 | 2153 | 1732 | 641 |
| 0-30 min | 3515 | 4509 | 5040 | 2275 |
| SE | 916 | 867 | 1308 | 729 |
| % CV | 82 | 58 | 78 | 96 |
| UCI | 5022 | 5935 | 7192 | 3474 |
| LCI | 2008 | 3083 | 2888 | 1076 |
| 0-45 min | 5902 | 6128 | 7752 | 3955 |
| SE | 1331 | 1116 | 1937 | 1279 |
| % CV | 71 | 55 | 75 | 97 |
| UCI | 8091 | 7964 | 10938 | 6059 |
| LCI | 3713 | 4294 | 4566 | 1851 |
| 0-60 min | 8086 | 7237 | 10609 | 5306 |
| SE | 1703 | 1240 | 2620 | 1738 |
| % CV | 67 | 51 | 74 | 98 |
| UCI | 10887 | 9277 | 14919 | 8165 |
| LCI | 5285 | 5197 | 6299 | 2447 |
| 0-120 min | 15628 | 10165 | 20503 | 9540 |
| SE | 3035 | 1458 | 5088 | 2734 |
| % CV | 61 | 43 | 74 | 86 |
| UCI | 20621 | 12563 | 28873 | 14037 |
| LCI | 10635 | 7767 | 12133 | 5043 |

48

TABLE 10-continued

Partial Area Under the Curve Plasma Epinephrine Data for Intranasal and Intramuscular Doses

| | N | | | |
|---|---|---|---|---|
| AUC | 10 4.5 mg IN | 9 0.3 mg EAI | 9 5.5 mg IN | 9 NAC 4.5 mg IN |
| 0-240 min | 25677 | 14103 | 32717 | 15484 |
| SE | 4606 | 1856 | 7773 | 3989 |
| % CV | 57 | 39 | 71 | 77 |
| UCI | 33254 | 17156 | 45504 | 22046 |
| LCI | 18100 | 11050 | 19930 | 8922 |

Figure 92:
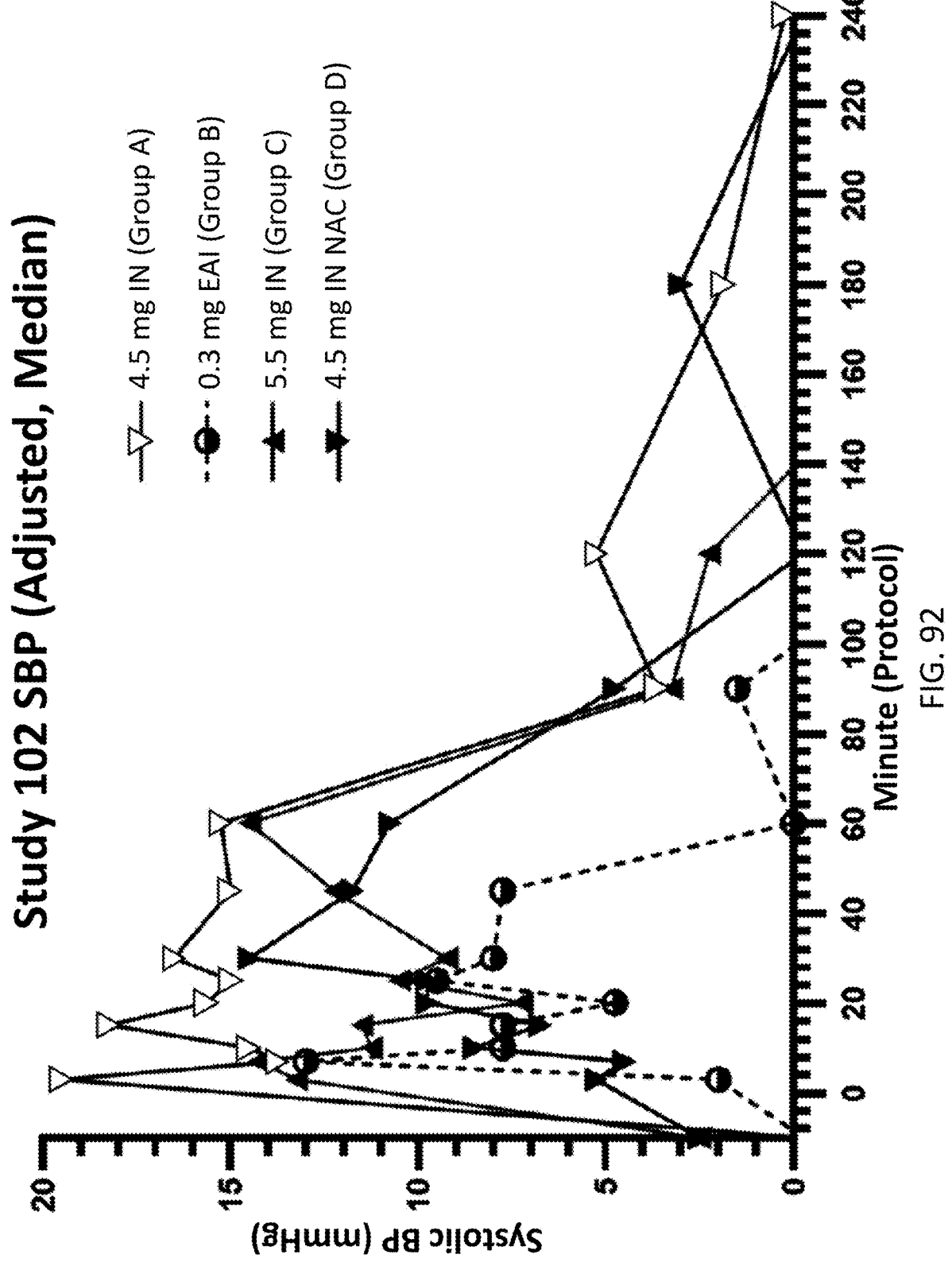
FIG. 92 is a graph comparing systolic blood pressure of patients over time after treatment with autoinjector doses and various intranasal doses of epinephrine.
Figure 93:
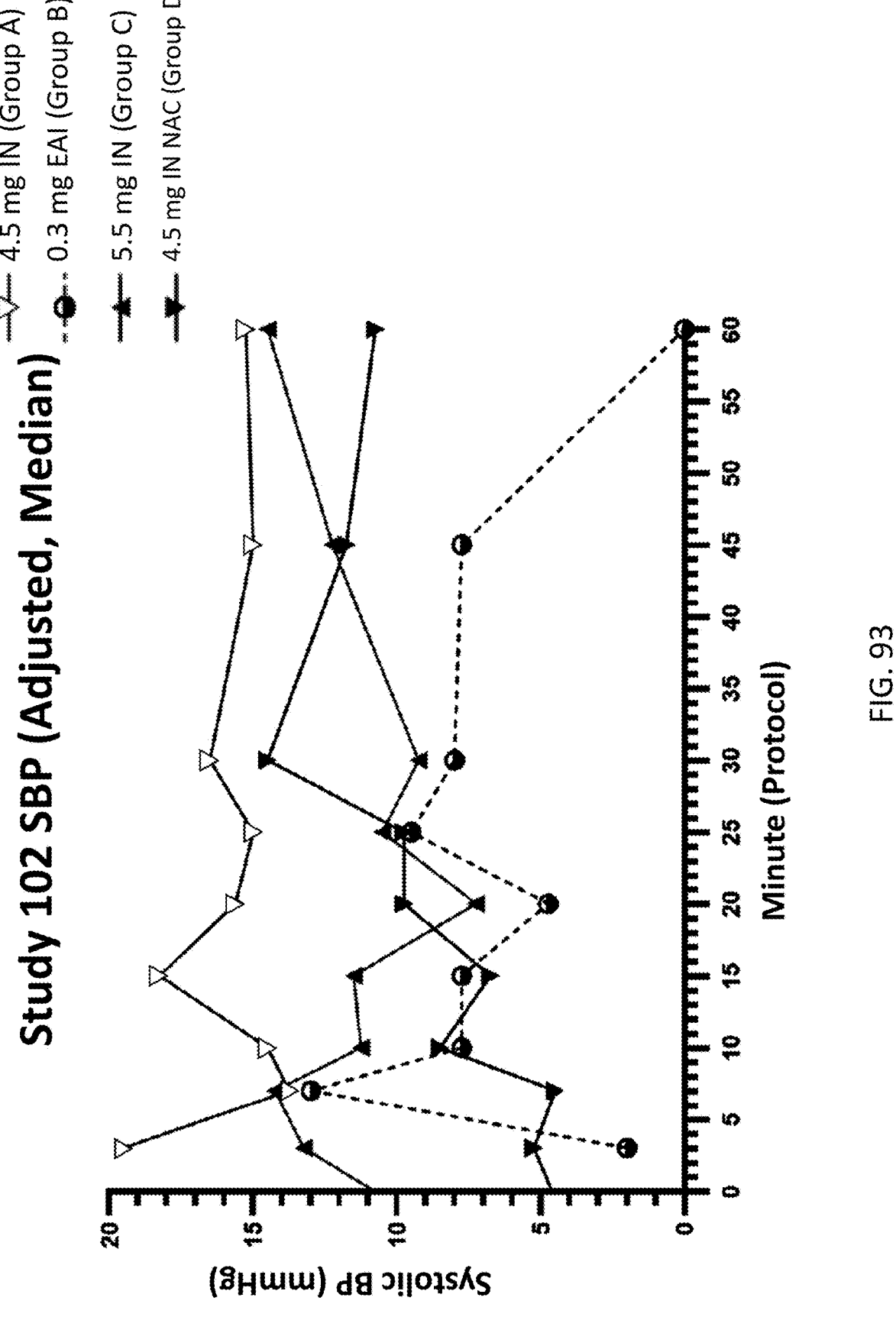
FIG. 93 is a graph comparing systolic blood pressure of patients over time focusing on the first hour after treatment with autoinjector doses and various intranasal doses of epinephrine.

FIGS. 92 and 93 show comparisons of systolic blood pressure of patients over time after treatment with both the intramuscular dose and intranasal doses of the composition of the present invention. As shown in FIGS. 92 and 93, both the high and low intranasal doses according to the present invention caused a more pronounced and earlier onset increase in systolic blood pressure compared to either intramuscular dose, while still being within a safe range of physiological effects. Additionally, both the high and low intranasal doses according to the present invention cause a sustained increase in systolic blood pressure compared to the intramuscular dose. These results indicate that the intranasal doses act faster and longer in providing relief than comparable intramuscular doses. A low or no dose response was observed between both the high and low intranasal doses according to the present invention. These results confirm the results of Study 101.

Figure 94:
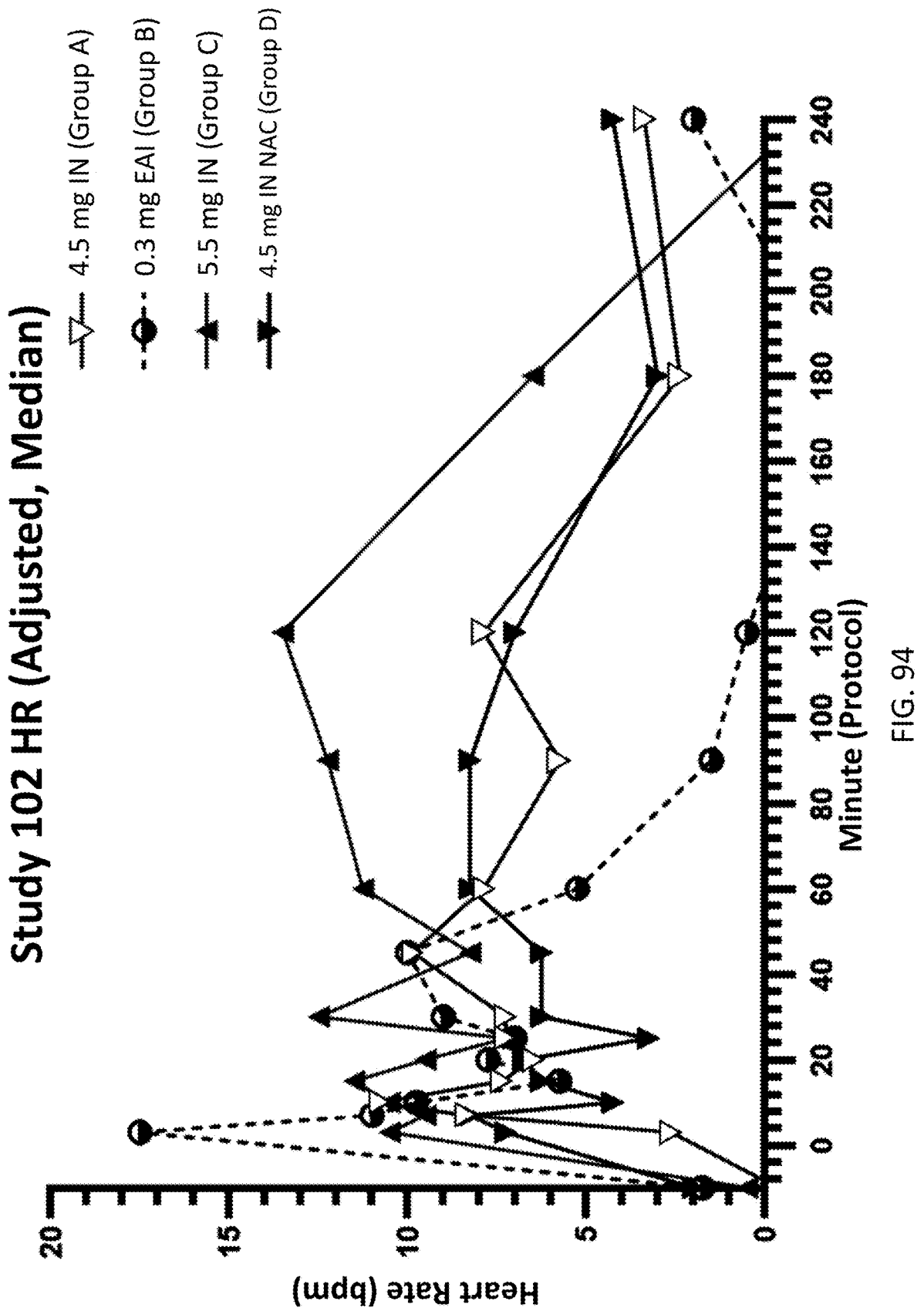
FIG. 94 is a graph comparing heart rate of patients over time after treatment with autoinjector doses and various intranasal doses of epinephrine.
Figure 95:
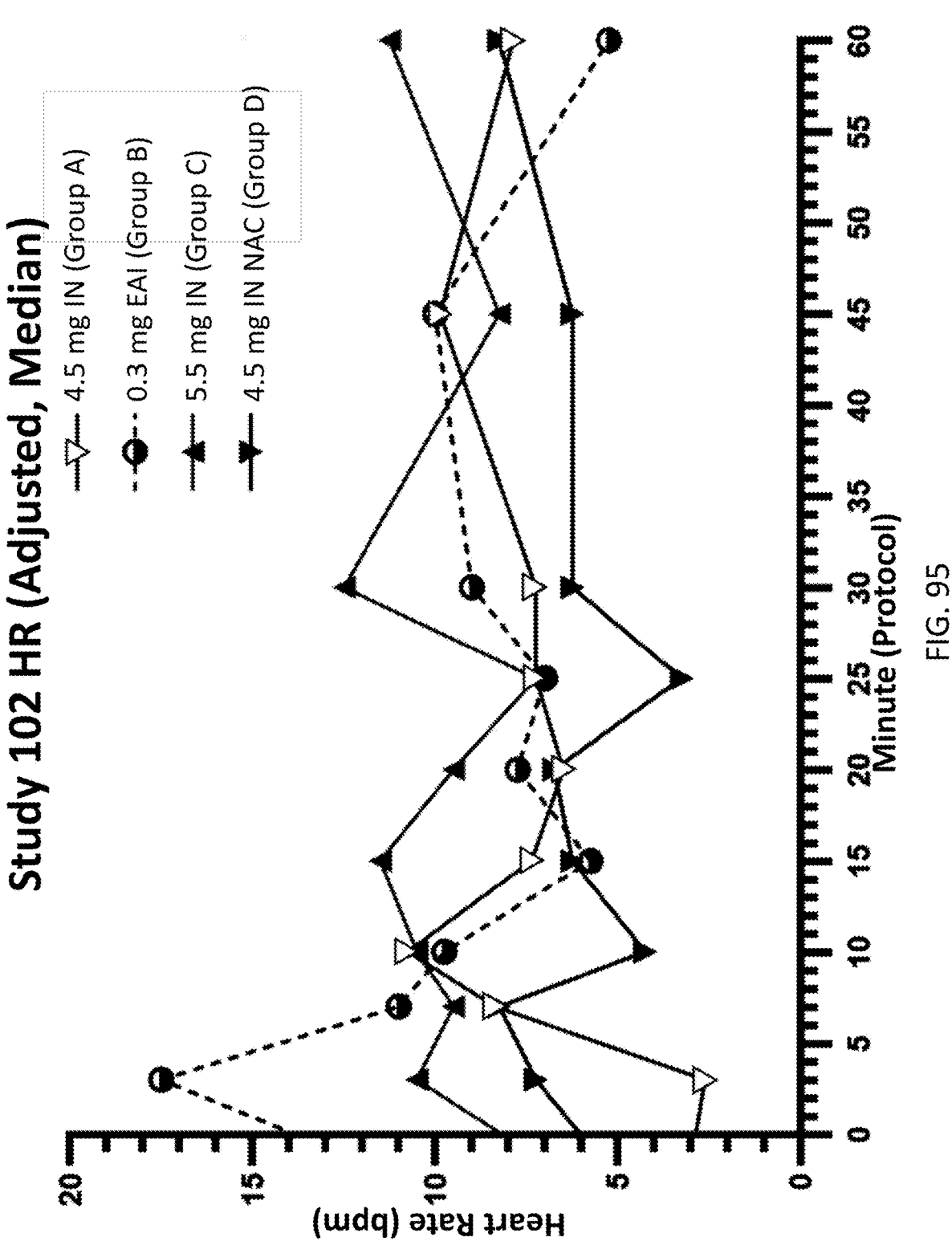
FIG. 95 is a graph comparing heart rate of patients over time focusing on the first hour after treatment with autoinjector doses and various intranasal doses of epinephrine.

FIGS. 94 and 95 show comparisons of heart rate of patients over time after treatment with the intramuscular dose and intranasal doses of the composition of the present invention. Similar to the effects on systolic blood pressure, the intranasal doses produced a more pronounced increase in heart rate in patients relative to the intramuscular doses, while still being within a safe range of physiological effects. However, the timing of the peak heart rate effects of the intranasal doses appears to be comparable to the timing of the peak heart rate effects of the intramuscular doses. Additionally, both the high and low intranasal doses according to the present invention cause a sustained increase in heart rate compared to the intramuscular dose. A low or no dose response was observed between both the high and low intranasal doses according to the present invention. These results confirm the results of Study 101.

Figure 96:
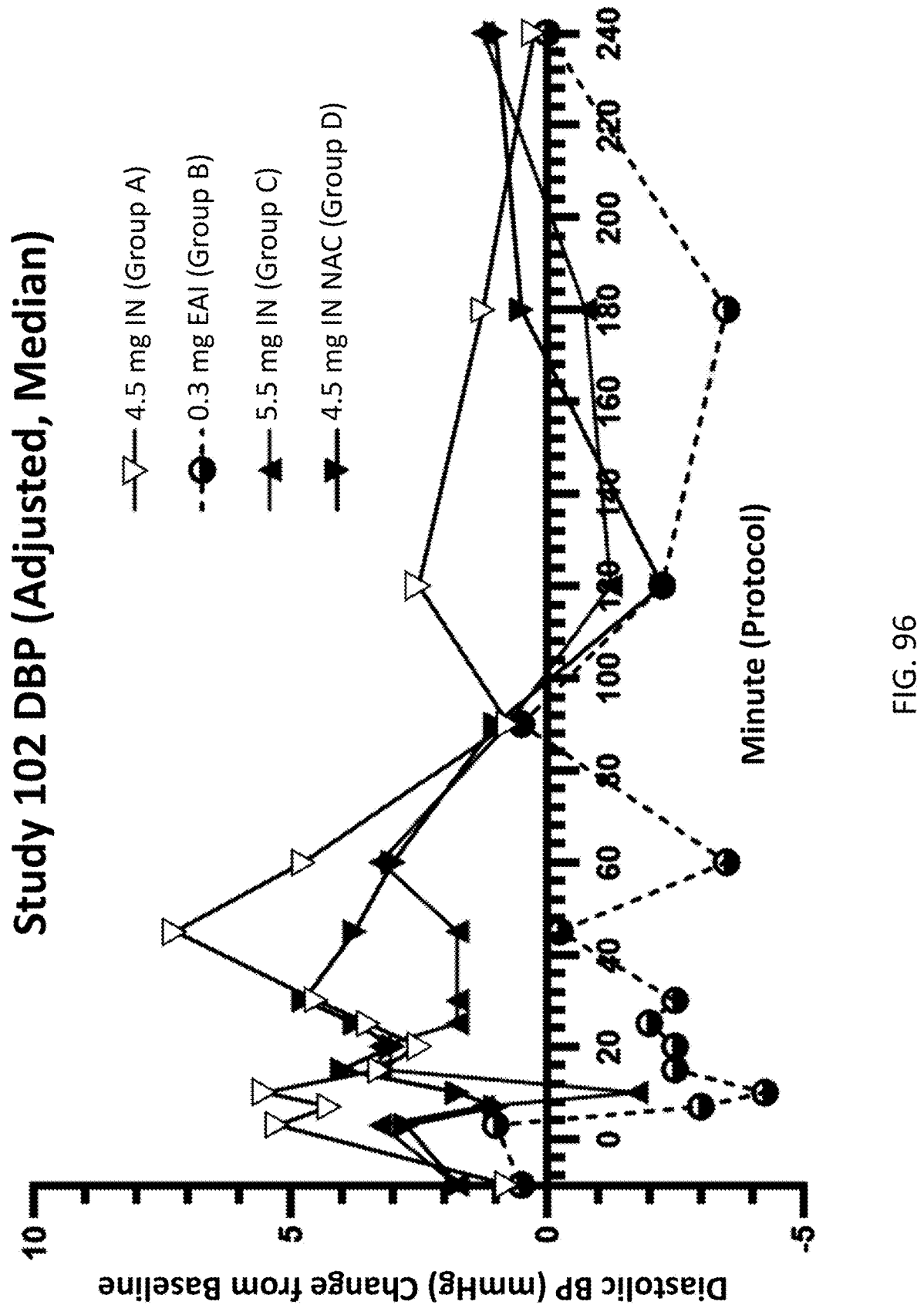
FIG. 96 is a graph comparing diastolic blood pressure of patients over time after treatment with autoinjector doses and various intranasal doses of epinephrine.
Figure 97:
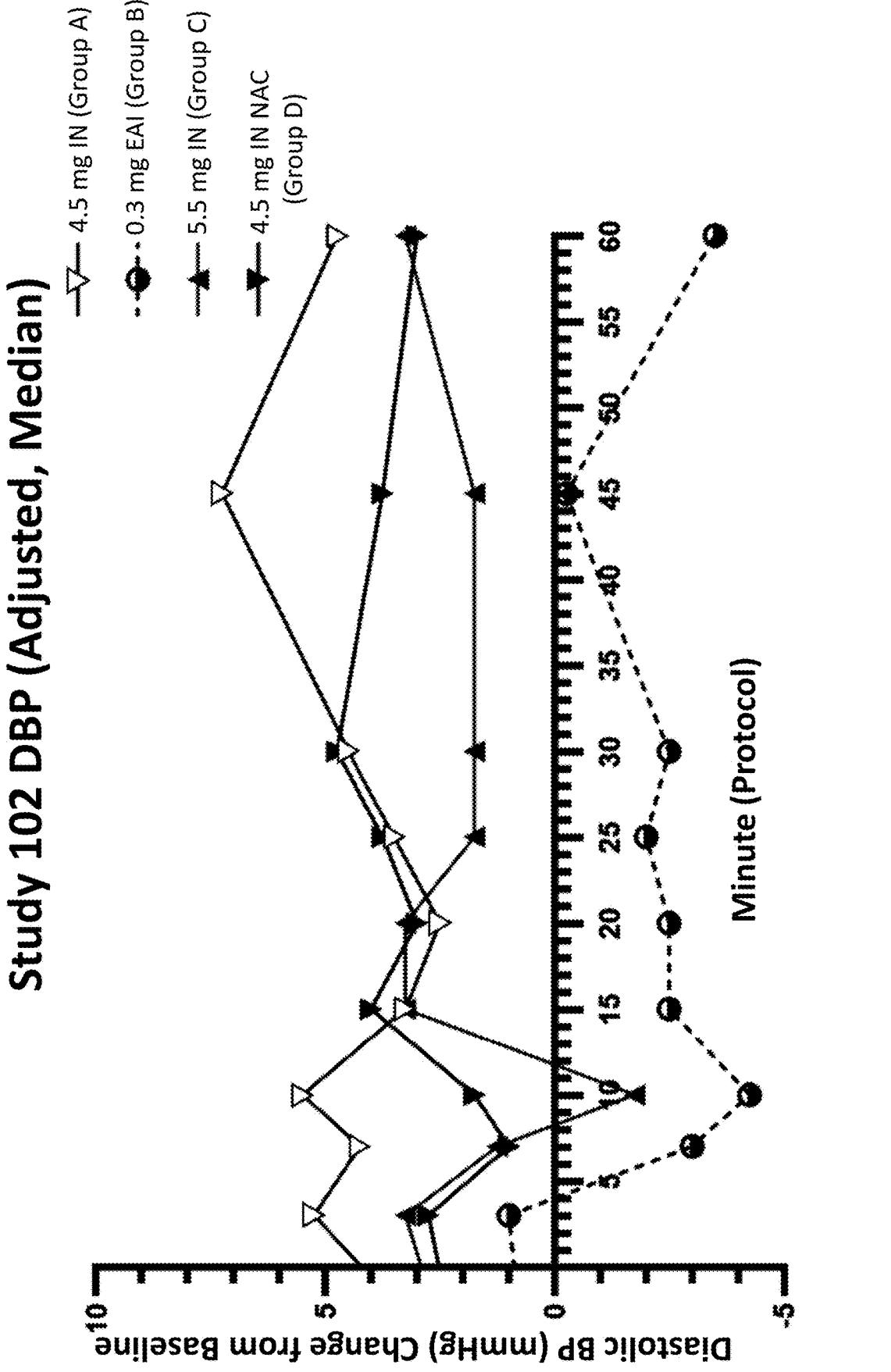
FIG. 97 is a graph comparing diastolic blood pressure of patients over time focusing on the first hour after treatment with autoinjector doses and various intranasal doses of epinephrine.

FIGS. 96 and 97 show comparisons of diastolic blood pressure of patients over time after treatment with the intramuscular dose and intranasal doses of the composition of the present invention. As shown in FIGS. 96 and 97, both the high and low intranasal doses according to the present invention caused a more pronounced and earlier onset increase in diastolic blood pressure compared to the intramuscular dose, while still being within a safe range of physiological effects. Additionally, both the high and low intranasal doses according to the present invention cause a sustained increase in diastolic blood pressure compared to the intramuscular dose. These results indicate that the intranasal doses act faster and longer in providing relief than comparable intramuscular doses. A low or no dose response was observed between both the high and low intranasal doses according to the present invention. These results confirm the results of Study 101.

Figure 98:
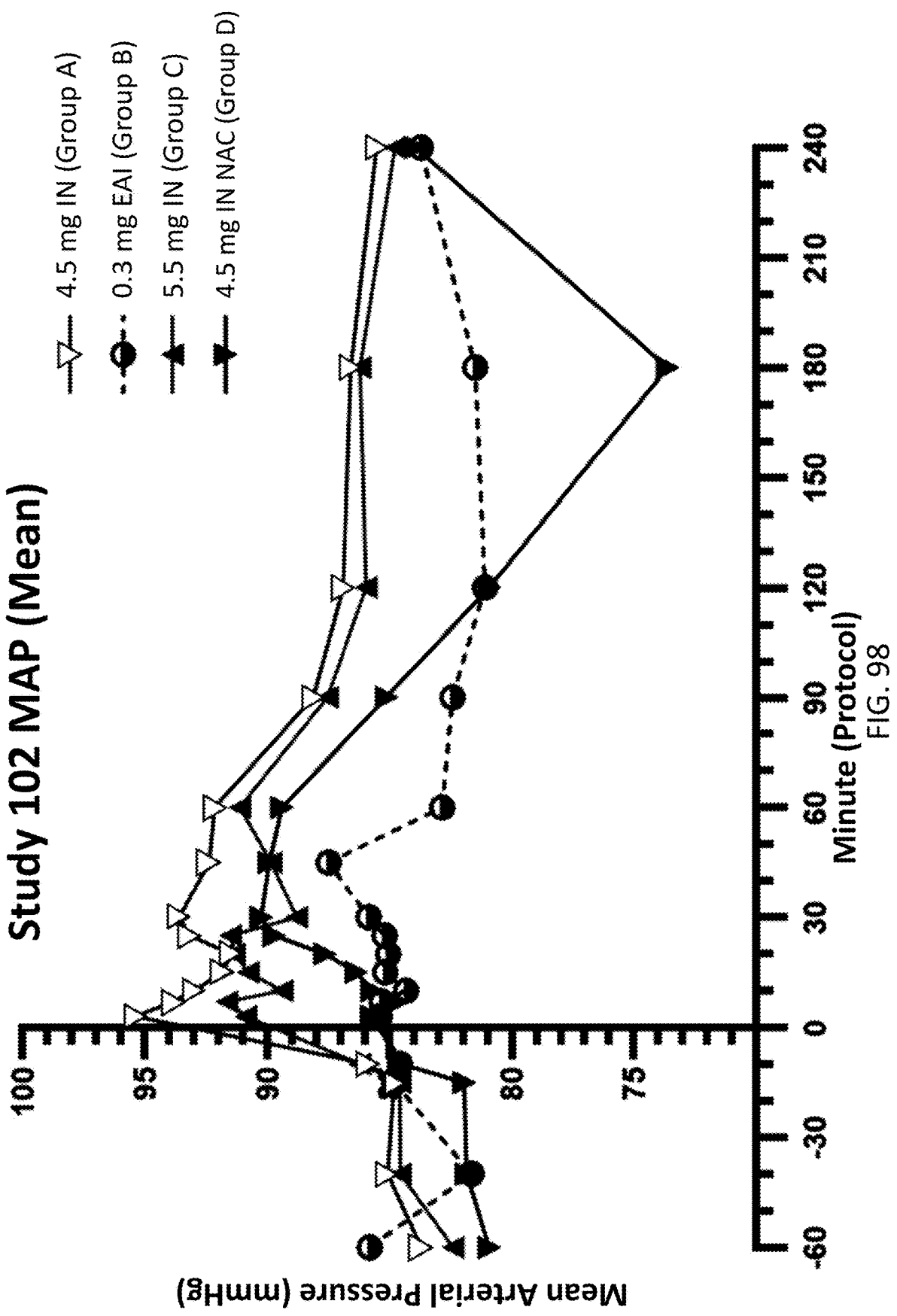
FIG. 98 is a graph comparing mean arterial pressure of patients over time after treatment with autoinjector doses and various intranasal doses of epinephrine.
Figure 99:
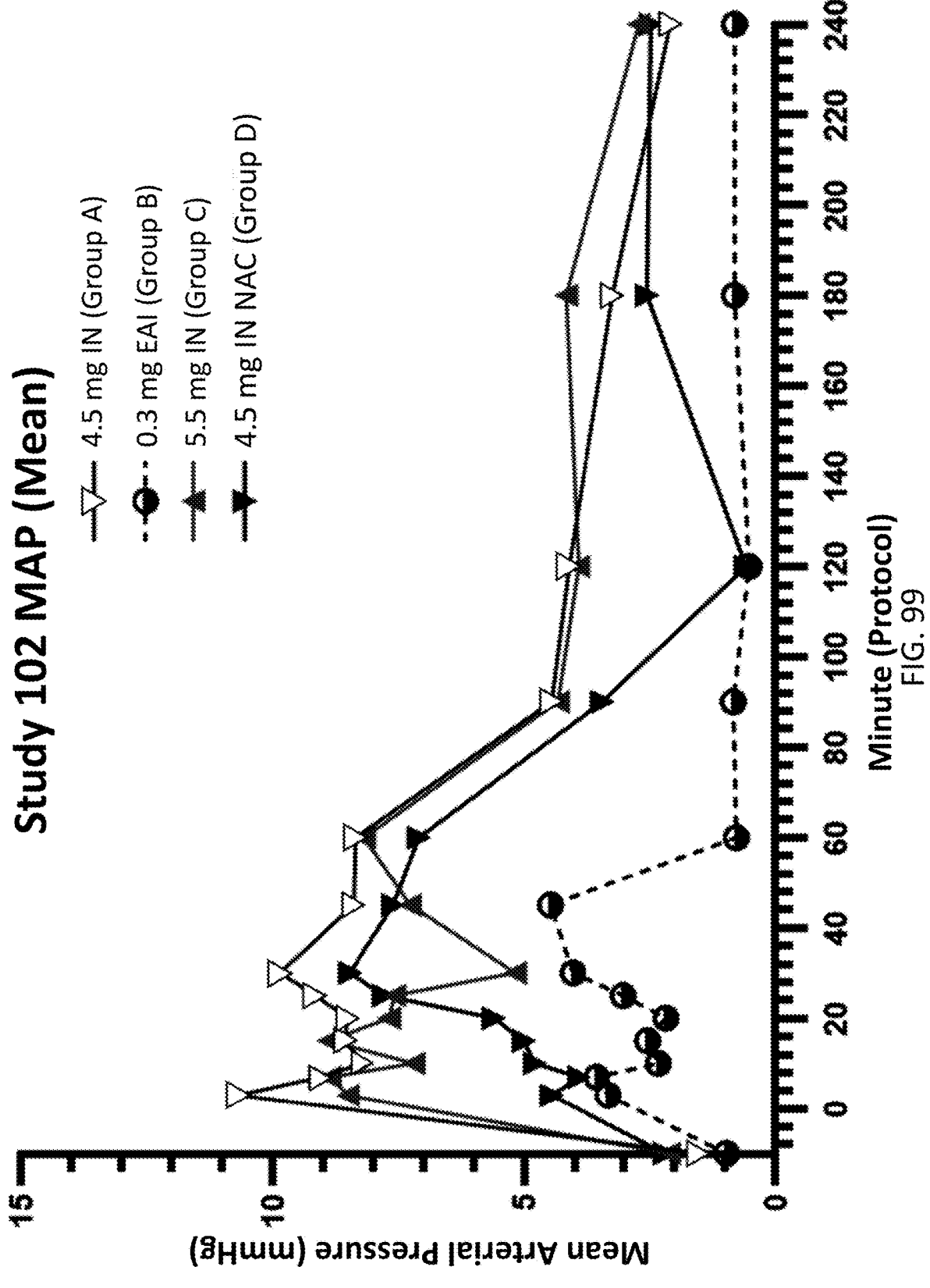
FIG. 99 is a graph comparing mean arterial pressure of patients over time focusing on the first hour after treatment with autoinjector doses and various intranasal doses of epinephrine.

FIGS. 98 and 99 show comparisons of mean arterial pressure (MAP) of patients over time after treatment with the intramuscular dose and intranasal doses of the composition of the present invention. As shown in FIGS. 98 and 99, both the high and low intranasal doses according to the present invention caused a more pronounced and earlier onset increase in mean arterial pressure compared to the intramuscular dose, while still being within a safe range of physiological effects. Additionally, both the high and low intranasal doses according to the present invention cause a sustained increase in mean arterial pressure compared to the intramuscular dose. A low or no dose response was observed between both the high and low intranasal doses according to the present invention. These results confirm the results of Study 101.

Figure 100:
FIG. 100 is a graph of mean unadjusted plasma epinephrine concentration relative to time of dose administration in humans after treatment with intramuscular doses, epinephrine autoinjector doses, intranasal doses of the composition of the present invention, and other intranasal dosing systems.

FIG. 100 is a graph of plasma epinephrine concentration relative to time post dose administration in humans after treatments from both Study 101 and Study 102. As shown in FIG. 100, the intranasal doses in Study 102 generally provide lower exposures than the intranasal doses in Study 101.

Figure 101:
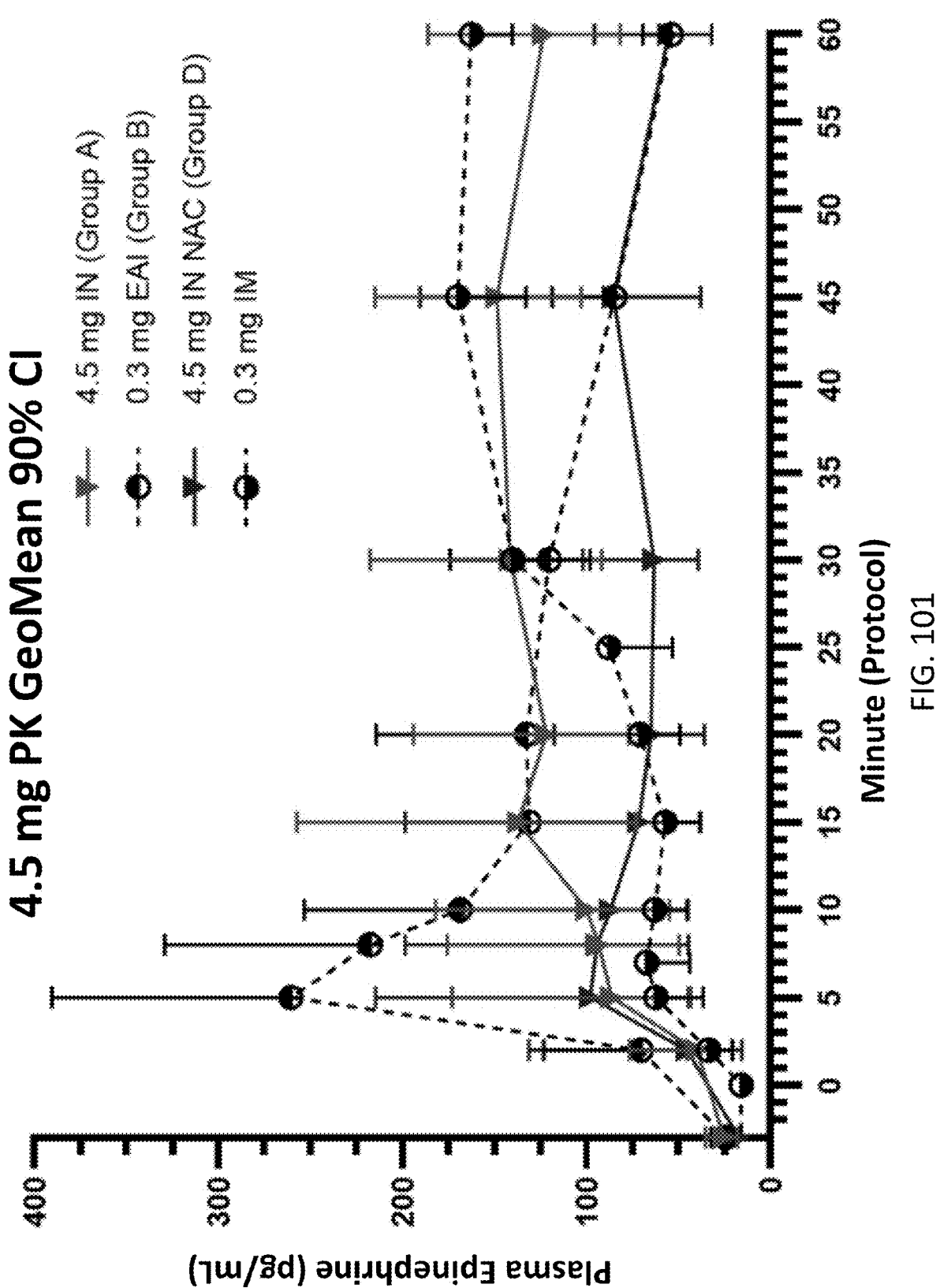
FIG. 101 is a graph of mean plasma epinephrine concentration, with 90% confidence intervals, relative to time of dose administration in humans after treatment with intramuscular doses, epinephrine autoinjector doses, intranasal doses of the composition of the present invention, and other intranasal dosing systems.

FIG. 101 is a graph of mean plasma epinephrine concentration, with 90% confidence intervals, relative to time of dose administration in humans after treatment with intramuscular doses, epinephrine autoinjector doses, intranasal doses of the composition of the present invention, and other intranasal dosing systems. As shown in FIG. 101, from 0 to 10 minutes, the 4.5 mg intranasal dose of the composition of the present invention exhibits a plasma epinephrine concentration that is less than the 0.3 mg epinephrine autoinjector dose and is greater than the 0.3 mg intramuscular dose. Thus, the 4.5 mg intranasal dose of the composition of the present invention provides bracketed time-concentration in the first 10 minutes, between the 0.3 mg intramuscular dose and the 0.3 mg epinephrine autoinjector delivered intramuscularly. Therefore, the 4.5 mg intranasal dose of the composition of the present invention provides at least comparable pharmacokinetic effects as the existing intramuscular dosing systems.

Figure 102:
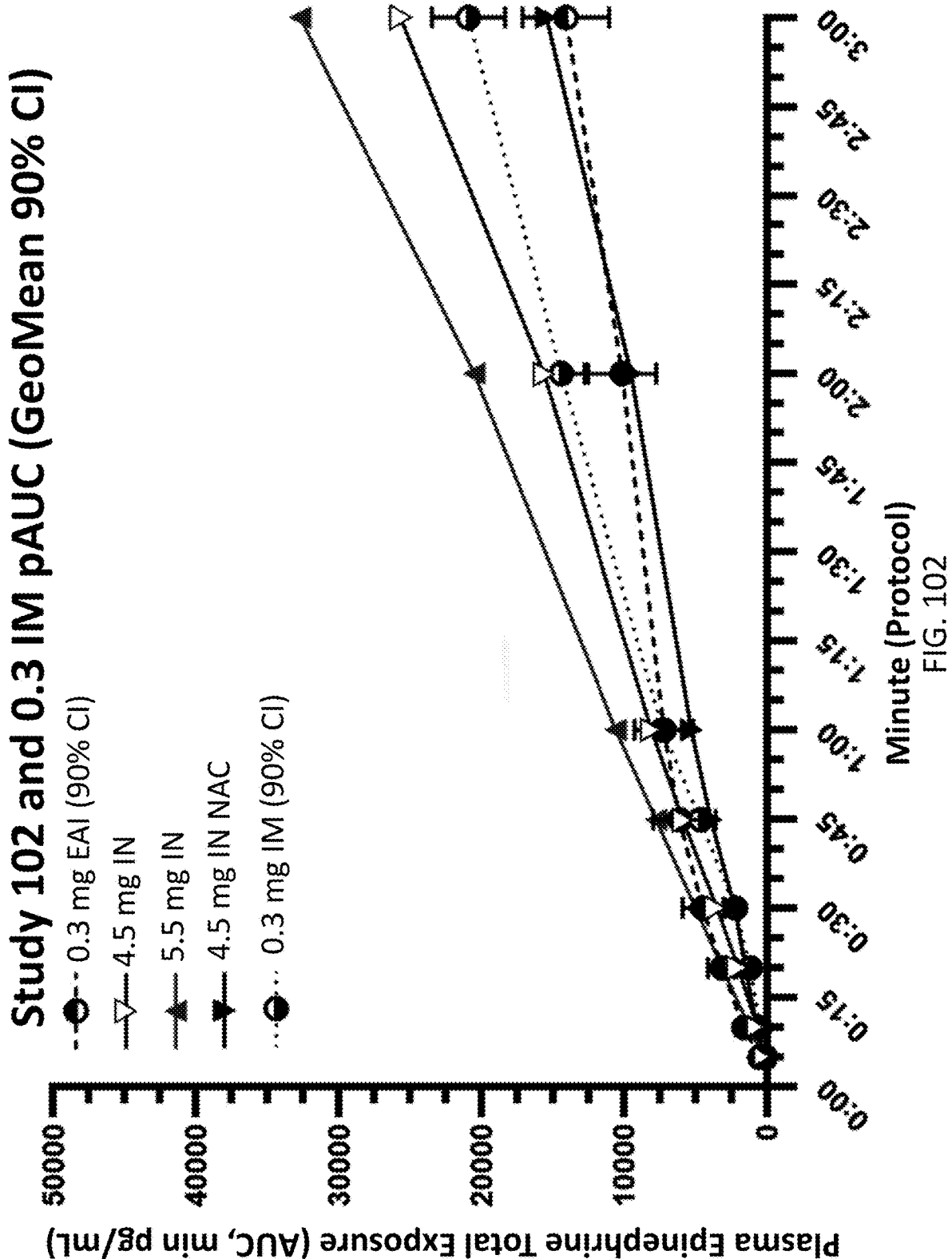
FIG. 102 is a graph comparing partial area under the curve for plasma epinephrine for autoinjector doses, intramuscular doses, and various intranasal doses of epinephrine.

FIG. 102 is a graph comparing partial area under the curve for plasma epinephrine for autoinjector doses, intramuscular doses, and various intranasal doses of epinephrine. As shown in FIG. 102, the 4.5 mg intranasal dose of the composition of the present invention is comparable to the epinephrine autoinjector dose delivered intramuscularly in the first 60 minutes. Additionally, as shown in FIG. 102, the 4.5 mg intranasal dose of the composition of the present invention is comparable to the 0.3 mg intramuscular dose from 1 to 3 hours.

Figure 103:
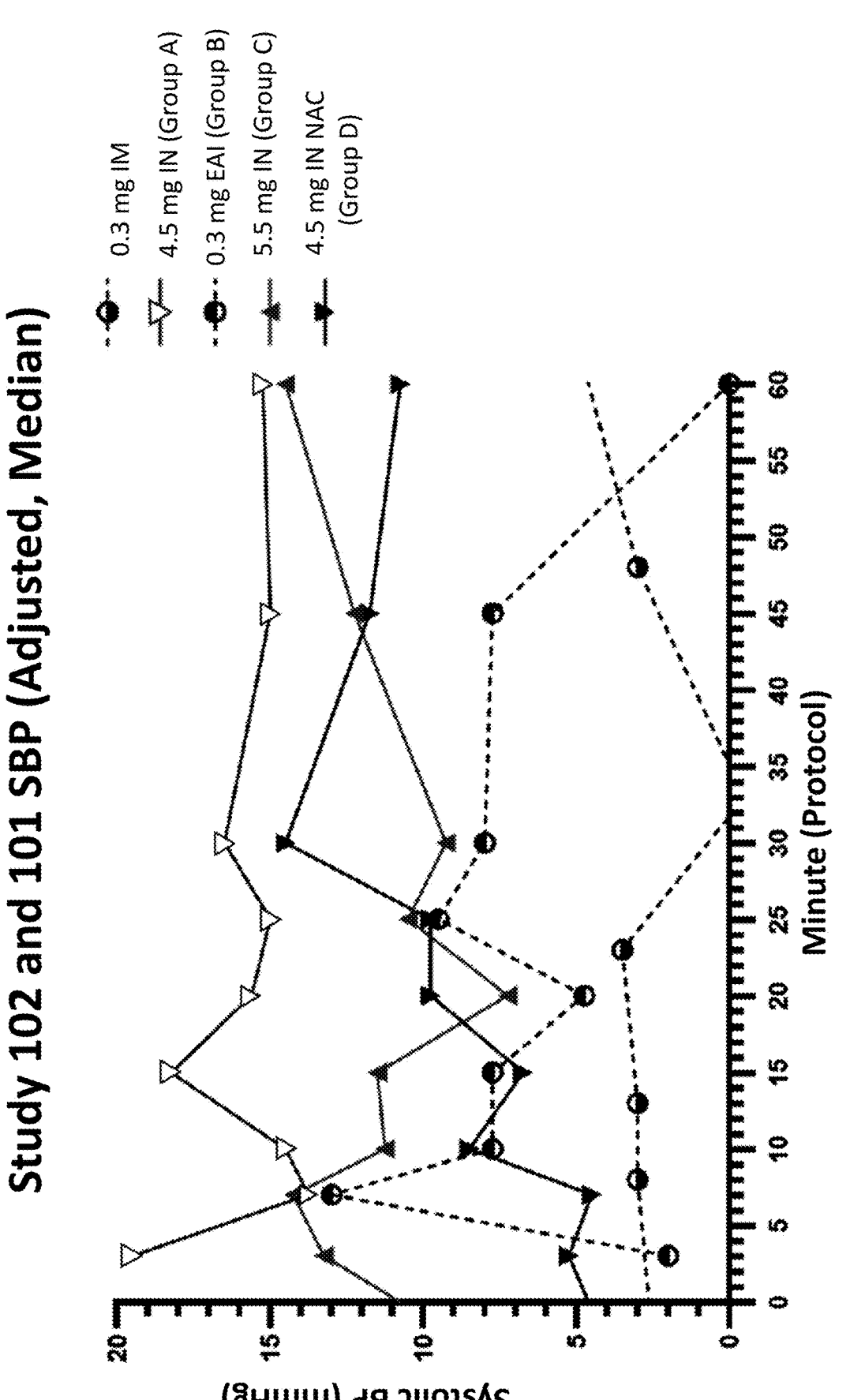
FIG. 103 is a graph comparing systolic blood pressure of patients over time after treatment with autoinjector doses, intramuscular doses, and various intranasal doses of epinephrine.

FIG. 103 is a graph comparing systolic blood pressure of patients over time after treatment with autoinjector doses, intramuscular doses, and various intranasal doses of epinephrine. As shown in FIG. 103, the 4.5 mg intranasal dose of the composition of the present invention provides slightly higher systolic blood pressure changes from baseline, as compared to the 0.3 mg epinephrine autoinjector delivered intramuscularly.

Figure 104:
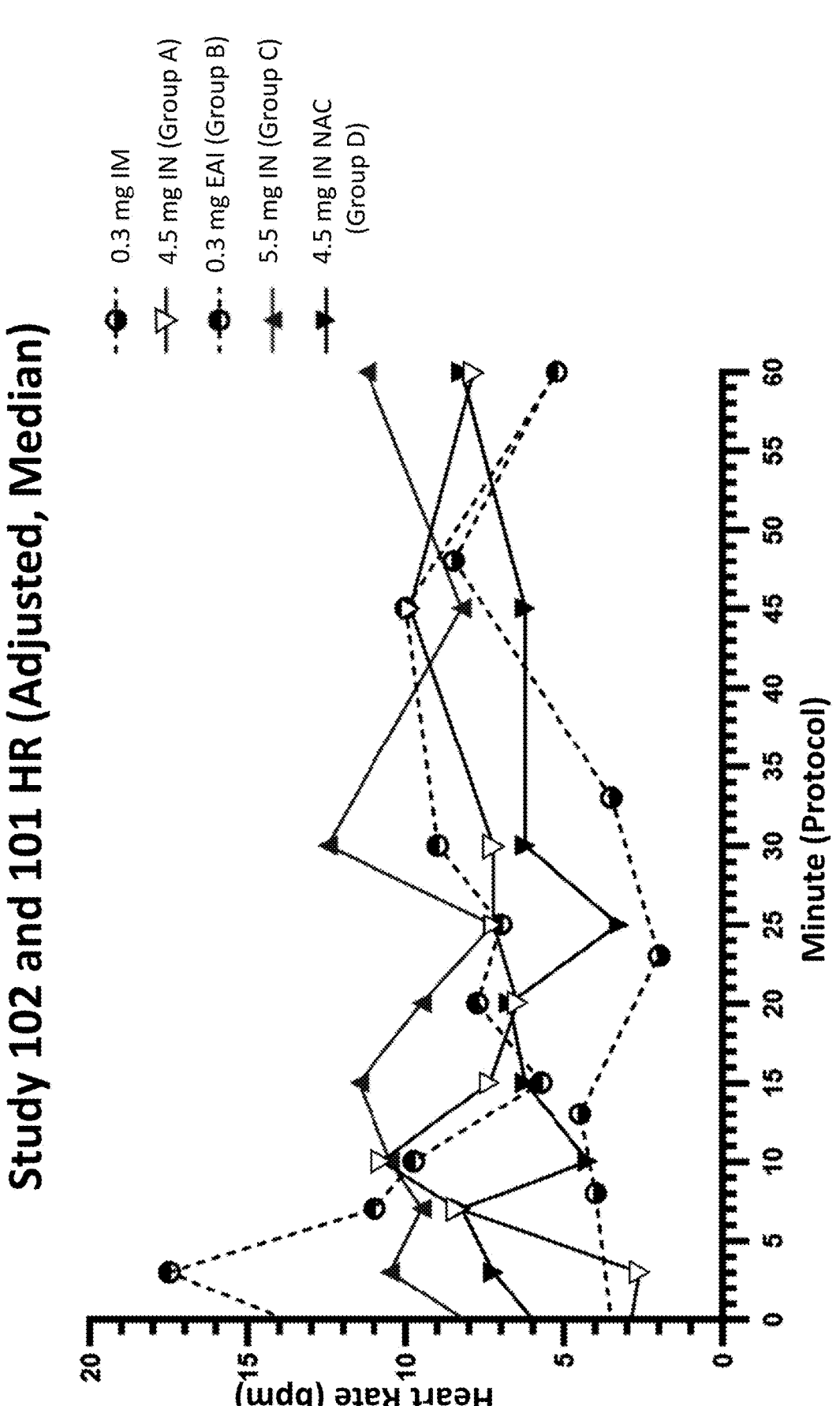
FIG. 104 is a graph comparing heart rates of patients over time after treatment with autoinjector doses, intramuscular doses, and various intranasal doses of epinephrine.

FIG. 104 is a graph comparing heart rates of patients over time after treatment with autoinjector doses, intramuscular doses, and various intranasal doses of epinephrine. As shown in FIG. 104, the 4.5 mg intranasal dose of the composition of the present invention provides slightly lower heart rate changes from baseline, as compared to the 0.3 mg epinephrine autoinjector delivered intramuscularly.

Additionally, both the high and low intranasal doses according to the present invention cause a maximum pharmacodynamic effect before causing a maximum pharmacokinetic effect, wherein both the high and low intranasal doses according to the present invention cause the maximum effect (Emax) to be achieved before Tmax.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments as discussed above.

Where methods and/or events described above indicate certain events and/or procedures occurring in certain order, the ordering of certain events and/or procedures may be modified. Additionally, certain events and/or procedures may be performed concurrently in a parallel process, when possible, as well as performed sequentially as described above.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

Certain modifications and improvements will occur to those skilled in the art upon a reading of the foregoing description. The above-mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the present invention.

The invention claimed is:

1. An apparatus for delivery of a spray dried powder pharmaceutical composition, the apparatus comprising:

a reservoir containing a dose of the spray dried powder pharmaceutical composition, wherein the spray dried powder pharmaceutical composition comprises epinephrine or a pharmaceutically acceptable salt thereof and a carrier, wherein the spray dried powder pharmaceutical composition has a bulk particle size distribution characterized by a Dv50 of between about 5 microns and about 30 microns;

an air delivery assembly configured to be placed in fluid communication with the reservoir; and a delivery head operatively coupled to the reservoir, wherein the delivery head defines a delivery aperture;

wherein upon actuation of the apparatus, the air delivery assembly is configured to produce an airflow through the reservoir to deliver a mixture of the airflow and the dose of the spray dried powder pharmaceutical composition via the delivery aperture, wherein the mixture has an emitted particle size distribution characterized by a Dv50 of between about 15 microns and about 200 microns and that is greater than the Dv50 of the bulk particle size distribution.

2. The apparatus of claim 1, wherein the bulk particle size distribution is characterized by a Dv10 of between about 1.5 microns and about 5 microns, wherein the emitted particle size distribution is characterized by a Dv10 of between about 5 microns and about 10 microns and is greater than the Dv10 of the bulk particle size distribution.

3. The apparatus of claim 1, wherein the bulk particle size distribution is characterized by a Dv90 of between about 13 microns and about 50 microns, wherein the emitted particle size distribution is characterized by a Dv90 of between about 475 microns and about 625 microns.

4. The apparatus of claim 1, wherein the Dv50 of the bulk particle size distribution is between about 5 microns and about 18 microns and wherein the Dv50 of the emitted particle size distribution is between about 20 microns and about 185 microns.

5. The apparatus of claim 1, wherein the spray dried powder pharmaceutical composition has a moisture content of between about 3% and about 6%.

6. The apparatus of claim 1, wherein the dose contains between about 3.5 mg and about 5.5 mg of the epinephrine or the pharmaceutically acceptable salt.

7. The apparatus of claim 1, wherein the spray dried powder pharmaceutical composition further comprises a dispersing agent.

8. The apparatus of claim 1, wherein the air delivery assembly includes an air chamber and a piston configured to be moved within the air chamber to produce the airflow through the reservoir.

9. The apparatus of claim 8, wherein the apparatus is configured to be manually actuated by the piston moving within the air chamber.

10. The apparatus of claim 1, wherein the spray dried powder pharmaceutical composition does not include an alpha-adrenergic blocker.

11. An apparatus for delivery of a spray dried powder pharmaceutical composition, the apparatus comprising:

a reservoir containing a dose of the spray dried powder pharmaceutical composition, wherein the spray dried powder pharmaceutical composition comprises epinephrine or a pharmaceutically acceptable salt thereof, wherein the spray dried powder pharmaceutical composition has a bulk particle size distribution characterized by a Dv50 of between about 5 microns and about 18 microns;

an air delivery assembly configured to be placed in fluid communication with the reservoir; and a delivery head operatively coupled to the reservoir, the delivery head defining a delivery aperture;

wherein upon actuation of the apparatus, the air delivery assembly is configured to produce an airflow through the reservoir to deliver a mixture of the airflow and the dose of the spray dried powder pharmaceutical composition via the delivery aperture, wherein the mixture has an emitted particle size distribution characterized by a Dv50 of between about 20 microns and about 185 microns and that is greater than the Dv50 of the bulk particle size distribution.

12. The apparatus of claim 11, wherein the spray dried powder composition further includes a carrier.

13. The apparatus of claim 12, wherein the carrier is lactose monohydrate.

14. The apparatus of claim 11, wherein the spray dried powder pharmaceutical composition does not include an alpha-adrenergic blocker.

15. The apparatus of claim 11, wherein the bulk particle size distribution is characterized by a Dv10 of between about 1.5 microns and about 5 microns, wherein the emitted particle size distribution is characterized by a Dv10 of between about 5 microns and about 10 microns and is greater than the Dv10 of the bulk particle size distribution.

16. The apparatus of claim 11, wherein the bulk particle size distribution is characterized by a Dv90 of between about 13 microns and about 50 microns, wherein the emitted particle size distribution is characterized by a Dv90 of between about 475 microns and about 625 microns.

17. The apparatus of claim 11, wherein the dose contains between about 3.5 mg and about 5.5 mg of the epinephrine or the pharmaceutically acceptable salt.

18. A spray dried powder pharmaceutical composition comprising:

epinephrine or a pharmaceutically acceptable salt thereof; and a carrier;

wherein a single dose of the spray dried powder pharmaceutical composition contains about 3.5 mg to about 5.5 mg of epinephrine or the pharmaceutically acceptable salt thereof;

wherein the spray dried powder pharmaceutical composition has a bulk particle size distribution characterized by a Dv50 of between about 5 microns and about 30 microns; and wherein the spray dried powder pharmaceutical composition is formulated such that intranasal delivery of the dose of the spray dried powder pharmaceutical composition through an apparatus comprising an air delivery assembly and a delivery aperture produces a spray having an emitted particle size distribution characterized by a Dv50 of between about 15 microns and about 200 microns and that is greater than the Dv50 of the bulk particle size distribution.

19. The spray dried powder pharmaceutical composition of claim 18, wherein the spray dried powder pharmaceutical composition does not include an alpha-adrenergic blocker.

20. The spray dried powder pharmaceutical composition of claim 18, wherein the carrier includes any of mannitol, a cyclodextrin, citric acid, lactose, or sodium carboxymethylcellulose.

* * * * *